United States Patent
Nelson et al.

(10) Patent No.: US 11,073,625 B2
(45) Date of Patent: Jul. 27, 2021

(54) STRUCTURED DETECTORS AND DETECTOR SYSTEMS FOR RADIATION IMAGING

(71) Applicant: Minnesota Imaging and Engineering LLC, Excelsior, MN (US)

(72) Inventors: Robert Sigurd Nelson, La Mesa, CA (US); William Bert Nelson, Excelsior, MN (US)

(73) Assignee: Minnesota Imaging and Engineering LLC, Excelsior, MN (US)

( * ) Notice: Subject to any disclaimer, the term of this patent is extended or adjusted under 35 U.S.C. 154(b) by 0 days.

(21) Appl. No.: 16/284,776

(22) Filed: Feb. 25, 2019

(65) Prior Publication Data

US 2019/0187302 A1    Jun. 20, 2019

Related U.S. Application Data

(60) Division of application No. 15/701,088, filed on Sep. 11, 2017, now Pat. No. 10,365,383, which is a
(Continued)

(51) Int. Cl.
*G01T 1/20* (2006.01)
*G01N 23/046* (2018.01)
(Continued)

(52) U.S. Cl.
CPC ............ *G01T 1/2018* (2013.01); *A61B 6/032* (2013.01); *A61B 6/037* (2013.01); *A61B 6/4233* (2013.01);
(Continued)

(58) Field of Classification Search
CPC ... G01T 1/2018; A61B 8/4416; A61B 6/4417; A61B 6/4233; A61B 6/032; A61B 6/037;
(Continued)

(56) References Cited

U.S. PATENT DOCUMENTS

| 4,160,997 A | 7/1979 | Schwartz |
| 4,209,908 A | 7/1980 | Fleer |

(Continued)

FOREIGN PATENT DOCUMENTS

| EP | 0363092 A2 | 4/1990 |
| EP | 1072717 A1 | 1/2001 |

(Continued)

OTHER PUBLICATIONS

"Third-party submission under 37 CFR 1.290 filed on Mar. 4, 2016 and entered in U.S. Appl. No. 14/804,799".
(Continued)

*Primary Examiner* — David P Porta
*Assistant Examiner* — Gisselle M Gutierrez
(74) *Attorney, Agent, or Firm* — Dorsey & Whitney LLP

(57) ABSTRACT

Detector module designs for radiographic include first and second layers of scintillator rods or pixel arrays oriented in first and second directions. The first and second directions are transversely oriented to define a light sharing region between the first and second layers. Encoding features may be disposed in, on or between the first and second layers, and configured to modulate propagation of optical signals therealong or therebetween.

44 Claims, 30 Drawing Sheets

Related U.S. Application Data continuation-in-part of application No. 15/699,458, filed on Sep. 8, 2017, now Pat. No. 10,274,610.

(60) Provisional application No. 62/385,466, filed on Sep. 9, 2016.

(51) Int. Cl.
*A61B 6/03* (2006.01)
*A61B 6/00* (2006.01)
*A61B 8/00* (2006.01)

(52) U.S. Cl.
CPC .......... *A61B 6/4417* (2013.01); *A61B 8/4416* (2013.01); *G01N 23/046* (2013.01); *G01N 2223/419* (2013.01); *G01N 2223/505* (2013.01)

(58) Field of Classification Search
CPC .......... G01N 23/046; G01N 2223/505; G01N 2223/419
USPC ...................................................... 250/370.11
See application file for complete search history.

(56) References Cited

U.S. PATENT DOCUMENTS

| | | |
|---|---|---|
| 4,260,054 A | 4/1981 | Bory et al. |
| 4,308,252 A | 12/1981 | Tomaich et al. |
| 4,525,628 A | 6/1985 | Dibianca et al. |
| 4,560,882 A | 12/1985 | Barbaric et al. |
| 4,564,005 A | 1/1986 | Marchand et al. |
| 4,666,037 A | 5/1987 | Weissman |
| 4,937,453 A | 6/1990 | Nelson |
| 4,950,907 A | 8/1990 | Kuhn |
| 4,978,297 A | 12/1990 | Vlock |
| 5,017,782 A | 5/1991 | Nelson |
| 5,258,145 A | 11/1993 | Nelson |
| 5,331,166 A | 7/1994 | Crosetto et al. |
| 5,376,806 A | 12/1994 | Hejazi |
| 5,434,417 A | 7/1995 | Nygren |
| 5,912,942 A | 6/1999 | Schick et al. |
| 6,097,902 A | 8/2000 | Blume |
| 6,117,471 A | 9/2000 | King |
| 6,315,444 B1 | 11/2001 | Koren |
| 6,352,949 B1 | 3/2002 | Willems et al. |
| 6,583,420 B1 | 6/2003 | Nelson et al. |
| 6,693,291 B2 | 2/2004 | Nelson et al. |
| 7,015,460 B2 | 3/2006 | Nelson et al. |
| 7,147,372 B2 | 12/2006 | Nelson et al. |
| 7,291,841 B2 | 11/2007 | Nelson et al. |
| 7,635,848 B2 | 12/2009 | Nelson |
| 7,692,156 B1 | 4/2010 | Nagarkar |
| 7,778,380 B2 | 8/2010 | Altman et al. |
| 7,968,853 B2 | 6/2011 | Altman et al. |
| 8,017,906 B2 | 9/2011 | Nelson et al. |
| 8,115,174 B2 | 2/2012 | Nelson |
| 8,115,175 B2 | 2/2012 | Nelson |
| 8,183,533 B2 | 5/2012 | Nelson |
| 8,183,535 B2 | 5/2012 | Danielsson et al. |
| 8,378,310 B2 | 2/2013 | Bornefalk et al. |
| 8,742,932 B2 | 6/2014 | Casares |
| 9,347,893 B2 | 5/2016 | Nelson et al. |
| 9,384,864 B2 | 7/2016 | Nelson et al. |
| 9,763,126 B2 | 9/2017 | Lee |
| 10,067,239 B2 | 9/2018 | Nelson et al. |
| 10,088,580 B2 | 10/2018 | Nelson et al. |
| 10,365,383 B2 | 7/2019 | Nelson et al. |
| 10,509,135 B2 | 12/2019 | Nelson et al. |
| 10,509,136 B2 | 12/2019 | Nelson et al. |
| 10,520,611 B2 | 12/2019 | Nelson et al. |
| 10,663,606 B2 | 5/2020 | Nelson et al. |
| 2001/0055368 A1 | 12/2001 | Carroll |
| 2002/0011571 A1 | 1/2002 | Lin et al. |
| 2003/0034455 A1 | 2/2003 | Schreiner et al. |
| 2003/0072419 A1 | 4/2003 | Bruder et al. |
| 2004/0251419 A1 | 12/2004 | Nelson et al. |
| 2005/0258373 A1 | 11/2005 | Lacy |
| 2006/0016877 A1 | 1/2006 | Bonalle et al. |
| 2006/0151708 A1 | 7/2006 | Bani-hashemi et al. |
| 2006/0214109 A1 | 9/2006 | Bueno et al. |
| 2007/0184998 A1 | 8/2007 | Evans et al. |
| 2007/0263764 A1 | 11/2007 | Mccallum et al. |
| 2007/0288263 A1 | 12/2007 | Rodgers |
| 2008/0099045 A1 | 5/2008 | Glenn et al. |
| 2008/0222963 A1 | 9/2008 | Zwart |
| 2008/0230704 A1 | 9/2008 | Daghighian |
| 2009/0089093 A1 | 4/2009 | Johnson et al. |
| 2009/0091458 A1 | 4/2009 | Deutsch |
| 2009/0224907 A1 | 9/2009 | Sinha et al. |
| 2010/0074401 A1 | 3/2010 | Kayzerman |
| 2010/0134296 A1 | 6/2010 | Hwang |
| 2010/0204942 A1 | 8/2010 | Danielsson et al. |
| 2010/0215230 A1 | 8/2010 | Bornefalk et al. |
| 2010/0270462 A1 | 10/2010 | Nelson et al. |
| 2010/0315244 A1 | 12/2010 | Tokhtuev et al. |
| 2011/0051895 A1 | 3/2011 | Vogtmeier et al. |
| 2011/0148586 A1 | 6/2011 | Anderson et al. |
| 2011/0150185 A1 | 6/2011 | Uzbelger |
| 2011/0168905 A1 | 7/2011 | Yabuta et al. |
| 2011/0297696 A1 | 12/2011 | Casares |
| 2012/0055986 A1 | 3/2012 | Sahud |
| 2012/0085006 A1 | 4/2012 | Phillips |
| 2012/0112914 A1 | 5/2012 | Wegelin et al. |
| 2012/0181437 A1 | 7/2012 | Nelson et al. |
| 2012/0249331 A1 | 10/2012 | Wegelin et al. |
| 2012/0261593 A1 | 10/2012 | Noori |
| 2012/0307109 A1 | 12/2012 | Morioka et al. |
| 2013/0026380 A1 | 1/2013 | Tkaczyk et al. |
| 2013/0028379 A1 | 1/2013 | Nelson et al. |
| 2013/0122807 A1 | 5/2013 | Tenarvitz et al. |
| 2013/0187053 A1 | 7/2013 | Colby |
| 2013/0229276 A1 | 9/2013 | Hunter |
| 2014/0018673 A1 | 1/2014 | Manion et al. |
| 2014/0110592 A1 | 4/2014 | Nelson et al. |
| 2014/0276018 A1 | 9/2014 | Mukdadi et al. |
| 2015/0323685 A1 | 11/2015 | Nelson et al. |
| 2015/0331115 A1 | 11/2015 | Nelson et al. |
| 2016/0021674 A1 | 1/2016 | Lee |
| 2017/0016999 A9 | 1/2017 | Nelson et al. |
| 2017/0079609 A1 | 3/2017 | Pani et al. |
| 2018/0136340 A1 | 5/2018 | Nelson et al. |
| 2018/0136344 A1 | 5/2018 | Nelson et al. |
| 2018/0172847 A1 | 6/2018 | Nelson et al. |
| 2018/0172848 A1 | 6/2018 | Nelson et al. |
| 2018/0172849 A1 | 6/2018 | Nelson et al. |
| 2018/0234731 A1 | 8/2018 | Das et al. |
| 2019/0107637 A1 | 4/2019 | Nelson et al. |
| 2019/0204460 A1 | 7/2019 | Nelson et al. |
| 2019/0279491 A9 | 9/2019 | Nelson et al. |
| 2019/0317227 A1 | 10/2019 | Nelson et al. |
| 2020/0003348 A1 | 1/2020 | Nelson et al. |
| 2020/0096656 A1 | 3/2020 | Nelson et al. |
| 2020/0142083 A1 | 5/2020 | Nelson et al. |

FOREIGN PATENT DOCUMENTS

| | | |
|---|---|---|
| GB | 2334666 A | 9/1999 |
| WO | 2012127257 A1 | 9/2012 |
| WO | 2017015473 A8 | 9/2017 |

OTHER PUBLICATIONS

"Third-party submission under 37 CFR 1.290 filed on Mar. 4, 2016 and entered in U.S. Appl. No. 14/804,838".

Cherry, Simon R. et al., "What is Nuclear Medicine", Physics in Nuclear Medicine, third edition, pp. 1-6, Saunders, New York, 2003.

Da Via C., et al., "Dual Readout—Strip / Pixel Systems," Nucl. Instr. Meth., 2008, pp. 7-12.

Knoll G., Radiation Detection and Measurement, 4th edition, Wiley (2010), p. 230 (table 8.2), p. 238 (Table 8.3) and p. 492 (Table 13.3).

Kroeger, et al., "Three Compton Telescope: Theory, Simulations,

(56) References Cited

OTHER PUBLICATIONS and Performance," IEEE Trans. Nucl. Sci., Aug. 2002, pp. 1887-1892, vol. 49, No. 4.
Kronberger, et al., "Proving the Concepts of Photonic Crystals on Scintillating Materials," IEEE Transactions on Nuclear Science, Jun. 2008, vol. 55, No. 3.
Nagarkar, et al., "Continuous Phoswich Detector for Molecular Imaging," IEEE NSS/MIC, Oct. 30-Nov. 6, 2010.
Nowotny, R., "Application of Si-Microstrip-Detectors in Medicine and Structural Analysis", Nuclear Instruments and Methods in Physics Research 226 (1984), pp. 34-39.
Parker, et al., "3DX: and X-ray Pixel Array Detector with Active Edges," IEEE Trans. Nucl. Sci., 2006, pp. 1676-1688, vol. 53.
Parker, et al., "Increased Speed: 3D Silicon Sensors; Fast Current Amplifiers," IEEE Trans. Nucl. Sci., 2011, pp. 404-417, vol. 58.
Phelps, PET Physics, Instrumentation, and Scanners, 2006.
Singh, et al., "An Electronically Collimated Gamma Camera for Single Photon Emission Computed Tomography. Part II: Image Reconstruction and Preliminary Experimental Measurements," Medical Physics, Jul./Aug. 1983, pp. 428-435, vol. 10, No. 4.
Singh, et al., "An Electronically Collimated Gamma Camera for Single Photon Emission Computerd Tomography. Part I: Theoretical Considerations and Design Criteria," Medical Physics, Jul./Aug. 1983, pp. 421-427, vol. 10, No. 4.
Urdaneta, et al., "Quantum Dot Composite Radiation Detector," IEEE Nuclear Science Symposium, 2010.
Yu, et al., "Compressed Sensing Based Interior Tomography," Phys. Med. Biol., 2009, pp. 2791-2805, vol. 54, No. 9.
Innovation in Reach, Kodak 9000C 3D Panoramic & Cephalometric System, 8 pages from <https://web.archive.org/web/20100105025036/http://kodakdental.com/?cookieCheck=true>.
International Search Report and Written Opinion, PCT application PCT/IB2011/000576, dated Dec. 13, 2011, 9 pages.
Chen G., et al., Journal of Non-crystalline Solids 352, pp. 610-614, 2006.
Johnson J., Schweizer S, J. Am. Ceram. Soc. 90 [3] pp. 693-698, Mar. 1, 2007.
Fronk, R.G. et al. "High-efficiency microstructured semiconductor neutron detectors for direct 3He replacement." Nuclear Instruments and Methods in Physics Research A 779, (2015), pp. 25-32.
Rowlands J., Phys. Med. Biol. 47, pp. 123-166, Dec. 7, 2002.
Kodak RVG Digital Radiography Systems, Kodak RVG 5100 and 6100 Digital Radiography User's Guide. 39 pages. Dec. 2010.
Edgar A., et al., Current Applied Physics 6, pp. 399-402, Dec. 27, 2005.
"Third-party submission under 37 CFR 1.290 entered in U.S. Appl. No. 14/804,799", Mar. 4, 2016.

"Third-party submission under 37 CFR 1.290 entered in U.S. Appl. No. 14/804,838", Mar. 4, 2016.
Anderson, E.W. et al., "A Scintillator Hodoscope at the Tevatron Collider", Fermi National Accelerator Laboratory FERMILAB-Pub-90/152-E [E-735], Jul. 1990.
Cherry, Simon et al., "Physics in Nuclear Medicine", 3rd Edition, Saunders, New York, 2003.
Da Via, C. et al., "Dual Readout—Strip/ Pixel Systems", Nucl. Instr. Meth A594, 2008, 7 pages.
Knoll, G "Radiation Detection and Measurement", 4th edition, Wiley, 2010, pp. 50-51, 189-202, 230, 238, 492.
Kroeger, R et al., "Three-Compton Telescope: Theory, Simulations, and Performance", IEEE Trans. Nucl. Sci., Aug. 2002, vol. 49(4), pp. 1887-1892.
Kronberger, Matthias et al., "Probing the Concepts of Photonic Crystals on Scintillating Materials", IEEE Transactions on Nuclear Science, Jun. 2008, vol. 55, No. 3.
Nagarkar, Vivek et al., "Continuous Phoswich Detector for Molecular Imaging", IEEE NSS/MIC, Knoxville, TN, Oct. 30-Nov. 6, 2010.
Parker, S et al., "3DX: an X-ray pixel array detector with active edges", IEEE Trans. Nucl. Sci., 2006, 53, 1676-1688.
Parker, S et al., "Increased speed: 30 silicon sensors; Fast current amplifiers", IEEE Trans. Nucl. Sci., 2011, 58, 404-417.
"International Preliminary Report on Patentability", Application No. PCT/IB2011/000576, dated Sep. 24, 2013, 6 pages.
"International Preliminary Report on Patentability", Application No. PCT/US2016/043361, dated Jan. 23, 2018, 8 pages.
"International Search Report and Written Opinion", Application No. PCT/US2016/043361, dated Dec. 16, 2016, 12 pages.
R., Nowotny "Application of Si-Microstrip-Detectors in Medicine and Structural Analysis", Elsevier Science Publications, Nuclear Instruments and Methods, in Physics Research, North-Holland, Amsterdam, 1984, vol. 226, pp. 34-39.
Singh, M "An electronically collimated gamma camera for single photon emission computed tomography. Part 1: Theoretical considerations and design criteria", Medical Physics, Jul./Aug. 1983, Aug. 1983, vol. 10(4) pp. 421-427.
Singh, M, "An electronically collimated gamma camera for single photon emission computed tomography. Part 2: Image reconstruction and preliminary experimental measurements", Medical Physics, Aug. 1983, vol. 10(4), pp. 428-435.
Turner, James E., "Atoms, Radiation, and Radiation Protection", Turner, "Atoms, Radiation, and Radiation Protection" book, 2007, pp. 274-296, 3rd Edition, WILEY-VCH Verlag GmbH & Co. KGaA, Germany.
Urdaneta, M et al., "Quantum dot composite radiation detectors", IEEE Nuclear Science Symposium, oral presentation, 2010.
Yu, H et al., "Compressed sensing based interior tomography", Phys Med Biol, 2009, vol. 54(9): p. 2791-2805.

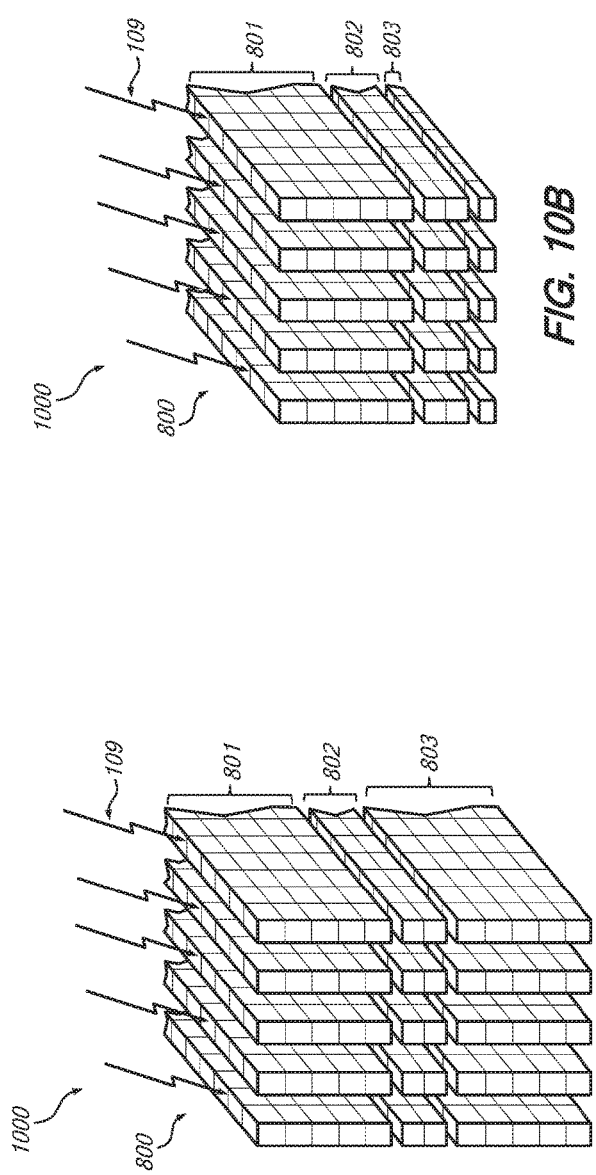
FIG. 10A
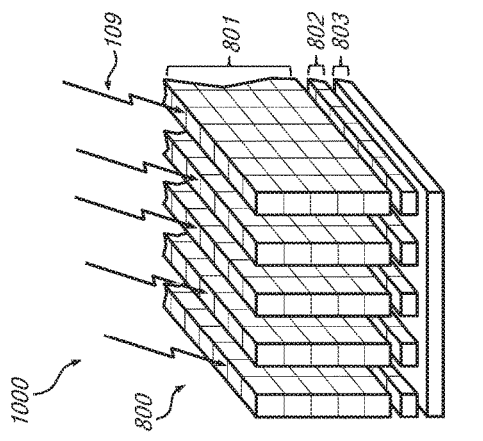
FIG. 10D
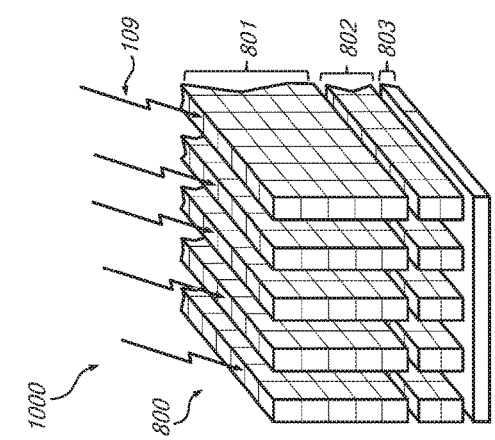
FIG. 10C
FIG. 10B

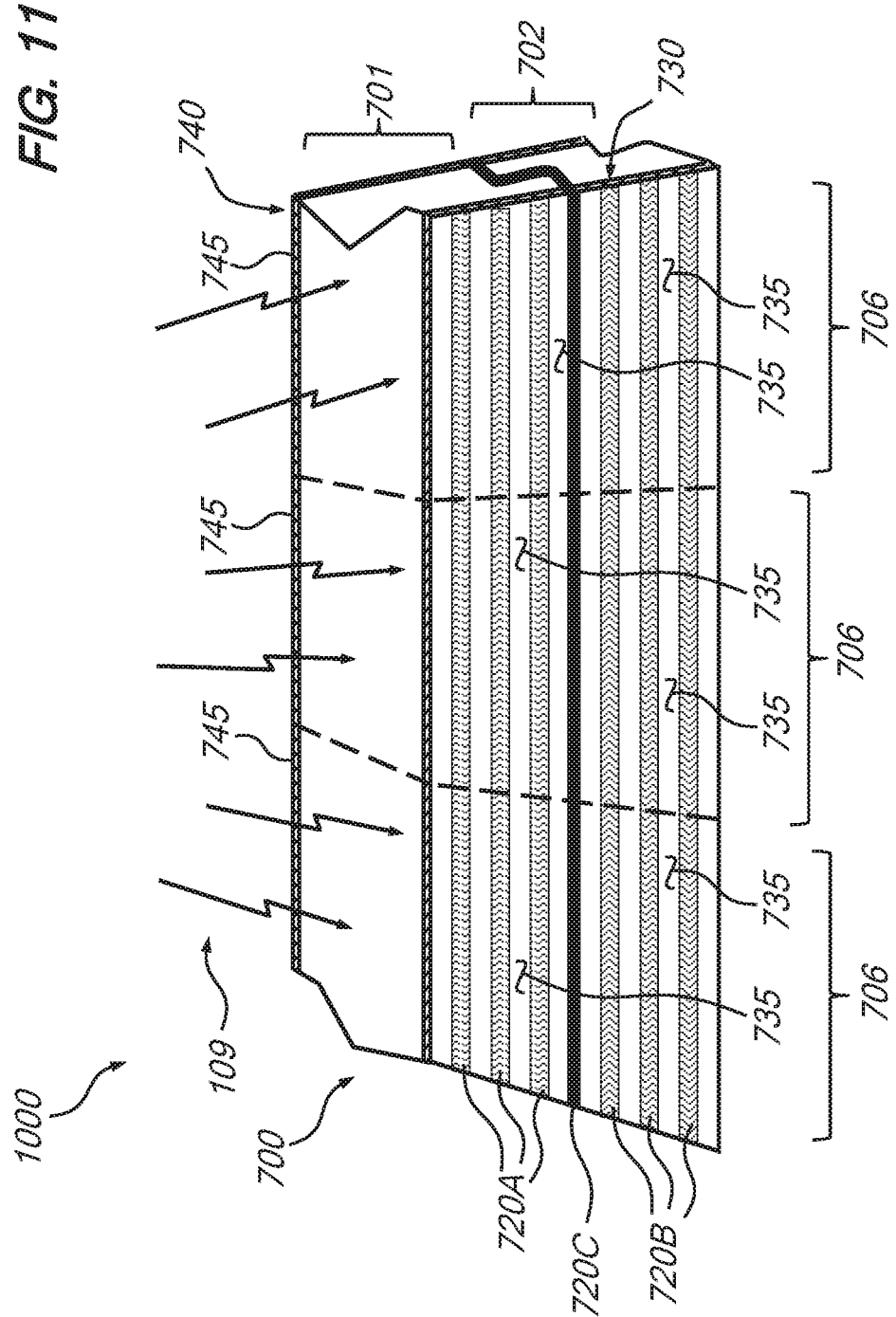

ic x-ray radiology (such as x-ray area, slit, slot, tomosynthesis, CT, dental and phase imaging), radiation therapy imaging, nuclear medicine imaging and/or PET imaging, as well as high energy physics, inspection, etc., to develop cost-effective, single purpose and multipurpose integrated detector systems.

The details of one or more embodiments of the invention are set forth in the accompanying drawings and description below. Other features, objects, and advantages of the embodiments of the invention will be apparent from the description and drawings, and from the claims. All publications, patents and patent applications cited herein are hereby expressly incorporated by reference herein, for all purposes.

STRUCTURED DETECTORS AND DETECTOR SYSTEMS FOR RADIATION IMAGING

CROSS-REFERENCE TO RELATED APPLICATIONS

This application is a divisional of U.S. patent application Ser. No. 15/701,088, filed Sep. 11, 2017 and issued Jul. 30, 2019 as U.S. Pat. No. 10,365,383, which is a continuation-in-part of U.S. patent application Ser. No. 15/699,458, filed Sep. 8, 2017 and issued Apr. 30, 2019 as U.S. Pat. No. 10,272,610, and claims priority to U.S. Provisional Patent Application No. 62/385,426, each entitled STRUCTURED DETECTORS AND DETECTOR SYSTEMS FOR RADIATION IMAGING, filed Sep. 9, 2016, each of which is incorporated by reference herein, in the entirety and for all purposes.

FIELD

This disclosure describes novel implementations of detectors and detector systems that can be employed for diagnostic x-ray and gamma ray medical and small animal imaging (diagnostic x-ray radiology including x-ray area, slit, slot, tomosynthesis, CT, phase imaging, intraoral/extraoral dental and radiation therapy imaging, nuclear medicine imaging, PET imaging, Compton imaging, small animal imaging), as well as in industrial, Homeland Security and scientific radiation imaging.

BACKGROUND

The combining of imaging modalities to offer increased functionality has produced a number of useful imaging systems, particularly in medical diagnostic and small animal imaging. For example, Gamma ray PET detector systems are frequently sold with x-ray computed tomography (CT) detector systems (although the PET and CT detector systems are physically separate and therefore do not share detectors or a common imaging space). A notable attempt at offering an integrated imaging system (in which detectors and the imaging space of the system are shared) was a SPECT-PET (nuclear medicine and PET) imaging system which reduced costs by sharing detectors and the imaging space (the volume in which the object is imaged). Although these SPECT-PET imaging systems were not well received commercially due to performance compromises nonetheless they offered interesting functionality since SPECT and PET images could be acquired separately or simultaneously in a shared imaging space (thereby avoiding registration error between separately acquired SPECT and PET images and reducing the total scan time). In addition, simultaneous CT-SPECT systems have been proposed (typically using CZT or CdTe) although issues arise due to generally differing collimation and flux rate requirements. Both shared and stand-alone imaging systems benefit from the implementation of enhanced radiation detectors.

SUMMARY

Embodiments of the invention utilize one or more different improvements in high speed detector electronics along with various detector materials developed for human and small animal medical diagnostic imaging including diagnostic x-ray radiology (such as x-ray area, slit, slot, tomosynthesis, CT, dental and phase imaging), radiation therapy

BRIEF DESCRIPTION OF THE DRAWINGS

FIG. 10A is a perspective view of an alternate multilayer detector system with N=3 layers used for CT and/or PET detector imaging.

FIG. 10B is a perspective view of a multilayer CT and/or PET detector imaging system with a face-on back-end detector layer.

FIG. 10C is a perspective view of a multilayer CT and/or PET detector imaging system with a face-on back-end detector layer.

FIG. 10D is a perspective view of a multilayer CT and/or PET detector imaging system with a face-on back-end detector layer.

FIG. 11 is a perspective view of a focused two-dimensional structured mold detector system with quantum dots or semiconductor detector materials.

DETAILED DESCRIPTION

Figure 1:
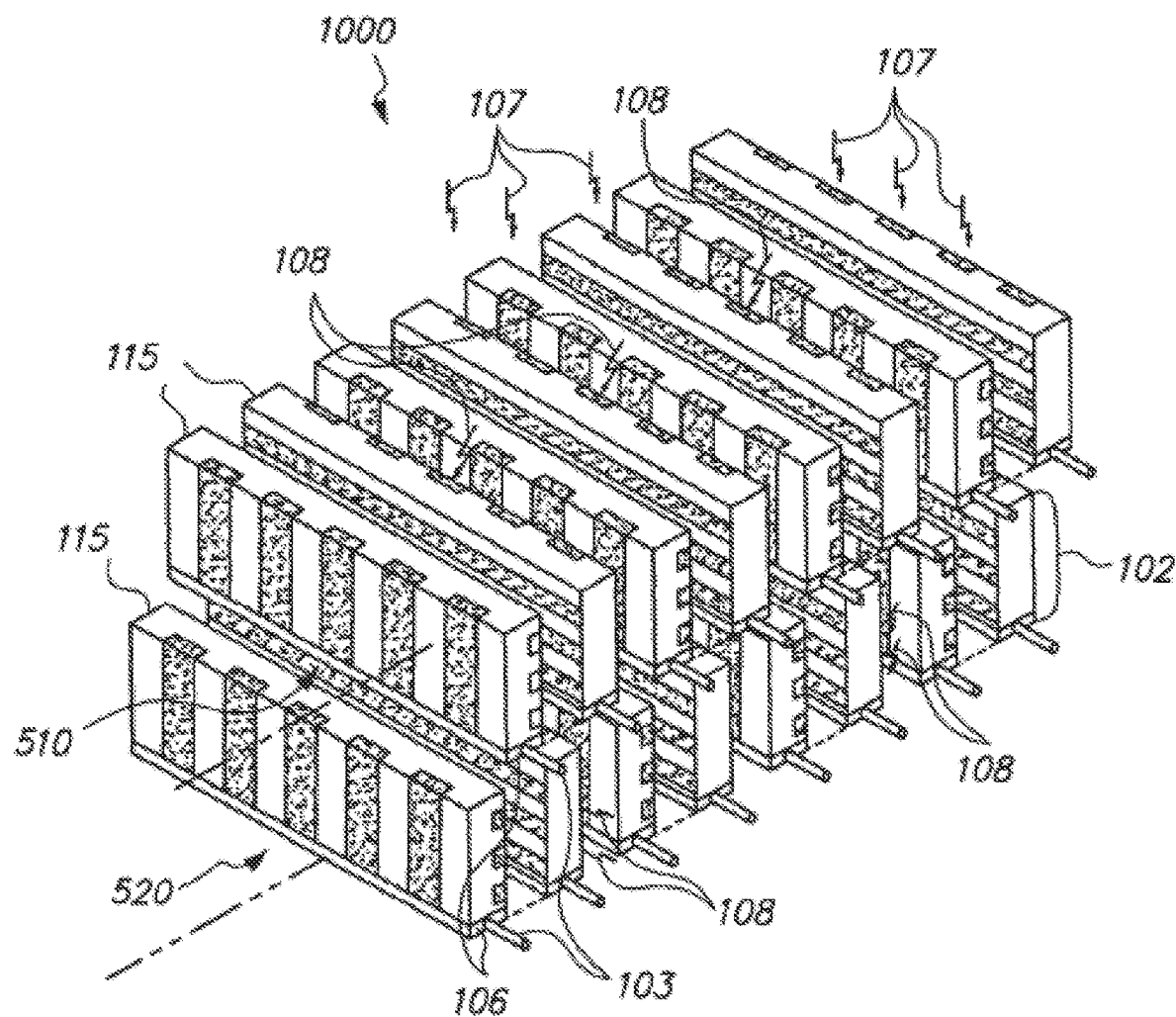
FIG. 1 is a perspective view of a non-coincidence Compton-PET detector imaging system.

Compton cameras are frequently implemented as multi-layer detectors. Photon-tracking Compton camera designs considered for photon energies encountered in applications such as nuclear medicine and PET imaging include a single layer (a front-end detector) which provides 3D detector properties by incorporating a stack of face-on detector planes of the same material such as low-Z Silicon (Si) or moderate-Z Germanium (Ge), essentially a multilayer detector, and a multilayer (dual-layer) configuration which combines a 2D detector first layer (the front-end detector) and a 2D detector second layer (the back-end detector). Note that the spatial resolution of the first layer and the second layer in the multilayer (dual-layer) detector design need not be the same. Furthermore, spatial resolution of detector elements within a layer need not be the same (e.g., a detector layer that offers higher spatial resolution in the center or a detector layer in which the pixel size increase with depth). Note that alternative single layer Compton cameras (mono layer Compton cameras) developed for nuclear medicine and PET typically employ a 3D semiconductor detector with tracking capability.

The dual-layer, front-end/back-end detector configuration typically consists of a face-on, planar, 2D Si (low-Z) or 2D Ge (moderate-Z) front-end detector combined with a face-on, 2D high-Z back-end detector. Thus, these two Compton camera configurations described herein can utilize detector layers of the same material (low-Z and moderate-Z for Compton scattering) or different materials (low-Z for Compton scattering and high-Z for photoelectric interactions) for the detection of photons in the diagnostic energy range of medical imaging. Flexibility in the selection of detector materials and configuration (often with different temporal and/or energy resolution) is not limited to separate layers, and different detector materials and configurations can be employed within a detector layer.

Clearly other choices of materials can be made depending on the photon energy range or if other types of particles (neutrons, muons, etc.) are to be detected. Compton camera designs (as well as x-ray scanning and CT, SPECT, PET, dental and hand-held probe designs are described in various U.S. patents and patent applications including: R. S. Nelson and Z. L. Barbaric, U.S. Pat. No. 4,560,882; R. S. Nelson, U.S. Pat. No. 4,937,453; R. S. Nelson, U.S. Pat. No. 5,258,145; R. S. and W. B. Nelson, U.S. Pat. No. 6,583,420; R. S. and W. B. Nelson, U.S. Pat. No. 7,291,841; R. S. Nelson, U.S. Pat. No. 7,635,848; R. S. and W. B. Nelson, U.S. Pat. No. 8,017,906; R. S. Nelson, U.S. Pat. No. 8,115,174; R. S. Nelson, U.S. Pat. No. 8,115,175; R. S. Nelson, U.S. Pat. No. 8,183,533; R. S. and W. B. Nelson, U.S. Pat. No. 9,384,864; R. S. and W. B. Nelson, U.S. patent application Ser. No. 13/199,612, filed Sep. 6, 2011 (U.S. Publication No. 2012/0181437); R. S. and W. B. Nelson, U.S. Pat. No. 9,347,893; R. S. and W. B. Nelson, U.S. patent application Ser. No. 14/804,777, filed Jul. 21, 2015 (U.S. Publication No. 2016/0021674); and R. S. and W. B. Nelson, U.S. patent application Ser. No. 14/804,838, filed Jul. 21, 2015 (U.S. Publication No. 2015/0331115), each of which is incorporated by reference herein, in the entirety and for all purposes.

This application also relates to the subject matter of U.S. patent application Ser. No. 14/804,777 (U.S. Publication No. 2016/0021674) and Ser. No. 14/804,838 (U.S. Publication No. 2015/0331115), each entitled DETECTOR SYSTEMS FOR RADIATION IMAGING and filed Jul. 21, 2015, which claim priority as continuations-in-part to U.S. patent application Ser. No. 13/573,981, entitled COMPTON CAMERA DETECTOR SYSTEMS FOR NOVEL INTEGRATED COMPTON-PET AND CT-COMPTON-PET RADIATION IMAGING, filed Oct. 18, 2012 (U.S. Publication No. 2014/0110592), which claims priority to U.S. Provisional Application No. 61/689,139, entitled COMPTON CAMERA DETECTOR SYSTEMS FOR INTEGRATED COMPTON-PET AND CT-COMPTON-PET RADIATION IMAGING, filed May 31, 2012, and U.S. Provisional Application No. 61/690,348, entitled COMPTON CAMERA DETECTOR SYSTEMS FOR NOVEL INTEGRATED COMPTON-PET AND CT-COMPTON-PET RADIATION IMAGING, filed Jun. 25, 2012, each of which is incorporated by reference herein, in the entirety and for all purposes. This application further relates to the subject matter of U.S. patent application Ser. No. 13/199,612, entitled HIGH RESOLUTION IMAGING SYSTEM FOR DIGITAL DENTISTRY, filed Sep. 6, 2011 (U.S. Publication No. 2012/0181437), which claims priority as a continuation-in-part to U.S. Pat. No. 9,384,864, also entitled HIGH RESOLUTION IMAGING SYSTEM FOR DIGITAL DENTISTRY, each of which is incorporated by reference herein, in the entirety and for all purposes.

Compton Camera Detector Systems

Compton camera detector systems exploit the Compton scatter interaction and can also exploit photoelectric interactions (and even pair production interactions at sufficiently high photon energies). Compton camera detector systems include the capability to track these interactions in terms of spatial location and energy deposition with a temporal resolution limited by the detector itself and the readout electronics.

A variant of the Compton camera design that is useful with high energy photons encountered in applications such as PET imaging employs only high-Z materials (in single layer or multilayer or 3D block configurations). If acolinearity angle errors are relatively small then the initial photoelectric interaction or initial Compton interaction position within the detector is important for reconstruction of coincidence events for PET imaging. The photoelectric event can be used directly in reconstruction whereas the Compton interaction event(s) (possibly correlated with a photoelectric event) can be used for PET reconstruction with or without applying Compton scatter equations (used to estimate the spatial position cone of the incident gamma photon).

Typically the interaction information is used to estimate the directionality and energy of the photon incident on the Compton camera detector system whether the photon is an x-ray, a gamma ray, or an annihilation gamma ray. Note that with the addition of collimation such as (for example) a pin hole or parallel hole collimator, the Compton camera can be converted into a nuclear medicine SPECT camera (Gamma camera). Compton camera features such as tracking capability can continue to be utilized. This is an example of a dual-use, integrated Compton detector system in which the types of applications are relatively unchanged but the capabilities of the detector system are modified (Nelson, U.S. Pat. No. 7,291,841; Nelson, U.S. Pat. No. 8,017,906).

The collimation now provides the directionality of an incident gamma ray independent of directionality determined by applying Compton camera reconstruction algorithms. It will be shown that the integrated Compton detector system design can be applied to a range of applications (including nuclear medicine). By employing two or more Compton camera detector systems with electronic coincidence circuitry (used in medical PET detector systems) coincidence PET imaging can be implemented.

The flexibility of the Compton camera detector system design (incorporating capabilities such as 3D spatial resolution, energy resolution, detection of photons of different energies, a single layer detector or a multiple layer detector with the same or different properties, photon tracking and coincidence capability) allows versatile non-coincidence Compton-PET and coincidence Compton-PET detector systems to be implemented. Furthermore, CT capability can be implemented in the Compton camera detector system design, including non-coincidence and coincidence Compton-PET designs resulting in CT-Compton-PET detector systems. A simplification of this design in which the CT detector and the Compton-PET detector (or just a PET detector) function independently will be referred to as a limited CT-Compton-PET detector system. Furthermore, limited implementations of Compton camera detector designs can be employed for dedicated applications such as (but not limited to) CT imaging or PET imaging.

Although applications discussed herein are primarily directed at medical diagnostic x-ray and gamma ray radiation detection, in principle the invention can also be used to detect radiation such as changed particles (alphas, betas, protons, muons, etc.) and neutrons (as well as other neutral particles) for the applications described. Furthermore, the detector systems described herein can be combined with or integrated with other imaging modalities such as MRI scanners, optical scanners, ultrasound scanners, opto-acoustic scanners, microwave scanners, etc. It should be understood that the variations of the dual-use detector systems (triple-use, etc. detector systems can also implemented) described herein can be employed for simultaneous or non-simultaneous imaging as required by the appropriate application.

The invention provides detector designs that employ one or more layers of detector modules comprised of edge-on or face-on (or tilted) detectors or a combination of edge-on and face-on detectors (as well as tilted detectors). Edge-on detectors (and tilted detectors) can incorporate sub-aperture resolution (SAR) capabilities and face-on detectors can incorporate depth-of-interaction (DOI) capabilities. One or more types of detectors can be employed, including: scintillator detectors, semiconductor detectors, gas detectors (including, but not limited to, straw arrays, microstrip gas chambers, multiwire proportional counters and crossed strips multilayer proportional counters, gas electron multiplier (GEM), micromegas (Micro-MEsh Gaseous Structure) and resistive plate chamber (RPC) detectors), low temperature (such as Ge or superconductor) detectors and structured detectors.

Detectors can offer block, 1D, 2D or 3D spatial resolution as well as adequate, fast or very fast temporal resolution (depending on the application requirements). Detectors can offer fixed or adjustable pixels sizes which can be uniform or non-uniform (for example, increasing pixel length along the depth dimension as a function of depth to compensate for beam hardening with depth in a CT detector). The effective pixel length along a detector column can be synthesized from the outputs of one or more uniformly spaced pixels. Parallel or focused pixel structures can be implemented. Detectors can operate as ionizing radiation energy integrators, photon counters (PCs) and photon counters with energy resolution (PCEs). Possible detector formats include, but are not limited to, planar (and focused planar) and focused structure (parallel planes, ring, partial ring as well as focused ring and focused partial ring) detector geometries.

The invention provides novel detector designs and systems for enhanced radiation imaging including Compton and nuclear medicine imaging, PET imaging and x-ray CT imaging. The invention also provides integrated detector systems based on Compton camera designs.

In one aspect, the invention provides integrated non-coincidence Compton-PET detector imaging systems. In another aspect, the invention provides integrated coincidence Compton-PET detector imaging systems. In yet another aspect, the invention provides limited integrated CT-Compton-PET detector imaging systems. In still another aspect, the invention provides integrated non-coincidence CT-Compton-PET detector imaging systems. In another aspect, the invention provides integrated coincidence CT-Compton-PET detector imaging systems. Since the integrated nature of these Compton camera detector design implementations is readily apparent the term "integrated" will frequently be omitted when referring to them. Therefore "integrated non-coincidence Compton-PET detector imaging systems" will also be referred to as "non-coincidence Compton-PET detector imaging systems," etc. In still another aspect, the invention provides variations of Compton camera detector designs that can be implemented for dedicated applications such as (but not limited to) CT imaging or PET imaging.

The invention employs a range of detector types and formats. The use of gas, scintillator, semiconductor, low temperature (such as Ge and superconductor) and structured detectors in edge-on and/or face-on geometries has been described for both medical and non-medical imaging applications. Medical imaging applications include diagnostic x-ray imaging (such as single and multiple x-ray tube sources or other x-ray sources (including, but are not limited to, constant voltage tubes or sources, switch voltage tubes or sources, split-beam x-ray tubes or sources, x-ray array sources, x-ray sources using scanning electron beams, and coherent x-ray sources) employed with single energy or multiple energy implementations of slit scanning, slot scanning, area radiography, (single or multi-layer) flat panel or planar cone beam CT, focused structure ring or partial ring fan beam CT, focused cone beam CT, tomosynthesis, phase (PCI), coherent scatter, radiation therapy and intraoral/extraoral dental imaging), radiation therapy, nuclear medicine imaging (Compton camera, SPECT/gamma camera detector imaging systems as well as hand held probe detectors) and PET imaging. Non-medical imaging applications include high energy physics, x-ray and gamma ray astronomy, industrial radiography, Home Land Security (HLS) and military applications. Furthermore it has been shown that detector spatial resolution can be enhanced using sub-aperture resolution (SIR) or depth-of-interaction (DOI) readout techniques with edge-on and face-on detector geometries, respectively.

Detectors may be layered (stacked) and detector modules within a layer can be partially or completely offset from neighboring detector modules. Individual detectors may function as energy integrators, photon counters (PCs) or photon counters with energy resolution (PCEs), depending on the application. One or more of these detector types can be employed within a detector imaging system. (Photon counting (PC) is often mixed up with photon counting with energy resolution (PCE) in the literature. Photon counting functions as a (one energy bin) single channel analyzer or SCA. Photon counting with energy resolution functions as a multi-channel analyzer or MCA).

High speed electronics is provided for tracking interactions and analyzing the readout signals. An electronic communications link is provided to a computer for data post-processing, storage, and display. One or more tracking capabilities such as examining nearest neighbor pixels for effects related to induced signals and charge diffusion, following scattered or characteristic x-ray radiation within a detector layer and between detector layers (if there is more than one detector layer), following Compton scattered electrons and photoelectrons and measuring coincidence events (for example, the detection of pairs of annihilations photons in PET imaging), etc., can be implemented. Tracking techniques are used in photon counting and spectral x-ray imaging, SPECT, PET, Compton cameras, hand-held radiation detector probes, neutron detectors, detectors with SAR or DOI capability and high energy physics particle detectors.

Tracking capabilities, if implemented in a detector system as described herein, can be implemented in all of or part of at least one detector module of the detector system, and between detector modules with tracking capability. For example, in one implementation of a CT-PET detector system tracking can be implemented in one or more PET detector modules (or in a portion of the detector modules used for both CT and PET imaging), but not necessarily in any or all of the CT detector modules.

Various Compton camera implementations incorporate one or multiple detector layers. These detector layers provide suitable 2D or 3D spatial resolution, energy resolution, temporal resolution, stopping and scattering power and tracking capability. Compton camera, nuclear medicine SPECT/gamma camera and PET detector imaging systems, tracking, x-ray CT and slit and slot scan detectors, hand held probe detectors, edge-on and face-on detectors (with or without SAR or DOI capability), integrating, PC, and PCE detectors, multi-material detectors along with planar and focused structure detector geometries have been described in various U.S. patents and patent applications including Nelson et al., U.S. Pat. Nos. 4,560,882; 4,937,453; 5,258,145; 6,583,420; 7,291,841; 7,635,848; 8,017,906; 8,115,174; 8,115,175; 8,183,533; U.S. patent application Ser. No. 13/199,612 (U.S. Publication No. 2012/0181437); U.S. Pat. No. 9,347,893; U.S. patent application Ser. No. 14/804,777 (U.S. Publication No. 2016/0021674) and U.S. patent application Ser. No. 14/804,838, (U.S. Publication No. 2015/0331115), each of which is incorporated by, reference herein, in the entirety and for all purposes.

X-ray or gamma ray interactions (in medical imaging applications) can be tracked between sufficiently thin detector layers, each with 2D spatial resolution capability. If the depth of a 2D detector layer is sufficiently small such that tracking position errors are acceptable then it effectively functions as a restricted 3D detector (its depth resolution is at most the thickness of the detector layer). If detectors offer 3D spatial resolution capability then interaction tracking (including multiple interactions) can be implemented internally within a 3D detector layer as well as between detector layers.

Energy resolution can be used to measure the position-dependent energy losses due to the interactions within detectors which in turn can provide an estimate of the energy of the initial incident x-ray or gamma ray. This information can be used to determine whether the initial incident photon energy is within an allowed energy range as well as its directionality.

Temporal resolution capability can be used to distinguish between independent incident x-rays or gamma rays interactions (as well as their subsequent interactions) within the Compton camera. It will be shown that very good temporal resolution can be beneficial if coincidence timing is of interest between Compton camera systems (for example, when coincidence PET imaging is implemented).

One implementation of a Compton camera using a dual-layer detector design wherein the first layer (front-end) was a small area, face-on, Si or Ge semiconductor pixelated detector offered 2D spatial resolution. The second layer (back-end) was a large area, face-on, scintillator (gamma camera) detector which also offered 2D spatial resolution (Singh, M., Medical Physics Vol. 10(4), pp. 421-427 (July/August 1983) and Singh, M., Doria D., Medical Physics Vol. 10(4), pp. 428-435 (July/August 1983)). Both front-end and back-end detectors offered appropriate levels of energy resolution for the photon energies employed and temporal resolution for the expected event interaction rates.

Since Compton scattered photons include a range of scatter angles the sensitivity of design is in part dependent on the separation distance and area of the second layer with respect to the first layer of detectors. A second layer which employs a smaller 3D detector may, in some instances, be more-cost effective than a larger 2D detector which suffers from parallax errors and needs to be positioned further away from the first layer.

Another implementation of the Compton camera, the (face-on) Compton telescope camera, consisted of only a first layer detector. This front-end detector was comprised of a stack (and thus could also be viewed as a multilayer detector) of 2D, face-on Si detectors which function together as a 3D detector (Krueger R, et al., IEEE Trans. Nucl. Sci., Vol. 49(4), pp. 1887-1892 (August 2002); Nelson, U.S. Pat. No. 8,017,906). A different single layer (mono-layer) design implemented a cylinder-like, 3D Ge detector defined by a positional readout implemented on the periphery and the hollow core of the detector.

A stack of 2D, face-on Ge detectors (or a thick 3D Ge detector with DOI capability) can also be implemented although the Ge semiconductor operates at a low temperature. The Compton telescope camera tracks multiple Compton scatters by a photon in order to determine its original direction and energy.

Low-Z (atomic number) semiconductor materials such as Si and diamond (and sometimes moderate-Z Ge) are often preferred for the front-end Compton scatter detector for photons of relatively low energies (e.g. medical diagnostic x-ray energies, 140.5 keV gamma rays from Tc-99m used in nuclear medicine) compared to the 511 keV gamma rays used in PET imaging.

The Compton scatter interaction cross section of the material dominates its photoelectric cross section and the relative contribution to the angular reconstruction error due to the Doppler shift is reduced as Z decreases and/or photon energy increases. As the photon energy increases semiconductor materials with moderate-Z values (such as Ge, GaAs, CdTe, CZT, etc.) or even high-Z values (PbO, PbS, $PbI_2$, $HgI_2$, TlBr, etc.) represent increasingly acceptable substitutes for low-Z semiconductor materials such as Silicon.

The amount of energy deposited by relatively low energy photons (commonly used in diagnostic x-ray imaging or nuclear medicine) due to a Compton scatter interaction is typically small and therefore semiconductors detectors are employed as front-end detectors because of their superior energy resolution compared to most scintillator detectors. In the dual-layer Compton camera design lower-cost 2D or 3D scintillator detectors (including scintillator fibers) may be employed in place of semiconductor detectors as back-end detectors or front-end detectors (or both back-end and front-end detectors) if they offer at least one of suitable spatial, temporal and energy resolution and stopping power.

For example, axially-orientated, fast scintillator rod or fiber array front-end detectors (including low-Z materials such as ZnO and moderate-to-high-Z materials such as $LaBr_3$, $BaF_2$, LSO, etc.) can be employed with back-end scintillator detectors (and/or semiconductor detectors, structured detectors, etc.) for Compton-PET/PET/TOFPET imaging (including whole-body PET imaging). The selection of detectors often involves tradeoffs. For example, fast plastic scintillator fiber arrays typically offer reduced cost and excellent temporal resolution and longer lengths than scintillator rods, but may suffer from a reduced photoelectric cross section at 511 keV, and reduced energy resolution. Overall detection efficiency at 511 keV can be improved by recording both photoelectric events and Compton scatter events (for tracking purposes) in the scintillator fibers, which can be combined with a back-end detector (which can be used to detect both Compton-scattered and photoelectric events).

The scintillating (scintillator) fibers described herein can be continuous or segmented and include plastic scintillator fibers, fibers embedded with particles (including nano-particles such as Quantum dots), glass scintillator fibers, and scintillator materials processed as crystal scintillator fibers LuAG or Lutetium Aluminum Garnet crystal scintillator fibers developed by the Crystal Clear Collaboration). The properties and surface treatments (including the coupled surfaces between segments) of scintillating fibers as described herein can be varied as a function as position. Scintillator fibers can be employed alone or with scintillator rods, scintillator pixel arrays, scintillator blocks and layers, light guides and fiber optics (light pipes), in the detector modules described herein.

Conventional optical coupling materials as well as WLS materials, nano-particle materials, surface treatments, etc., as described herein, can be used to couple scintillator fibers (and/or scintillator rods) to scintillator fibers, scintillator rods, scintillator pixel arrays, scintillator blocks/slabs/sheets, light guides, fiber optics (light pipes) and photodetectors. Furthermore, scintillator 2D and 3D arrays, blocks/slabs/sheets, rods and fibers (or segments thereof), including straws employing appropriate solid, liquid, gas or nanoparticle materials that can be electromagnetically pumped (e.g., via UV, visible, near-infrared, infrared, terahertz, or microwave) or pumped-probed externally (also referred to as optical pumping or optical encoding) can benefit from at least one of signal gain (improved energy resolution), improved spatial resolution, improved temporal resolution, and reduced dead time. Furthermore, optical pump-probe techniques can be implemented with semiconductor and structured detectors in the detector geometries described herein.

The detector materials described herein can be cooled (or warmed) as needed in order to improve one or more aspects of detector response. For some externally-pumped scintillator materials signal gain can be achieved due to superluminescence (nb: an optical cavity is not necessarily required). Numerous optical pumping techniques, ranging from continuous to modulated to pulsed optical pumping (including two-photon (non-linear) optical pumping techniques), can be applied herein.

Ionizing radiation event rates per detector element and detector element recovery time may influence the choice of pumping technique. Optical pumping techniques can be implemented with one or more (physical or virtual) detector elements within a detector. The external optical pumping geometry used with a radiation detector can include one or more pump beams (including recirculated beams). One or more properties of at least one pump beam (e.g., spectral composition, power levels, pulse length, pulse period, and phase) can be varied spatially in order to encode the radiation detector volume. Electromagnetic (optical) detectors (photodetectors) can be employed as needed to measure the effects of the pump beam(s) on the radiation detector, or modifications to the pump beam(s) due to ionizing radiation events within the radiation detector. Optical pumping of a direct (or indirect) ionizing radiation detector material can be considered to be an application of an optical encoding technique, as described herein.

Scintillator materials such as LuAG (and embodiments incorporating one or more dopants including, but not limited to, Ce, Pr, Eu, Tl), YAG, YAP, as well sa nanoparticles including quantum dots, etc., can act as both a scintillator crystal material and a laser material that can be pumped (for example) by an optical source as well as being pump-probed. The choice of dopants will affect both the intensity, spectrum and decay timing of LuAG (and therefor the pump beam parameters). Scintillator-laser materials can either be pumped externally or pumped within an appropriate optical cavity (e.g., a laser cavity). For example, an appropriate optical cavity could include one or more fibers, rods, blocks, slab and sheets of suitable optical material.

In addition to (or as an alternative to) measuring the scintillation signal strength and temporal properties of the ionizing radiation event, one or more properties of the laser output signal (e.g., temporal, intensity, phase, polarization, or spectral content) can be monitored using a variety of methods that are useful for event timing and/or energy deposition and/or spatial location estimates, as well as for timing correlation (coincidence) with other events (e.g., in PET imaging). These techniques can be implemented with any suitable scintillator, semiconductor, gas, chemical, biological, nanoparticle (etc.) ionizing radiation detector laser material, as well as with indirect ionizing radiation detector laser materials, indirect ionizing radiation detector materials are materials that exhibit a desired property such as optical two photon pump-probing or lasing (a process that could be altered at least locally by the interaction of the lasing material with ionizing radiation) but otherwise would not necessarily function as a useful ionizing radiation detector material (e.g., with acceptable temporal, energy, and spatial resolution properties).

Furthermore, these techniques can be extended to include any suitable direct or indirect ionizing radiation detector material that offers at least one of internal gain and multi-modal operation (e.g., with multiple states including, but not limited to, off-on states). For example, Si or GaAs APDs may offer internal gain whereas semiconductor transistors, super conductors, etc. may operate with multiple states, and SiPM materials offer internal gain and multiple states. Direct and/or indirect ionizing radiation detector materials that offer at least one of internal gain and multi-modal (multi-state) operation can be employed as radiation detectors in any of the detector formats described herein, and for the detector systems described herein. Furthermore, the detector systems described herein can incorporate both detectors that implement direct and/or indirect ionizing radiation detector materials that offer at least one of internal gain and multi-modal operation, and any other detector systems described herein. Direct and/or indirect ionizing radiation detector materials that offer at least one of internal gain and multi-modal operation can be implemented in many such types of radiation detector systems, including, but not limited to, x-ray, gamma ray, charged particle and neutral particle radiation detectors.

In a variation of the optical pumping technique, non-linear optical absorption (due to ionizing radiation-induced ultrafast transient phenomena) of short optical pulses (often in the femtosecond range) can be exploited, using two-photon pump-probe techniques. Pump-probe techniques may exploit recirculated pump light, for some implementations. With appropriate detector geometries, changes in interference effects can be measured. Furthermore, crystal defect-related absorption can also be measured.

A variety of optical pumping techniques (the imposition of an external uniform or pulsed/patterned radiation field), as well as pump-probe techniques, are implemented with linear and non-linear optical systems (including laser designs) as described herein, suitable for use in Chemistry, Physics, Meteorology, Geology, materials analysis, inspection, etc. For example, in one implementation pump-probe beams are injected (or one beam is recirculated) from opposite sides or faces of a scintillator rod or fiber, block/slab/sheet, parallel rod array, crossed rod array, etc., or other suitable radiation detector. As previously noted, if multiple pump beams are present then one or more properties of at least one pump beam can be varied spatially in order to optically encode the radiation detector volume. One or more optical detectors (e.g., photodetectors) can be employed to monitor variations in the pump-probe signals within the radiation detector volume. In one implementation, the existing scintillation readout photodetectors used to measure the scintillation signals are also used to measure the pump-probe beam(s).

Once an ultrafast transient phenomena is detected, the pump and/or probe beams could be temporarily switched off or diverted or absorbed while the scintillation readout photodetectors record the delayed scintillation signal. In another implementation, the pump-probe beam(s) and scintillation signals are read out with separate optical detectors coupled to different surfaces, or to the same surface (e.g., employing a wavelength-sensitive and/or polarization-sensitive filter to divert the pump-probe beam from the scintillation signal, or an ultrafast optical switch to block the pump-probe beam once the ultrafast transient phenomena is detected). If needed, the scintillation readout photodetectors can be shielded optically (e.g., using at least one of wavelength-dependent absorbers or filters, converters and reflectors, including electronically-switchable implementations thereof), and/or selector to offer reduced or substantially no response over the optical pump wavelength band or interest the pump-probe wavelength bands).

Fast on-off switching of the scintillation readout photodetectors can be implemented based on optical pump timing or pump-probe timing. For example, if optical pump (pump-probe) intervals are of limited duration, then the scintillation readout photodetector output may be ignored during the optical pump (pump-probe) intervals. These optical pump-probe techniques can be implemented with any suitable scintillator, semiconductor, gas, chemical, biological, or nanoparticle (etc.) ionizing radiation detector material, as well as with suitable ionizing radiation non-detector materials (e.g., indirect ionizing radiation detector materials).

Although ionizing radiation scintillator and non-scintillator (direct) detector materials (as well as indirect ionizing radiation materials) can be pumped (or pumped-probed) externally, they can also be pumped (or pumped-probed) within a cavity (e.g., a laser cavity). For example, pumped or pump-probed ionizing radiation scintillator detector materials and non-scintillator (e.g., semiconductor, etc.) ionizing radiation detector materials can be employed in the various SPECT, PET and Compton camera and CT detector configurations described herein. These materials can be employed in multilayer radiation detector configurations, in one or more detector layers. For example, although in one implementation the front end detector layer (or layers) could employ a pumped or pump-probe scintillator material, in another implementation a non-scintillator pump-probe material such as a semiconductor detector would be employed in the front end detector layer(s) to provide ultrafast timing resolution and initial (or even final) interaction position information. The back end radiation detector would provide temporal, spatial, and energy deposition measurements. In another implementation, the roles of front end and back end radiation detectors are reversed.

The optical-pumped (direct) ionizing radiation detectors and (indirect) ionizing radiation detectors described herein are suitable for use in many fields where radiation detectors are employed (Medical imaging, Physics, Chemistry, Biology, Geology, industry, etc.). Changes to one or more optical properties due to ionizing radiation interactions can be measured, such as the index of refraction of the direct or indirect detector material. Additional techniques of altering optical properties such as the refractive index of the materials (including, but not limited to, semiconductor materials) include applying external electric and/or magnetic fields.

Linear and non-linear electro-optic effects (including, but not limited to, Pockels and Kerr effects) are included. The Kerr electro-optical effect, by varying an external electric field, is used to modulate (encode) transmitted light beams at frequencies in the multi-gigahertz range by inducing birefringence within a medium. For example, the degree of rotation of a continuous or encoded (e.g., modulated, pulsed) polarized optical beam passing through a non-centrosymmetric semiconductor material used in radiation detection (such as CZT, CdTe or InP) can be measured with an applied external electric field (standard Pockels effect), as the result of an ionization event. Thus, the Pockels effect, Kerr effect, etc. can be exploited with rod, fiber, block/slab/sheet, linear array, 2D and 3D ionizing radiation detectors (including structured radiation detectors), as described herein. This technique can be used to enhance at least one of timing resolution, spatial resolution, and energy resolution of the detector system, using one or more polarized optical beams (including crossed beams) to sample the detector medium.

Calibration of the electro-optic properties of the detector medium is desirable in many instances, since the applied electric field(s) may be selectively encoded or otherwise non-uniform through the detector medium (e.g., due to the presence of manufacturing defects or other inhomogeneous features in the detector medium). Furthermore, as previously described, the choice of detector medium is no longer limited to conventional (solid, liquid, gas) ionizing radiation detector materials, since electro-optic effects such as the Pockels effect can be observed and utilized in non-detector materials that experience ionizing radiation events (such ionizing radiation sensitive, non-detector materials may also be referred to as indirect ionizing radiation detector materials).

For example, if the conventional refractive index or externally-modified (by any technique including those described herein) refractive index of a non-detector material can be altered sufficiently by an ionizing radiation event, then the measured optical effects may provide at least one of position information, timing information, and energy deposition information. (Note that the same principle could also be implemented with conventional or externally-modified acoustic properties of a non-detector material.) Furthermore, this principle can be implemented with switched materials and structures in general (including, but not limited to, materials and structures that can be used in fast and ultrafast electronics and optoelectronics), where an ionizing radiation event switches the state of the material or structure.

For some applications, only one type (or two types) of information is (are) needed. For example, prior art PET detector systems have been implemented with adequate timing and spatial resolution, but negligible energy resolution (scatter rejection capability is sacrificed). If an ionizing radiation non-detector material (indirect ionizing radiation detector material) offers adequate spatial resolution and fast timing resolution (e.g., for TOF PET), a fraction of the accepted scatter radiation could be rejected, despite otherwise relatively poor energy resolution.

The semiconductor front-end detector may be replaced by a low temperature front-end detector or by a scintillator (or gas) front-end detector although energy resolution may suffer. Any significant reduction in accuracy of the calculated incident photon directionality by Compton reconstruction algorithms can be augmented or supplanted by additional information such as coincidence between detectors (used in coincidence PET imaging).

Compton electron tracking in a gas detector can be implemented although this is typically very time-consuming. Cherenkov radiation, despite the relatively weak optical signals, can be exploited for time-of-flight (TOF) measurements. (Cherenkov radiation can be detected when generated in optically-transparent mediums including fluids such as liquids and gases, scintillators and non-scintillators such as transparent plastics, glasses, fibers, diamond films, etc. Thus, transparent dielectric mediums other than scintillators and gases can be also be employed as Compton scatter or photoelectron detectors within a Compton camera detector system although energy resolution could suffer based on the detection of Cherenkov radiation alone. Inexpensive dielectric materials may be acceptable for those applications in which radiation scatter within the object is of reduced importance and therefor lower detector energy resolution is acceptable. Variations of detector designs described herein can include measuring only a Cherenkov signal or a Cherenkov signal and a fluorescence signal or an electronic signal.)

Potential advantages of this dual-layer implementation of a multilayer design may include a less-expensive front-end detector and/or a front-end detector that offers a feature such as fast (greater than 1 nanosecond) or very fast (less than 1 nanosecond) temporal resolution. Very fast temporal resolution is of interest for TOF PET. Benefits of TOF PET include improved image resolution and lower patient radiation dose. Furthermore, the use of coincidence information can also simplify the requirements of the back-end detector.

Compton electron tracking can also be implemented within a detector layer and between detector layers that employ at least one of scintillator-photodetector detector, semiconductor, structured and low temperature detectors.

Since electrons readily interact with matter electron tracking is preferably implemented when detecting energetic photons which are Compton scattered, typically generating more-energetic electrons with a more-directional nature. (A similar concept applies to energetic photoelectric interactions which typically generate more-energetic photoelectrons with a more-directional nature. Thus, a Compton camera could utilize sufficiently energetic photoelectric interactions for image reconstruction by tracking the highly directional photoelectrons.)

Figure 3:
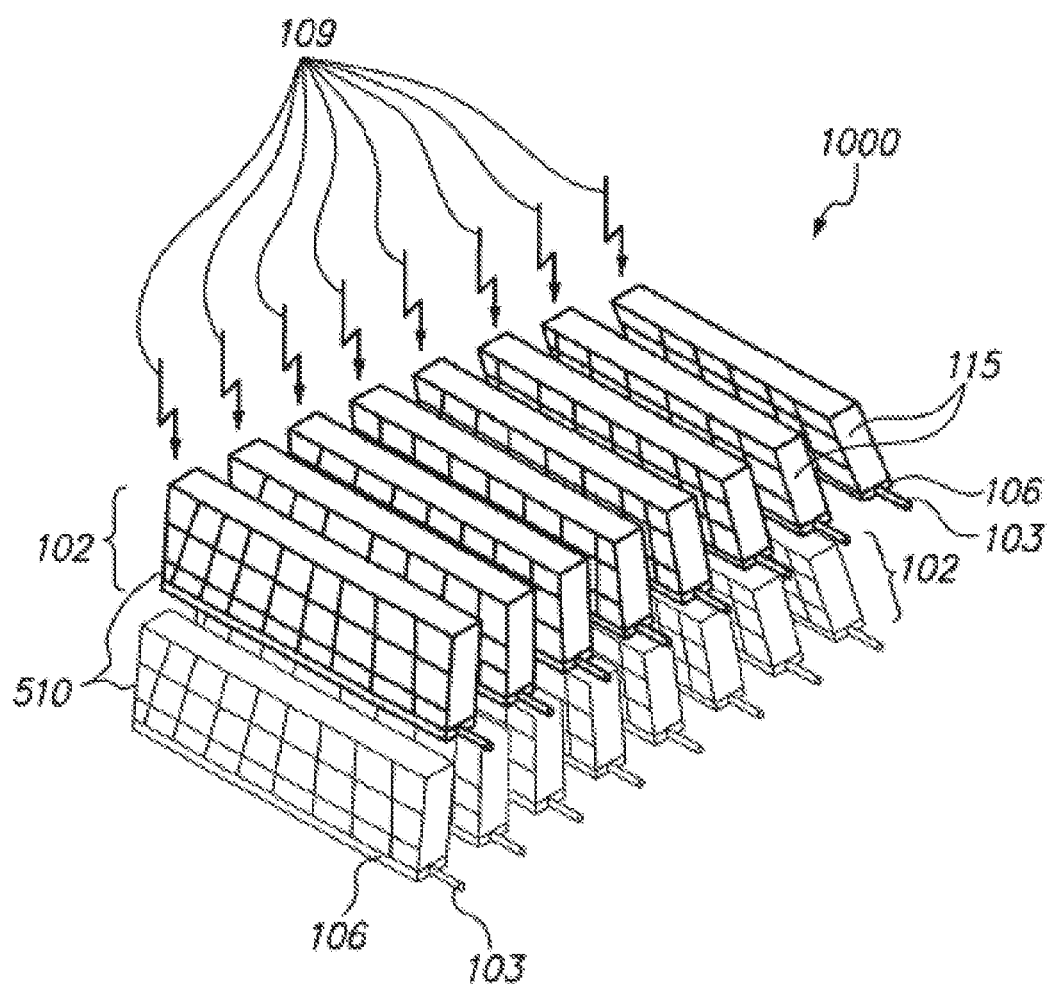
FIG. 3 is a perspective view of a focused planar detector.
Figure 5:
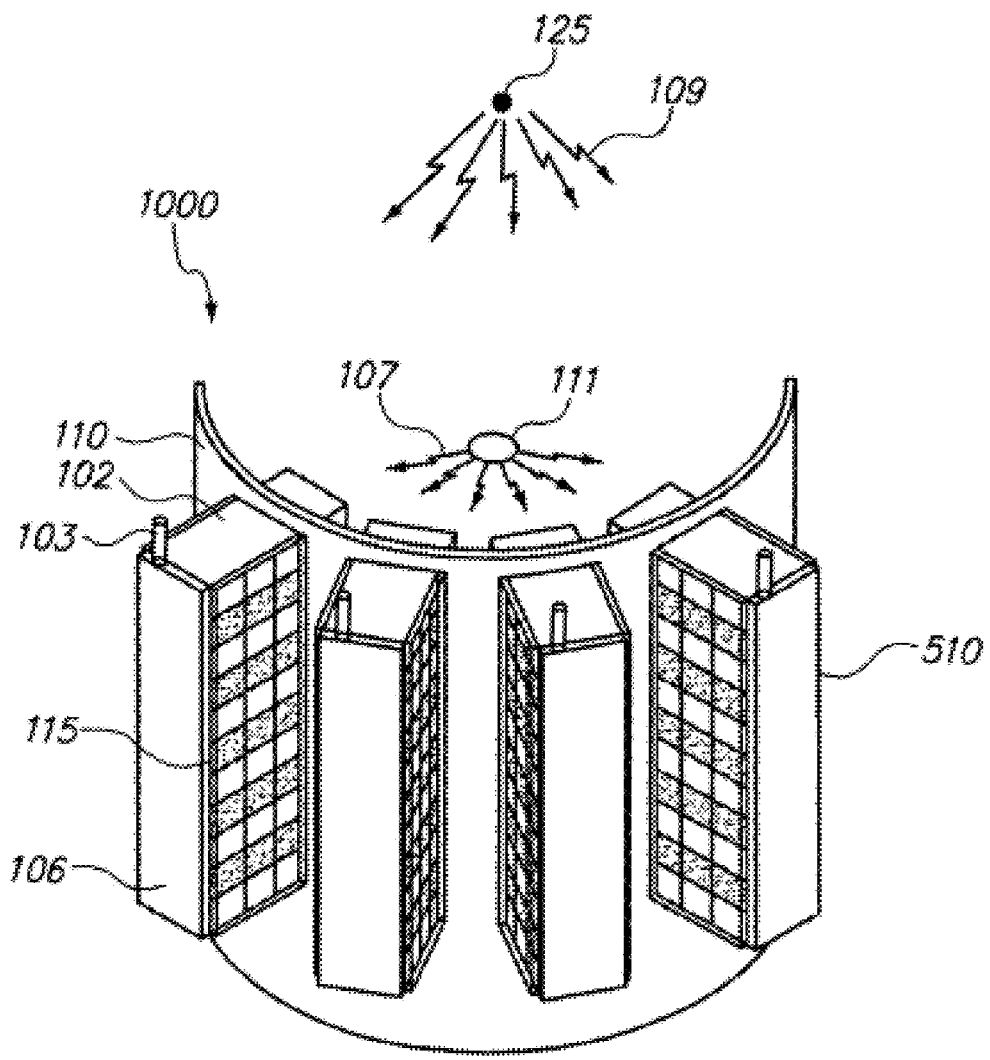
FIG. 5 is a perspective view of a non-coincidence CT-Compton-PET detector imaging system.

The tracking of Compton scattered electrons as well as Compton scattered photons can be simplified by enabling longer path lengths for the scattered particles, improving the estimates of scattering angles. Examples of relatively thin, edge-on detector configurations that incorporate gaps between adjacent detectors (including partially- or completely-offset detectors are shown in FIGS. 1, 3 and 5.

Face-on detector configurations with gaps between detector layers can also be implemented. Compton camera image reconstruction can be improved if both the Compton scattered photon and electron are tracked since the solution can be limited to a fraction of a cone surface rather than the full cone surface.

The flexibility of the Compton camera design can be understood by considering front-end (single layer) detector and front-end with back-end (dual-layer) detector implementations of multilayer, edge-on detector Compton camera designs which can be used for low energy and high energy photon imaging. In one dual-layer implementation the front-end detector is used to detect low energy x-rays or gammas and the back-end detector acts to detect higher energy gammas as an edge-on SPECT/gamma camera or PET camera (Nelson, U.S. Pat. No. 7,291,841). Front-end detectors and back-end detectors can be differentiated based on functionality and/or position. The front-end and back-end detectors should have at least one or more different properties such as position, size, geometry (planar, box, partial-box, ring, partial-ring, full or partial D-shape, etc.), directionality (focused, unfocused), spatial resolution, temporal resolution, energy resolution, interaction probability (material density, thickness, interaction coefficients), orientation (edge-on, face-on, tilt), continuity (continuous, discontinuous), noise characteristics, detector operation (integrator, PC, PCE), etc.

A multilayer detector can include one or more front-end detectors and back-end detectors. Detector properties within a detector layer can be uniform or non-uniform (continuous, discontinuous, mixing one or more of detector materials, detector operation capabilities, detector orientations, detector temporal characteristics, etc.). A special case of a multilayer detector is a single detector layer that incorporates one or more front-end detectors and back-end detectors. This can be implemented in structured detectors (such as edge-on structured semiconductor detectors including structured 3D semiconductor detectors and structured mold semiconductor detectors (including implementations that use segmented holes and/or channels), structured scintillator detectors including 3D edge-on or face-on stacked cross-coupled scintillator rod detectors, multilayer scintillator block detectors, scintillating fiber bundle detectors, straw array detectors, etc.).

For example, stacked cross-coupled scintillator rods can vary the scintillator rod properties (material, interaction probabilities, density, temporal characteristics, brightness, etc.) as a function of depth (as well as within a layer and even within individual rods). Front-end stacked cross-coupled layers might use, for example, a scintillator(s)

preferred for lower energies encountered in SPECT or a very fast scintillator or scintillator fiber suitable for TOF PET) while back-end stacked cross-coupled layers might use a scintillator(s) preferred for moderate or fast or very fast PET. Furthermore, scintillator rod properties can be varied within at least one of a rod, a layer, between cross-coupled layers. Varying scintillator temporal characteristic as a function of position could be used to improve event localization based on both optical signal sharing and different temporal decay characteristics of scintillator rods.

Other means of event localization, including signal wave form analysis based on calibration of the detector volume using at least one of the direct (event) signal, reflected signals, cross-coupled signals and wavelength shifted signals (including reflected signals) can also be employed. For example, since the effective rod length is approximately double the physical rod length when the paths (including scatter) of the direct signal and the reflected signal are evaluated this information can be incorporated into a calibration procedure. Event localization information can be used to correct for optical signal (including Cherenkov radiation) propagation time in TOF PET for cross-coupled scintillator rods (and crossed-fiber scintillator rods) involving at least one of the direct event signal, a reflected event signal from the rod end opposite the photodetector readout, a cross-coupled event signal, a reflected cross-coupled event signal, a reflected cross-coupled signal, a wavelength shifted signal (including a reflected wavelength shifted signal), indirect signals and reflected indirect signals. In the case of a cross-coupled event signal commonly employed WLS materials (with nanosecond response) may be problematic unless the delays can be accurately calibrated.

DOI or SAR event localization can be implemented (or enhanced) and/or ambiguity issues resolved by comparing one or more components of the temporal response patterns of multiple readout photodetectors (independently or in conjunction with other localization methods and encoding techniques described herein). Event localization using readout photodetector temporal response pattern information can be employed with scintillator blocks, slabs, sheets, fiber arrays, rod arrays, structured arrays (including various crossed-rod implementations), dual readout arrays, Compton cameras and variants thereof, etc., and other radiation detector systems as described herein.

For example, a scintillator block/slab with at least one sparse or continuous 2D SiPM array photodetector readout can be optically coupled to at least one face of the block/slab/sheet (optionally, at least one additional block/slab/sheet face can be optically coupled, partially or completely, to a single photodetector or to a linear array photodetector readout, providing additional signal intensity and/or temporal response pattern information). The first direct photon detection component of the temporal response pattern of individual elements of a 2D SiPM array can be compared. Furthermore, additional components (e.g., first or higher-ordered reflected photon detection components, gradients, etc.) of the temporal response pattern of individual elements of a 2D SiPM array can be compared and/or analyzed individually (as well as other localization information, such as measured signal intensity). This information can be combined with timing and/or measured signal intensity from additional photodetector readout elements, in order to estimate the position of the scintillation event within the scintillator block, slab, sheet, fiber array, rod array, structured array, Compton camera, etc., and other radiation detector systems as described herein.

In one implementation, a simple slab Anger camera with 2D photodetector readout (eg., as employed in nuclear medicine and PET imaging) can function as a 3D detector by incorporating temporal response pattern information. In another implementation, a (structured) crossed rod scintillator array radiation detector utilizes both signal intensity and temporal response pattern information from multiple photodetectors to enhance event localization estimates and/or reduce ambiguity.

In some implementations, one or more scintillator rod dimensions within at least one layer can be increased (e.g., rod length, rod cross section width and/or height), due to the use of the additional temporal response pattern information for event localization. For example, individual rods within a layer could implement a geometry associated with a sheet or slab. In yet another implementation, a (structured) crossed sheet (or slab) scintillator array radiation detector utilizes both signal intensity and temporal response pattern information from multiple photodetectors to enhance event localization estimates and/or reduce ambiguity.

Individual scintillator sheets can have different properties for encoding purposes. Parallel or crossed scintillator sheet (slab) array configurations can be implemented within the simple slab Anger camera with 2D photodetector readout, as previously described herein.

Very fast WLS materials (including quantum dots), if available, can be deployed otherwise other techniques to direct the cross-coupled event signal to the photodetector readout should be implemented. Cross-coupled scintillator rods incorporate aspects of single-sided and two-sided readout scintillator rods. The use of event localization information to improve TOF information can be employed with other detector geometries described herein (for example, a transparent layer coupled to one or more layers of scintillator rods, a pixelated layer coupled to one or more layers of scintillator rods, scintillator sheets with imposed rod and/or pixel and/or intermediate layer structures, scintillating fibers, scintillator rods with a single-sided or two-sided readout, etc.).

Consider a planar or ring multilayer detector geometry with two (discontinuous) detector layers in which adjacent 3D edge-on silicon detector modules with PCE capability in the front-end and back-end detector layers are tilted with respect to one another to achieve a focused detector geometry with respect to diverging radiation from at least one source, with the adjacent detector modules in the back-end detector layer offset to fill gaps between the adjacent modules in the front-end detector layer and define a substantially continuous detector configuration. (Optionally, these two layers can be treated as a single detector layer.)

Furthermore, consider a multilayer detector with three detector layers (treat the two focused 3D edge-on silicon with PCE capability detector layers as a single detector layer followed by a 2D face-on scintillator with integration capability followed by a 3D edge-on scintillator with PCE capability) employed as a PET camera and x-ray CT imaging system. The 3D edge-on silicon layer and 2D face-on scintillator layer both function as the front-end detector for CT (experiencing different energy spectrums) and alternatively one or both layers could be employed in a dedicated CT imaging system. The 3D edge-on silicon layer also functions as a front-end detector for PET (detecting gammas or scattering gammas). The 3D edge-on scintillator layer acts as the back-end detector for PET (detecting non-scattered gamma rays and scattered gamma rays due to the 3D edge-on silicon layer).

A focused, edge-on Compton camera design was described that can employ one or multiple (of the same or different materials) detector layers as well as implementing additional features such as the offset (complete or partial) of adjacent (neighboring) detector modules within a layer. Completely offset detector modules can be used to create two or more detector layers (offset layers) which when employed together can approximate a continuous detector (and therefor can be referred to as either a single layer or two layers (front-end and back-end layers) of detector modules). The offset layer feature of an edge-on Compton camera design can be implemented in PC, PCE and energy integration versions of diagnostic CT detector, including ring and cone beam CT as well as tomosynthesis, PET, CT-PET, Compton-PET, Compton-PET-CT, gamma camera, etc. (as described in Nelson, U.S. Pat. Nos. 7,291,841; 7,635,848; 8,017,906; 8,115,174; 8,115,175; and 8,183,533; Danielsson, U.S. Pat. No. 8,183,535; and Bornefalk, U.S. Pat. No. 8,378,310). This complete or partial offset feature can be used for not only edge-on detector implementations but also face-on detector implementations for ring and cone beam CT (for example, a planar or cylindrical arrangement of linear arrays of face-on detectors, each oriented parallel to the axial direction of the scanner) as well as tomosynthesis. It should be understood that the modifications and improvements described herein for ring CT detector implementations are also applicable for cone beam CT and tomosynthesis detector implementations.

Implementations of the Compton camera design are described herein that are suitable for use as Compton-PET imaging systems and CT-Compton-PET imaging systems. In addition, the positioning of nuclear medicine collimator hardware such as focused, parallel or pin hole collimators between the object being imaged and the Compton camera permits the system of collimator and Compton camera to provide nuclear medicine imaging capabilities (the imaging capabilities of a SPECT/Gamma camera) for those applications in which the Compton camera does not offer adequate imaging properties.

Limited implementations of the Compton camera designs described herein include versions that function only as CT or PET (and SPECT) detector designs. The Compton camera imaging systems described herein will find use in diagnostic medical x-ray CT, nuclear medicine and PET imaging, x-ray micro-CT imaging, dental CT, medium and small animal imaging, radiation therapy imaging, industrial imaging, HLS and military imaging, and scientific imaging.

Compton-Pet Detector Systems

One implementation of the Compton camera is referred to as the Compton-PET detector system (Nelson, U.S. Pat. No. 7,291,841). The Compton-PET detector system design allows flexibility in the choice of detector materials as well as detector geometries. This flexibility is constrained by the intended imaging applications (such as PET only, nuclear medicine and PET, x-ray and PET).

Face-on, edge-on, and combinations of face-on and edge-on detectors can be employed. One, two or more than two layers of detectors can be employed. Detector modules that comprise a detector layer can optionally be partially-offset or completely-offset from their adjacent neighbors within a layer.

PET image acquisition formats based on planar and focused structure (such as ring and or partial ring) geometries are implemented. Compton-PET detector systems are based on block, 1D, 2D or 3D edge-on, face-on, or mixtures of edge-on and face-on detectors (including edge-on detectors with SAR capability and face-on detectors with DOI capability) (Nelson, U.S. Pat. Nos. 4,560,882; 4,937,453; 5,258,145; 6,583,420; 7,291,841; 7,635,818; 8,017,906; 8,115,174; 8,115,175; and 8,183,533). The non-coincidence and coincidence Compton-PET detector systems described herein include focused and unfocused planar detector formats and focused structure (such as ring and partial ring as well as focused ring and focused partial ring) detector formats.

A non-coincidence Compton-PET (one-sided PET) detector system is implemented by extending Compton camera designs that have been developed for nuclear medicine imaging devices such as hand held probes or SPECT/Gamma cameras so that the detector system can operate with the lower gamma ray energies used in nuclear medicine as well as the higher energy range of PET with good detection efficiency. A highly flexible implementation of a Compton camera design is a dual-layer, 3D Compton camera. A specific implementation, a non-coincidence Compton-PET detector system, employs a (preferably, but not exclusively) Compton scattering front-end detector and a (preferably, but not exclusively) high-stopping power back-end detector in which both front-end and back-end detectors offer suitable 3D spatial resolution, energy resolution and temporal resolution (Nelson, U.S. Pat. No. 8,017,906).

Both the front-end and back-end 3D detectors provide adequate temporal resolution for an expected event rate, such that accurate event tracking can be enabled both within the front-end and back-end detectors and between the front-end and back-end detectors. Both the front-end and back-end 3D detectors can record Compton scatter and photoelectric interactions.

In some instances Raleigh scattering interactions (angle change with insignificant energy loss) can be identified based on tracking information. The front-end and back-end detectors, either separately or together, can operate as two layer Compton cameras and Compton telescope cameras (Nelson, U.S. Pat. No. 8,017,906).

In one scenario the 3D front-end detector can function as a single (or multiple) Compton scatter device and the 3D back-end detector can be used to measure the energy and interaction location of the Compton scattered photon. The front-end and back-end detectors have 3D spatial resolution. Front-end and back-end 3D detectors can also Compton-scatter a photon (measuring position and energy deposited) and detect the (single or multiple) Compton-scattered photon (measuring its energy and interaction location). Therefore this two layer Compton camera with 3D detector layers incorporates the capabilities of three two layer Compton cameras (in which one layer Compton-scatters the photon and the other layer detects (stops) the Compton-scattered photon). A variant of this configuration includes the use of photoelectric events detected in the front-end and/or back-end layer for (coincidence) PET image reconstruction.

Compton telescope camera designs exploit multiple Compton scattering for reconstruction. The Compton telescope camera capability can be implemented in the 3D front-end detector, in the 3D back-end detector and between the 3D front-end and back-end detectors (providing the capabilities of three (multilayer, face-on 2D array detectors) Compton telescope cameras).

Appropriate two layer Compton camera and Compton telescope camera reconstruction algorithms are used to form an image. When this Compton camera is used to image single annihilation gamma rays created during a PET scan it is referred to as a one-sided PET detector system or a non-coincidence Compton-PET detector system. (This dual-layer, 3D Compton camera design is clearly not limited to PET imaging alone and therefore may be adapted for use in imaging applications at other photon energies. Furthermore more than two layers of 3D detectors can be employed and non-3D layers of detectors can be mixed with 3D layers of detectors, thereby introducing additional flexibility in the types of imaging applications for which this Compton cameras design is suitable.)

This one-sided PET detector can be implemented in a focused or unfocused planar detector geometry or a focused structure detector geometry such as a ring or partial ring (as well as focused ring and focused partial ring detector geometry). This avoids the expense of employing a coincidence PET detector system based on opposing (or nearly-opposing) sets of PET detectors.

EXAMPLES

FIG. 1 illustrates a dual-layer Compton-PET detector imaging system 1000 that incorporates 3D, edge-on detector arrays 510 and 520 (a first layer of detectors and a second layer of detectors, respectively). The individual, 2D edge-on detector modules 102 use crossed strip radiation detectors 115. Alternatives include 2D pixelated arrays (or 3D pixelated arrays if SAR capability is enabled) in an edge-on geometry.

Incident radiation photons 107 from gamma ray radiation source, with energy less than the pair production threshold, can undergo Rayleigh scattering, Compton scattering or photoelectric interactions. Compton scattered gamma ray photons 108 can be detected by the edge-on radiation detector within the module 102 responsible for the initial scattering, by other edge-on detector modules within the front-end detector layer 510 (detector layer 1) or by detector modules within the back-end detector layer 520 (detector layer 2).

Each module 102 also includes a base 106 and a communications link 103. The base 106 preferably contains detector electronics including signal conditioners and read-out ASICs, power management components, temperature control components, and a data or information channel for communicating with the computer system. The communications link 103 can be used to provide power to the module 102 and connects the base 106 to a computer system.

The communication link 103 preferably is used to off-load the digitized detector radiation data to a computer system for analysis and image reconstruction. The computer system, which can include general purpose, dedicated, and embedded computers, provides monitor and control services to modules 102, to the detector layers 510 and 520 and to the entire Compton-PET detector imaging system 1000.

The computer system evaluates module parameters, detector layer parameters, and the detected radiation image data. The detected data is processed and can be displayed and stored if desired. Additional relevant module information, such as temperature, amplifier settings, detector voltages, position, orientation, and motion information, can be transmitted to this computer system over the communication link 103. The computer system transmits instructions that update the detector modules 102 and detector layers 510 and 520. This establishes a dynamic information feedback loop that is useful for adaptive imaging (Nelson, U.S. Pat. No. 7,291,841).

Note that the electronic functionality of the detector base 106 can be implemented along the side of a detector module or attached to the surface of the detector module (integrated electronics). Another option when the detector substrate is a semiconductor such as Si is to etch an indentation along the bottom of (opposite the radiation entrance surface) and mount the readout ASICs and radiation shielding in the indentation and directly to the substrate along the bottom edge.

If the length of the edge-on detector is greater than its height then this configuration allows the readout ASICs to be closer to a set of detector pixels than for the case wherein the readout ASICs are mounted along the side in order to avoid the direct x-ray beam. Preferably the combined thickness of the etched substrate and mounted readout ASIC with shielding would be less than or equal to the thickness of the substrate (avoiding problems if the readout ASIC and any shielding stick out from the substrate and possibly interfering with the x-ray beam seen by offset detectors).

Figure 2:
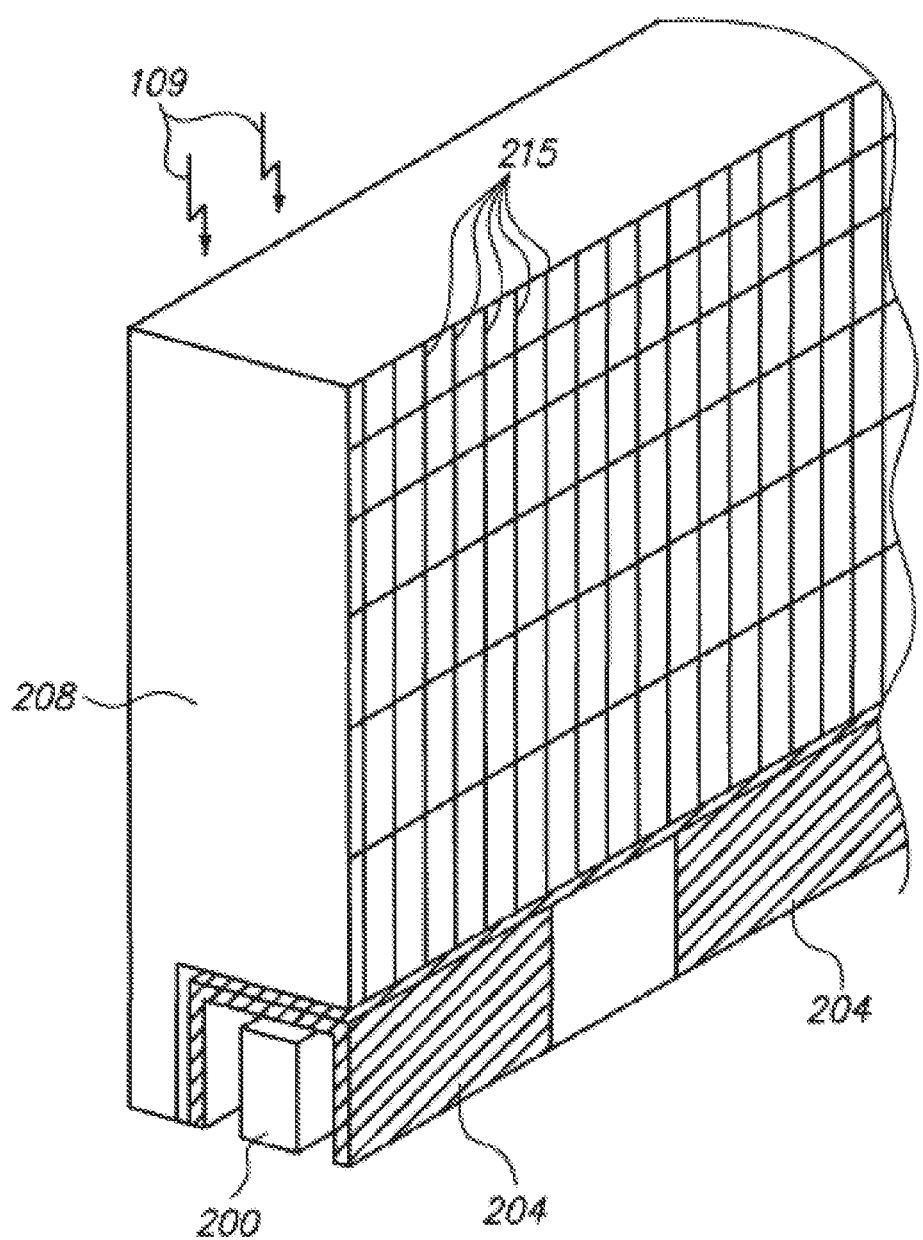
FIG. 2 is a perspective view of an edge-on silicon detector substrate in which shielded readout ASICs are mounted within an etched region along the bottom edge of the semiconductor detector substrate.

FIG. 2 illustrates a perspective of readout ASICs 200 with radiation shielding 204 mounted in an etched Si substrate 208 (or another suitable semiconductor substrate), with a pixel size 215 that varies with height which is positioned edge-on to incident radiation photons 109. Other techniques of delivering power to the detector modules as well as wireless communication can be employed in place of communication link 103 (FIG. 1). It should be understood that readout ASICs can be mounted along the side and the bottom edge.

Two or more non-coincidence Compton-PET detector systems (an enhanced non-coincidence Compton-PET detector system) can be employed for a PET imaging application. Furthermore, with the addition of coincidence circuitry, pairs of non-coincidence Compton-PET detector systems (preferably facing each other and positioned on opposite sides of an object) can function as a coincidence Compton-PET detector system.

The cost of a two layer non-coincidence Compton-PET (one-sided PET) detector system can be reduced if either one or both of the 3D front-end and back-end detectors can be replaced by a suitable 2D detector with acceptable energy and temporal resolution and stopping or scattering power. The caveat is that photon detection efficiency and reconstruction image quality may suffer as a result. A compromise in terms of cost is to leave the front-end detector with 3D spatial resolution (and therefore retaining the previously herein-listed capabilities: to function as a Compton scatterer, a two layer Compton camera, a Compton telescope camera), and employ a back-end detector with 2D spatial resolution. The back-end detector would offer acceptable stopping power, energy resolution and temporal resolution for the expected gamma ray event rate and gamma ray energies.

For a planar detector geometry the front-end and back-end detectors can consist of single-layer face-on detector plane modules, a multilayer (stack) of face-on detector plane modules, a single-layer of edge-on detector modules, a stack of edge-on detector modules or a combination of face-on and edge-on detector modules. Face-on detector modules can include DOI capability whereas edge-on detector modules can include SAR capability.

One implementation of a focused planar detector geometry (suitable for cone beam CT, tomosynthesis, etc.) employs a front-end detector that consists of either a single layer (offset or non-offset) or multiple layers (offset or non-offset) of tilted edge-on (and/or face-on) detector modules. A degree of physical focusing (promoting directionality) is achieved by tilting the detector modules (detector modules with fixed or adjustable tilt angles can be implemented depending on the imaging requirements). As an alternative to a parallel pixel structure a focused pixel structure can be implemented along the lengths of the edge-on tilted (or parallel) detector modules to account for x-ray beam divergence (which can also be implemented in a ring or partial ring CT detector geometry). A focused collimator can be implemented in order to reduce x-ray scatter.

Furthermore, an additional degree of physical focusing be achieved by positioning detector modules (using parallel and/or focused pixel structures in a curved geometry and thereby approximating arc-shaped detector lines (suitable for a focused, near-planar detector geometry as well as ring or partial ring CT detector geometries). Each of the offset or non-offset edge-on detector module comprising the first layer of tilted edge-on detector modules can have at least a second (offset or non-offset) edge-on or face-on detector module (comprising the at least second layer of detector modules), tilted or not tilted, positioned beneath it. For example, the first layer can implement offset tilted edge-on silicon detector modules with each offset silicon detector module followed by one or more semiconductor or scintillator face-on or edge-on detector modules comprising one or more additional layers (typically employing moderate-to-high Z detector materials).

FIG. 3 illustrates a perspective of a focused planar detector system 1000 in which detector modules 102 are tilted so as to focus on diverging radiation 109 from a radiation source. In addition the pixel structure 115 within the individual detector modules 102 is angled so as to focus on the same radiation source.

The tilting of the detector modules may create unacceptable gaps between neighboring detector modules within the detector layer 510. These gaps are shown to be effectively filled by the complete offset of every other detector module comprising the offset detector layer 510.

One implementation of a focused structure detector geometry such as a ring (or partial ring) employs a front-end detector comprised of a single layer (non-offset) or single layer with an offset layer (which can be treated in this application as a single layer) of tilted edge-on detector modules. As in the case of planar detectors, a focused pixel structure can be implemented along the lengths of the edge-on tilted detector modules (creating focused ring and focused partial ring detector geometries).

Suitable detector configurations and materials have been described for Compton, PET, nuclear medicine and x-ray imaging (Nelson, U.S. Pat. Nos. 6,583,420; 7,291,841; 7,635,848; 8,017,906; 8,115,174; 8,115,175; 8,183,533; U.S. patent application Ser. No. 13/199,612 (U.S. Publication No. 2012/0181437); and U.S. Pat. No. 9,347,893). Examples of suitable detector configurations include a single or multilayer face-on detector, a single or multilayer edge-on detector and a multilayer detector comprised of face-on and edge-on detectors.

Edge-on detectors may incorporate SAR capability and face-on detectors may incorporate DOI capability. Examples of suitable detector materials and formats include semiconductor detectors, structured detectors such as single and double sided structured 3D silicon as well as other structured 3D semiconductor materials (Diamond, carbon nanotubes, Ge, Se, GaAs, CdTe, CZT, etc.), structured quantum dots, structured scintillators, and scintillators. Structured mold quantum dot detectors (also referred to as structured quantum dot detectors) offer flexibility since a variety of cell shapes (including trenches) can be implemented. Furthermore, the selection of (and density of) quantum dot (nanoparticle) materials can be varied as a function of position within the substrate in order to enhance a type of interaction such as Compton scattering or the photoelectric effect. Silicon is frequently used as a mold material in the form of porous silicon or micromachined silicon for semiconductor quantum dots (nano-particle semiconductor materials), as well as polycrystalline and amorphous semiconductor materials. Silicon and other mold materials can be used with scintillator quantum dots as well as scintillator materials.

Structured mold semiconductor detectors implement (but are not limited to) either semiconductor quantum dots (nanoparticles) or amorphous semiconductors or polycrystalline semiconductors (semiconductor materials). Structured mold semiconductor detectors (also referred to as structured mold detectors), including segmented anode and/or cathode variations thereof as well as other implementations of structured mold detectors (and structured 3D semiconductors) described herein, are not limited to a pixelated readout. Strip, crossed strip, area and pixelated readout geometries can be employed (or combinations thereof).

Note that potential costs and benefits should be weighed against possible reductions in one or more detector module response (performance) parameters (e.g., energy resolution, spatial resolution, temporal resolution, volume-dependent dead time, positioning errors, etc.). For example, a crossed strip readout geometry (perpendicular anode and cathode strips on opposite side of a semiconductor slab) can be employed with silicon, germanium or CZT detector materials, etc., offering 2D resolution (or 3D DOI or SAR resolution, if differences between electron and hole mobility are exploited). The flexibility of the structured mold architecture enables incorporating not only two or more semiconductor materials within a structured mold but also implementations such as one or more semiconductor materials with one or more scintillator materials and/or gases, one or more scintillator materials with one or more gases, etc. within a structured mold. For example, an edge-on dual-layer detector with a semiconductor detector first (front-end) layer and a scintillator detector second (back-end) layer can be manufactured as a single, edge-on structured mold detector with semiconductor and scintillator components (or other combinations of two or more detector types described herein, including semiconductor, scintillator, gas, or superconductor detectors, etc.).

The first layer within the structured mold could implement one or more semiconductor quantum dot (nanoparticle), amorphous semiconductor and/or polycrystalline semiconductor materials in appropriate geometries (in this implementation the first layer is comprised of one or more layers) for the incident radiation field. The second layer could implement one or more organic and inorganic scintillator materials including, but not limited to, scintillator quantum dot (nanoparticle), polycrystalline scintillator, nanophosphor scintillator, liquid scintillator, gas scintillator, etc. materials in appropriate geometries (in this implementation the second layer is comprised of one or more layers) for the incident radiation field.

Partial lists of suitable organic and inorganic scintillators and semiconductors are provided, e.g., in Knoll G., Radiation Detection and Measurement, 4th edition, Wiley (2010) which is incorporated by reference for these teachings as described herein. Suitable materials include, but are not limited to, organic crystal scintillators, inorganic crystal scintillators, plastic (polymer) scintillators and (plastic and non-plastic) scintillating fibers and fiber bundles (strips) (scintillating fiber bundles (strips) represent one implementation of a structured detector), gel scintillators, liquid scintillators, deuterated liquid scintillators, and loaded liquid scintillators (loaded, e.g., with B, Gd or Sn). Suitable gas scintillators include, but are not limited to, xenon, krypton, argon, helium, and nitrogen. Glass scintillators may also be used (e.g., silicate glass containing lithium activated with cerium).

Additional detector options include structured, gas-filled straw detectors with appropriate low-Z or moderate-Z material annuli which provide suitable energy, spatial and temporal resolution and stopping or scattering power (Nelson, U.S. Pat. No. 8,017,906), liquefied gas based detectors (such as Xenon), semiconductor-based or gas-based Medipix detectors and low temperature (such as GE and superconductor) detectors. Multiple Compton-PET (one-sided PET) views of a volume of an object to be imaged can be acquired as a result of detector system rotation about the object to be imaged.

An alternative imaging format is to rotate the object and keep the detector system stationary. Additional object volumes can be imaged, if needed, by translating (typically) the object through the scanner system.

It should be noted that if the Compton camera image quality isn't suitable for the nuclear medicine imaging applications of interest then a collimator can be inserted in front of the detector so that the system of collimator and detector can function as a SPECT/gamma camera. Since the collimator imposes a degree of directionality then the SPECT/gamma camera implementation of a Compton camera can utilize both Compton scatter interactions (and tracking capabilities) as well as direct photo-electric interactions (which have a much higher probability of occurring at lower energies such as 140.5 keV versus 511 keV in low-Z and high-Z detectors). The direct photo-electric interactions would not be used in conventional (no electron tracking) Compton camera imaging. Furthermore, a miniature version of the Compton-PET detector system can be implemented as a Compton-PET hand-held detector probe. The addition of a nuclear medicine collimator permits the Compton-PET detector probe to function as a gamma camera hand-held detector probe. Versions of probes can be operated in non-coincidence or coincidence mode with non-coincidence Compton-PET detector systems (as well as coincidence Compton-PET detector system) to offer enhanced resolution.

Coincidence Compton-PET detector systems extend the implementations of a non-coincidence Compton-PET detector system by including a second Compton-PET detector system and coincidence circuitry between the pair of Compton-PET detector systems, for example, employing a pair of planar or partial ring Compton-PET detector systems with coincidence circuitry.

Figure 4:
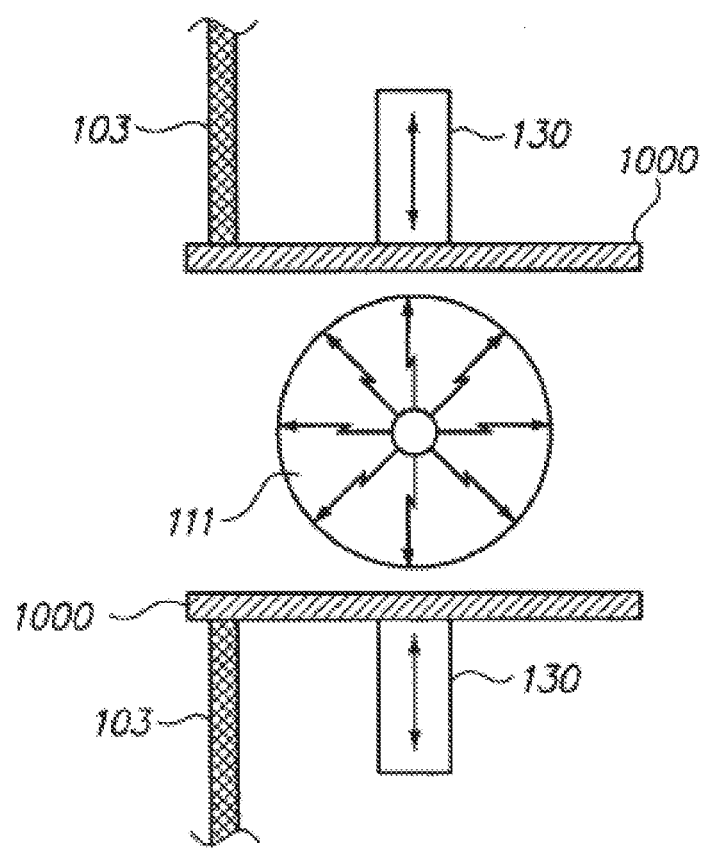
FIG. 4 is a schematic view of a coincidence Compton-PET detector imaging system.

FIG. 4 illustrates a coincidence Compton-PET detector system which is comprised of a pair of planar Compton-PET detector systems 1000 with communications links 103 operated in coincidence for imaging an object 111. (for example, the heart). Each planar Compton-PET detector system 1000 is positioned by an electronically controlled actuator arm 130.

For the case of a partial ring Compton-PET detector system, if a sufficient number of pairs of partial ring Compton-PET detector systems and coincidence circuitry (linking all detectors) are employed, then a complete ring coincidence Compton-PET detector system can be implemented. The complete ring geometry can be achieved with a single pair of partial ring Compton-PET detector systems if each partial ring covers an angular aperture of 180 degrees.

If the Compton scatter capability of a front-end detector is not needed (for example, if only one complete Compton camera is needed for non-PET image applications), then there is the option of employing only a PET-compatible detector for the second detector system. Additional pairs of Compton-PET and/or PET-compatible (or combinations of both) detectors with appropriate coincidence circuitry can be combined to form an enhanced coincidence Compton-PET detector system. (Note that a dummy or non-functional equivalent of the front-end detector can be used to make a stand-alone PET-compatible detector unit "see" a comparable radiation field to what the back-end detector experiences in a coincidence Compton-PET system without the cost of an active front-end detector).

The description of a flexible non-coincidence Compton-PET detector system applies to the Compton-PET detector systems used in a coincidence Compton-PET detector system. Consider the case in which at least one of the two detector system is a Compton-PET detector system. The front-end and back-end detectors offer suitable 3D spatial resolution, energy resolution and temporal resolution and stopping or scattering power. Both the front-end and back-end detectors provide adequate temporal resolution for an expected event rate such that accurate event tracking can be enabled both within the front-end and back-end detectors and between the front-end and back-end detectors, since Compton scatter and photoelectric interactions can be recorded in both front-end and back-end detectors.

As described for non-coincidence Compton-PET detector systems this combination of front-end and back-end detectors incorporates the capability of three two-layer Compton cameras and three Compton telescope cameras. The addition of coincidence detection capability introduces additional flexibility in that events involving a single photoelectric interaction (in which no Compton scattering occurs) in the front-end or back-end detector can be used for coincidence detection as well as events involving one or more Compton scatter interactions.

In a conventional Compton camera design a photoelectric interaction in the front-end detector layer is not useful. A fast or very fast detector (including, but not limited to, silicon, GaAs, various structured 3D detectors such as 3D silicon, structured mold, etc.) can provide timing information for coincidence PET using either photoelectric or Compton scatter interactions. The capability to use photoelectric events without Compton scattering leads to an alternative detector system design in which the front-end detector layer employs a moderate-to-high Z detector material with tracking capability. In this implementation both photoelectric events and Compton scattering can be exploited but now the photoelectric interaction relative probability is more significant compared to a material such as silicon. Tracking capability for Compton scattered photons (as well as characteristic x-rays) can be used for estimating the deposited energy for each detected event even if Compton scatter reconstruction is not employed. If the front-end detector is sufficiently fast then the TOF PET imaging can be implemented. For example, an edge-on, structured mold detector implementing at least one of high-Z (semiconductor) quantum dots, amorphous semiconductors, and polycrystalline semiconductors can replace an edge-on silicon or structured 3D silicon detector. If the edge-on, structured mold detector offers significant attenuation it can be used in place of both the front-end and back-end detectors. Furthermore, this alternative detector system design can be readily extended for use with CT-Compton-PET, CT-PET, PET Compton-PET and CT detector systems.

Since very fast coincidence timing (TOF) can be used to improve reconstruction accuracy and reduce patient dose and/or image acquisition time there can be a benefit from having one or both of the front-end and back-end detectors capable of very fast timing resolution. If both front-end and back-end detectors are involved in the detection process then coincidence timing can be based on using at least one of the front-end and back-end interaction timings. Timing resolution corrections are made for the response of one or both detectors (depending on whether one or both of the front-end and back-end detectors are involved in detection) and gamma ray travel times between interaction locations within one or both detectors and between detectors (Nelson, U.S. Pat. No. 8,017,906).

Commercial TOF PET systems are capable of very fast temporal resolution (on the order of or less than one nanosecond). Very fast temporal response capabilities can influence the choice of detector materials for front-end and back-end detectors. If the front-end detector has a reasonable probability per photon of a Compton scatter interaction then one option is to select a front-end detector material with a very fast temporal response and select a (possibly much less expensive) back-end detector material with a much slower temporal response. Suitable front-end detectors (including externally-modified implementations of these detectors) that incorporate at least one of fast or very fast temporal resolution, good spatial resolution and good energy resolution include, but are not limited to, edge-on and face-on scintillators with photodetector readouts (indirect detectors), semiconductors, 3D semiconductors, structured mold detectors, nanowires, and spintronics direct detectors, etc., as described herein.

Alternative front-end detectors such as, but not limited to, microchannel plates (MCPs), externally-modified non-scintillator and semiconductor materials, etc., as described herein, can be implemented as direct ionizing radiation detectors, although energy resolution may range from acceptable levels for these detectors. For example, a single-layer or multi-layer (e.g., Chevron, Z-stack) microchannel plate direct detector unit (or a stack of such direct detector units), with a suitable fast or very fast (potentially below 10 picosecond resolution) 1D or 2D readout (e.g., strip line, multi-anode array, crossed strips, resistive anode, etc.), can be positioned edge-on or face-on with respect to the radiation source in a single layer or a multilayer detector configuration.

An optional converter material or materials can be coupled to at least one face of at least one microchannel plate direct detector unit (e.g., a hybrid MCP direct detector), and employed within a suitable detector system. Converter materials can include, but are not limited to, thin foils to convert ionizing radiation into charged particles, thin foils coupled to scintillators, scintillators, scintillator and non-scintillator materials adapted to generate Cherenkov radiation, scintillating fibers, etc. For the detection of visible optical signals, a photocathode layer is employed (e.g., as used in conventional microchannel plate detectors or MCPs), such that the MCP direct detector (or a hybrid MCP direct detector) unit can exploit direct (internal) interactions and indirect (external) interactions. Fast timing and position of ionization events within the microchannel plate unit (or a converter material if present) can be measured. Energy resolution is dependent upon the ionizing event interaction location (e.g., within a single layer, within a multi-layer, or within a converter material if present).

Corrections for event interaction depth, position and/or energy resolution within the MCP or converter material (if present) can be estimated using at least one of temporal and spatial signal distribution information (providing DOI/SAR for face-on/edge-on geometries). Excellent temporal resolution, spatial resolution and energy resolution (if suitable) can be used to track one or more secondary events within an MCP unit, and between MCP units (or other detectors) within a detector system, where the secondary event is due to a primary event (such as an initial x-ray or gamma ray Compton scatter event, a neutron interaction, etc.).

For some applications such as x-ray photon counting detectors that can be employed in x-ray diagnostic radiology and CT scanners, or for certain implementations of PET/TOFPET scanners, only limited energy resolution is required. Although the microchannel fibers used in conventional microchannel plates are typically comprised of lead-glass fibers or relatively low-Z borosilicate glass fibers, the interaction cross sections for one or more types of ionizing radiation (x-rays, gamma rays, neutrons, etc.) can be enhanced by altering the composition or coatings of the glass fibers, or by implementing microchannel arrays with non-glass materials of the desired properties (metals, semiconductors, scintillators, etc.). For example, for most x-ray and gamma ray energies encountered in medical imaging applications, Compton scattering is promoted over photoelectric interaction by the use of borosilicate glass fibers (or other low-Z materials), rather than lead glass fibers.

The properties of MCP units within a face-on or edge-on stack can be the same or different depending on the application (e.g., slit/slot/area diagnostic x-ray, radiation therapy, CT, PET, PET-CT, therapy-CT, therapy-PET, therapy-PET-CT, x-ray and neutron imaging, etc.), and depending on the detector geometries (single layer, multiple layers, etc.). Furthermore, the properties of the microchannel fibers (including amplification coatings, fiber length, fiber diameter, fiber materials), both within a microchannel layer and between microchannel layers within a multilayer MCP unit, can be varied according to the ionizing radiation detection application.

The use of MCP direct detectors (ionization MCPs) is described in high energy physics applications such as the detection of minimum ionizing particles, or within calorimeters. Issues that affect x-ray and gamma ray (Compton and photoelectric) interaction probabilities such as the choice of microchannel material (relevant for medical imaging applications) may be of minor importance for applications in high energy physics, in which the cost for large area detectors (e.g., 20×20 $cm^2$ MCP detectors) has driven the development of low-Z borosilicate glass fibers as a replacement for lead glass fibers as used in smaller commercial MCP units.

Note that in general, a microchannel plate, direct detector unit or an alternative direct detector unit that offers internal gain (including, but not limited to, semiconductor photomultipliers, semiconductor APD detectors, etc.), and hybrid implementations thereof (as well as hybrid direct detectors without internal gain such as photosensitive or electron-sensitive Si, GaAs detectors, semiconductor photodiodes/arrays, etc.) can be employed within a single layer detector system or a multi-layer detector system (e.g., for CT, PET, SPECT, or Compton imaging, or combinations thereof), and is not limited for use as a front-end detector. Therefore, microchannel plate detectors (edge-on, face-on, with or without converter materials) can be employed for at least one of front-end, intermediate, and back-end detectors, or for stand-alone detectors within the detector systems described herein. Furthermore, these microchannel plate detectors can operate in at least one of the previously described detector modes (with one or more of integration, photon counting, and energy resolution). For example, a single energy or a dual energy (or multiple energy), edge-on CT detector as described can incorporate an edge-on or face-on microchannel plate detector (with or without converter materials), as a suitable detector system for use in CT, PET, SPECT, or Compton imaging, or any combination thereof.

MCP detectors (conventional photodetectors, direct and hybrid direct implementations) with fast or very fast readout capabilities are useful for their potential to reduce costs in particle and/or photon ionizing radiation detector systems, including, but not limited to, CT, PET, SPECT and Compton imaging systems (or combinations thereof), where the MCPs implement at least one of a single readout sensor, a linear array readout sensor, a 2D array of individual readout sensors, and a single readout strip or an array of readout strips with a readout sensor at each end. The location of the signal due to an event along the strip can be estimated using differences in propagation times (TOF) to the two readout sensors, and/or differences in signal levels measured at the two readout sensors. Readout strips lengths can be selected based on the required number of pixels (spatial resolution), temporal resolution, and energy resolution, for the desired implementations of edge-on and face-on detector geometries described herein.

The readout strips can be relatively long (on a scale of centimeters), while offering spatial resolution suitable for moderate and high resolution applications such as single layer or multilayer CT, PET, SPECT and Compton imaging (or combinations thereof). For example, an axial CT, axial PET, axial SPECT or axial Compton implementation (or any combination thereof) could employ one or more detector modules that implement at least one of a single readout sensor MCP detector, a linear array readout sensor MCP detector, an MCP detector with a 2D array of individual readout sensors, a single strip MCP detector (e.g., with dual-ended readout sensors), or an array of single strip MCP detectors (with dual-ended readouts) of sufficient length to cover at least a useful fraction of the axial field of view.

Alternatively, multiple single strip MCP detectors (or multiple arrays of single strip MCP detectors) could be employed butted end-to-end to cover at least a fraction of the axial field of view. Detector systems employing one or more detector modules that incorporate at least one MCP can implement the active and/or passive encoding techniques described herein within at least one detector module (and/or a material sample), including, but not limited to, an optical pump encoding, an optical pump-probe encoding, an applied electric field encoding, an applied magnetic field encoding, a passive electromagnetic encoding, an active electromagnetic encoding, an active acoustic encoding and passive acoustic encoding, and an active thermal encoding.

If a gamma ray undergoes a Compton scatter interaction in at least one of the front-end and back-end detectors as well as additional interactions such that the energy of the incident particle can be estimated, then photon directionality based on the appropriate Compton camera reconstruction algorithm (for the Compton camera designs described for non-coincidence Compton-PET detector system) can be compared with photon directionality based on coincidence (line-of-sight) between the Compton-PET detector systems operating in coincidence. The Compton-based directionality can be used to estimate the degree of validity of the coincidence (line-of-sight) assumption, including acollinearity. This capability can be used to help reject some of the photons that undergo Raleigh and/or Compton scattering within the object and its surroundings as well as Rayleigh scattering or difficult to detect Compton scattering within the detectors.

In addition, a (combined) non-coincidence Compton-PET (one-sided PET) reconstructed image can be compared to (or combined with) a coincidence PET reconstruction image, (Nelson, U.S. Pat. No. 8,017,906). Unpaired detected events (in which coincidence fails since only one of the two annihilation photons is detected and is considered legitimate) by a Compton camera can still contribute to the Compton scatter reconstruction image.

As described for the case of non-coincidence Compton-PET (one-sided PET) detector systems, system cost (in some cases) may be reduced if the back-end detector 3D spatial resolution capability is lowered to 2D capability while maintaining adequate energy and temporal resolution. The 2D spatial resolution of the back-end detector implies that it offers limited performance as a stand-alone PET detector for gamma rays that aren't Compton scattered by the front-end detector.

The back-end detector should provide good stopping power. The Compton scattering front-end detector offers suitable 3D spatial, temporal and energy resolution and scattering interaction probability. Single and multiple Compton scattering (as well as photoelectric) interactions can occur in the front-end detector, allowing the front-end detector to function as a Compton camera, as a PET camera, as the first layer of a multilayer Compton camera and as the first layer in a multilayer PET camera in which it records the initial interaction location, energy deposition and event timing information. (Note that if the multilayer Compton camera capability is sacrificed then the 2D spatial resolution capability of the back-end detector can be reduced to 1D or even block detector spatial resolution, further reducing costs. The back-end detector primarily provides stopping power along with appropriate energy and temporal resolution. The front-end detector should offer an acceptable probability of undergoing at least one Compton scatter interaction so that an initial location of interaction, timing and energy deposition can be established. If TOF PET imaging is desired then the front-end detector can offer very fast temporal resolution. The front-end detector, due to its 3D spatial resolution capability, can still track multiple scatter interactions as well as photoelectric events. The front-end detector retains the capabilities of a Compton camera and a PET detector. Event tracking between the front-end and back-end detectors is employed.)

The back-end detector can also offer fast or very fast temporal resolution. The front-end detector can maintain fast or very fast temporal resolution capability but an alternative is to implement a front-end detector (with suitable temporal resolution) primarily for establishing spatial resolution via photoelectric and Compton interactions while relying on the fast or very fast back-end detector (with suitable spatial resolution) to establish coincidence timing for the front-end detector Compton scattered photons. In some implementations cost savings may be realized and the choice of front-end and back-end detectors may be expanded by moving some temporal resolution capabilities from the front-end detector to the back-end detector. For example, the 3D front-end detector could use low, moderate or high-Z semiconductor materials with less emphasis on temporal resolution and more emphasis on spatial resolution while the back-end detector could offer reduced spatial resolution while emphasizing temporal resolution (employing fast scintillators such as LSO, LYSO, $BaFl_2$, $LaBr_2$, etc. coupled to PMTs, microchannel plates, SiPMs, SPADs, APDs, silicon nanowires, etc.). Implementations of these dual-layer detector configuration are suitable for use in CT-PET imaging systems wherein the front-end detector is used for CT and PET and the back-end detector is used for CT and PET or PET. Furthermore, the front-end detector and back-end detector layers can always be implemented as independent detector layers leading to cost savings. For example, the CT front-end detector can be a simple face-on scintillator (energy integrator), a dual-energy edge-on scintillator, a PCE edge-on semiconductor detector, etc. but the needed for capabilities such as tracking electronics between layers, etc. are removed.

Multiple Compton-PET or PET views of an object volume to be imaged can be acquired as a result of detector rotation about the object. The alternative imaging format is to rotate the object and keep the detector system stationary. If the Compton camera image quality isn't suitable for the nuclear medicine imaging applications of interest then a collimator can be inserted in front of the detector so that the system of collimator and detector can function as a SPECT/gamma camera (collimators can also be used with PET cameras).

For the coincident and non-coincident Compton-PET configurations described there are many options for detector materials based on cost and performance requirements. Assuming that acceptable-to-good energy resolution is desirable, then block, 1D, 2D and 3D back-end detectors and 2D and 3D front-end detectors can use semiconductors, polycrystalline and amorphous semiconductors, structured 3D semiconductors, structured mold semiconductor quantum dots (nanoparticles) as well as amorphous semiconductors and polycrystalline semiconductors, moderate-to-bright nanophosphors (scintillator quantum dots), organic and inorganic scintillators, gas and liquid detectors, and amplified detectors. Furthermore these detectors can incorporate edge-on SAR or face-on DOI (positional encoding) capabilities.

Semiconductor and gas detectors typically offer a Fano factor noticeably less than 1.0. If stopping power is important, then sufficient detector material can be present in order to provide good to excellent attenuation. Detector response time (for example, scintillator decay time) properties should be suitable for at least event tracking at expected event rates. Very fast detectors would permit the use of TOF information to be utilized in PET reconstruction algorithms.

Possible scintillators with at east one of these properties include, but are not limited to: $BaF_2$, $LaBr_3$ (including co-doped), $Tl_2LiLaBr_6$, $LaCl_2$, LSO, LYSO, GSO, $GdI_3$, $LuI_3$, $SrI_2$, $BaHfO_3$, $SrHfO_3$, $PbWO_4$, LuAP, CsI:Tl,Sm, NaI:Tl, BGO, CsI:Tl, $Lu_2O_3$:Eu, ZnO-based fast scintillators as well as glass, plastic and fiber scintillators, liquid scintillators, gas scintillators, quantum dot scintillators, ceramic scintillators, polycrystalline scintillators and various fast-to-very fast organic scintillators. Possible semiconductor detectors (and variants thereof) with at least one of these properties include, but are not limited to: diamond, carbon nanotubes, Si, Si(Li), SiC, Se, Ge, GaAs, GaAs:Cr, CdTe, CZT, $HgI_2$, PbO, $PbI_2$, TlBr (as well as low noise implementations such as silicon drift detectors or those with gain such as Si-APDs or SiPMs or silicon nanowires or iDADs, Se-APDs, GaAsPMs and DiamondPMs) detectors; one dimensional structures such as rods and wires, structured single and double sided 3D Si and other semiconductor material detectors and structured mold semiconductor quantum dot (nanoparticle), amorphous semiconductor, and polycrystalline semiconductor detectors.

A number of these semiconductor detectors can be configured as fast or very fast photodetectors and so they can be coupled with fast or very fast scintillators such as quantum dot, organic, or inorganic scintillators. Suitable detector packages (a detector material coupled to a readout ASIC) include Medipix-based detectors. Additional structured detectors with gain include, but are not limited to, gas-filled straw detectors (Nelson, U.S. Pat. No. 8,017,906).

In addition, the choice of detector material can be influenced by the detector format. For example, a 10 mm thick (or greater) CdTe or CZT face-on detector (used primarily for photo-detection) for PET imaging may offer limited temporal resolution, whereas a 1 mm thick (or less) CdTe or CZT edge-on detector (used for photo-detection and/or Compton scattering) may qualify as a fast detector (even if SAR or DOI corrections are not implemented). From a similar perspective a 1 mm or 0.5 mm (or less) thick Si or Ge edge-on detector (used for Compton scattering or Compton scattering and photo-detection) can be employed as a fast or very fast detector.

If SAR or DOI capabilities are implemented to estimate the interaction location of an event, then timing corrections can be made based on the propagation times of electrons or holes to the anode and cathode, respectively (Nelson, U.S. Pat. Nos. 7,635,848; 8,017,906). An edge-on or face-on structured 3D semiconductor or structured mold semiconductor quantum dot detector can be employed as a fast or very fast detector since charge propagation distances can often be less than 40-100 microns.

The flexibility of this Compton-PET design also allows alternative choices for the front-end detector and back-end detector based on factors such as lower cost and non-redundancy of features (if possible) as well as spatial resolution, energy resolution, temporal resolution and the likelihood of Compton scatter and photoelectric interactions. For example, a Compton-scatter front-end scintillator detector could be employed based on suitable (excellent) timing resolution and/or spatial resolution despite reduced (or minimal) energy resolution compared to a semiconductor detector. Compton reconstruction techniques, in some instances, can be employed to estimate the photon energy loss due to the front-end detector Compton scatter event.

Suitable, front-end detector candidates with at least one of these properties include, but are not limited to: low-Z or moderate-Z, fast and very fast organic or inorganic scintillators (or scintillating fibers) with a suitable high-speed, sensitive optical readout detectors (such as photodiodes, graphene photodetectors, APDs, semiconductor photomultipliers such as SiPMs, silicon nanowires and GaAsPMs, electron multiplier CODs, microchannel plates, etc.), semiconductor-based, scintillator-based or gas-based Medipix detectors, and structured, gas-filled straw, RPC, etc. detectors with appropriate low-Z or moderate-Z material which function as a source of Compton electrons. In additional examples, straw and plastic (or non-plastic) scintillating fiber detector formats, when implemented in an edge-on geometry used for PET imaging, could implement SAR (permitting position estimates as well as energy and timing corrections). Furthermore, plastic scintillating fibers (as well as non-plastic scintillating fibers) can be coated with thin films of moderate-to-high-Z materials to enhance their photoelectric cross section (permitting the properties of the front-end detector layer to be tuned in terms of the Compton scatter and photoelectric interaction probabilities). Alternatively, high-Z detector materials can be employed as front-end detectors if photoelectric interactions (e.g., used in coincidence PET imaging) or both photoelectric and Compton interactions are to be emphasized. As noted previously, Compton interactions can be used in Compton image reconstruction, coincidence PET image reconstruction or both Compton and PET image reconstruction.

Previously, structured straw (gas-filled) detectors incorporated only high-Z annuli in order to enhance the photoelectric effect (Nelson, U.S. Pat. No. 8,017,906). The same design technique can be used with low-Z and moderate-Z annuli in order to enhance the Compton scatter effect. Furthermore, combinations of low/moderate-Z annuli straw detectors followed by high-Z annuli straw detectors (or other high-Z detectors) can be employed. Gas-filled detectors including, but not limited to, structured straw detectors and RPC detectors can be manufactured in sizes appropriate for conventional PET or extended axial field of view whole body PET (potentially lowering detector cost).

Furthermore, the relatively high photon energies encountered in PET imaging favor forward scattering of Compton electrons. For a single RPC detector the incident annihilation photons initially encounter a thin sheet of glass, plastic, bakelite, etc. in the upper surface, with a relatively small probability of undergoing Compton scattering and a much smaller probability of undergoing a photoelectric interaction. The upper surface is the dominant source of ionizing electrons events.

An alternative to stacking single RPC detectors to form a multilayer RPC detector is to construct a multilayer RPC detector in which the lower surface of one RPC detector is utilized as the upper surface of the next RPC detector in the stack (this has limits in terms of voltage division between plates). This can be a problem for a multilayer straw detector which emphasizes Compton scatter events for PET imaging (whether it is oriented face-on or edge-on or at an intermediate angle with respect to the incoming annihilation photons). For example, for a face-on geometry the potential ionizing electron events generated within the bottom surface wall of a straw must then penetrate the upper surface wall of a straw in the next layer in order to be detected. (Note that the straw detectors walls can be manufactured from a variety of low-Z materials (glass, plastic, carbon (including nanotubes), Al, etc.).

Detectors should offer an acceptable probability of experiencing at least one Compton scatter interaction so that an initial location of interaction can be established. Event tracking within and between the front-end and back-end detectors can be employed. If the front-end detector offers excellent temporal resolution then TOF information can be used to improve the reconstructed image along with a reduction in patient dose and/or image acquisition time. If a front-end detector lacks good energy resolution it still can be effective if the front-end and back-end detectors offer good spatial resolution and the back-end detector offers good energy resolution.

Coincidence (line-of-sight or line-of-reaction) directionality can be exploited along with the scattered photon angle in order to estimate the incident gamma ray energy for cases of simple Compton scatter. Once the properties of the front-end or back-end detector have been defined, then the properties of the other detector can be selected on the basis of which properties need to be accentuated or can be allowed to diminish (such as stopping power, energy resolution, spatial resolution and temporal resolution).

The back-end detector may primarily offer stopping power and energy resolution if the front-end detector offers 3D spatial resolution and energy resolution. Then a cost-based decision can be made as to whether the front-end or back-end detector (or both) should provide acceptable, fast or very fast temporal resolution. Alternatively, a feature such as detector energy resolution may be sacrificed for lower cost and/or for fast or very fast temporal resolution.

Thus a single detector implementation does not have to embody all of the coveted PET detector properties (high stopping power, 3D spatial resolution, fast or very fast temporal resolution). For example, the coincidence Compton-PET detector system can implement features such as TOF imaging with a range of detector options that is much greater than with commercial (conventional) TOF PET systems. Nonexclusive lists of suitable scintillator and semiconductor materials are provided herein. Partial lists of suitable organic and inorganic scintillators and semiconductor materials including some of their properties are provided in Knoll G., Radiation Detection and Measurement, 4th edition, Wiley (2010), p. 230 (table 8.2), p. 238 (Table 8.3) and p. 492 (Table 13.3), respectively, each of which is incorporated by reference herein, in the entirety and for all purposes.

The flexibility of using front-end and back-end detectors for PET which can offer different spatial, temporal and energy resolution for PET results in different PET images based on which detectors interact with the pair of gamma rays from an annihilation event. For example, a Compton-PET front-end detector could Compton scatter one gamma of a pair which is then detected by the back-end detector. Another Compton-PET front-end detector might fail to scatter the other gamma of the pair which is detected by the back-end detector. Coincidence can be established but the timing or spatial resolution (or both) of the front-end detector that detects one gamma may be much better than the timing or spatial resolution of back-end detector that detects the other gamma of the pair.

The use of front-end and back-end detectors permits flexibility as to which detector parameters to adapt (temporal, spatial, energy resolution) as well as selected detector material properties (density, Compton scatter versus photoelectric interaction probability, Compton or photoelectric electron range), for the front-end and back-end detectors. Cost-sensitive decisions can made based on detector characteristics and geometries in terms of how they influence various PET parameters including energy resolution, spatial resolution, temporal resolution, sensitivity, NECR (noise equivalent count rate), true counts, incorrectly classified events, random events, characteristic radiation, Rayleigh scatter, acollinearity, etc.

For example, it may be suitable to employ 0.5 mm thick, high-resistivity or detector grade pixelated silicon or a structured (3D) silicon (or structured mold) detector arranged edge-on (for adequate energy resolution, improved spatial resolution, faster timing), rather than 1.0 mm thick, detector grade Silicon arranged face-on. Or a material with a higher Z than Silicon could be employed to increase photoelectric interaction probability (Ge, GaAs CdTe, CZT, structured 3D and structured mold detectors, etc.). One possibility is that a front-end detector alone will be adequate. For a dual-layer (or multilayer) detector system all detector interaction combinations and thus a range of PET images with different properties) need to be considered.

Consider a dual-layer detector in which the two layers may have one or more different properties such as stopping power, spatial resolution and timing resolution. The first layer could, for example, be comprised of an array of edge-on, high spatial resolution (typically small pixels), fast or very fast temporal resolution, (low-Z) silicon or structured silicon 3D detector planes (or structured mold detectors) providing 3D detector capability. The second layer could be an array of edge-on or face-on, moderate or high-Z, semiconductor or scintillator or structured 1D or 2D detector planes (providing 2D or 3D detector capability, respectively) of the same or lower spatial and temporal resolution (typically slower, larger pixels). Alternatively, the first layer could implement a moderate-Z or high-Z detector and thereby change the percentages or relative probability of Compton and photoelectric interactions in the respective detector layers.

Photoelectric interactions that occur in the first layer or second layer as well as valid reconstructed events (the result of tracking of single scatter or multiple scattered photons as well as shared energy within or between layers) can be used in coincidence detection with an opposing dual-layer detector. Note that this will result in multiple PET images. Coincidence between opposing (typically faster, smaller pixels) first layer detectors (based on photoelectric events or tracked scatter events interacting within the first layer) may be best for spatial and timing resolution information followed by coincidence between a first layer detector and an opposing second layer detector. The poorest spatial and timing resolution would be provided by coincidence between (typically slower, larger pixel) second layer detectors.

As in the case of a dual-layer or "telescope" Compton camera which employs tracking the synergistic interaction of the detector layers enables the recovery of a fraction of the scatter events that interact within one or both layers. A low-Z semiconductor material such as silicon, in which Compton scattering dominates the photoelectric effect at 511 keV, can be used in high resolution PET imaging since the photoelectric and scattering effects can be exploited. If Compton reconstruction algorithms can be employed the effects of acollinearity and scatter may be reduced in some instances and some non-coincidence detected events can be used to form a non-coincidence PET image (Compton-PET image). If advantageous, data from one or more types of acquired PET images can be combined to reconstruct enhanced PET images. Note that low-Z semiconductor detectors such as silicon as well as structured mold semiconductor detectors and other structured semiconductor detectors (for example, structured 3D silicon detectors) are also suitable for use in PET detector systems as well as CT detector systems (ring, partial ring, cone beam, tomosynthesis) in single layer or multilayer or off-set layer detector formats.

CT-Compton-Pet Detector Systems

The flexibility of the Compton camera design allows it to be adapted for PET (and nuclear medicine) imaging. The Compton camera design can also be adapted for use in diagnostic x-ray imaging applications such as CT (including full ring, partial ring, focused full ring, focused partial ring, cone-beam and tomosynthesis) and projection radiography (with the understanding that typical data rate requirements will be much higher, spatial resolution requirements may increase, and the operational energy range for diagnostic medical CT is typically lower than for PET and nuclear medicine imaging).

Various coincidence and non-coincidence Compton-PET detector system implementations have been described. An extension of this dual-use concept is to describe a multi-use CT-Compton-PET detector system design (with the understanding that nuclear medicine imaging capability can also be implemented).

The incorporation of CT features can be explained by examining a special case of a Compton-PET detector system design, the CT-Compton-PET detector system design. This is of interest because CT-PET detector imaging systems are commercially available. However, the CT and PET detector imaging sub-systems (which use face-on detectors) are physically distinct. This commercial configuration involves moving the patient with respect to the typical partial ring geometry (or alternatively a cone beam geometry) CT scanner into a physically separate PET scanner. These CT and PET detector sub-systems do not share detectors or the image acquisition space.

An alternative to the existing commercial CT-PET detector imaging systems are improved CT-PET detector systems in which the CT scanner or PET scanner (or both) are replaced with novel edge-on CT scanners and/or PET scanners (including Compton-PET detectors) described in this application. For example, the face-on detector CT configuration is replaced with an edge-on CT detector system capable of performing at least one of energy integration, PC, and PCE (Nelson, U.S. Pat. Nos. 6,583,420; 7,291,841; 7,635,848; 8,017,906; 8,115,174; 8,115,175; and 8,183,533).

For example, one CT implementation would employ a single layer using an array of edge-on semiconductor detectors operating in PCE mode (such as an edge-on semiconductor silicon detector or an edge-on structured semiconductor detector). Suitable edge-on structured semiconductor detectors include at least one of a 3D semiconductor detector such as 3D silicon, a structured mold semiconductor detector incorporating one or more of semiconductor quantum dots, amorphous semiconductors, and polycrystalline semiconductors. If additional stopping power is needed a second layer of moderate-to-high Z semiconductor or scintillator detectors could be implemented.

One implementation of a second detector layer is to employ face-on or edge-on semiconductor arrays chiding structured detectors) which operate in PCE mode (based on factors such as cost, detector response limitations, and/or information content of the radiation field). Less-costly implementations operate in limited PCE mode (two or more energy bins) or PE mode. An alternative (less-costly) implementation is for the second layer to employ a face-on or edge-on scintillator array operating in integration mode or PC mode to primarily detect the more energetic x-rays (providing additional information about the radiation field to compliment the spectral information acquired with the first detector layer). If advantageous, detectors can implement mode switching circuitry (for example, from PCE mode to integration mode or PC mode; from PE or PC mode to integration mode) as a technique for compensating for excessive event rates.

A fast, improved CT-PET detector system incorporates multiple x-ray tubes (two, three or more) or x-ray sources (such as carbon nanotubes, scanning electron beams, etc.), including split-beam variations thereof, to reduce image acquisition times (providing improved temporal imaging resolution), and/or to provide multiple energy imaging. Novel PET detectors include, but are not limited to, 3D crossed rod, crossed fiber-rod and encoded PET detectors. The physically separate PET or Compton-PET scanner preferably provides one or more detector features such as suitable or excellent energy resolution, 3D spatial resolution and TOF capability. If reduced PET performance is acceptable then one or more of energy, spatial and temporal resolution can be degraded.

PET designs described in this patent application can be employed with commercial face-on CT scanners to comprise enhanced CT-PET detector systems. Physically separate commercial PET scanners can also be used with an edge-on CT detector system in another version of an enhanced dual CT-PET imaging system. Still another version of an enhanced dual CT-PET imaging system employs physically separate edge-on CT and PET designs described in this application and prior patents. Yet another version of an enhanced CT-PET imaging system is to employ a face-on detector or edge-on detector CT scanner with a physically separate Compton-PET detector system.

Alternative to commercial and enhanced dual CT-PET detector designs are CT-Compton-PET systems in which detector components and/or space are shared, representing a cost effective and compact design compared with the benefit that the patient remains stationary and so registration between CT and PET images is straightforward. Furthermore current CT imaging sub-systems in commercial dual CT-PET systems do not offer PC or PCE capabilities which are available in enhanced dual CT-PET and CT-Compton-PET detector systems.

PC or PCE capabilities can be used for dose reduction and/or multispectral imaging. Furthermore, multispectral imaging can be implemented with a PC detector system by implementing x-ray tube voltage switch (currently employed with dual-energy CT detector systems). X-ray source voltage switching (which includes x-ray tube voltage switching) and/or split-beam techniques can be used with any of the single or multiple x-ray tube (x-ray source) imaging systems described herein (including, but not limited to, implementations that incorporate full ring and partial-ring CT, cone beam CT, split-beam CT and tomosynthesis). Furthermore, x-ray source (tube) voltage switching and/or split-beam techniques can be implemented with any of the x-ray detectors that implement at least one of energy integration, PC and PCE capabilities, as described herein.

CT-Compton-PET detector systems designs incorporate the capabilities described for Compton-PET detector systems. One or more layers of detectors can be employed. PET options include non-coincidence (one-sided) and coincidence PET imaging capabilities. The incorporation of x-ray CT capabilities may impose additional requirements on the design of the radiation detectors, depending on the energy range for the application (small animal, pediatric, adult, therapy, industrial, HLS, synchrotrons) and the event (data) rates (which, for medical CT imaging, are typically much higher than the event rates encountered in nuclear medicine imaging).

In addition, collimation may be introduced into the CT detector which would be of a relatively fine nature. The type and amount of collimation introduced into the CT detector configuration is preferably sufficient to at least result in a beneficial reduction in radiation cross talk between detector elements during CT imaging without substantially reducing the efficiency of the PET detector component of the imaging system. If external collimation is employed to reduce the intensity of x-ray's scattered by the object from reaching the CT detector, and this external collimation has an undesirable impact on PET imaging efficiency or image quality, then the external collimation is preferably moveable so that it can rotate or slide out of the detector field of view (FOV) during PET imaging.

X-ray scatter correction algorithms in CT imaging can also be employed with or without collimation along with corrections for detector effects such as induced charges in nearest-neighbor detector elements, charge cloud diffusion and radiation cross talk (energetic electrons, characteristic x-rays, bremsstrahlung) between detector elements (Nelson, U.S. Pat. Nos. 7,291,841; 8,017,906). If the PET detector imaging is not implemented simultaneously with the CT detector imaging then an optional movable, attenuating shield (such as, but not limited to Cu, W, Pb, a multilayer material) can be inserted during CT imaging to protect the PET detector from unnecessary radiation damage, and then removed during PET imaging.

The insertion of nuclear medicine collimation hardware such as parallel or pin hole (pinhole) collimators into these Compton camera designs can provide nuclear medicine imaging capabilities for those cases in which the Compton camera does not offer adequate imaging properties. CT detector modes of operation can include energy integration, PC or PCE. One implementation of a CT-Compton-PET detector system is to simply operate the back-end PET detector independently of the front-end CT detector and accept that the CT detector acts as an attenuator and scatterer of the 511 keV PET gamma rays.

More sophisticated CT-Compton-PET detector systems will be described next. Implementations of detector geometries include planar (and focused planar) configurations and focused structure configurations such as rings and partial rings (as well as focused rings and focused partial rings). Planar, ring, and partial ring detector geometries are encountered in medical diagnostic x-ray CT.

CT-Compton-PET detector system designs described herein are based on implementations of coincidence and non-coincidence Compton-PET detector systems with additional constraints imposed by CT imaging. X-ray fluence rates for diagnostic medical x-ray CT are typically sufficiently high that features such as PC and PCE are easier to implement if the distribution of detected events during a time interval is spread out over a number of detector channels. Other constraints on detector selection are related to problems such as dose-dependent pixel performance degradation (including polarization issues) and detector effects described herein.

This tends to limit the selection of edge-on or face-on detector to one or more fast-to-very fast, low-to-moderate Z semiconductors (and variants thereof) with or without gain capability (including, but not limited to, Si, Ge, GaAs, diamond, carbon nanotubes, Se, Si-APDs, SiPMs, silicon nanowires, iDADs, Se-APDs, GaAsPMs, DiamondPMs), structured 3D semiconductor detectors and structured mold (quantum dot, amorphous, polycrystalline) semiconductor detectors coupled to high speed readout circuitry (such as a custom readout ASIC or a Medipix chip). Other options include configurations such as gas-based Medipix detectors and fast-to-very fast, bright scintillators coupled to photo-detectors.

Other semiconductor material such as CdTe or CZT may be employed if they are sufficiently thin (typically less than 1 mm) such that issues related to high data rates can be mitigated. Their pixel performance degradation rates and detector effects should be acceptable (or can, in part, be compensated by evaluating whether any correlated charge was deposited in neighboring pixels (charge sharing) as in the case of the Medipix detector chip). For conventional semiconductor detector designs (including silicon detectors) the importance of implementing corrections for charge sharing (as well as x-ray cross talk) typically increases as the photon energy increases, the pixel size decreases and pixel thickness increases. For edge-on and face-n detector designs charge sharing can occur between neighboring pixels within the same detector array and between neighboring detector arrays (for example, adjacent edge-on detector arrays or adjacent face-on detector layers).

For the case of a focused structure detector geometry such as a ring the detector modules can form partial rings, with detectors in a single partial ring that have small gaps or gaps comparable in thickness to 2D edge-on detector plane modules (with optional collimation between the detector plane modules). If gaps are of comparable thickness to the 2D edge-on detector plane modules then the x-ray source is preferably collimated to match the gaps in the detector plane and the collimators and detector need to move along the ring by one pixel width (detector plane width) to acquire a complete projection for reconstruction. This compensating motion and matching x-ray source collimation is not needed if at least two sets of partially-offset or completely-offset detector rings (alternate detector modules are located at two different radii) with gaps comparable to the thickness of 2D edge-on detector modules are employed (Nelson, U.S. Pat. No. 7,291,841).

The CT edge-on detector modules employed in a focused structure ring geometry can also be employed in a planar CT detector geometry. One or more layers of edge-on detector modules can be configured to be parallel or tilted with respect to adjacent detector modules in order to achieve a focusing effect. As with the ring geometry implementations, layers of tilted edge-on detector modules can also be partially offset or completely offset so that tilted edge-on detector modules in a lower layer fill gaps between edge-on detector modules in the upper layer(s) so that a reasonably continuous detector is emulated.

As described, a focused pixel structure can be implemented along the lengths of the edge-on tilted (or parallel) detector modules. Various configurations of edge-on or face-on (single or multilayer) detector modules or combinations of face-on and edge-on detector modules may also be employed in planar and ring detector geometries. Optionally, SAR and DOI capabilities can be incorporated into the edge-on and face-on detector modules, respectively.

If the front-end CT detector and the back-end Compton-PET (or PET) detector operate independently of each other, then the CT-Compton-PET detector system can be considered a limited CT-Compton-PET detector system (an integrated limited CT-Compton-PET detector system). In this case the range of front-end CT detector designs extends from planar to focused structure (ring and partial ring) geometries and from traditional (low-cost) energy integration detectors to PC to PCE detectors.

The front-end CT detector attenuates a fraction of annihilation gamma rays directed toward the back-end Compton-PET (or PET) detector. The planar or focused structure back-end Compton-PET (or PET) detector does not have to occupy the same FOV as the CT detector; larger or smaller FOVs can be implemented according to hardware constraints, cost and desired acquisition times. The back-end Compton-PET (or PET) detector can be designed to operate with 2D or 3D spatial resolution.

Non-coincidence PET (one-sided PET) imaging can be implemented with a limited CT-Compton-PET system in which the back-end detector is a Compton-PET detector. For coincidence PET imaging, the back-end Compton-PET (or PET) detector can provide either 2D or 3D spatial resolution capability.

Coincidence PET imaging may require the addition of a second PET detector system and the appropriate coincidence circuitry. If the Compton-PET detector offers 3D resolution and tracking capability then both coincidence and non-coincidence PET imaging can be conducted simultaneously. Another implementation of a limited CT-Compton-PET detector system is to position the Compton-PET (or PET) detector outside the FOV of the CT detector. A radiation shield may be inserted between the CT detector and the Compton-PET (or PET) detector during CT operation to limit unnecessary radiation dose to the Compton-PET (or PET) detector system.

For example, consider the case wherein at least one CT detector array (also referred to as a CT detector) is employed (high speed acquisition may require multiple distinct CT detector arrays and x-ray sources or even a full ring CT detector array). An implementation for a ring-like acquisition geometry can employ at least one front-end (inner layer) CT detector as a partial ring detector (or a planar detector) for PET (preferably) aligned with a pair of back-end (outer layer) opposing partial ring (or planar) PET detectors or a full ring PET detector.

Optionally, a fraction of the CT detector can be implemented with PET detection features. (For the case of a dedicated PET or Compton-PET imaging system the one or more partial ring (or planar) CT detector arrays or a full ring CT detector array can be replaced with comparable (or smaller) detector arrays with the advantage that the pixel geometry and readout electronics can be adapted for PET or Compton-PET imaging without consideration for CT pixel geometry or CT readout electronics.) Note that in an alternative implementation at least one front-end CT detector array with a planar format can be aligned with a pair of back-end opposing planar or partial ring PET detectors or a full ring (or square/rectangular) PET detector. One or more (aligned or unaligned) additional front-end (AFE) detectors (not necessarily used for CT) can be incorporated into the detector geometry in order to improve PET imaging system capabilities such as detection efficiency and/or timing resolution.

For example, an AFE detector could be paired with the CT detector (or a fraction thereof). Extra AFE detectors can be added, either positioned independently or positioned as opposing pairs. The case of a single front-end partial ring CT detector aligned with a pair of back-end opposing partial ring PET detectors permits many interactions to be considered (the partial ring CT detector can also interact with partially-aligned or unaligned PET detectors). A Compton image can be acquired by using the CT detector for scattering gammas, a fraction of which are then preferably detected by either the aligned PET detector behind it or by the CT detector alone (e.g., if it has 3D capability). Another option is for the PET detector alone (if it has 3D capability) to scatter and detect incident gammas that did not interact with the CT detector. The information from Compton scattering a sufficient number of times within or between detectors can be used for Compton image reconstruction based on multiple scattering.

Alternatively, the information from Compton scattering one or more times terminating with a photoelectric event can be used for Compton image reconstruction. Compton image reconstruction can also be implemented in the opposing, aligned PET detector (e.g., if it has 3D capability). If a Compton image event can also be used for PET coincidence imaging then the Compton image information may be used to enhance the PET image since additional information concerning the directionality of the detected gamma is available. PET coincidence images can be acquired based on coincidence between a PET detector with a PET detector, a CT detector or a CT/PET detector (a CT/PET detector represents, e.g., a CT detector interacting with preferably an aligned back-end PET detector although the CT detector can also interact with partially-aligned and unaligned back-end PET detectors).

If at least one AFE detector is present then new coincidence images can be acquired including AFE detector coincidence with a CT detector (and AFE/PET if the AFE can interact with a PET detector), a PET detector, a CT/PET detector and other AFE (as well as AFE/PET) detectors (if present). Furthermore, AFE (and AFE/PET, if present) Compton images can be acquired. Image data can be combined when appropriate to synthesize enhanced diagnostic images. The dual-layer detector formats described herein can also be implemented as dedicated PET detectors (or nuclear medicine/PET detectors) including the benefits of generating multiple types of coincidence images and/or Compton images, using Compton image information to enhance coincidence PET imaging and the synthesis of enhanced diagnostic images. Note that each layer in the dual-layer detector formats described can be comprised of sub-layers (and/or have a detector with a structure that is equivalent to having sub-layers). Furthermore, detector properties within a layer or sub-layer can vary (a design feature also applicable for dedicated multilayer and single layer PET systems).

For example, consider the front-end partial ring CT detector used with a back-end PET ring detector with detectors that offer only moderate temporal resolution (not necessarily suitable for TOF PET). The front-end partial ring CT detector typically offers high spatial resolution but it may or may not offer high temporal (fast or very fast) resolution. If high temporal resolution for the PET image associated with the CT detector is desired and the CT detector is not fast then the aligned PET detector segments behind and opposite the CT detector should preferably implement suitably fast detectors (e.g., replacing both of the moderate temporal resolution PET detector segments with fast PET detector segments). Alternatively, if the CT detector is fast then the aligned PET detector segment opposite the CT detector should be suitably fast whereas the aligned PET detector behind the CT detector can be fast but it is not required to be fast (if the interaction probability of 511 keV gammas with the front-end CT detector is satisfactory for generating sufficient coincidence events with the opposing PET detector segment during image acquisition). Then one or both moderate temporal resolution PET detector segments may be replaced with suitably fast or very fast detector segments.

Since the back-end PET detector segments are expected to detect a fraction of non-scattered gammas another option is to implement fast PET detector segments regardless of the temporal response of the front-end detectors. Yet another option is to introduce at least one AFE detector that may or may not offer high temporal resolution to operate with the opposing PET detector segment permitting increased flexibility with respect to properties implemented for the opposing PET detector segment. The PET detector segments for CT-Compton-PET or dedicated PET systems can optionally be designed to include positioning capability permitting greater flexibility for improved image acquisition. Cost can factor into the decision if the fast PET detector segments cost substantially more than the PET detector segments they would replace. Other tradeoffs such as differences in detector stopping power and readout electronics requirements need to be considered.

For CT-Compton-PET detector systems the front-end CT detector also serves as front-end detector layer for a Compton-PET detector system. The readout electronics should be suitable to handle event data rates that are on a comparable scale to the event data rates experienced by CT detectors, or the CT detector pixel geometry can be modified to reduce the effective data rate per pixel and so reduce the requirements of the readout electronics. The front-end and back-end detector layers preferably include appropriate internal and intra-layer event tracking capabilities (for coincidence and non-coincidence Compton-PET systems) depending on their intended use.

For CT applications which utilize PC or PCE capabilities several edge-on pixel geometries have been described including uniform pixel sizes (1D or 2D pixel array) and non-uniform pixel sizes (Nelson, U.S. Pat. Nos. 7,635,848; 8,115,174; 8,115,175; and 8,183,533). Issues arise as to x-ray beam hardening with depth of penetration and the benefit of imposing a more-uniform distribution of interaction rates between pixels along the x-ray beam direction (reducing readout errors and readout electronics costs).

If the event rate is sufficiently low a uniform pixel distribution may be adequate even if beam hardening occurs with penetration depth. If the event rate is high (as expected in many diagnostic medical x-ray CT applications) and PC or PCE capability is required, then a static, uniform 2D pixel array may not offer a good balance in detected event rate per pixel unless the pixel dimensions are relatively small in terms of the stopping power of the detector material. Implementing such relatively small pixels allows a degree of flexibility since a variable effective pixel size versus depth could be synthesized by combining the output signals from two or more pixels.

Unfortunately, as pixel size decreases the number of pixels and readout electronics increases which raises the cost of the detector modules. In addition to detector effects pixel readout noise can increase due to leakage issues associated with some small pixel implementations.

High event rates and x-ray beam hardening with penetration depth may favor the use of a non-uniform pixel size with increasing detector depth along a pixel column. The pixel length within a column can increased with increasing depth, resulting in a non-uniform (variable) readout element pitch in order to provide a more-balanced count rate per pixel for the readout electronics.

Detector pixel distributions as well as the use of collimating septa and/or side shielding for detector modules used in CT systems have been described (Nelson, U.S. Pat. Nos. 6,583,420; 7,291,841; 7,635,848; 8,017,906; 8,115,174; 8,115,175; and 8,183,533). Furthermore, the pixel size in the axial direction (the slice thickness) can be non-uniform (benefitting dose reduction). For example, a high resolution pixel size (thin slices) could be implemented near the center of the detector in the axial direction with a lower resolution pixel size (thicker slices) implemented on both sides of the center.

Additional non-uniform pixel size distributions can be implemented based on imaging requirements. Additional flexibility is provided when the outputs of two or more pixels in the axial direction can be combined electronically in order to synthesize the desired distribution of pixel sizes in the axial direction. A non-uniform pixel size in the axial direction can be implemented with edge-on detectors and/or face-on detectors. A non-uniform pixel size distribution can be implemented along an arc segment.

For example, in one implementation of a non-uniform detector pixel size in the axial direction the high resolution detector pixels could be centered mid-way between the axial limits of the detector arc with low spatial resolution detectors on either side. In this case the region of interest within the object being scanned that benefits from higher spatial resolution is radially-opposite the high resolution detector pixels whereas the regions of interest on either side (for which lower spatial resolution is acceptable) are radially-opposite the low resolution detector pixels. Arrangements of non-uniform detector pixels distributions include at least one detector region with high or moderate resolution detector pixels (detector regions with graded spatial resolution can also be employed).

Relative positioning of the high resolution, moderate resolution and low resolution detector pixels in the axial direction can be adapted for a specific imaging application. The choice of PCE, PC, and integrating readout electronics (or combinations thereof) can be adapted for the imaging requirements of individual detector regions. Furthermore, edge-on detectors, face-on detectors or combinations thereof can be used to implement these arrangements of non-uniform detector pixels.

With edge-on detectors the low spatial resolution detectors can be synthesized by combining the outputs of two or more pixels with the same coordinates as measured with respect to the edge-on detectors themselves. Thus, comparable pixels from adjacent edge-on detectors (even if they are offset with respect to their neighbor) are combined. The same capability to combine the outputs of two or more pixels in order to reduce spatial resolution can be implemented with face-on detectors. The ability to synthesize larger pixels dynamically allows the edge-on or face-on detector to operate with either uniform or a non-uniform spatial resolution.

An alternative is to implement the edge-on or face-on detector with a fixed, non-uniform spatial resolution. The advantage of positioning detectors with higher spatial resolution closer to the region of interest is not limited to CT imaging, this approach to non-uniform detector spatial resolution can also be implemented for Compton, SPECT and PET imaging (as well as scientific and industrial imaging). Detector non-uniformity can be implemented along at least one of the axial direction, the radial direction, an arc. Detector non-uniformity can also be implemented as an insert to an existing detector system.

Furthermore, this approach to employing detectors with non-uniform properties such as spatial resolution can be implemented for other detector properties including temporal resolution and energy resolution (and even radiation resistance), independent of employing detectors with non-uniform spatial resolution. One or multiple detector materials can be employed including scintillators, semiconductors, structured detectors, etc. and combinations thereof. PCE, PC, and integrating readout electronics can be employed as well as combinations thereof. For example, a CT scanner (full ring, partial ring, focused full ring, focused partial ring, or cone beam, including tomosynthesis) could implement detector regions in which PCE is employed, whereas other detector regions may employ PC or integrating electronics. This approach can also implemented in point scanning, slit scanning, slot scanning and area detectors employed in diagnostic radiography, as well as in industrial and scientific applications.

Both PCE and PC readout modes can be deployed as needed according to the imaging requirements along the axial direction and along the arc (such as the need for energy subtraction in a limited region of image). Alternatively, an integration readout mode can be implemented if a PCE or PC readout mode is or will be saturated (or is not needed). Appropriate beam collimation and filtration can be employed to match the pixel distribution in the axial direction and along the arc. Furthermore, non-uniformity can be extended to include the detector geometry type (mixing of edge-on and face-on detectors). For example, high spatial resolution edge-on detectors are (in one implementation) positioned at the middle of the detector arc (that images the region of interest within the object being scanned), with low spatial resolution face-on detectors on either side (potentially reducing the over-all cost of the detector system).

The principles of non-uniformity in pixel size (as well as temporal resolution, energy resolution, radiation resistance) and detector geometry type can be applied to both ring and planar detector systems. Detector configurations of reduced size can be employed if region of interest CT is implemented (retaining the high spatial resolution detectors that image the region of interest within the object being scanned while eliminating the low spatial resolution detectors on either side).

A focused structure, ring geometry Compton camera design (Nelson, U.S. Pat. No. 7,291,841), may or may not offer optimal performance as a CT-Compton-PET camera for high event (data) rate, fan beam CT diagnostic imaging. The Compton camera would preferably use edge-on detector modules with a uniform pixel size along a column (uniform 3D spatial resolution), whereas the PC or PCE CT system would preferably use edge-on detector modules with a variable readout element pitch along a column.

The variable readout element pitch for CT allows the readout rate requirements of the readout ASIC-based electronics to be better balanced between readout elements (pixels) near the entrance surface and pixels distant from the entrance surface, which experience reduced beam intensity. Thus the number of readout elements can be reduced noticeably and fewer readout ASICs of a given performance level are needed compared to a uniform pixel array with many small pixels. If the readout ASICs electronics offer high readout data rates sufficient to handle the maximum expected CT data rates for any pixel in a uniform pixel detector which is preferred for use in a Compton camera or Compton-PET detector, then this not an insurmountable constraint.

A potential drawback is a likely increase in cost due to a need for more high speed readout ASICs than would be utilized in a dedicate CT scanner with similar PC or PCE capabilities, but a non-uniform pixel distribution with depth. Other issues that may arise due to this CT-COMPTON-PET detector system design and the increased use of high speed readout ASICs are related to an increase in heat generation and therefore new cooling requirements to avoid increased detector noise and thermal expansion issues. There is also a possibility that some readout ASICs may be moved closer to the pixels (which may result in certain readout ASICs positioned within the x-ray beam path and therefore altering shielding requirements).

Note that this issue of CT detectors with uniform and non-uniform pixel arrays in CT-Compton-PET detector systems affects both the focused structure ring (or partial ring) detector format used in fan beam CT and the planar detector format used in cone beam CT. One alternative is to use readout ASICs of varying performance with respect to depth. The highest speed readout ASICs would read out the pixels close to the entrance surface, whereas readout ASICs of progressively slower speeds (but still sufficient for both CT and Compton camera applications) could be used to read out pixels at greater depths.

Another alternative is to enable the edge-on detector module electronics to redefine the readout element pitch according to whether the CT-Compton-PET detector system is functioning as a PET detector system or a CT detector system. Thus, a detector module can have a selectable (fixed or variable) effective pixel width along a detector row and/or an effective pixel length along a detector column in which the effective pixel width or length is synthesized from the outputs of one or more (typically) uniformly spaced pixels.

For example, a variable, effective pixel length can be selected for CT imaging based on the beam spectrum and the beam intensity. A softer x-ray beam would preferentially be attenuated closer to the detector entrance surface than a harder x-ray beam, for a given detector material (for energies away from a detector material k-edge). For the case of a softer x-ray beam of a given intensity the balancing of event rates between successive effective pixels in a column would benefit from electronically synthesizing relatively smaller effective pixel lengths near the entrance surface. Relatively larger effective pixel lengths would create a better balance of event rates between effective pixels in the case of a harder x-ray beam of a given intensity.

The advantage of a synthesized readout is that it can be adapted according to the energy spectrum and the desired readout rates, thus expanding the use of a PC or PCE CT system to a broad range of beam spectrums (applications) while retaining the uniform detector pixel geometry useful for PET (and Compton camera) imaging. Since a SPECT camera employs collimation to define directionality of the incident photons, either uniform or non-uniform detector pixel geometry can be employed (making a CT-SPECT detector system relatively straightforward to implement with appropriate collimation in place).

If tracking of Compton-scattered photons within the SPECT camera is implemented, then a uniform detector pixel geometry may be beneficial. Features such as redefining the readout element pitch (synthesizing an effective pixel length or width) or employing readout ASICs of varying performance with detector depth can be implemented in dedicated CT detector systems, as well as CT-Compton-PET detector systems and CT-SPECT detector systems. Furthermore, CT-SPECT detector systems can employ a single detector layer or multiple detector layers.

CT-Compton-PET detector system geometries include planar and focused planar detector systems and focused structure detector systems such as ring and partial ring (as well as focused ring and focused partial ring) detector systems. Non-coincidence and coincidence CT-Compton-PET configurations are described herein based on non-coincidence and coincidence Compton-PET configurations. The CT x-ray detectors offer suitable 3D spatial resolution, energy resolution (PCE capability) and temporal resolution to be useful for the high x-ray fluence rates encountered in medical and non-medical CT scanning as well as for use as the front-end detector in non-coincidence and coincidence Compton-PET detector systems. Event tracking capability may be required for CT-Compton-PET systems.

Non-coincidence CT-Compton-PET detector systems combine CT imaging capability with one-sided PET imaging capability by employing the CT x-ray detector as the front-end detector layer that would be used in a non-coincidence Compton-PET detector system in conjunction with a high-stopping power back-end detector. A flexible design employs front-end and back-end detectors that offer suitable 3D spatial resolution, energy resolution and temporal resolution.

Both the front-end and back-end detector layers provide adequate temporal resolution for an expected event rate, such that accurate event tracking can be enabled both within the front-end and back-end detectors and between the front-end and back-end detectors, since Compton scatter and photoelectric interactions can be recorded in both front-end and back-end detectors. AN implementations described for non-coincidence Compton-PET (three two-layer Compton cameras and three Compton telescope cameras) are applicable, possibly with the added constraint that the front-end detector should offer suitable detection efficiency for the x-ray energy spectrums that would be used in CT imaging, should be compatible with the event rates for CT imaging, and should offer a spatial resolution with depth that is reasonably uniform when Compton and/or PET imaging modalities are employed.

FIG. 5 illustrates a perspective of a CT-Compton-PET detector system 1000 in a focused structure (partial ring) geometry which includes a point-like x-ray 109 radiation source 125 and a gamma ray 107 radiation source 111. The front-end detector layer 510, comprised of detector modules 102 which use 2D pixelated array radiation detectors 115 in an edge-on geometry with base 106 and communication links 103, performs the dual role as an x-ray CT detector and a front-end detector layer (detector layer 1) for a Compton-PET detector system.

The detector modules 102 are mounted in a rigid structure 110. The back-end detector layer 520 (detector layer 2) could be of a planar or focused structure geometry. For comparison, FIG. 1 can be understood to show the front-end and back-end detector layers 510 and 520 (detector layers 1 and 2) for a planar CT-Compton-Pet detector geometry if the front-end detector layer 510 is suitable for CT imaging.

A reduction in cost can be realized if the Compton-PET capability is implemented only within a sub-region of the CT detector (for example, a segment of a partial ring detector geometry or a region of a planar detector geometry). In these instances segments of CT detector modules or regions of CT detector modules that are not involved in PET imaging do not need to implement features such as synthesizing variable effective pixel lengths or employing readout ASICs of varying performance with detector depth. Multiple Compton-PET views can still be acquired as a result of detector rotation (in some applications the object can rotate and the detector is stationary).

By reducing the active detector area the detection efficiency will be reduced and acquisition times will, in general, increase. Alternatively, acquisition times can be typically be reduced by increasing the PET detector FOV beyond the CT detector FOV. As described, if the Compton camera image quality isn't suitable for the nuclear medicine imaging applications of interest then a collimator can be inserted in front of the detector so that the system of collimator and detector can function as a SPECT/gamma camera.

Coincidence CT-Compton-PET detector systems extend the implementations of non-coincidence CT-Compton-PET detector systems with the addition of coincidence detection capability by introducing a second Compton-PET detector system along with appropriate coincidence circuitry. If the Compton scatter capability of a front-end detector is not needed then only a PET-compatible detector may be needed for the second detector system.

Implementations described for coincidence Compton-PET detector systems are applicable. Thus, the detector geometries shown in FIG. 1 and FIG. 5 are applicable when employed in a coincidence detection configuration such as FIG. 4. Again, a reduction in cost can be realized if the coincidence Compton-PET or coincidence PET capability is implemented only within a sub-region of the CT detector (for example, a segment of a partial ring or complete ring detector geometry or a region of a planar detector geometry) and a matching Compton-PET or a PET-compatible back-end detector of comparable dimensions is positioned opposite that segment or region of the CT detector.

Additional cost savings may be realized if the second coincidence Compton-PET detector system employs a front-end detector that offers comparable performance to the CT detector when used as part of a Compton-PET detector system, but lacks the extreme performance capability of a CT detector. Acquisition times can be typically be reduced by increasing the PET detector FOV beyond the CT detector FOV.

Multiple Compton-PET or PET views of a limited volume of the subject can be acquired as a result of detector rotation about the subject. In some applications the subject can rotate and the detector is stationary. By reducing the active detector area detection efficiency may be reduced and acquisition times may increase. If the Compton camera image quality isn't suitable for the nuclear medicine imaging applications of interest, then a collimator can be inserted so that the detector can function as a SPECT/gamma camera.

The CT-COMPTON-PET scanner assigns the CT detector to the role of a front-end detector in a Compton-PET detector system when Compton camera or PET (or nuclear medicine) imaging is implemented. In an implementation of a coincidence Compton-PET detector, the front-end detector primarily acted as a Compton scatterer (with photoelectric detection capability) and the back-end detector provided stopping power, energy resolution and temporal resolution sufficient for event tracking with respect to the front-end detector. Options described for the front-end detector include, but are not limited to, sufficiently thin planar semiconductor detectors, structured 3D semiconductor detectors, structured mold quantum dot or amorphous or polycrystalline semiconductor detectors, detectors with SAR or DOI capability, low/moderate-Z scintillator detectors and structured low/moderate-Z straw detectors (which typically require lower data rates than the semiconductor-based detectors).

Furthermore, the front-end CT detector may be a multi-layer detector, as described herein. For example, one implementation employs a front-end detector comprised of a first layer of an edge-on semiconductor followed by an edge-on or face-on scintillator second layer followed by a back-end PET detector which now functions as a third layer (a variation of this detector design employs a suitably-designed back-end PET detector to function in the role of the second layer of the front-end CT detector). (Similar detector implementations may be used for the back-end detector although the detector properties may differ between front-end and back-end detectors.)

If the front-end detector offers an acceptable Compton interaction probability with annihilation gammas and it is fast enough to provide the required coincidence timing resolution (or very fast coincidence timing if TOF PET imaging is desired), then the back-end PET detector requirements can be simplified since its role is primarily to detect (typically through the photoelectric effect) Compton-scattered gammas from the front-end detector. If the back-end detector is required to provide coincidence resolution (including TOF resolution if desired), then the selection of suitable detector materials and detector designs may be reduced. In one implementation the back-end PET detector is also used to detect annihilation gammas that don't interact with the front-end detector (requiring coincidence resolution or TOF resolution). (Front-end and back-end detectors can function independently as PET coincidence detectors, front-end and back-end detectors can function cooperatively as a PET coincidence detector, and front-end and back-end detectors can function cooperatively as a Compton gamma camera.)

Reduced spatial resolution could be acceptable for a back-end detector (although Compton camera reconstruction accuracy will be reduced or lost) used in coincidence PET imaging, if the front-end detector provides adequate 3D Compton-scatter information including moderate-to-high spatial resolution. For example, a single detector block, a 1D or a 2D detector array could be implemented based on factors such as expected count rate, required energy resolution, cost and desired flexibility.

In general, for both coincidence and non-coincidence Compton-PET detector systems, a combination of a 3D back-end detector with a 3D front-end detector could improve overall detection efficiency. In this implementation the back-end detector could detect Compton scattered photons from the front-end detector, non-scattered (primary) photons using the photoelectric effect, and photons scattered within the back-end detector itself. Pace-on and edge-on (or angled) detector designs can be employed for the back-end detector as well as the front-end detector.

PET scan times can be improved by employing additional partial-ring or planar PET or Compton-PET detector systems that operate with or are independent of the coincidence or non-coincidence CT-Compton-PET detector system. These systems are referred to as enhanced coincidence or non-coincidence CT-Compton-PET detector systems. The amount of rotation about the object to acquire a more-complete PET image can be reduced.

Another option is to implement a coincidence CT-Compton-PET detector system based on a multiple (two or more) x-ray tube or x-ray source system. For example, the angular arc of a commercial, dual x-ray tube CT partial ring detector is approximately twice that of a single x-ray tube system. Multiple cone beam imaging can be implemented if there are two or more x-ray tubes or x-ray sources and corresponding single layer or multiple layer (multiple energy resolution) planar detectors. (An example of a multi-planar detector/x-ray tube CT system developed for high speed cardiac and lung CT was the Mayo Dynamic Spatial Reconstructor or DSR first implemented in the late 1970s.) Note that if interior tomography techniques can be implemented, then x-ray intensities and/or areas of planar detectors (depending on the application) may be reduced (Yu, H. and Wang, G., Phys. Med. Biol., Vol. 54(9): pp. 2791-2805 (2009)).

For the case of the focused structure partial ring geometry the CT partial ring detector (the front-end detector) used in a dual x-ray tube configuration can be split into two equal CT partial ring detector sections so that at least one CT partial ring detector section (and its back-end detector) can be rotated through 180 degrees when coincidence PET scanning is initiated. This could be particularly beneficial for applications such as fast scan Cardiac CT in conjunction with Cardiac PET CT. Other applications that could benefit from high resolution CT and PET or SPECT (nuclear medicine) imaging capabilities of this system include head imaging and small animal imaging. Note that the back-end detector might cover only a segment of a CT partial ring or complete ring detector (or a region for a planar detector). If coincidence CT-Compton-PET system is implemented the second planar or partial ring PET detector may only need to be comparable in size to the actual PET detector implemented with the first CT planar or partial ring detector.

The efficiency of a PET detector system can be improved by adding additional front-end detectors (and corresponding back-end detectors) opposite to, adjacent to or separate from the CT partial ring detector or the CT planar detector. These front-end detectors could utilize less demanding readout electronics and may not require features such as pixel synthesis since they would only be used for PET imaging and not CT imaging. Note that for the various PET implementations in which an opposing PET detector would block the x-ray beam path the opposing PET detector is either rotated out of the beam path (the x-ray tube or x-ray source may be physically retracted when not in use) or a small opening is made in the opposing PET detector to pass the collimated x-ray beam (the PET detector rotates with the x-ray tube or x-ray source). If physical gaps are present within the PET detector due to the presence of one-or-more x-ray sources then the gaps can be filled by removable PET detector modules or the PET detector can be rotated to sample the missing PET detector volumes.

Multiple x-ray tubes or x-ray sources (as described for fast, improved CT-PET detector imaging systems) can be employed with enhanced integrated non-coincidence or enhanced coincidence CT-Compton-PET detector imaging systems and enhanced limited integrated CT-Compton-PET detector imaging systems. Both stationary and rotating x-ray tube-detector systems can be implemented (both designs have been used with dedicated CT imaging systems). Multiple x-ray tubes or x-ray sources using voltage switching and/or split-beam techniques can also be used to implement multiple energy imaging.

Dedicated (stand-alone) CT detector imaging system in a ring or planar detector geometry can be implemented by reducing the functionality of the CT-Compton-PET detector imaging systems described herein. As detailed, detectors with fixed (or variable) uniform or non-uniform pixels can be implemented with the requirement that the detectors can perform efficiently at the event count rates per pixel encountered in medical CT imaging.

CT detectors include single layer and multilayer detectors comprised of face-on detectors and/or edge-on detectors including gas, scintillator, semiconductor, low temperature (such as Ge and superconductor) and structured detectors (such as structured 3D semiconductor, structured mold quantum dot and scintillator-photodetector structured detectors). Single layer and multilayer detector designs of Compton cameras described herein can be implemented in a dedicated CT detector imaging system with PCE capability (a simplification would be a design that provides PC capability and/or energy integration capability). Multilayer designs typically maintain or increase the atomic number of the detector material for progressively deeper detector layers with respect to the radiation entrance surface.

Consider a single layer, edge-on detector implementation for a medical CT imaging system in which detector planes are aligned with the Z-axis in a ring geometry. 2D Si edge-on detectors with a wafer thickness of (for example) approximately 500 microns ($\mu$m) as currently implemented may be preferred over relatively thick, expensive, face-on CdTe or CZT detectors in terms of operational lifetime and temporal response. Alternative edge-on detectors of comparable thickness (approximately 500 microns) which can offer improvements with respect to the stopping power and/or temporal response performance of 2D Si at reduced cost compared to the relatively thick, face-on CdTe or CZT detectors include, but are not limited to, 2D ZnO (which is also a fast, relatively low-Z scintillator making ZnO attractive as a semiconductor or scintillator detector material for TOF PET), 2D GaAs, 2D Ge. 2D CdTe and 2D CZT detectors (including low noise implementations, implementations with gain) and structured detectors (structured 3D semiconductor detectors such as 3D Si, 3D GaAs, 3D CdTe, 3D CZT, 3D Ge, etc., as well as structured mold (amorphous, polycrystalline, quantum dot/nanoparticle) semiconductor detectors.

If cost is an issue and reduced capabilities (such as reduced energy resolution) are acceptable then a structured mold scintillator quantum dot detector could be employed (for example, functioning as an energy integrator detector for single or multiple energy CT). Since quantum dot density can be varied with position and a single quantum dot material or multiple quantum dot materials can be employed as a function of position it is readily apparent that the equivalent of a multilayer detector can be synthesized within a single structured mold quantum dot detector by varying quantum dot density and/or material as a function of position in regular or irregular patterns, as described below.

This concept of varying material (and/or material density) is readily extended to structured mold amorphous and polycrystalline semiconductor detectors, structured mold scintillator detectors, etc. This design can be further generalized to structured mold semiconductor detectors that include two or more of quantum dots, amorphous semiconductors, and polycrystalline semiconductors, as well as structured mold detectors that incorporate (for example) semiconductors and scintillators, semiconductors with gases, scintillators with gases, etc., and structured mold detectors with segmented anodes (with a single semiconductor material, or with multiple semiconductor materials).

In addition, detectors with thickness greater than or less than 500 microns can be implemented depending on the image resolution requirements for the CT detector imaging system (medical diagnostic, dental panoramic imaging, dental cone beam CT imaging, dental 3D tomosynthesis (single tooth) intraoral imaging, radiation therapy, industrial, Homeland security, etc.). This single layer, edge-on detector CT imaging system can be employed as a single layer PET imaging system and/or a Compton camera/nuclear medicine imaging system.

As described, multiple Compton-PET implementations are possible. Furthermore, PET and Compton camera/nuclear medicine imaging can be conducted simultaneously. Depending on the fraction of the ring circumference covered by edge-on detectors, additional detectors (of the same or different design) may need to be added to increase coincidence detection efficiency.

For the relatively small (hardware) pixel sizes employed in current medical CT imaging systems, Si is a reasonably efficient detector for the lower x-ray energies encountered in mammography CT and pediatric CT. For adult CT the efficiency of Si may suffer, particularly for x-ray energies above (approximately) 40 keV. A compromise, multilayer detector configuration (for example) could employ edge-on, 2D semiconductor or structured semiconductor detectors (such as 3D Si or GaAs detectors or a structured mold semiconductor detectors (including segmented anodes) with materials such as semiconductor quantum dots, amorphous semiconductors, polycrystalline semiconductors) as the low-Z or moderate-Z front-end detector, with moderate-Z or high-Z, edge-on or face-on, back-end detector. (Note that if temperature requirements can be met then Ge is a candidate as a moderate-Z, face-on or edge-on detector.) The back-end detector, with appropriate capabilities, may not only improve the overall CT detector performance but also may be suitable for a different imaging modality such as PET (as described herein). A simplification is to implement a single layer or offset detector layer format for CT or PET using at least one of edge-on, 2D semiconductor detectors, structured semiconductor detectors (such as 3D semiconductor detectors or structured mold semiconductor detectors with or without segmented anodes), structured scintillator detectors.

Consider the case of a multilayer (in this case, a dual-layer) detector configuration in which an edge-on, 2D Si front-end detector (alternatives such as 3D silicon, etc. may also be employed) is employed as the first detector layer. It would be of reduced height compared to a single layer, edge-on, 2D Si detector implementation and thus less expensive as well as reducing the pixel count and limiting the maximum pixel size. The back-end, second detector layer (edge-on or face-on) is typically comprised of a moderate-Z material (including semiconductors such as GaAs or CdTe or CLT, scintillators, gas, liquid and/or structured detectors), or a high-Z material (including semiconductors, scintillators, and/or structured detectors) which would emphasize photoelectric interactions with the high energy photons that penetrate the front-end detector.

One or more types of back-end, face-on detectors can be configured as 1D detectors that are positioned beneath each of the 2D Si edge-on detectors. The thicknesses of appropriate face-on on detectors should not be so great that detrimental effects such as polarization or light losses (for scintillators) cannot be mitigated. The cost of manufacturing such 1D detectors (material yields, butting pixels, bonding to readout electronics) should be reduced relative to 2D detectors. More than one layer of 1D, face-on detectors can be employed and layers can consist of the same or different materials. Furthermore, if enhanced detector performance is desired (one or more of: higher spatial resolution, higher temporal resolution, higher energy resolution) in the back-end detector, a 2D face-on detector can be implemented even if SAR is not implemented in the front-end edge-on detector (as noted previously herein, the detector layers need not have the same spatial, temporal or energy resolution). If 3D information is desired then DOI capability can be introduced or additional layers can be added. Note that in some applications (e.g., due to issues that may be related to cost, temporal resolution, spatial resolution, energy resolution) it may be desirable to employ face-on 1D or 2D (or 3D) detectors in the front-end and edge-on detectors (1D, 2D or 3D) in the back-end. The useful information that can be extracted from the radiation detected within each layer (as well as cost) will determine whether individual detectors operate as energy integrators, PCs or PCEs.

An alternative is to position a back-end, edge-on 1D or 2D detector (including structured 3D semiconductor and structured mold semiconductor quantum dot, amorphous semiconductor and polycrystalline semiconductor detector implementations) below each front-end, 2D Si edge-on detector. The edge-on, 1D detector is less-costly to manufacture whereas the 2D array will typically handle higher data rates and offer better energy resolution. This dual-layer CT design could be used for both low energy and high energy imaging applications. Any combination of suitable edge-on detectors including 2D detectors, structured 3D semiconductor detectors and structured mold semiconductor detectors such as semiconductor quantum dot detectors can be employed for the front-end and back-end detectors. In this case the semiconductor quantum dots function as semiconductor detector materials and therefore a structured mold semiconductor quantum dot detector can also be described as a specific implementation of a structured mold semiconductor detector.

It should be noted (as described previously herein) that a single layer implementation based only on an edge-on structured 3D semiconductor detector or a structured mold semiconductor detector of a single low, moderate or high-Z material may be implemented in place of a dual-layer CT design. Structured mold semiconductor quantum dot detectors offer additional flexibility, beyond simply varying the dimension of the pixel versus depth to control count rates, in that the density of quantum dots can be varied from low-to-high for individual pixels that constitute the structured quantum dot detector. Another technique to vary quantum dot density is to vary the number of holes within a pixel that are filled with a quantum dot material. For example, pixels could be of a uniform dimensions while energy-dependent attenuation could increase with depth by increasing the density of quantum dots with depth. Thus, the quantum dot (detector) material can be varied as a function of depth in an edge-on orientation. Similar functionality can be implemented with structured mold amorphous and polycrystalline semiconductor detectors. As described herein, structured mold detectors can incorporate more than one type of semiconductor material as well as mixtures of detector material types (semiconductor, scintillator, gas, superconductor).

Furthermore, the selection of back-end detector materials is not limited to semiconductors or structured detectors. The back-end detectors can be face-on or (1D or 2D) edge-on scintillator detectors (Nelson, U.S. Pat. No. 7,291,841). (Additional face-on detector layers can be implemented as needed and different scintillator materials can be employed in different layers.) In general, the back-end detectors can operate as PC, PCE or integrating detectors depending on the application. For example, a PC or integrating back-end scintillator detector can be paired with a PCE front-end detector simplifying detector design. The filtered beam spectrum reaching the back-end detector can be estimated.

In addition, the flexible design permits either or both front-end and back-end detectors to be scintillator-photodetector detectors. For example, the (first layer) front-end detector could be a low-to-moderate Z (or high-Z) scintillator-photodetector detector with a (second layer) back-end moderate-to-high Z structured mold quantum dot detector. As noted, the detectors in each layer can operate as either PC or PCE or energy integrating detectors. Thus, one implementation would use a low-Z Si detector with PCE capability for the first layer with a high-Z scintillator-photodetector detector with energy integration capability for the second layer. Furthermore, the flexible design described for dual-layer detector systems can be implemented for multi-layer detector system with three or more layers. The single layer and multilayer detector systems described herein can incorporate one or more non-detector materials including attenuating materials, scattering materials and conversion materials depending on the interacting radiation field (e.g., particle types, energies).

It should be noted that a single layer implementation based only on an edge-on structured 3D semiconductor detector or a structured mold semiconductor detector (implementing at least one of semiconductor quantum dots, amorphous semiconductors, and polycrystalline semiconductors) of a single low, moderate or high-Z material may be implemented in place of a dual-layer CT design. Structured mold semiconductor detectors offer additional flexibility, beyond simply varying the dimension of the pixel versus depth to control count rates, in that the density of semiconductor materials such as quantum dots (nanoparticles) can be varied from low-to-high for individual pixels that constitute the structured mold semiconductor detector. For example, pixels could be of a uniform dimensions while energy-dependent attenuation could increase with depth by increasing the density of semiconductor quantum dots with depth. Furthermore, structured mold semiconductor detectors in face-on or edge-on (or tilted) orientation can implement segmented anodes.

Structured Mold Detectors

Structured mold semiconductor quantum dot (nanoparticle) detectors (including segmented anode implementations) may deploy a single semiconductor quantum dot (nanoparticle) material. The use of edge-on, structured mold semiconductor quantum dot (nanoparticle) detectors creates an opportunity to implement a more flexible detector design. For example, multiple semiconductor quantum dot materials can also be deployed such that low-Z/moderate-Z/high-Z semiconductor quantum dot materials are positioned near the radiation entrance surface and moderate-Z/high-Z semiconductor quantum dot materials are positioned further from the radiation entrance surface (a multilayer structured mold quantum dot detector). Thus, the selection of semiconductor quantum dot (nanoparticle) materials can be selected for different energy ranges and the count rate per pixel as a function of distance from the radiation entrance surface can be more-balanced. Furthermore, as noted, the densities of each of the multiple semiconductor quantum dot (nanoparticle) materials can be varied for individual pixels from low-to-high for purposes of improved operation and imaging. Structured mold semiconductor detectors may also be referred to as structured semiconductor conductive mold detectors or semiconductor conductive mold detectors.

The semiconductor quantum dot (nanoparticle) materials can be distributed in appropriate patterns for the incident radiation field utilized for imaging and the modified radiation field within the detector (examples include Compton cameras, spectral CT, etc.). For example, a geometric pattern such as a series of partial concentric rings can be employed to create a focused edge-on detector (with the ability to vary semiconductor quantum dot material and density within a ring and between rings). Furthermore, the partial concentric rings can be comprised of offset pixels (gaps between neighboring pixels in a partial concentric ring that are covered by offset pixels in a neighboring partial concentric ring) rather than a continuum of pixels (FIG. 3 demonstrates a similar design wherein the gaps between offset pixels in the upper edge-on semiconductor detector layer are covered by the offset pixels in the lower edge-on semiconductor detector layer).

Other semiconductor detector materials than quantum dots (nanoparticles) can also be employed to fill a 1D or 2D array of channels or a 2D array of holes of a conductive mold material, including, but not limited to, polycrystalline and amorphous semiconductor detector materials (e.g., silicon is frequently used as a conductive mold material, in the form of porous silicon or micromachined silicon). When appropriate, both channels and holes can be present in the conductive mold material. In an edge-on orientation the detector material density distribution can be adjusted as a function of depth if desired. For example, a non-uniform detector material density distribution can be implemented to compensate for beam hardening with depth for an edge-on CT detector. In order to attain reasonable signal collection efficiency the practical cross section dimensions for holes (diameters for the case of circular holes) or practical channel widths are limited in part by the travel ranges of the information carriers. Typically, as a cross section dimension (or dimensions) increase the difficulty of chemical etching or micromachining of holes and channels of a desired depth is reduced as well as the difficulty of attaining an acceptable degree of uniform filling of holes or channels with semiconductor detector materials.

Adjusting the density distribution of a semiconductor detector material within the detector can be implemented in conjunction with pixel size adjustments to provide even greater flexibility in detector adaptation for an incident radiation field. Thus, semiconductor detector materials (including semiconductor quantum dot (nanoparticle) materials) can be distributed according to appropriate patterns for the properties of the incident radiation field (types of particles, energies, angular distribution, intensity distribution, etc.) utilized for imaging. A specific implementation (but not the only possible implementation) of SAR involves segmenting the holes or channels into at least two parts such that separate signals can be read out from the segments. These segmented anodes can incorporate one semiconductor material or multiple semiconductor materials (enabling variation in at least one of energy response and temporal response as a function of segment position).

Structured mold detectors that employ a single detector material (such as a single quantum dot (nanoparticle) semiconductor material, a single quantum dot (nanoparticle) scintillator material, etc.) are basic structured mold detectors. Hybrid structured mold detectors can be comprised of multiple detector materials of a single type (for example, multiple semiconductor materials or multiple scintillator materials) or multiple types of detector materials (for example, one or more semiconductor materials combined with one or more scintillator materials and/or gas materials, etc.). An example is a hybrid structured mold semiconductor detector that is comprised of a mixture of semiconductor quantum dot materials and/or other semiconductor materials such as polycrystalline and/or amorphous semiconductor detector materials wherein low-to-moderate Z materials are positioned to intercept the x-ray beam in the front-end while moderate-to-high Z materials are positioned in the back-end of the edge-on detector. Furthermore, hybrid structured mold detectors can also incorporate structured 3D detectors such that a region of the structured mold detector is nonporous (the structured 3D detector region) and another region is porous (with pores incorporating detector materials). For example, low-Z 3D silicon is positioned in the nonporous front-end of the edge-on detector and moderate-to-high Z semiconductor materials are positioned in the porous back-end of the edge-on detector.

Furthermore, basic structured mold detectors and hybrid structured mold detectors can incorporate one or more non-detector materials including attenuating materials, scattering materials and conversion materials to provide transverse filtering and/or lateral shielding. Thus, basic structured mold semiconductor detectors and hybrid structured mold semiconductor detectors can incorporate attenuating materials, scattering materials and conversion materials. For example, patterns of holes or channels can be filled with materials that contain (e.g., for the case of x-ray and gamma ray radiation) moderate-to-high Z attenuating elements (iron, copper, lead, tungsten, uranium, gold, etc.) or alloys in order to create collimation for the radiation field incident on the detector, to reduce inter-detector cross talk elements (lateral shielding), to incorporate spectral (and/or particle type) filters such as gratings (diffraction, absorption, phase). Scattering and conversion materials can be employed in order to alter the properties of the incident radiation field prior to being detected (transverse filtering). For example, conversion materials can be used to transform x-rays to electrons, neutrons to photons, fast neutrons to thermal neutrons, etc. for the benefit of the detector. Scattering materials could be used, for example, to degrade photons or neutrons with undesirable energies. The densities of selected attenuating, scattering and converting materials can also be varied with position in order to improve detector performance.

Although the advantages of basic structured mold (and hybrid structured mold) semiconductor detectors have been described for an edge-on detector orientation it should be apparent that similar advantages can be realized for basic structured mold detectors and hybrid structured mold detectors employed in a face-on orientation (or tilted orientation). For example, semiconductor detector materials can be distributed in appropriate patterns for the incident radiation field utilized for imaging, and semiconductor detector material densities can be varied as needed within a single face-on detector layer or with multiple face-on detector layers. Furthermore, patterns of holes or channels can be filled with attenuating materials, conversions materials, spectral (and/or particle type) filters such as gratings (diffraction, absorption, phase), etc. in a face-on basic structured detector or a face-on hybrid structured detector.

For example, one implementation would create an attenuating grid pattern providing lateral (side) shielding between face-on detector elements. Non-detector materials such as attenuators, scatterers and converters can also be applied in appropriate patterns on the surface of the face-on basic structured detector or hybrid structured detector (this represents an alternative to introducing a structured layer that only implements appropriate patterns of non-detector materials prior to a structured detector layer). Note that an edge-on SAR capability (implementing segmented anodes) becomes a face-on DOI capability. These segmented anodes can incorporate one semiconductor material (enabling a variation in energy response as a function of segment position for a multi-energy radiation source), or multiple semiconductor materials (enabling variation in at least one of energy response and temporal response as a function of segment position for a single energy or multi-energy radiation source).

The benefits of basic structured detectors and hybrid structured detectors are not limited to the implementation of semiconductor detector materials, these benefits are also available for implementations wherein scintillator detector materials (or other detector materials such as gas and low temperature detectors) are employed. Thus, scintillator materials can be arranged in patterns, scintillator density can be varied multiple scintillator materials can be employed, scintillator and non-scintillator detectors can be employed in the same edge-on or face-on basic or hybrid structured detector and non-detector materials can be employed.

The positioning of detector materials and density distribution of detector materials (as well as non-detector materials) within edge-on and face-on basic structured detectors and hybrid structured detectors can be adapted according to the properties of the radiation field being detected (including mixed radiation fields). In a layered detector system either edge-on detectors or face-on detectors or both edge-on and face-on detectors (as well as tilted detectors) can be employed. Furthermore, both structured detectors and more conventional detectors can be employed within a layered detector system. For example, in a two layer system an edge-on, basic structured semiconductor quantum dot detector could be aligned with and followed by a 1D scintillator array coupled to a photodetector (or amplified photodetector) array.

Structured mold semiconductor and scintillator quantum dot (nanoparticle) detectors (as well as structured 3D detectors and 2D semiconductor detectors) can be implemented with fixed or adjustable pixel sizes which can be uniform or non-uniform. Furthermore, the density of quantum dot material can be varied with position. Typically the lowest density of quantum dot material could be positioned near the radiation entrance surface.

A moderate-Z or high-Z structured mold semiconductor quantum dot (nanoparticle) detector can also be employed in a face-on orientation as a 1D (or 2D) detector positioned after a (for example) low-Z, 2D Si edge-on detector. Furthermore, moderate-Z or high-Z, fast, bright scintillator-photodetector 1D (or 2D) array detectors (including structured scintillator and nanophosphor detectors), face-on or edge-on, can be employed after a (for example) low-Z, 2D Si edge-on detector (providing limited energy resolution or simply providing photon counting or integration capability or acting as an energy integrators).

The photodetector is a fast, sensitive 1D photodetector that can be chosen from (but is not limited to) photodiodes and amplified photodetectors including, but not limited to, APDs, SiPMs, silicon nanowires, GaAsPMs, DiamondPMs, electron multiplier CCDs and microchannel plates with a pixel structure or a dual-readout structure. Scintillator-photodetector detectors can employ scintillator screens, deposited scintillator films, ceramic scintillators and cut scintillator sheets (including thick sheets which can also referred to as blocks or slabs). Scintillator-photodetector structured detectors can employ structured scintillators (such as manufactured scintillator arrays, scintillators that demonstrate columnar growth and scintillators coupled to fiber arrays) as well as scintillating or minifying scintillating, focused or unfocused, fiber arrays.

Scintillating fiber materials include, but are not limited to, phosphors, granular phosphors, nanophosphors and scintillator quantum dots. If limited energy resolution is acceptable or only photon counting is needed for CT then a moderate-Z or high-Z, fast, bright, scintillator-photodetector or scintillator-photodetector structured detector (wherein the photodetector is a fast, sensitive photodetector) can be used in place of the single layer or dual-layer detector implementations as described herein (see Nelson et al., U.S. Pat. Nos. 4,560,882; 5,258,145; 8,017,906; and 9,347,893).

Figure 6:
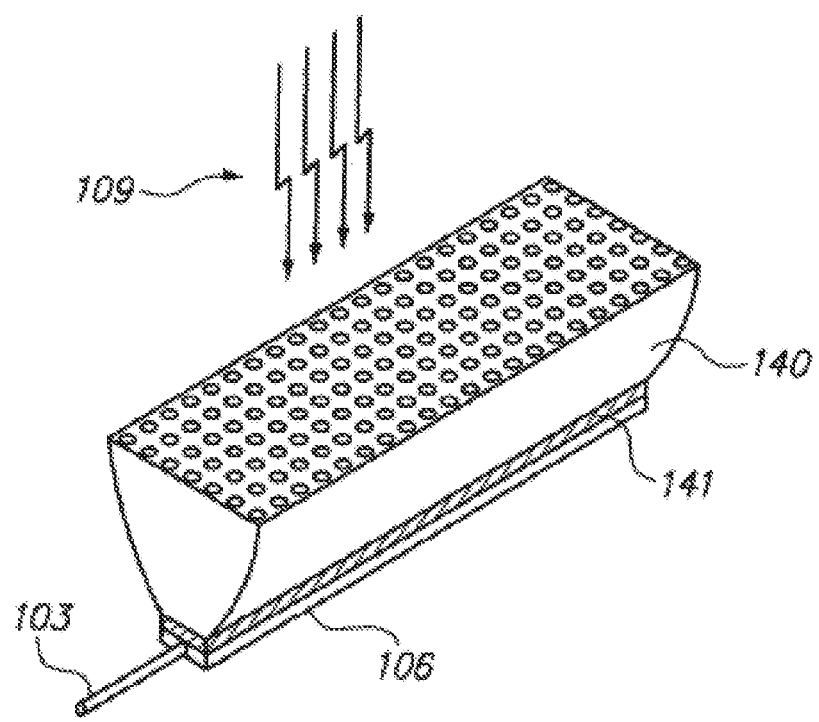
FIG. 6 is a perspective view of a minifying scintillating fiber array coupled to a 1D photodetector structured detector suitable for PC or limited PCE CT imaging.

FIG. 6 illustrates a minifying scintillating fiber array 140 coupled to a 1D photodetector 141 which is incorporated into the base unit 106. The scintillating fiber array coupled to a photodetector readout comprises a structured detector that can be deployed in place of an edge-on detector in a CT scanner. Adjacent structured detectors such as this can be positioned in a continuous, partially-offset or completely offset configuration.

This ring detector geometry comprised of an array of 1D scintillator-photodetector detectors oriented parallel to the axial direction can be extended to multiple pixel widths along the circumference, since planar or shaped entrance surface scintillating fiber optic arrays and small, 2D high speed photodetector arrays are available. The use of 1D (or 2D) scintillator-photodetector detectors may offer advantages since manufacturing costs are typically reduced, although butting of 1D detectors is generally easier than butting of 2D detectors.

The same approach applies to a planar geometry concerning the use of 1D or 2D scintillator-photodetector detectors. Although readout electronics such as ASICs can be attached to the 1D or 2D photodetector sensors externally, the readout electronics can alternatively be integrated directly on the substrate of the 1D or 2D photodetector sensors.

Orientation, Interaction Height and Sub-Aperture Resolution

Consider a scenario in which radiation is incident upon a planar edge-on detector. The detector thickness (height) now defines the maximum detector entrance aperture while the length or width of the detector area now defines the maximum attenuation distance for edge-on radiation detector designs including semiconductor drift chamber, single-sided strip, and double sided strip detectors, including micro-strip detector versions.

The interaction position along the height of the edge-on detector aperture will be referred to as the interaction height. When a scintillator, semiconductor, gas, or liquid detector is irradiated face-on the 1D positional information along the thickness direction of the detector is referred to as the interaction depth. The electronically-measured face-on detector DOI positional information defines the edge-on detector sub-aperture resolution (SAR).

Strip widths can be tapered or curved if focusing is desired. In the case of double-sided parallel strip detectors in which opposing strips are parallel, both electrons and holes can be collected to provide 2D position information across the aperture. If strips on one side run perpendicular to those on the other side, then depth-of-interaction information can be obtained. If strips are segmented in either a single-sided or double-sided parallel strip detector then depth-of-interaction information can be obtained and readout rates can be improved.

In the case of double-sided parallel strip detectors (in which opposing strips are parallel) or crossed strip or 2D pixelated array detectors, both electrons and holes produced by a radiation event can be collected to provide 1D positional information between the anode and the cathode sides of the aperture. This 1D positional information is used to determine electronically the sub-aperture spatial resolution.

Sub-aperture spatial resolution can be achieved by measuring either the transit times of electrons and holes to the anodes and cathodes, respectively, or the ratio of anode and cathode signals. A significant benefit may be gained by implementing sub-aperture resolution (e.g., resulting from electronically-defined detector elements) because the edge-on detector aperture height no longer limits spatial resolution along that direction. Furthermore this 1D positional information may, in some situations, be used to estimate meaningful corrections to the expected signal losses as a function of interaction height and thus improve energy resolution. Other benefits include an increase in available image detector volume due to a decrease in the number of edge-on detector physical boundaries (detector material properties typically degrade near the perimeter) and the number of gaps that may be present between edge-on detector planes.

The benefits of sub-aperture resolution (increased spatial resolution, signal loss compensation, fewer readout detectors, increased detector volume) that are possible with edge-on semiconductor detectors can also be attained using scintillator arrays in an edge-on detector geometry. Depth-of-interaction and interaction height information (e.g., for sub-aperture resolution) can be acquired using 1D and 2D scintillator arrays, for example by adding dual-readout (photodetector readout) capability.

The semiconductor detector DOI accuracy is affected by parameters such as the detector depth, electron and hole mobility, signal diffusion, and the number of defects (such as traps) in the bulk semiconductor material. The specific parameters that affect scintillator detector DOI accuracy vary with the DOI measurement technique.

Coupling a 2D photodetector readout array to the side of an edge-on scintillator array permits an analysis of the relative signal strength measured at both ends of individual scintillator elements in the array. By calibrating the relative signal strength versus interaction location in the direction of the aperture (interaction height), sub-aperture resolution can be achieved. With sufficiently fast readout detectors, time-of-flight measurements could also be used to determine the interaction location. Thus, sub-aperture resolution can be attained for 1D and 2D edge-on scintillator detectors, and a 2D, edge-on scintillator array detector can function as a 3D, edge-on scintillator array detector.

In many instances the one-side readout implementations of edge-on SAR designs emulate the face-on DOI designs. In both face-on DOI and edge-on SAR scintillator detector designs, a one-sided or a multi-sided readout can be implemented. Thus, encoding techniques developed for one-sided or two-sided (or multi-sided), face-on DOI scintillator elements can be applied to edge-on SAR scintillator elements. Furthermore, edge-on or edge-on with face-on 2D photodetectors coupled to two or more adjacent faces of a scintillator block (e.g., a block geometry) can be employed to implement a 3D scintillator block detector using encoding techniques (e.g., providing SAR and DOI information).

A potential problem with face-on DOI scintillator detectors is that Compton scattering of incident radiation is biased in the forward direction such that the probability of detecting the scatter event downstream from the initial off-axis event within the same scintillator may not be small (resulting in an inaccurate DOI estimate). The edge-on SAR scintillator detector design reduces the likelihood that a Compton scatter photon will be detected in the same scintillator for a relatively large range of incident angles. This simplifies the tracking of most subsequent interactions or events after a primary interaction.

The number of edge-on scintillator or semiconductor detector planes required to assemble an edge-on detector module can be reduced by implementing the techniques developed for measuring the depth of interaction (DOI) within face-on scintillator and semiconductor detectors. The benefits of this approach can be illustrated by considering a scenario in which radiation is incident face-on upon the anode or cathode side of a planar semiconductor detector of known depth or thickness (height). The DOI spatial resolution can be determined by measuring either the transit times of electrons and holes to anodes and cathodes, respectively, or the ratio of anode and cathode signals.

Radiation incident approximately perpendicular to the plane or irradiation from the left or right side (approximately parallel to the plane) of an edge-on detector array is also allowed. The side-irradiation geometry may be useful for specific applications. For example, it may be desirable to collimate the radiation so that the detector region near the base and relevant readout electronics are removed from direct irradiation. In addition, irradiation from the right or left side would allow two edge-on detector arrays to be oriented such that one array faces the other array in close proximity. In general, spatial and energy resolution may be enhanced if sub-aperture height information is acquired for edge-on detectors that are irradiated from the side.

Figure 7:
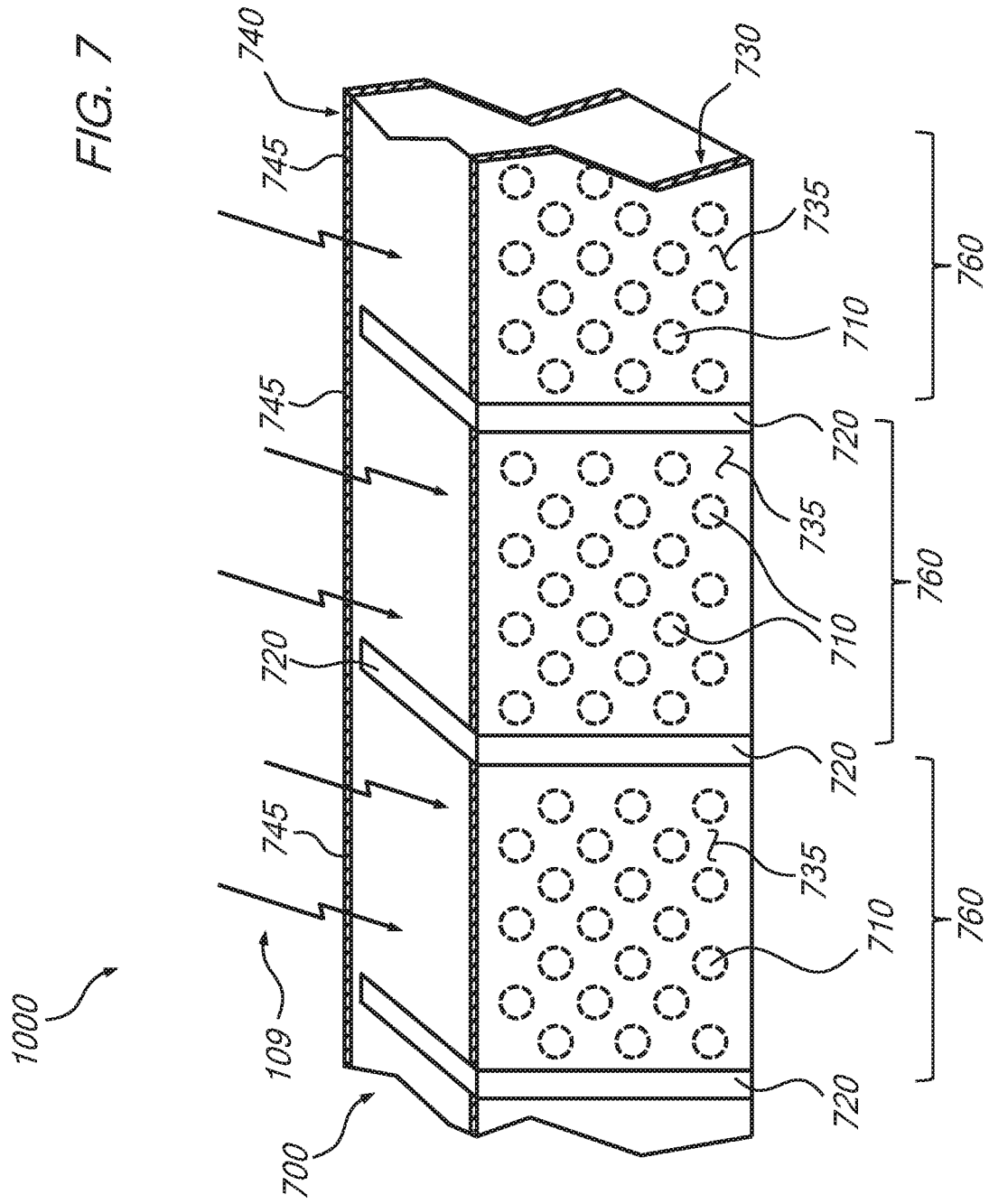
FIG. 7 is a perspective view of a one-dimensional structured mold detector system with quantum dots or semiconductor detector materials.

FIG. 7 illustrates a perspective of a detector imaging system 1000 with a one-dimensional (1D) edge-on structured mold detector 700. As shown in FIG. 7, radiation 109 is incident onto the top surface of detector 700, in an edge-on 1D pixelated structured mold detector (silicon block) configuration. Holes 710 of structured mold detector 700 are filled with semiconductor quantum dots or semiconductor detector materials. Channels 720 are filled with attenuation material. These features are not to scale.

In this view, anode face 730 is oriented toward the front of detector 700, showing three separate anode elements 735 separated by the attenuating material in channels 720. Cathode face 740 is oriented toward the back of detector 700, with one or more cathode elements 745. Holes 710 and channels 720 can be etched or micromachined into (e.g., silicon block) detector 700. For example, channels 720 may extend from anode face 730 partially through detector 700 toward cathode face 740, as shown in FIG. 7, or channels 720 may extend completely through detector 700 to (or through) cathode face 740. Alternatively, the front (anode) and back (cathode) faces 730 and 740 can be reversed, and the placement, arrangement, and configurations of channels 720 and holes 710 may vary.

In the particular embodiment of FIG. 7, structured mold detector 700 has holes 710 and channels 720 in which holes 710 are filled with quantum dot materials or other semiconductor detector materials. Channels 720 are filled with an attenuating material to isolate or help isolate neighboring pixels 760. Detector 700 is irradiated in an edge-on configuration, with radiation 109 incident from the top, and front and back faces 730 and 740 of detector 700 are represented by conductive anode and cathode elements 735 and 745, respectively. The top (front-end) and bottom (back-end) layers of detector 700 can also be interchanged, without loss of generality.

For illustrative purposes, an implementation of detector 700 with only a single layer of pixels 760 is shown. A cathode sheet covers back (cathode) face 740 of detector 700, and an anode sheet covers front (anode) face 730. Both the anode sheet on front face 730 and the cathode sheet on back face 740 can be segmented to create individual pixels 760 in detector 700.

Selection of the radius (or other dimensions) of holes 710 and the depth and width of channels 720 is influenced by transport properties of the information carriers (or attenuation properties of the material if used for isolation purposes), and these quantities are selected in a suitable range for detector 700 to identify interactions of radiation 109 within pixels 760. In PbS quantum dots, for example, excitons have a range of about 20 nm, and holes 710 may be selected with a radius of about 50 nm, so that the excitons have acceptable probability of reaching the PbS silicon heterojunction. Cost is also a design issue for choice of quantum dot or semiconductor detectors materials (such as amorphous or polycrystalline semiconductor materials).

Figure 8:
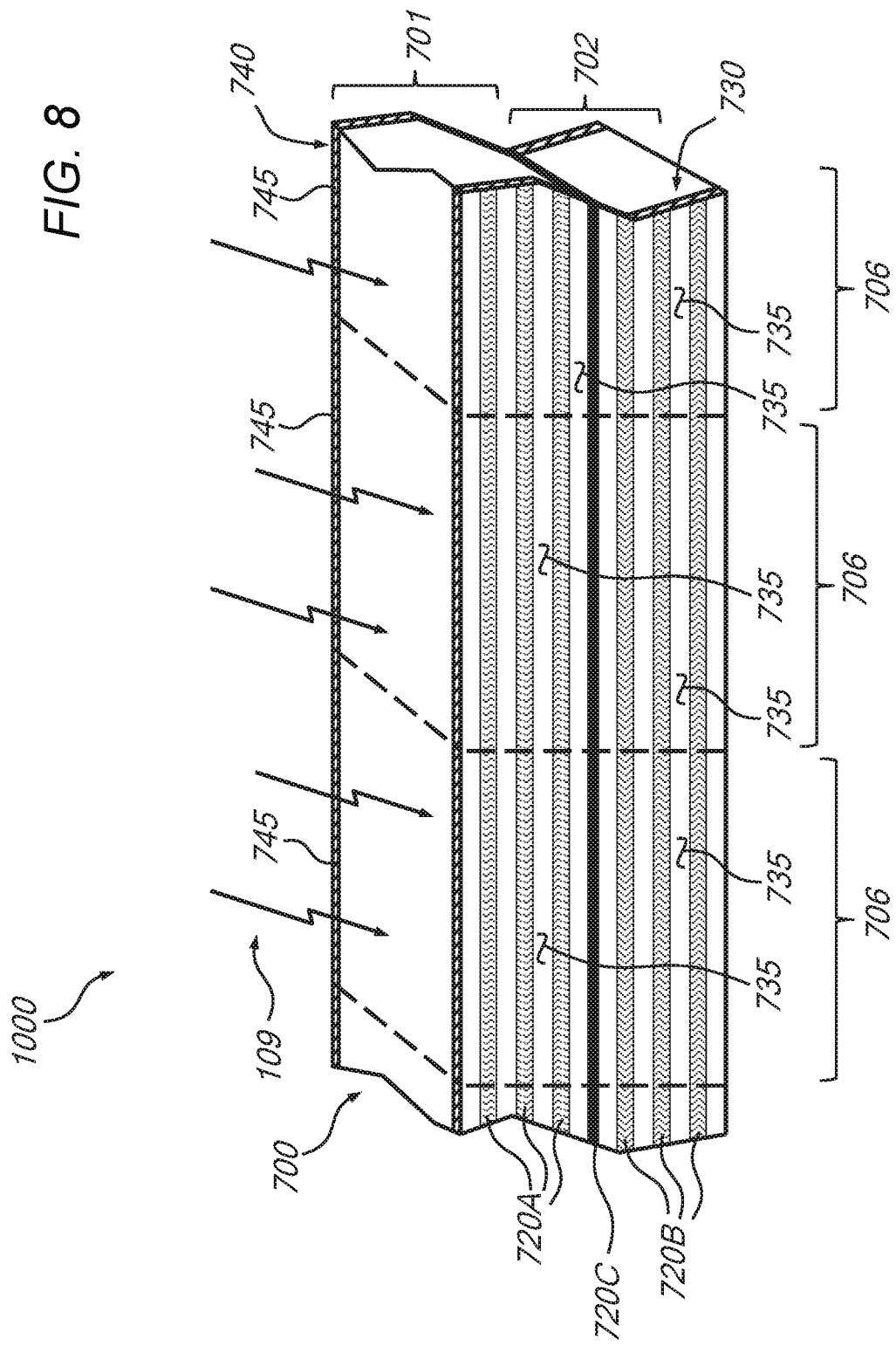
FIG. 8 is a perspective view of a two-dimensional structured mold detector system with quantum dots or semiconductor detector materials.

FIG. 8 illustrates a perspective of a detector imaging system 1000 with a two-dimensional (2D), layered, edge-on structured mold detector (silicon block) 700. In this configuration, channels 720A are provided with relatively low-Z detector material, e.g., in the first or top layer 701 of detector 700, and channels 720B are filled or provided with relatively moderate or high-Z detector material, e.g., in the second or lower layer 702 of detector 700. These features are not to scale. As noted previously, a moderate-Z/high-Z semiconductor material offering suitable energy and/or temporal resolution can be substituted for a relatively low-Z material such as silicon in the first layer (alternatively, scintillator or gas or liquid detector materials can also be employed), although the ratio of Compton scattering to photoelectric interactions may be reduced for typical x-ray, nuclear medicine and PET patient imaging energies. This could affect the choice of detector materials in the second layer (or any additional layers for detector systems using more than two layers), or even the need for a second layer.

Channel 720C is provided with a filter material, e.g., between top (low-Z) layer 701 and bottom (moderate or high-Z) layer 702 of detector 700. Anode elements 735 are segmented both by layer 710, 702 and by pixel 706 within each layer 701, 702. Cathode elements 745 can be similarly divided.

In the particular embodiment of FIG. 8, structured mold detector 700 has channels 720A and 720B filled with semiconductor quantum dots or semiconductor detector materials. Hole structures are not necessarily required. As shown, two layers 701, 702 of pixels 706 are provided, with relatively low-Z (or lower-Z) detector materials in channels 720A of first layer 701 (e.g., the top layer, where radiation 109 is incident onto edge-on detector 700), and moderate or relatively high-Z (or higher-Z) materials in second layer 702 (e.g., the bottom layer of detector 700, reached by radiation 109 passing though top layer 701).

For illustrative purposes, the implementations of anode face or layer 730 and cathode face or layer 740 are represented with only one level of pixels 706 per detector layer 701, 702. Alternatively, there may be multiple pixels 706 per detector layer, and/or multiple anode and cathode elements 735 and 745. The selection of channel width (or hole radius) for detector system 700 is influenced by the transport properties of the information carriers, as described above.

Figure 9:
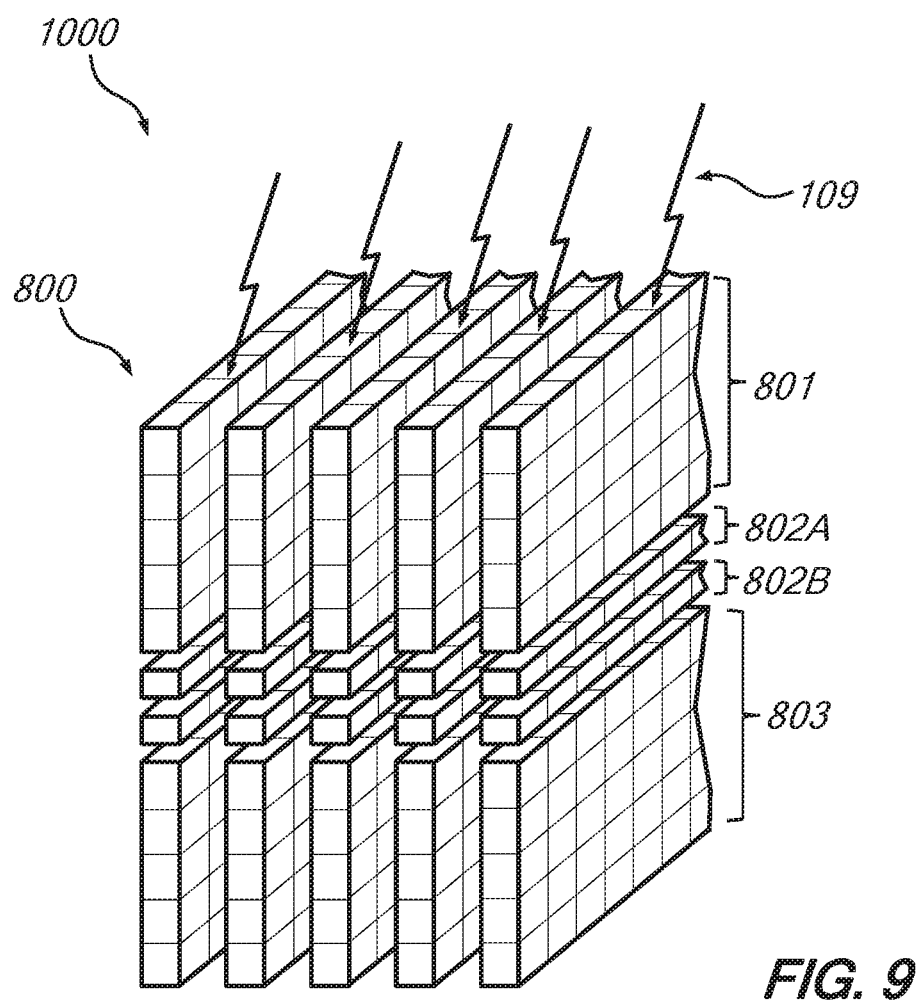
FIG. 9 is a perspective view of a multilayer detector system with N=4 layers used for CT and/or PET detector imaging.

FIG. 9 illustrates a perspective of a multilayer detector system 800 for a CT and/or PET detector imaging system 1000. In this particular example, detector system 800 includes N=4 (four) individual layers: a top or front-end layer 801, two middle layers 802A and 802B, and a bottom or back-end layer 803.

As shown in FIG. 9, the first (top or front-end) layer 801 is formed with an array of edge on, 2D pixelated detectors, e.g., using a relatively low-Z semiconductor detector material such as silicon (which offers good energy and temporal resolution). The two middle layers 802A and 802B are formed with arrays of face-on 1D or 2D pixelated detectors, e.g., using a moderate-Z semiconductor detector material such as CZT or CdTe or a high-Z semiconductor detector material or a moderate-Z/high-Z scintillator (or gas or liquid) detector material with suitable energy and temporal resolution properties. The bottom (or back-end) layer 803 is formed with an array of edge-on, 2D pixelated detectors, e.g., using a moderate or relatively high-Z scintillator or semiconductor detector material. As noted previously, a moderate-Z/high-Z semiconductor material offering suitable energy and/or temporal resolution can be substituted for a relatively low-Z material such as silicon in the first layer (alternatively, scintillator or gas or liquid detector materials can be employed), although the ratio of Compton scattering to photoelectric interactions will be reduced for typical x-ray and nuclear medicine or PET patient imaging energies. This could affect the choice of detector materials in the other layers, as well as the number of layers employed.

The dimensions of pixels within a layer or within different layers may be different. Therefore, the spatial resolution (as well as temporal and energy resolution) properties of individual detector layers (as well as the pixels within a detector layer) need not be the same and are dictated by the imaging requirements as well as cost. This principle applies for one detector layer, two detector layers, three detector layers, four detector layers, etc. For example, although detector layer 803 pixels are depicted with the same surface area (e.g., 1×1) as pixels in detector layers 801 and 802, imaging and cost requirements may indicate (or dictate) a different relationship A×B where each of A and B can be less than, equal to or greater than one (including block detectors).

Depending on application, first (top) layer 801 can be used for CT and PET imaging (e.g., employing a combination of x-ray and gamma ray photoelectric and Compton scatter interactions). Middle layers 802A and 802B could also be used for CT and/or PET imaging, while bottom layer 803 can be used primarily for PET imaging. In some embodiments, middle layers 802A and 802B are provided as removable/insertable units, which are configured for insertion into and removal from imaging system 1000 between top and bottom layers 801 and 803 of detector 800. Bottom (PET) layer 803 can also be provided in the form of a 3D sub-aperture resolution (SAR) detector, for example as described in Nelson, U.S. Pat. No. 7,635,848. In general, the N detector layer design is appropriate for at least one of Compton (including gamma camera/SPECT) imaging, Compton-PET imaging, PET (including TOF PET) imaging, high resolution CT imaging, CT imaging. Either energy integration or PC or PCE capability can be implemented in individual detector layers depending on the detector capabilities and imaging requirements.

FIG. 10A illustrates a perspective of an alternate multi-layer detector system 800 for, in one implementation, a CT and/or PET detector imaging system 1000. In this particular example, detector system 800 includes N=3 (three) layers: first (top) layer 801, second (middle) layer 802 and third (bottom) layer 803.

As shown in FIG. 10A, first (top or front-end) layer 801 is formed with an array of edge-on, 2D pixelated semiconductor detectors, e.g., using a relatively low-Z semiconductor detector material such as silicon. Second (middle) layer 802 is formed with an array of edge-on pixelated detectors, e.g., using a moderate-Z or high-Z semiconductor or scintillator detector material (alternatively, layer 802 can be implemented using an array of face-on pixelated detectors). Third (bottom or back-end) layer 803 is formed with an array of edge-on, 2D pixelated detectors, e.g., using a moderate or high-Z detector material. Second (middle) detector layer 802 can also be configured in removable/replaceable form (e.g., if detector layer 803 is not implemented then N=2 layers), and third (bottom) layer can be replaced (for example) by a 3D DOI detector or a 3D SAR detector, as described above for the four-layer embodiment of Ha 9. Depending upon embodiment, one goal is to provide a three-layer configuration including an edge-on Si, face-on scintillator or semiconductor detector layer and an edge-on semiconductor or scintillator detector layer (e.g., in the front-end and/or back-end layers). A face-on middle detector layer could include an integrator to handle high fluence, e.g., in an x-ray CT imaging system (or combined CT/nuclear medicine system), with the awareness that 511 keV photons may not be entirely contained. Thus, such a face-on layer may provide limited energy resolution, or incorporate photon counting or integration capability, as described herein.

FIG. 10B illustrates a perspective of CT and/or PET detector imaging system 1000 with a face-on back-end detector layer 803. As shown in FIG. 10B, first (top or front-end) layer 801 and one or more middle layers 802 of detector system 800 are formed with arrays of edge-on, 1D or 2D pixelated detectors. Third (bottom) layer 803 is formed with an array of face-on, 1D or 2D pixelated detectors.

FIG. 10C illustrates a perspective of a multilayer CT and/or PET detector imaging system 1000 with a face-on back-end detector layer. FIGS. 10B and 10C show one or more middle detector layers 802 of detector system 800 are formed with arrays of edge-on, 1D or 2D pixelated detectors.

FIG. 10D illustrates a perspective of a multilayer CT and/or PET detector imaging system 1000 with a face-on back-end detector layer. FIG. 10D illustrates a middle detector layer 802 of detector system 800 formed with an array of face-on pixelated detectors.

FIGS. 10B, 10C and 10D illustrate CT and/or PET detector imaging system 1000 with an edge-on first (top or front-end) detector layer 801, one or more middle detector layers 802 and a face-on back-end detector layer 803. As shown in FIGS. 10B, 10C and 10D, first (top or front-end) detector layer 801 of detector system 800 is formed with arrays of edge-on, 1D or 2D pixelated detectors. FIGS. 10B and 10C show one or more middle detector layers 802 of detector system 800 formed with arrays of edge-on, 1D or 2D pixelated detectors. FIG. 10D illustrates middle detector layer 802 of detector system 800 formed with an array of face-on pixelated detectors.

FIGS. 10B, 10C and 10D show a third (bottom) detector layer 803 formed with face-on block, 1D, 2D (or 3D if DOI is implemented) pixelated detectors. As described herein, one or more of the layers could combine edge-on and face-on detector elements (varying at least one of spatial resolution, energy resolution, temporal resolution and stopping power within a detector layer). The dimensions of pixels within a layer or within different layers may be different. The spatial resolution (as well as temporal and energy resolution) properties of individual detector layers (as well as the pixels within a detector layer) need not be the same and are indicated (or dictated) by imaging requirements as well as cost.

This principle applies for one detector layer, two detector layers, three detector layers, four detector layers, etc. For example, in one implementation the surface area of a pixel of third detector layer 803 as shown in FIG. 10C is depicted, for illustrative purposes, as being (approximately) the surface area of a 5×5 array of pixels in first detector layer 801 or middle detector layer 802. In this instance the pixel size employed in detector layers 801 and 802 may be appropriate for high resolution CT imaging (with a pixel surface dimension ranging from approximately 0.2-1.0 mm at this time) whereas the pixel size employed in detector layer 803 may be appropriate for at east one of Compton (including gamma camera/SPECT) imaging, Compton-PET imaging, PET (including TOF PET) imaging, CT imaging. Other implementations may result in third detector layer 803 pixels being smaller, the same or larger than pixels in first detector layer 801 pixels or second detector layer 802.

For the multilayer detectors described herein, the choice of detector material or materials used within a layer, the thickness of a layer, the detector element size within a layer, and the detector readout technology (including photosensors if present) can all be selected for a single application (e.g., Compton, CT, PET, SPECT, charged particle detection, neutron detection, etc.), or for multi-use applications as described herein (CT-PET, CT-SPECT, CT-Compton, Compton-PET, etc.). For example, one implementation of a multilayer CT-PET detector could include one or more relatively thin front-end detector layers and one or more relatively thick back-end detector layers. If two or more front-end (back-end) detector layers are present, the detector layer thickness may become progressively greater to compensate for a hardened energy spectrum with penetration depth, and/or to better-equalize count rates between detector layers within the front-end (and back-end) detectors. For example, if the front-end and back-end detector layer materials are scintillators, one choice for readout photodetectors for the front-end scintillator layer (or layers) may be lower-cost photodetectors such as photodiodes (or other energy integrators). SiPM detectors (providing temporal and energy resolution) could be coupled to the back-end scintillator(s) used for PET imaging. SiPMs may also be employed in front-end scintillator layers, e.g., if those layers are also configured to be used as PET detector layers.

FIG. 10D depicts detector layer 803 with a pixel area which is more block-like. In this instance detector layer 803 might be comprised of one or more blocks used primarily for timing and/or energy determination for scattered PET photons from detector layer 801 or detector layers 801 and 802 (if detector layer 802 is not present then this represents an implementation of an N=2 detector layer imaging system 1000). (Note that various implementations of block detectors are possible including simple 1D block detectors, 2D block detectors (including, but not limited to, 1D arrays or gamma cameras) and 3D block detectors). Features including fast or very fast temporal response, present in one or both layers of the above-described two layer, coincidence (including TOF) PET detector system implementation, can be present in one or more of the detector layers for the three-layer CT and/or PET, Compton-PET, and Compton (including gamma camera) detector imaging systems. Either energy integration or PC or PCE capability can be implemented in individual detector layers depending on detector capabilities and imaging requirements.

Middle detector layer (or layers) 802 may be provided in a removable configuration and bottom (back-end) detector layer 803 may be replaced with an SAR detector, as described above. In addition, the orientation of first (front-end) and third (back-end) layers 801 and 803 can be interchanged with respect to the direction of incident radiation 109, without loss of generality.

FIG. 11 illustrates a perspective of a detector imaging system 1000 with a focused two-dimensional (2D), layered, edge-on, pixelated structured mold (silicon block) detector 700. As shown in FIG. 11, individual pixels 706 diverge in width along the direction of incident radiation 109, e.g. with respect to the direction of radiation. 109 from a diverging source such as an internal radionuclide or a diverging x-ray beam. This provides pixels 706 and detector 700 with a focused structure geometry, as described herein.

Channels 720A are provided with relatively low-Z detector material, e.g., in the first or top layer 701 of focused detector 700, and channels 720B are filled or provided with relatively moderate or high-Z detector material, e.g., in the second or lower layer 702 of focused detector 700. Channel 720C is filled or provided with a filter material, e.g., between top (low-Z) layer 701 and bottom (moderate or high-Z) layer 702 of focused detector 700. Anode elements 735 and cathode elements 745 can be segmented both by layer 710, 702 and by pixel 706 within each layer 701, 702.

In the particular embodiment of FIG. 11, focused, structured mold detector 700 has channels 720A and 720B filled with semiconductor quantum dot materials or semiconductor detector materials. Hole structures are not necessarily required. As shown, two layers 701, 702 of pixels 706 are provided, with relatively low-Z materials in channels 720A of first layer 701, and moderate or relatively high-Z materials in second layer 702. Anode layer 730 and cathode layer 740 may have multiple anode and cathode elements 735 and 745 per detector layer, with multiple pixels in one or both of layers 701 and 702. As noted previously, a moderate-Z/high-Z semiconductor material offering suitable energy and temporal resolution can be substituted for a relatively low-Z material such as silicon in the first layer, although the ratio of Compton scattering to photoelectric interactions maybe reduced for typical x-ray and nuclear medicine or PET patient imaging energies. This could affect the choice of detector materials in the second layer, or even the need for a second layer.

Discrete and Semi-Continuous Structured 3D Scintillator Detectors

Nelson (U.S. Pat. No. 7,635,848) teaches planar, discrete structured 3D scintillator detector modules (that can be stacked), using crossed top and bottom (planar) layers of parallel arrays of discrete scintillator rods with light sharing and an optical readout at one end of each array of discrete scintillator rods. Various photodetector implementations (photodiodes and amplified photodetectors including, but not limited to: PMTs, PSPMTs, APDs, SiPMs, silicon nanowires, iDADs, Se-APDs, GaAsPMs, DiamondPMs, other semiconductor APDs and PMs, microchannel plates, etc.) and electronic readout implementations are described (e.g., integrating, photon counting, photon counting with energy resolution, coincidence, etc.).

The single end optical readout of each array of discrete scintillator rods (or fibers) can be enhanced (at additional cost) by reading out the opposite end of one or more rods in least one layer of the scintillator rods, e.g., with a complete or sparse photodetector array, enabling an increase of at least one of timing resolution, spatial resolution, energy resolution and scintillator rod length. An alternative to the crossed rod geometry 3D detector format (which typically employs more extensive optical encoding techniques) implements two parallel layers (rather than crossed layers) of parallel scintillator rods, with dual-end readout (discrete element photodetectors, array photodetectors, position sensitive photodetectors) coupled to at least one intermediate scintillator layer, or a single parallel layer with dual-end readout coupled to at least one scintillator layer on one or both sides.

If suitable, spacers can be used to separate scintillator layers from scintillator rod layers. Suitable scintillator layers include, but are not limited to, continuous scintillator sheet layers, parallel rod scintillator layers and 2D pixelated scintillator layers. Parallel rod scintillator layers can be positioned parallel, perpendicular or at an angle to the parallel scintillator rods with dual-end readout. Individual scintillator layers can also have different properties, e.g., if more than one scintillator layer is present in a 3D detector unit, and the scintillator layers can have different properties from the scintillator rod layer to which they are coupled. Furthermore, scintillator rods with at least one different property (such as material, decay time, or emission spectrum) can be employed within a rod layer, or between layers, to enhance and/or encode the 3D detector unit properties.

The 3D detector unit design can be extended to include additional layers of rods (e.g., rods-layer-rods-layer-rods, layer-rods-layer-rods-layer, etc.). Combinations of any of these 3D detector units (rods-layer-rods, layer-rods, layer-rods-layer, and extended implementations thereof) can be stacked to provide greater stopping power. These dual-end readout detector implementations with a pixelated scintillator array layer or an intermediate scintillator layer provide a reduction in the number of readout elements relative to conventional (uniform) dual-end readout implementations, in which each of the parallel scintillator rods employs dual-end readout photodetectors.

An alternative implementation that may result in reduced readout costs is the sparse dual-end readout scintillator rod detector format, in which a crossed layer of parallel scintillator rods (each rod with a photodetector readout) is rotated parallel to the other layer such that the sets of photodetectors coupled to the two adjacent layers are at 180 degrees (on opposites sides). The sparse dual-end readout format utilizes the same number of photodetector readouts as crossed rod geometry (e.g., one per rod), but typically requires more extensive encoding due to increased light sharing complexity (including light sharing between layers, and optional light sharing within a layer).

A further reduction in the number of photodetector readouts can be implemented with the crossed rod or sparse dual-end readout detectors, e.g., by enabling optically coupling (and possibly additional encoding) between rods within a layer and between layers, while employing readout photodetectors coupled to only a reduced number (subset) of the scintillator rods within a layer (e.g., reduced crossed rod detectors, reduced sparse dual-end readout detectors). For example, in one implementation every other scintillator rod within a layer (crossed rod detector, sparse dual-end readout detector) is coupled to a photodetector readout. Dual-end readout detectors, sparse dual-end readout detectors, reduced sparse dual-end readout detectors and reduced crossed rod detectors can utilize the enhancement and encoding techniques as well as the photodetectors described herein, for use with crossed rod detectors as described herein, including implementations that utilize three or more layers of scintillator rods, or curved geometries or offset rods.

Photodetector configurations can include, but are not limited to, discrete pixel photodetectors, linear and 2D arrays including position-sensitive area and photodetector strips with readout circuitry at the ends of the strips (measuring relative signal strength and/or propagation time), as well as linear and 2D arrays with on-board analog and/or digital processing readout circuitry (permitting timing, position, energy and relevant waveform information to be output for at least one detected event), and photo-emissive detector strips and area photodetectors. Suitable strip and area photodetectors include, but are not limited to, pixelated PMTs (PSPMTs) photodetectors, 1D/2D pixelated, strip or area APD/SiPM/iDADs/silicon nanowires/microchannel plate photodetectors (as well as implementations utilizing Se-APDs, GaAsPMs, DiamondPMs, etc.). Area photodetectors can implement readout circuitry at the four corners.

Position-sensitive area photodetectors can also implement readout circuitry at the four corners. Position-sensitive strip and/or area photodetectors can be employed with arrays of parallel scintillator rods (or fibers), and with various crossed scintillator rod (crossed fiber) and crossed scintillator rod and fiber 3D detectors, in order to reduce the number of readout elements for the detector modules as described herein. For example, position-sensitive photodetectors could be coupled to one or both ends of an N×N array of parallel scintillator rods (e.g., with an N×N photodetector array coupled to the opposite end). A simplification of this design is to replace either the position-sensitive photodetectors or the N×N 2D photodetector array with a 1D photodetector (e.g., a PMT) or with a combination of position-sensitive and 1D photodetector or 2D photodetector arrays. (Note that an N×N scintillator array is only used for illustrative purposes, and in general N×M scintillator arrays can be used with the detector modules described herein, where M is equal or different from N.)

Another implementation employed with the detector modules described herein uses a photodetector optically coupled to a fiberoptic or light pipe, which is optically-coupled to at least one end of one or more scintillator rods (or fibers). For example, with an N×N array of parallel scintillator rods (N rows and N columns), a fiber optic or light pipe could be optically coupled to each of the N rows and thus form an N-element fiber optic or light pipe array. This N-element fiber optic or light pipe array could be read out by an N-element photodetector array, or even a photodetector strip (including strip array embodiments) with position-sensing capability. Thus, one possible alternative to an N×N photodetector array readout is an N photodetector readout (which could be reduced further by using a positions-sensitive photodetector strip).

N-element fiber optic or light pipe arrays optically coupled to both ends of an N×N scintillator rod array (and at 90 degrees to each other) could significantly reduce the total number of photodetector readout elements, e.g., from 2(N×N) to either 2N or substantially less than 2N (with position-sensitive photodetectors), while providing 3D spatial resolution using DOI (face-on) or SAR (edge-on) capability. Alternative implementations include N fiber optics optically-coupled to one end and an N×N photodetector array or N×N position-sensitive photodetectors, or a 1D photodetector (e.g., a PMT) coupled to the other end of the scintillator rod array.

Yet another variation implements a combination of optical fibers/light pipes and at least one of position-sensitive photodetectors, individual photodetectors or 1D or 2D photodetectors coupled to one or both ends of the scintillator rod array. The detector module implementations described herein (scintillator-based, semiconductor-based, etc.) typically represent trade-offs in terms of cost and one or more aspects of detector module response (performance) parameters (e.g., energy resolution, spatial resolution, temporal resolution, volume-dependent dead time, positioning errors, etc.).

For example, consider the simple case of the volume-dependent dead time for a single, localized photoelectric event recorded within one (1) scintillator rod of an N×N array of isolated scintillator rods with N×N photodetector arrays (which may incorporate integrated digital signal processing circuitry) at both ends of the scintillator rod array. In this scenario, the volume-dependent dead time is the volume of one (1) scintillator rod times the effective scintillator decay time (influenced by the inherent scintillator decay time, and to a lesser extent the light-sharing geometry), and taking into account the signal shape processing capabilities of the readout circuitry. Replace the N×N photodetector arrays with position-sensitive area photodetectors (with comparable gain and photosensitivity), with readouts at the four corners. Assume that the signal shape processing capabilities of the readout circuitry are unchanged. Since the scintillator rod array light-sharing geometry has not changed, the volume-dependent dead time has increased by a factor of N×N (the readout volume increased from 1 to N×N scintillator rods). The potential cost saving is in reducing the number of photodetector elements from 2(N×N) to eight (8).

A second photoelectric event in a second scintillator rod that significantly overlaps in time with the fluorescence decay due to the first photoelectric event can still be detected by the 2(N×N) photodetector array configuration, but may result in a positioning error and (two) rejected events, for the position-sensitive area photodetector configuration. Note that the position-sensitive area photodetector configuration experiences a similar problem with single or multiple Compton scatter events followed by photoelectric events in different scintillator rods, resulting in the correct total energy but with a possible positioning error.

Variations on this discrete structured 3D scintillator detector module design implement two (or more) layers. A two layer detector module can employ top and bottom layers of the same or different scintillator rod (fiber) materials, discrete scintillator rods in the top and bottom layers with the same or different spatial dimensions, shared photodetector sensors, applied reflective materials and patterns, applied absorptive and/or scattering materials and patterns, applied wavelength shifting (WLS) materials (including conventional fluorescent dopants as well as quantum dots and other nano-particles and microdots) and patterns (including WLS materials combined with reflectors), WLS fibers (including WLS fibers combined with reflectors), structured surfaces, etc. (see Nelson, U.S. Pat. No. 8,017,906). This approach can be extended such that scintillator rod parameters (material, physical properties, dimensions) within a layer and between layers can be varied. Note that implementations of quantum dots, other nano-particles and microdots can function as wavelength shifting materials and/or direct ionizing radiation conversion materials and can be employed on the surface as well as within the volume of a scintillator pixel, rod, sheet, block or fiber.

For example, reflective (and/or absorptive) coatings between at least two adjacent scintillator rod walls within a layer and/or between layers can be replaced with patterns of reflectors (and/or absorbers, scatters, WLS, Quantum dots/ nanoparticles, etc.) as encoding elements that partially couple optical energy into at least one adjacent scintillator rod (enabling light sharing), or that impede (reduce or delay) optical coupling into at least one adjacent scintillator rod. Furthermore, reflective (and/or absorptive) coatings on at least one area of at least one uncoupled scintillator rod surface can be replaced by a sparse or continuous photodetector, enabling an increase of at least one of timing resolution, spatial resolution, energy resolution and scintillator rod length. This approach can be extended to allow light sharing between three or more layers of scintillator rods. This approach can also be extended such that scintillator rod parameters (material, physical properties, dimensions) within a layer and between layers can be varied.

Furthermore, at least one scintillator rod (fiber) within at least one layer can be encoded by means of segmentation, and uniform and/or non-uniform segmentation patterns can be implemented for at least two scintillator rods within the same layer or optically-coupled layers. Scintillator rod (fiber) segmentation, e.g., as described herein within a layer, can be extended to segmentation within one or more pixels of a 2D pixel array (or one or more rods within a 2D rod array), and thereby provide DOI (face-on geometry) or SAR (edge-on geometry) 3D resolution capability. Thus, a single scintillator rod layer (as well as 2D pixel or 2D rod arrays) can include at least one of rods, segmented rods, scintillator pixels/elements as well as other elements for controlling light propagation (reflectors, absorbers, scattering materials, WLS materials, Quantum dots/nanoparticles, etc.). Segmenting of scintillator rods (including scintillator fibers), as described herein, allows increased event position (and/or timing) encoding flexibility, since the interfaces between rod (fiber) segments can be varied in terms of reflective, absorptive and transmissive properties, as well as via the use of WLS materials, coupling materials, spacers, nano-patterning with photonic crystals, or by implementing photonic hypercrystals, optical antennas, etc.

Furthermore, the properties of individual rod (fiber) segments as described herein can be altered to enhance spatial and/or temporal resolution. For example, an existing rod (fiber) segment can be replaced with a rod (fiber) segment of the same material with the same or different scintillation properties (e.g., to alter the dopant concentration and/or use of a co-dopant), or even by a rod (fiber) segment comprised of a different scintillator rod (fiber) material (e.g., a GSO or LYSO rod segment in place of a LSO rod segment). The principle of replacing a rod (fiber) segment with another rod (fiber) segment that has different properties is readily extended to replacing one or more rod pixels (fibers) in an array with rod pixels (fibers) that have different properties, thereby encoding the rod pixel (fiber) array and/or the segmented rod pixels (fibers).

Furthermore, a continuous or patterned gradient in scintillator dopant(s) concentration can be introduced along the length of a rod (fiber) or a rod (fiber) segment (or a rod pixel (fiber) array), in order to encode scintillator temporal properties as a function of length. In principle, the scintillator dopant gradient can be employed in any face-on and/or edge-on scintillator and/or fiber detector geometry, including single-sided readout, double-sided readout, crossed rods, crossed rods with layers, crossed rods and fibers, fibers, crossed fibers, etc. Note that implementations of quantum dots, other nano-particles and microdots can function as wavelength shifting materials and/or direct ionizing radiation conversion materials, and can be employed on the surface as well as within the volume of a scintillator pixel, rod, sheet, block or fiber.

Thus, different scintillator materials can be employed as well as variations of a scintillator material (different properties such as temporal decay characteristics, spectral distribution, conversion efficiency, light transport directionality and/or absorption, etc.). Furthermore, arrays of discrete scintillator pixels can replace one or more discrete rods (or all rods) within a layer. Scintillator pixel parameters (spatial dimensions, scintillator materials, physical and virtual internal and external structures, the application of WLS materials and patterns of WLS materials, etc.) within a layer and between layers can be varied.

Readout photodetectors employed with the scintillator detector implementations described herein rods, fibers, segmented rod or fibers, parallel and crossed rod/fiber arrays and variations thereof, including blocks, etc.) can use spectral sensitivity capabilities (e.g., using inherent spectral response of the photodetectors and/or optical absorption filters, gratings, WLS materials, etc.), in order to discriminate between scintillators (and scintillator fibers) with different optical emission spectra (including spatially-varying emission spectra within a single scintillator or fiber material). For example, two or more photodetectors (with the same or different dimensions) having different spectral sensitivities can be employed to read out one end of a scintillator rod (or scintillator fiber), or both ends of a scintillator rod (or scintillator fiber). If both ends of the scintillator rod (or fiber) are read out, one option is to have a single photodetector at each end but in an embodiment where each photodetector has a different spectral response. This approach can be extended to read out linear and 2D photodetector arrays used at one or both ends of a parallel or crossed scintillator rod (or fiber) array detector, or using scintillator rods crossed with fibers, according to the various detector implementations described herein.

In another implementation, a separate photodetector (or at least one of the photodetectors, if more than one is present) with a different spectral sensitivity from the photodetector at the end (or ends) of the scintillator rod or scintillator fiber is coupled to the side, of the rod or fiber. This approach can be extended to coupling a linear or 2D photodetector array (or arrays) to the side (or sides) of an array of parallel or crossed scintillator rods or scintillator fibers (or scintillator rods crossed with fibers), according to the various detector implementations described herein.

In yet another implementation, a photodetector (or at least one of the photodetectors if more than one is present) with different spectral sensitivity from the photodetector at the end (or ends) of the scintillator rod or scintillator fiber (and with the same or different dimensions) is coupled to the end(s) or side(s) of the scintillator rod (or fiber) by a fiber optic or light pipe. This approach can be extended to coupling readout fiber optics or light pipes to one or both ends and/or to the side(s) of an array of parallel or crossed scintillator rods or scintillator fibers or scintillator rods crossed with fibers, according to the various detector implementations described herein.

One or more layers of discrete scintillator rods and/or discrete scintillator pixels can be replaced by a scintillator sheet or multiple scintillator sheets which can be continuous or structured (physical and virtual structures can be introduced into, or onto, scintillator sheets). Physical and virtual internal structures include, but are not limited to, rods and/or pixels. Virtual internal structures can include, but are not limited to, vertical barriers, horizontal barriers, angled barriers, grids, fibers and dispersive formations. Physical and virtual surface and/or internal structures can be formed by roughening, sawing, drilling, sub-surface laser engraving, ion implanting, photolithography, deposition, gluing, embedding, etc. Scintillator sheet parameters within a layer (s) or between layers can be varied. A single scintillator sheet (continuous or structured) can be positioned between two layers of discrete scintillator rods and/or pixels. Physical and virtual surface and/or internal structures can be employed with scintillator sheets, scintillator rods and any coatings.

Individual scintillator sheets can employ a single scintillator material, a single scintillator material with spatially varying properties such as a dopant gradient, or multiple scintillator materials that differ in at least one of material composition, temporal emission properties, ionizing radiation conversion efficiency and/or linearity, and spectral emission. Patterns of WLS materials can be incorporated into the scintillator sheets with a discrete internal structure (such as a pixelated array). Furthermore, different scintillator sheets can employ the same or different scintillator materials, or different configurations of scintillator materials. The design flexibility (encoding) provided in these scintillator sheet formats is readily extended to scintillator rod formats (varying scintillator properties within a rod, assembling a rod from scintillator rod pieces or segments with the same or different material properties, including the use of WLS materials etc.,) and similarly to scintillator fiber formats, as described herein.

Multiple scintillator sheets can be coupled to implement a 3D scintillator detector) module. A 3D scintillator detector module stack can incorporate 3D scintillator detector modules with the same or different properties. WLS materials and (encoded) patterns of WLS materials can be applied to one or more scintillator rod, pixel, sheet surfaces. Scintillator sheets, as well as layers of discrete scintillator rods and/or pixels can implement at least one non-scintillator supporting layer to provide at least one of: additional structure integrity, reflection and/or redirection of the fluorescence signal, WLS materials (including encoded patterns of WLS materials), radiation filtering/conversion.

Physical or virtual structures can be introduced into, or onto, one or more discrete scintillator rods (as well as discrete scintillator pixels and scintillator sheets, if present) in order to improve spatial and/or temporal and/or energy resolution. Top and bottom layer scintillator rod (or pixel) surfaces that contact each other (as well as readout surfaces and other readout surfaces) can be modified to increase and/or direct light transmission by implementing at least one of: physical or virtual surface microstructures and/or macrostructure patterns attached to, deposited onto or cut/etched into or implanted (by ion implantation, sub-surface laser engraving or other techniques) into the scintillator crystal surface(s), surface macrostructures patterns, surface coatings, WLS materials including, but not limited to, WLS quantum dots and WLS films (see Nelson, U.S. Pat. No. 8,017,906). For example, rough surface patterns can be employed to diffuse directional light transmission whereas more sophisticated patterns such chevron designs (curved or angled channels) can be employed to help direct light transmission between crossed scintillator rods. For example, physical or virtual angled channels can be created on one or both contact surfaces for discrete crossed scintillator rods, or incorporated into a thin intermediate layer (which may incorporate WLS materials) between the discrete crossed scintillator rods, with the goal of directing transmitted light toward the photodetector coupled to that scintillator rod. Cherenkov radiation can also be recorded. Various techniques have been described for creating structures within or on the surface of scintillator rods (and therefor scintillator pixels), rod coatings, etc., and these techniques are readily extended to structured and continuous scintillator sheets and blocks.

Another variation of the discrete structured 3D scintillator detector module design (applicable to the other 3D detector designs described herein) implements discrete scintillator rods (or scintillator pixels or scintillator rods and pixels) or a continuous or structured (with discrete or virtual rods and/or pixels) scintillator sheet in which one or more scintillator properties of a scintillator rod (or scintillator pixels or a scintillator sheet) such as temporal decay distribution, spectral distribution, conversion efficiency is varied spatially along the length of a scintillator rod (or between scintillator pixels or over the area of a scintillator sheet) according to an encoded pattern. Positional information can thereby be encoded into the scintillator rods (or scintillator pixels or a scintillator sheet). The implementation of encoded scintillator rods (or scintillator pixels or scintillator sheet) in structured 3D scintillator detectors may be used to enhance resolution for crossed (or uncrossed) scintillator rod layers, or scintillator pixels layers or (continuous or structured) scintillator sheets. These encoding techniques can be used with discrete or continuous scintillator rods.

Yet another method of encoding position information along the length of a scintillator rod for the discrete structured 3D scintillator detector module is to apply WLS materials (including quantum dots/nanoparticles, photonic structured material, etc.) at selective locations and/or as continuous or discrete patterns (including 1D and 2D patterns) on one end face and/or at least one side along the lengths of the rods, such that wavelength and/or pulse shape properties (including time delays in emission) vary with position (see Nelson, U.S. Pat. No. 8,017,906). Pulse shape discrimination (PSI)) techniques are also employed in practice of the detector systems described herein. This encoding method can be implemented with scintillator pixels, rods, fibers, and arrays, as well as with scintillator blocks and slabs or sheets. Two or more WLS materials can be present at a location within the pattern. This design can be extended to the case of fibers crossed with scintillator rods (or pixels) in which scintillator rods (or pixels) are encoded, fibers are encoded or fibers and scintillator rods (or pixels) are encoded. Furthermore, this multiple-WLS design can be combined with (or replaced by) one or more of absorbers, scatterers, reflectors, surface and/or internal implementations of physical and/or virtual structures (including implementations employing patterns) and can be employed with a single layer of rods with one sided or two-side readout to implement a single layer 2D or 3D scintillator detector that can be employed in a single layer or multiple layer detector module.

Furthermore, discrete or continuous patterns of scintillator rod coatings or coupling materials can be applied along the length of the rod, such that the coating or coupling material index of refraction changes with position and thereby encodes how the optical signal is shared with an adjacent scintillator rod (within the same layer and/or between layers). Optical sharing is not limited to rods between layers. Patterned or continuous light sharing between two or more rods within a layer can also be implemented using the techniques described herein for controlling light sharing between coupled rods in different layers.

Patterns can also be implemented internally and/or on at least one side of individual rods in a single layer. An adjacent layer can be optically coupled with or optically isolated from this single layer of rods. For example, if the adjacent layer is continuous or pixelated then optical coupling is typically employed (the adjacent layer can be an intermediate layer). If the adjacent layer is comprised of rods parallel to the single layer rods then optical isolation is typically employed the adjacent layer is comprised of rods at an angle (such as perpendicular) to the single layer rods then optical isolation or optical coupling (if beneficial) can be employed.

Another method of encoding position information along the length of a scintillator rod (for a single-sided readout) is to evaluate the readout waveform representing the initial scintillation event followed by the delayed reflected signal from the opposite end face of the scintillator rod. This delayed reflected signal method can be combined with previously described positioning of WLS materials (quantum dots/nanoparticles, photonic structured materials, etc.) on at least one face of the scintillator rods, to enhance the accuracy of event position estimates. The opposite end face of the scintillator rod can implement a reflector, a WLS material (quantum dots/nanoparticles, photonic structured material, etc.), or both.

Furthermore, this multiple-WLS design (and variants thereof) can be used with scintillator sheets, slabs and blocks as well as scintillator rods and fibers. Potential benefits include improved spatial resolution, energy resolution and/or reduced ambiguity concerning the detection of multiple events within the coincidence resolution limits of the discrete structured 3D scintillator detector(s). For example, a fiber array can be shared across multiple discrete structured 3D scintillator detectors. This approach to encoding can be readily extended to a continuous or structured scintillator sheet (including a rod and/or pixelated scintillator sheet) by implementing a 2D pattern of WLS materials. Multiple-WLS designs, in general, can be combined with (or replaced by) one or more of absorbers, scatterers, reflectors, surface and/or internal implementations of physical and/or virtual structures (including implementations employing patterns). Physical internal structures can include embedded quantum dots, nano-particles and microdots.

Furthermore, be employed with other discrete or shared-light output 2D and 3D detector designs (including thick scintillator sheet detectors) implemented for nuclear medicine and/or PET imaging. Spatial positioning can be determined by employing photodetectors at both ends of an array of scintillator rods within a layer (or a scintillator sheet) using signal weighting to compare signal strength at both ends and/or TOF resolution techniques to compare pulses arrival times at both ends. Spatial positioning can also be determined by employing photodetectors at one end of an array of scintillator rods within a layer (or a scintillator sheet) using TOF resolution to compare arrival times of the initial pulse with the direct reflected pulse or an effective reflected pulse (a delayed signal) from the opposite end. Note that an effective reflected pulse (delayed signal) can be provided by a (passive) WLS material positioned at the scintillator face opposite the photodetector readout face is but one technique for providing a delayed signal. Other passive or active photo-activated signal delay mechanisms can be implemented, including quantum dots/nanoparticles, photonic structured materials, etc.

Sources of scintillator rods (structured or continuous scintillator rods) include a discrete 1D array of scintillator rods, (one multiple layer implementation could employ a discrete 2D array of scintillator rods), a structured scintillator sheet, a single-sided semi-continuous structured scintillator sheet, a double-sided semi-continuous structured scintillator sheet, a double-sided semi-continuous structured scintillator sheet with an intermediate layer. In addition, this approach can be readily implemented with (structured or continuous) scintillator fiber layers (or 2D arrays) as well as fiber optic layers (or 2D arrays). One or more non-scintillator supporting layers (as previously described herein) can be employed.

Patterns of light sharing between readout photodetectors may be used to improve estimates of depth of interaction (DOI) or sub-aperture resolution (SAR). One or more encoding techniques can be implemented with the detectors taught herein. A previously herein-described variation on the discrete structured 3D scintillator detector module is a discrete rod-structured, pixel-structured 3D scintillator detector module which implements a parallel array of discrete scintillator rods with light sharing and optical readouts at one or both ends of the array of discrete scintillator rods coupled to a second layer comprised of a discrete 2D pixel scintillator array. (Note that implementations can include not only arrays of rods or 2D arrays of pixels but also mixed arrays of rods and pixels.) Furthermore, a discrete pixel-structured, pixel-structured 3D scintillator detector module can be implemented in which both layers employ 2D arrays of discrete scintillator pixels (the two layers of discrete 2D scintillator pixel arrays can be aligned or offset). One or more encoding techniques can be implemented.

The discrete 2D pixel scintillator array layer can be replaced with a scintillator sheet (a structured scintillator sheet) with an imposed pixel structure including at least one of physical pixels (cut/sawed/etched) and virtual scintillator pixels (for example, via ion implantation). The physical and virtual pixels need not extend through the entire thickness of the scintillator sheet layer. Variations in the physical or virtual gap (divider) depth used to define a scintillator pixel may be employed in order to modify (locally) the distribution of fluorescence (or other optical) signals. Furthermore, encoding techniques such as spatially varying scintillator properties and/or applying continuous or discrete patterns (including 1D and 2D patterns) of WLS materials along the lengths of the rods or on the pixels of the 2D pixel arrays such that wavelength and/or pulse shape properties (including time delays in emission) vary with position can be used to enhance resolution.

Additional variations on the use of a scintillator sheet layer include a scintillator sheet layer with an imposed rod array structure (replacing a layer of discrete scintillator rods in a crossed rod geometry or in a discrete rod-structured, 2D pixel-structured geometry), or a patterned gradient in one or more scintillator dopant concentrations, or a scintillator sheet layer with no structure. For the case of a scintillator sheet layer with an imposed rod structure an optical readout can be positioned at one end of each array of scintillator rods or the optical readouts can be positioned at both ends of the array of discrete scintillator rods. For the case of a scintillator sheet layer with no structure the optical readouts can be positioned at one end or both ends of the array of discrete scintillator rods.

The implementation of spatial encoding through techniques such as spatially varying scintillator properties and/or applying continuous or discrete patterns of WLS materials on one or more surfaces for discrete scintillator rods (and/or pixels) and a scintillator sheet layer (imposed rod/pixel structure, no structure) can be used to improve resolution and/or enable the use of optical readouts at a single end of the array of discrete scintillator rods. It should be understood that encoding techniques described herein can be employed with any of the planar or non-planar scintillator configurations (discrete scintillator rod, discrete scintillator pixel array, structured or continuous scintillator sheet, scintillator block, fiber arrays, scintillator fiber arrays, etc.) taught in this specification.

Photodetector configurations can include, but are not limited to, discrete pixel photodetectors, photodetector strips with readout circuitry at the ends of the strips (measuring relative signal strength and/or propagation time), photo-emissive detector strips and area photodetectors. Strip and area photodetectors include, but are not limited to, pixelated PMTs (PSPMTs) photodetectors, 1D/2D pixelated, strip or area APD/SiPM/iDADs/silicon nanowires/microchannel plate photodetectors (as well as implementations utilizing Se-APDs, GaAsPMs, DiamondPMs, etc.). Area, photodetectors can implement readout circuitry at the four corners. Note that applications include not only medical x-ray and gamma ray detection and imaging but also the detection and imaging of charged and uncharged particles in general.

Figure 12A:
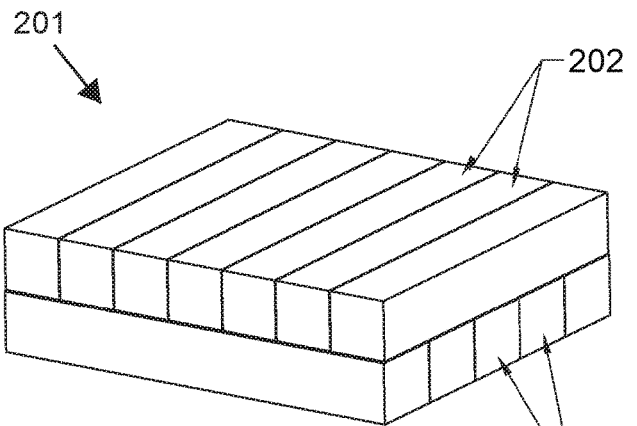
FIG. 12A is a perspective view of a non-uniform discrete structured 3D scintillator detector module with crossed top and bottom layers that implement different scintillator rod materials with different dimensions.

FIG. 12A shows a discrete structured 3D scintillator detector module 201 with crossed top (first) and bottom (second) layers that implement different scintillator rod materials with different dimensions 202, 203 (non-uniform discrete structured 3D scintillator detector module). An alternative implementation uses different scintillator materials but with the same dimensions. Yet another alternative implementation uses the same scintillator material with different dimensions. Furthermore, the scintillator rods 202, 203 within a layer may implement scintillator rod materials and/or dimensions with the same or different properties. Scintillator rod lengths in the top and bottom layers can be the same or different.

Potential benefits for implementing physical (or virtual) scintillator rods of different lengths in the top and bottom layers may include at least one of improved spatial resolution, energy resolution, and timing resolution, and/or an increase in usable rod length for one layer of rods. For example, a detector module with a rectangular geometry using a layer with 25 mm long rods crossed with a layer of 100 mm long rods may be preferred over a 50 mm long rod square geometry (with the same detector module volume), or a 100 mm long rod square geometry (despite a 75% reduction in detector volume).

Physical structures or virtual structures (using ion implantation, subsurface laser, etc. techniques) that modify optical propagation can be introduced into, onto and between scintillator rods (within a layer and between layers) in order to improve at least one of event positional accuracy, timing and detected signal levels. The physical structures (linear and non-linear) can include, but are not limited to, air structures, coating structures, coupling material structures, photonic crystal structures, nano-layered metamaterials (including nanocavities) structures (e.g. metasurfaces), refracting structures, diffracting structures, lens structures, micro-spheres and related micro-structures, fiber plates, WLS material structures, specular reflector structures, diffuse reflector structures, absorbing structures, scattering structures, polished surfaces, roughened surfaces, etched surfaces, shaped surfaces. Photodetector readout geometries can include discrete pixels, linear pixelated arrays, position sensitive linear arrays (e.g., using PSPMTs), position-sensitive strip detectors with readouts at the ends, position sensitive area detectors and variations thereof, with on-board analog and/or digital processing readout circuitry (permitting timing, position, energy and relevant waveform information to be output for at least one detected event). Position-sensitive photo-emissive strip detectors are implemented with microchannel plates. Digital processing readout circuitry is implemented in dSiPM photodetectors.

The detector module 201 could be used to detect and/or track photons and/or particles with different energies (different properties), including scattered photons and/or particles. 3D spatial resolution is different for events detected in the top and bottom layers. Both uniform and non-uniform discrete structured 3D scintillator detector modules 201 can be positioned (stacked), one on top of another, to form a stacked discrete structured 3D scintillator detector module Individual rod surfaces can be polished or unpolished (or a patterned combination of polished and unpolished). One or more of the non-readout surfaces of the rods (or segments of rod surfaces) can be coated and/or etched/roughened, notched, etc. in order to direct more light to the preferred readout photodetector(s). Zero, one or multiple scintillator coatings and/or surface treatments (including surface treatments to the scintillator coatings) or combinations thereof can be applied in continuous or discrete patterns to the individual rod surfaces.

Optionally, patterns of reflective and/or absorptive optical barriers can be introduced within one or more of the scintillator coatings to control the propagation of the scintillator and/or WLS optical photons within the scintillator coating or coatings and between scintillator layers. A simple optical barrier pattern could be a grid pattern implemented between 2 layers of crossed rods with the same or different rod cross sections. The optical barrier grid pattern corresponds to the pattern formed by the crossed rods (for example, crossed rods with 1×1 mm$^2$ and 2×2 mm$^2$ cross sections would implement an optical barrier grid pattern with element dimensions of 1×2 mm$^2$ or finer).

Scintillator coatings can include, but are not limited to, one or more low index coatings (which can function as reflective coatings when applied to scintillators with a higher index of refraction), high index coatings, reflective coatings, absorptive coatings, diffuse coatings, diffuse reflective coatings, WLS coatings, and patterns thereof. Coatings can be applied uniformly or non-uniformly, including continuous and discrete patterns of coatings. Physical and/or virtual surface and internal structures can be introduced into or onto coatings and/or scintillator rods by roughening, sawing, drilling, notching, sub-surface laser engraving, ion implanting, photolithography, deposition, gluing, embedding, etc. to help direct (and/or encode) the distribution of the fluorescence signal to the preferred readout photodetector(s). For example, an embedded physical internal structure could include a discrete or continuous pattern of quantum dots (and/or other suitable nano-particles or microdots) distributed internally along the length of a scintillator rod such that one or more properties (such as emission spectrum and/or temporal response) of the quantum dots and/or density vary with 2D (or 3D) position within the scintillator rod (a technique readily extended to encoding of scintillator sheets and blocks as well as scintillator fibers).

Examples of quantum dot patterns include, but are not limited to, varying quantum dot density versus position (a gradient) along at least one dimension (such as the length) of the scintillator rod, varying quantum dot property versus position along at least one dimension (such as length) of the scintillator rod, varying quantum dot density and property versus position along at least one dimension (such as length) of the scintillator rod. Embedded physical internal structures can also be implemented within scintillator pixels, sheets, blocks and fibers. Non-imaging optics techniques, photonic crystal structures, nano-layered materials (including nano-cavities) structures, WLS structures, refracting structures, diffracting structures, lens structures, micro-sphere structures, etc. can be applied. Introducing one or more notches to a scintillator rod surface can be used to couple a fluorescence signal to at least one of a fiber optic detector element, a scintillator fiber detector element, a scintillator rod detector element, and a photodetector. Notches can also be employed with scintillator fibers and rods.

For example, in one implementation a relatively high index scintillator rod can be coated on one or more surfaces with at least one relatively low index of refraction coating in order to exploit high reflectivity for angles of incidence near or greater than the critical angle (the fiber optic effect). A WLS coating or WLS structures, in one instance, can be applied to the rod surface in contact with the other scintillator rod layer to modify (in this case broaden) the angular distribution of the incident light and shift the fluorescence spectrum. Other technique of modifying the angular distribution include, but are not limited to, roughening the coating surface, creating/applying photonic crystal structures, nano-layered metamaterials (including nanocavities) structures (e.g. metasurfaces), refracting structures, diffracting structures, or lens structures at the coating surface, applying microspheres or fiber plates at the coating surface. Coatings and/or physical (and/or virtual) structures can be applied to other rod surfaces to enhance at least one of spatial resolution, energy resolution, temporal resolution.

These 3D scintillator detector designs (as well as other optical radiation detector designs described herein) can be used to detect Cherenkov and/or scintillation optical radiation. Alternative implementations employ relatively high-Z, non-scintillator materials to detect Cherenkov optical radiation.

Figure 12B:
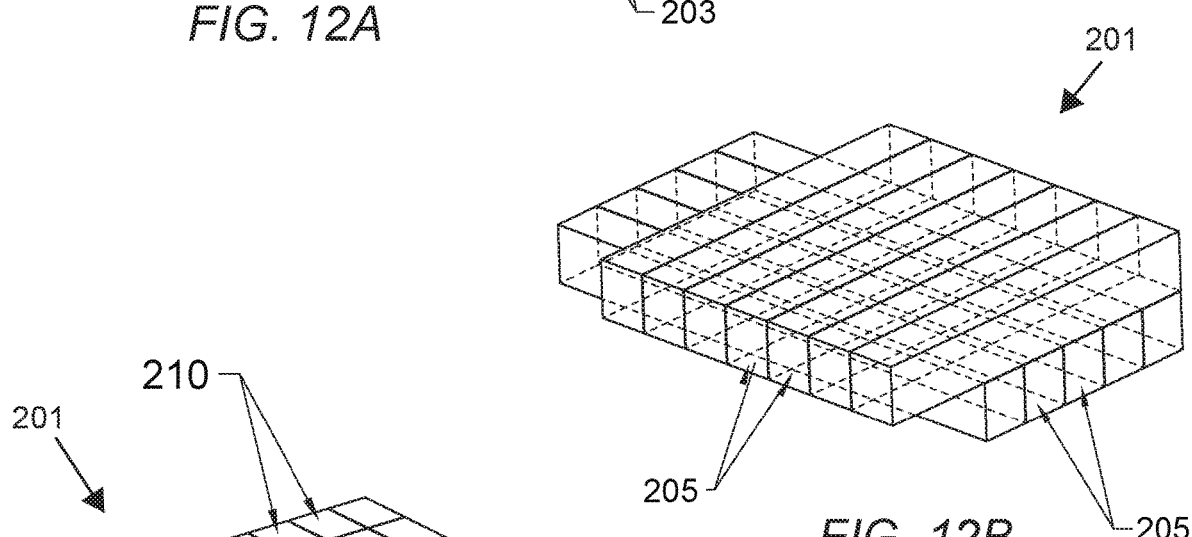
FIG. 12B is a perspective view of a uniform discrete structured 3D scintillator detector module with crossed top and bottom layers that implement the same scintillator rod materials with the same dimensions with the top layer and bottom layer overhanging their common surface employed for light sharing.

FIG. 12B illustrates a perspective of a uniform discrete structured 3D scintillator detector module 201 with crossed top and bottom layers that implement the same scintillator rod materials with the same dimensions with the top (first) layer and bottom layer overhanging their common surface employed for light sharing. While the sides of the discrete structured 3D scintillator detector module 201 in FIG. 12A are shown as uniform, an alternative arrangement in FIG. 12B illustrates a uniform discrete structured 3D scintillator detector module with crossed top and bottom layers that implement the same scintillator rod materials with the same dimensions 205 wherein the top layer and the bottom layers of rods 205 extend (overhang) their common surface that is employed for light sharing. These rod extensions can be very small (permitting the photodetector to be offset from the other layer) or sufficiently large so as to gain one or more extra pixels (defined by an absence of direct light sharing) while also providing an offset for the photodetector from the other layer. An alternative implementation results in an underhang of the readout ends of the top and bottom layers. This geometry allows the photodetectors coupled to one end of a scintillator layer to be slightly recessed with respect to the adjacent scintillator layer (e.g., of scintillator rods and/or scintillator pixels), and thereby increase packing density of adjacent detector modules.

One or more of the non-readout surfaces of the rod extensions can be provided with a coating and/or etched, etc. in order to direct more light to the readout photodetector. The implementation of scintillator layers that overhang their common surface is not limited to the use of a single scintillator material or a single rod dimension, a double-sided semi-continuous structured scintillator sheet with a rod structure can implement rod extensions. Furthermore, this approach is readily extended to include scintillator sheet extensions.

Figure 12C:
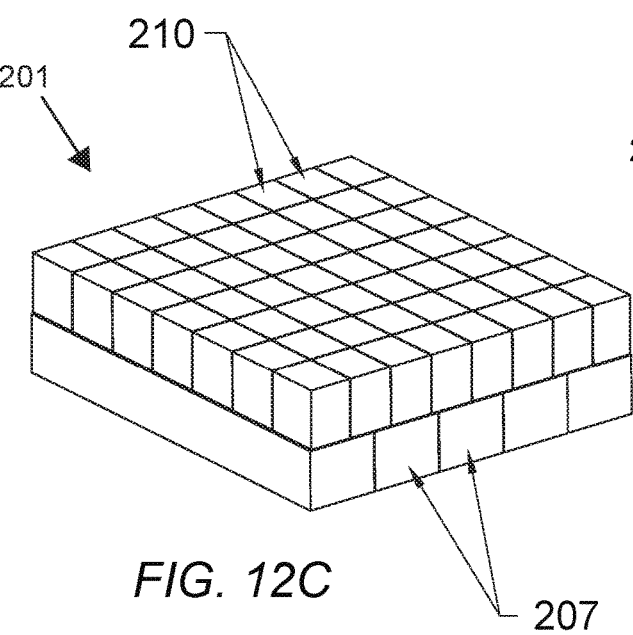
FIG. 12C is a perspective view of a discrete rod-structured, pixel-structured 3D scintillator detector module which implements a parallel array of discrete scintillator rods with light sharing and optical readouts at both ends of the array of discrete scintillator rods coupled to a second layer comprised of an array of discrete scintillator pixels.

FIG. 12C illustrates a discrete rod-structured, pixel-structured 3D scintillator detector module 201 which implements a parallel array of discrete scintillator rods 207 with light sharing and optical readouts at one or both ends of the array of discrete scintillator rods in the bottom (second) layer are coupled to a top (first) layer comprised of an array of discrete (or virtual) scintillator pixels 210.

The first and second (or top and bottom) layers can be interchanged without loss of generality. The scintillator materials employed in the first and second layer can be the same or different in terms of at least one of fluorescence decay properties, fluorescence efficiency, radiation interaction cross sections. In general, one or more additional (structured or continuous) scintillator layers (including single and multiple layer virtual structured scintillator sheets) can be inserted between the top and bottom scintillator layers.

For example, the 2D pixelated scintillator layer shown in FIG. 12C can be positioned between the two layers of crossed scintillator rods shown in FIG. 12A. This format can be extended to include a 2D pixelated scintillator layer positioned between the two layers of crossed scintillator rods (fibers), e.g., with a second 2D pixelated scintillator layer coupled to the top or bottom layer of rods followed by a third layer of crossed rods (with respect to the layer of rods coupled to the opposite face of the second 2D pixelated scintillator layer). The original pattern of three layers in a detector module with two readout layers can be extended to five layers in a detector module with three readout layers. This can be continued to seven layers in a detector module with four readout layers, etc. A variation is to couple a 2D pixelated scintillator layer to the top and/or bottom layers in the detector module. The 2D pixelated scintillator (array) layers described herein can have a different thickness than the scintillator layer or layers to which they are coupled.

Furthermore, a 2D pixelated scintillator rod (fiber) layer of extended thickness can employ one or more light-sharing encoding techniques and/or other encoding techniques described herein (e.g., segmentation, segmentation with different scintillator materials, varying scintillator dopant concentration), for scintillator rods and 2D pixelated scintillator layers such as patterns of reflectors, absorbers, rough surfaces, index of refraction changes in coatings or coupling materials, changes in scintillator material or properties, WLS materials, rod segmentation, etc., and thereby enable or enhance DOI or SAR spatial resolution capability (essentially, a 3D pixelated scintillator layer). 2D pixelated arrays of scintillator rods coupled to a 2D photodetector readout on only one face typically provide DOI or SAR resolution by implementing encoding techniques. 2D pixelated arrays of scintillator with a 2D photodetector readout on each face may or may not implement encoding techniques. Both 2D pixelated scintillator array readout formats are described.

A further variation is to replace one or more 2D pixelated scintillator layers within a detector module with a continuous scintillator layer. Yet a further variation is to implement any of the detector module configurations described herein with at least two parallel layers of scintillator rods. Yet another variation of this detector module design is to couple a single layer of rods (fibers) to at least one face of a 2D pixelated scintillator layer (with or without DOI or SAR resolution capability), and thereby form at least a two layer detector module. A variation of this two layer configuration is to read out the single layer of rods and read out the 2D pixelated scintillator face not coupled to the rods using a 1D or 2D photodetector.

More generally, 1D and 2D photodetector readouts can be combined with scintillator rod (fiber) readouts employed in the detector modules described herein (potentially enhancing one or more performance metrics such as spatial resolution, energy resolution, temporal resolution and detector dead time but with increased cost). Single and multiple layer virtual structured scintillator sheets can be employed in the detector module design described herein. One or more rods (fibers) in any of layer of any detector module described herein can be read out at one end or both ends (if detector performance gains warrant increased complexity and/or cost).

The preferred photodetector readout geometry for the discrete or virtual scintillator rods (fibers) within a layer described herein can be influenced by rod dimensions as well as encoding techniques (e.g., light sharing, segmentation, etc.) within a layer of rods, and by other layers optically coupled to the layer of rods. For example, as the length of the rods within a layer increases, a readout at both ends of a rod may be preferred over a reflector at one end and a readout at the other end. If the layer of rods (fibers) is cross-coupled to a layer with shorter rods (fibers), both layers of rods can employ reflectors at one end, and a readout at the opposite end of each layer.

In yet another example, if light sharing is implemented between neighboring rods within a layer (and/or with an optically coupled layer), an alternative rod configuration within a layer can implement a pattern in which the photodetector readout end of one rod is adjacent to the reflector end of the neighboring rod (e.g., in a sparse photodetector configuration). A variation of this pattern implements one or more rods with readouts at both ends (at additional cost), within the pattern. Yet another variation implements readout photodetectors for all rods on one end, while alternating photodetectors and reflectors (a sparse photodetector array) on the opposite end within a layer.

Sparse photodetector arrays can be implemented with 2D pixel scintillator arrays including rod (fiber) arrays. If acceptable ionizing radiation stopping power is maintained, one or more scintillator rods (up to and including all the rods) within any layer of any detector module described herein can be replaced by fiber optics, including conventional or encoded scintillator fibers or non-scintillator fibers (or rods). In addition to cost benefits over scintillator rods, fibers and non-scintillator rods typically offer better optical transparency and longer lengths than scintillator rods, and simplified surface treatments (or the embedding of materials) to promote at least one of optical coupling, optical channeling and encoding.

An alternative to implementing crossed layers (referred to as the top and bottom layers for convenience) of discrete scintillator rods is to implement a version of a structured scintillator sheet by introducing physical or virtual structures (such as scintillator rods) to define the top (first) and bottom (second) layers of a scintillator sheet so that the top and bottom layers of scintillator rods defined within the scintillator sheet are crossed. This structured scintillator sheet represents one implementation of a semi-continuous structured scintillator sheet. Multiple variations of a semi-continuous structured scintillator sheet can be implemented including two layers and two layers with an intermediate layer (which may be continuous or have structures). Physical and virtual structures can be introduced into, or onto, semi-continuous structured scintillator sheets.

For example, suitable physical structures could include, but are not limited to, continuous or patterned roughness, absorbers, scattering materials, reflectors, directional reflectors, WLS materials, notches, Fresnel lenses, etc., as applied to one or more external surfaces. Virtual structures could also be introduced within the scintillator sheet, for example, to help redirect light toward the readout photodetectors.

Note that the ends of discrete physical scintillator rods or scintillator rods formed within semi-continuous scintillator sheets that are not coupled to photodetectors are not constrained to be only flat surfaces. A loss of stopping power due to the implementation of focused surfaces can be partially mitigated by interleaving layers in adjacent detector modules, such that the focused surface ends of scintillator rods do not overlap.

The top and bottom layers of a scintillator sheet are not limited to implementing arrays of rods. For example, the bottom layer can implement rods (with a readout at one or both ends), whereas the top (first) layer can implement a 2D pixel array or be continuous (no imposed structure). A bottom layer can implement a 2D array of pixels whereas the top layer can be continuous (no imposed structure) or a 2D pixel array (in this case the top and bottom layers of pixel arrays can be aligned or offset). In yet another example, the top and bottom layers can implement at least one of a 2D pixel array or a continuous scintillator layer, whereas the intermediate layer or layers can implement at least one of a single layer of scintillator rods, two layers of crossed scintillator rods, or two layers of crossed scintillator rods with an intermediate 2D pixel array (or a continuous scintillator layer). Both rods and pixels can be implemented within a given top and/or bottom layer.

More generally, the 2D pixel arrays described herein include implementations that incorporate DOI (face-on geometry) or SAR (edge-on geometry) capability (and alternatively can be described as 3D pixel arrays). One or more rods in any of the layers described herein can be read out at one end or both ends. Furthermore, the 2D pixel arrays, continuous scintillator layers, and scintillator rods including scintillator fibers) described herein can be coupled by fiber optic (light pipes) to photodetector readout. For example, an array of scintillator rods coupled to a 2D pixel array can be replaced by an array of fiber optics (light pipes). In another example, a fiber optic (light pipe) array can be coupled to one face of a 2D pixel array and scintillator rods can be cross-coupled to the opposite face. Alternatively, 2D pixel arrays can be read out directly at one or both faces using position sensitive photodetectors (e.g., PSPMTs, 2D SiPM arrays, strip or 2D array microchannel plates, etc.), or using 2D photodetector arrays and/or single pixel photodetectors.

Encoding techniques described herein can be implemented to enhance at least one of spatial resolution, temporal resolution, energy resolution and/or reduce cost, including varying individual scintillator rod (scintillator fiber) and scintillator pixel materials and/or properties (including segmentation of rods or pixels). Crossed layers of scintillator rods can be read out with fiber optics by coupling the ends of aligned scintillator rods in at least two alternate layers (e.g., with N rods in each alternate layer) to an array of N optical fibers (light pipes) coupled to N photodetector pixels. Alternatively, a position-sensitive readout could be employed). If optical fibers are read out at a single end (or 2N photodetectors if fibers are readout at both ends), either technique can be used. Note that potential cost benefits are weighed against possible reductions in one or more detector module response (performance) parameters, in order to determine the desired design.

The dimensions of rod or pixels within an array can be uniform but need not be uniform. Encoding techniques can include, but are not limited to, implementing scintillator in which one or more scintillator properties vary spatially and/or applying surface treatments such as continuous and patterned WLS materials. A semi-continuous structured scintillator sheet (a single scintillator layer) can be employed directly as a 3D scintillator detector module (since it is comprised of at least two sub-layers that can be modeled as scintillator layers). A semi-continuous structured scintillator sheet can be employed with a layer of discrete scintillator rods or between two layers of scintillator rods to form a 3D scintillator detector module. A semi-continuous structured scintillator sheet can be employed with one or more of: a scintillator sheet, a second continuous structured scintillator sheet, a layer with discrete scintillator rods or a layer with a discrete 2D pixel scintillator array to form a 3D scintillator detector module.

The flexibility of this design enables multiple implementations that permit simplifications in manufacturing of this design compared to the discrete structured 3D scintillator detector module design (although design attributes such as the ability to employ different scintillator materials within a layer or between layers require using scintillator sheets with non-uniform properties). Cherenkov radiation can also be recorded. Increased light sharing between readout photodetectors compared to typical discrete structured 3D scintillator detector module implementations can be used to further improve estimates of depth of interaction (DOI) or sub-aperture resolution (SAR).

One implementation of a semi-continuous structured 3D scintillator detector module is the double-sided, semi-continuous structured 3D scintillator detector module that implements a single scintillator sheet into which physical gaps (cut/sawed/etched) and/or virtual gaps (for example, via ion implantation or sub-surface laser engraving) are made with respect to the top and bottom surfaces creating semi-continuous discrete or virtual scintillator rods, respectively (a double-sided semi-continuous structured scintillator sheet with a rod structure). Since the depth of the rod structures of the top and bottom surfaces can be controlled at least one of overlap (creating pixels in the overlap region), contact or a gap between top and bottom surface rods can be implemented in a desired pattern within the scintillator sheet. (Note that a physical or virtual partial pixel structure can optionally be implemented in a desired pattern within discreet scintillator rods.)

Arrays of semi-continuous discrete or virtual scintillator rods (or combinations of semi-continuous and discrete scintillator rods) are thereby created within the top and/or bottom layers of the scintillator sheet in order to form a double-sided, semi-continuous structured 3D scintillator detector using a double-sided semi-continuous structured scintillator sheet with a rod structure. As previously described herein, physical and/or virtual structures can be introduced into, or applied to, one or more of the semi-continuous scintillator rods in order to improve spatial and/or temporal and/or energy resolution. The crossing angle of the semi-continuous discrete or virtual scintillator rods is typically 90 degrees although other crossing angles can be implemented as needed.

Readout photodetectors are coupled to one end of each array of semi-continuous discrete and/or virtual scintillator rods comprising the top and bottom layers. The dimensions (thicknesses, width) of the semi-continuous discrete and/or virtual rods within the top and bottom layers can be different (as is the case for the discrete structured 3D scintillator detector) with the total thickness of rods from both layers being comparable to the thickness of the scintillator sheet. Furthermore, the width of individual rods within the top layer and/or bottom layer can be uniform or non-uniform.

The double-sided semi-continuous structured 3D scintillator detector module can, for suitable applications, offer reduced manufacturing costs compared to the discrete structured 3D scintillator detector. For example, as a discrete scintillator rod cross section becomes finer manufacturing yields tend to decrease and assembly costs tend to increase. As previously described herein, encoding techniques such as spatially varying scintillator properties and/or applying continuous or discrete patterns (including 1D and 2D patterns) of WLS materials, etc. can be used to enhance resolution.

Another variation on the double-sided, semi-continuous structured 3D scintillator detector module is a double-sided, semi-continuous structured 3D scintillator detector module with a rod structure and a pixel structure which implements a single scintillator sheet into which physical gaps (cut/sawed/etched) and/or virtual gaps (for example, via ion implantation or sub-surface laser engraving) are made with respect to the top and bottom surfaces creating semi-continuous discrete or virtual scintillator rods in one layer and semi-continuous discrete or virtual scintillator 2D array of pixels in the other layer (a double-sided semi-continuous structured scintillator sheet with a rod structure and a pixel structure). In this implementation the readout photodetectors are coupled to one or both ends of the array of semi-continuous discrete and/or virtual scintillator rods in one layer. Alternatively, readout photodetectors (pixelated, strip, area) can be coupled to the 2D array of pixels or a combination of readout photodetectors can be coupled to one or more rods and pixels.

Yet another variation implements semi-continuous discrete or virtual scintillator 2D array of pixels in the top and bottom layers (pixels can be aligned or offset between top and bottom layers). Improvements in one or more detector resolution parameters (spatial, temporal, energy) can be attained by sampling additional surfaces with readout photodetectors (including all or part of the face of a pixelated scintillator array) and/or by implementing encoding techniques such as implementing scintillators with spatially-varying parameters and/or applying patterns of WLS materials on at least one of the rod layer, the 2D pixel array layer.

Although examples of planar, square or rectangular sheets are shown in the figures for discrete and semi-continuous structured 3D scintillator detector modules other planar geometries (geometric and non-geometric) and non-planar geometries may be implemented. For example, a planar disk with crossed rods can be implemented. Readout techniques can be modified to compensate for non-planar readout surfaces.

Figure 13:
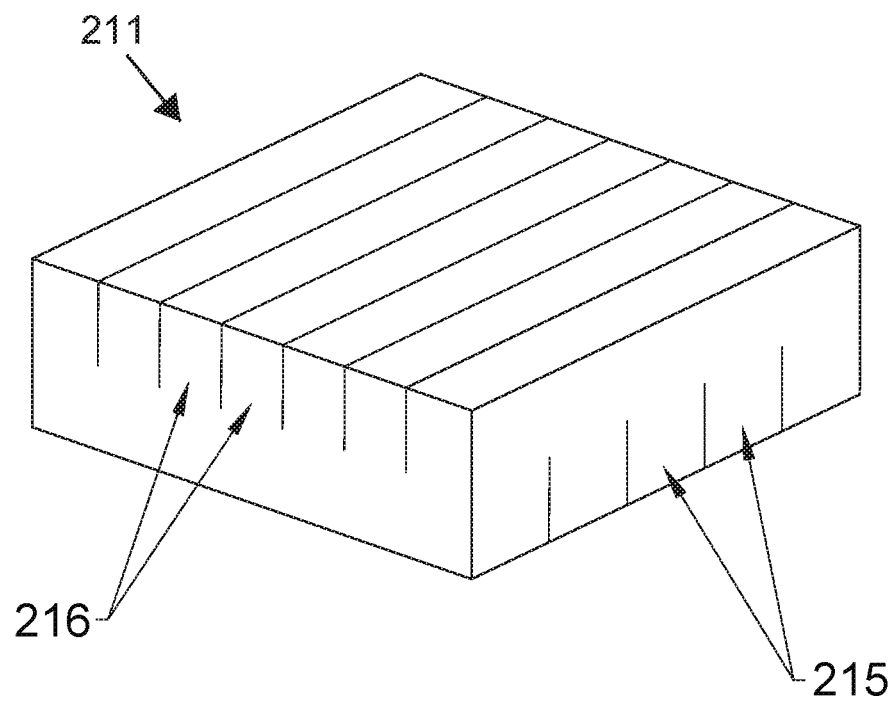
FIG. 13 is a perspective view of a double-sided, semi-continuous rod-structured 3D scintillator detector module with a crossing angle of 90 degrees comprised of a single scintillator sheet into which physical gaps (cut/sawed/etched) are introduced with respect to the top and bottom surfaces creating arrays of semi-continuous discrete scintillator rods.

FIG. 13 illustrates a double-sided, semi-continuous rod-structured 3D scintillator detector module 211 with a crossing angle of 90 degrees comprised of a single scintillator sheet (a double-sided semi-continuous structured scintillator sheet with a rod structure) into which uniform and/or non-uniform physical gaps (cut/sawed/etched) are introduced with respect to the top and bottom surfaces creating semi-continuous arrays of discrete rods 215, 216, respectively. Gaps can be unfilled, partially-filled or completely filled with one or more absorbing, scattering, reflective and WLS materials, including structured materials. Alternatively, some or all of the physical gaps can be replaced by virtual gaps (implemented using ion implantation, subsurface laser engraving or other techniques known in the art). Variations in gap depth may be employed in order to modify (locally) the distribution of fluorescence (or other optical) signals.

A variation of the double-sided, semi-continuous rod-structured 3D scintillator detector module implements a single scintillator sheet (a single-sided semi-continuous structured scintillator sheet with a rod structure) into which physical gaps or virtual gaps (for example, via ion implantation) are introduced from only the top or bottom surface to a depth that is less than the thickness of the scintillator sheet and thereby defining two layers in the scintillator sheet (one structured layer and one continuous layer). The structured layer is comprised of an array of semi-continuous discrete or virtual scintillator rods. This implementation of a dual layer scintillator sheet is referred to as a single-sided semi-continuous structured scintillator sheet with a rod structure that can be employed as a single-sided semi-continuous rod-structured 3D scintillator detector module or with at least one additional scintillator layer to implement additional variation of 3D scintillator detector modules.

As previously described herein, physical or virtual structures can be introduced into (and on the surface of) one or more of the semi-continuous scintillator rods (as well as the layer lacking an array of semi-continuous scintillator rods, for example, a 2D grid) in order to improve at least one of spatial, temporal and energy resolution. Furthermore, previously herein-described encoding techniques can be employed in order to enhance resolution. Readout photodetectors can be positioned at one or both ends of the array of semi-continuous scintillator rods comprising either the top or bottom layer. Readout resolution can be enhanced by implementing additional readout photodetectors positioned along one or more sides (including the face) of the scintillator sheet layer lacking an array of semi-continuous scintillator rods. The thicknesses of the top and bottom layers can be different.

Although single-sided and double-sided semi-continuous structured scintillator sheets are described as being comprised of two scintillator layers an equivalent description is a single scintillator layer comprised of two scintillator sub-layers. Double-sided semi-continuous structured scintillator sheets with an intermediate layer can be described as a single scintillator layer comprised of three scintillator sub-layers. Thus, variations of a 3D scintillator detector module can implement a single scintillator layer (a single scintillator sheet that is comprised of at least two scintillator sub-layers).

Another variation on the single-sided, semi-continuous rod-structured 3D scintillator detector module design is to implement a 2D array of semi-continuous discrete or virtual scintillator pixels on only the top or bottom layer (surface) of the scintillator sheet (a single-sided semi-continuous structured scintillator sheet with a pixel structure), forming a single-sided, semi-continuous pixel-structured 3D scintillator detector module. Variations on this single-sided, semi-continuous rod-structured or pixel-structured 3D scintillator detector module design is to implement a discrete scintillator M rod array or a 2D pixel array layer coupled to a continuous or semi-continuous scintillator sheet layer. One readout configuration implements readout photodetectors (discrete, strip, area) on the surface of at least one of the pixelated layer, the continuous scintillator layer. Readout resolution can be enhanced by implementing additional readout photodetectors positioned along one or more sides of the continuous scintillator sheet layer. As previously described herein, encoding techniques can be employed in order to enhance resolution.

Figure 14:
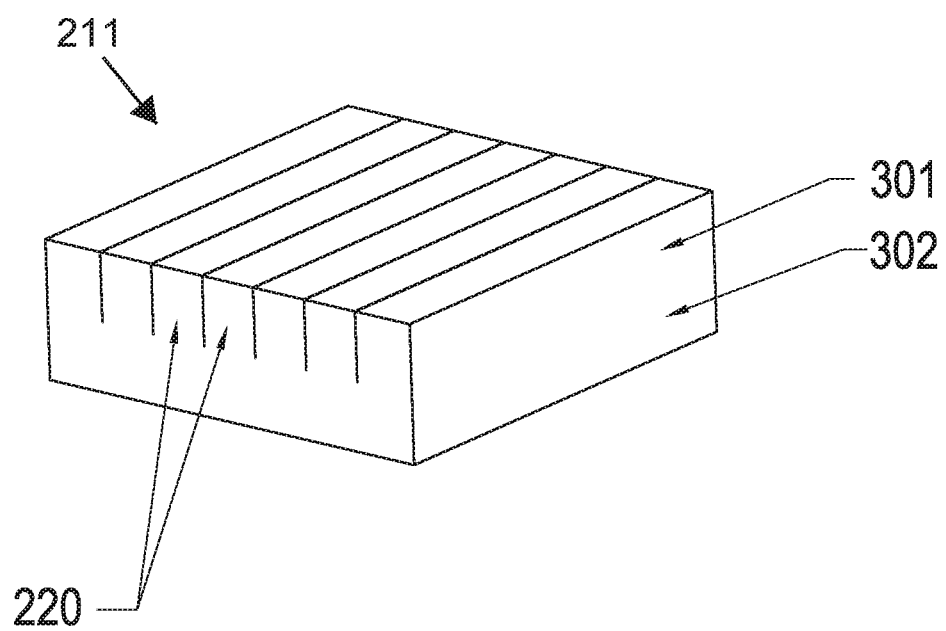
FIG. 14 is a perspective view of a single-sided, semi-continuous rod-structured 3D scintillator detector module implements a single scintillator sheet (a single-sided semi-continuous structured scintillator sheet with a rod structure) into which physical gaps are introduced in order to create an array of semi-continuous discrete scintillator rods in the top layer of the scintillator sheet.

FIG. 14 illustrates a single-sided, semi-continuous rod-structured 3D scintillator detector module 211 comprised of a single scintillator sheet (a single-sided semi-continuous structured scintillator sheet with a rod structure) into which physical gaps 220 of uniform depth are introduced in order to create an array of semi-continuous discrete scintillator rods in only one (here, the top layer 301) of two layers. The bottom (second) layer 302 is shown as continuous with no gaps. (These layers can also be referred to as virtual layers since there is no discrete boundary to separate the two layers.) The depth of the top (first) layer, for example, is defined by the depths of the individual gaps. Gap depths can be uniform or non-uniform within the array of semi-continuous scintillator rods (variations in depth could be irregular or follow a geometric pattern such as a circular arc, a parabolic arc, an elliptic arc, a sinusoid, etc.). Variations in gap depth may be employed in order to modify (locally) the distribution fluorescence (or other optical) signals.

Depending upon the application, the sheet can be inverted such that the top and bottom layers reverse their positions with respect to the location of the radiation source. Alternatively, one or more physical gaps can be replaced with virtual gaps creating one or more virtual scintillator rods. Readout photodetectors are positioned at both ends of the array of semi-continuous discrete or virtual scintillator rods. For the semi-continuous rod-structured or pixel-structured 3D scintillator detector module described herein previously described encoding techniques can be employed in order to enhance resolution.

The discrete structured 3D scintillator detector module and the double-sided, semi-continuous structured 3D scintillator detector module implementations (including implementations previously described herein such as arrays of crossed scintillator rods or an array of scintillator rods with a pixelated scintillator array configurations) can be modified to incorporate at least one (discrete or continuous) intermediate layer. An intermediate layer can implement a different thickness than the top and bottom layers. The Nelson (U.S. Pat. No. 7,635,848) discrete structured 3D scintillator detector module implementation can be modified to incorporate at least one discrete intermediate layer of rods (see Nelson, U.S. Pat. No. 8,017,906) or a transparent non-scintillator layer.

The scintillator or non-scintillator intermediate lay s) can be structured or unstructured (continuous). A transparent, structured or unstructured non-scintillator layer (as well as a scintillator layer) can be used to control the propagation of the fluorescence signals within and/or between top and bottom layers of scintillator rods. It can also be used to modify the radiation field interacting with the bottom scintillator layer (as well as backscattered radiation from the bottom scintillator layer). The properties of a scintillator intermediate layer (material, fluorescence efficiency, temporal decay, etc.) can be the same or be different from the properties of the top and bottom scintillator layers.

Thus, one variation implements an unstructured scintillator intermediate layer (a continuous scintillator sheet). Another variation implements at least one structured 2D pixelated scintillator intermediate layer (or a scintillator sheet with a 2D pixelated array). Yet another variation implements at least one structured parallel rod array scintillator intermediate layer (or a scintillator sheet with a parallel rod array). These parallel scintillator rods can be angled with respect to the top and bottom layers of crossed (arrays of) scintillator rods. The intermediate layer(s) of parallel scintillator rods can implement photodetectors at one end face or both end faces of the parallel scintillator rods or forgo photodetectors (reducing cost).

Yet a further variation implements a structured parallel rod array scintillator intermediate layer(s) (or a scintillator sheet with a parallel rod array) that is crossed with respect to the top and bottom layers of arrays of scintillator rods (for example, the top and bottom layers of arrays of scintillator are now parallel to each other if there is one intermediate layer). The intermediate layer(s) of parallel scintillator rods (or a scintillator sheet with a parallel rod array) can implement photodetectors at one end or both end faces of the parallel array of scintillator rods.

Another variation with a discrete intermediate layer replaces one layer of discrete scintillator rods and the discrete intermediate layer with one single-sided semi-continuous structured scintillator sheet (which implements either a scintillator rod array structure and/or a pixelated scintillator array structure). Yet another variation replaces the remaining layer of discrete scintillator rods with a second scintillator sheet (with a rod and/or pixel structure) a single-sided semi-continuous structured scintillator sheet with either a rod and/or pixel structure.

For the case of the double-sided, semi-continuous structured 3D scintillator detector module with an intermediate layer the total thicknesses of the semi-continuous discrete and/or virtual rods (or pixelated array) within the top and bottom layers of the double-sided semi-continuous structured scintillator sheet with a rod structure and/or a pixel structure) is now less than the thickness of the scintillator sheet. Previously herein-described physical or virtual structures can be introduced into or onto one or more of the discrete and/or semi-continuous scintillator rods and/or a discrete intermediate layer (for example, a 1D or 2D pattern of semi-continuous or virtual pixels can be introduced into discrete or virtual scintillator rods) or a continuous scintillator sheet intermediate layer in order to improve spatial and/or temporal and/or energy resolution. As previously described herein, encoding techniques can be employed in order to enhance resolution.

It should be understood, even if not explicitly stated, that the previously herein-described encoding techniques can be employed in order to enhance resolution for the detector inventions described herein. Furthermore, continuous or discrete patterns of WLS materials can be implemented with CT scintillator detectors (face-on or edge-on) as well as scintillator and non-scintillator materials in which Cherenkov radiation is generated and thereby provide at least one of: spatial encoding, wave length shifting, spatial redistribution of shifted-fluorescence signals, temporal shifting.

The WLS materials can be applied to one or more surfaces of scintillator rods or pixels used for CT x-ray detectors. For example, a scintillator with an emission spectrum that offers a poor optical match to the spectral response of a photodetector may be suitable for x-ray and/or gamma ray imaging with the application on appropriate scintillator surfaces of one or more WLS materials of a more desirable emission spectrum(s). In a similar manner the detection of short-wavelength optical Cherenkov radiation signals can also benefit from the application of WLS materials.

Temporal shifting (and wavelength shifting) can be used as a technique for spatial encoding for scintillator fluorescence radiation as well as Cherenkov radiation. The spatial redistribution of shifted-fluorescence signals can be used to reduce light trapping of a fraction of the scintillator fluorescence signal (or Cherenkov radiation) emitted within the scintillator volume, including optical fibers, scintillator fibers, face-on and edge-on scintillator detectors employed in CT, SPECT and PET detectors (or combinations thereof).

Readout configurations can vary according to resolution (spatial, energy, temporal) requirements. In general, photodetector readout densities for pixelated arrays (as well as block, slab, sheet, etc. scintillator geometries) can vary from one photodetector per scintillator pixel to less expensive implementations employing sparse arrays as well as readout photodetector arrays with non-negligible dead spaces (often with light guides) or strip detectors (with end readouts, or a single digital readout). Other approaches to compensate for photodetector readout arrays with non-negligible dead spaces include tapering the readout surfaces of the scintillator rods, and/or controlled light sharing between adjacent scintillator rods to improve optical coupling to the active photodetector areas. These readout configurations can be employed with the scintillator detectors (and detector modules) described herein.

In many instances a crossed rod geometry typically employs readout photodetectors at one end of each of the scintillator rod arrays, whereas a geometry that employs only an axially-oriented array of relatively long (e.g., longer than approximately 20-30 mm) parallel scintillator rods typically employs readout photodetectors at both ends of the scintillator rod array. (Note that previously herein-described variations include a readout at one end with or without encoding techniques.)

The crossed rod detector modules described herein, including crossed rod detector module geometries that employ relatively long scintillator rods in at least one layer, can implement readout photodetectors at one or both ends of at least one layer. Furthermore, the scintillator rods can be discrete or continuous (or a mixture thereof). Furthermore, arrays of parallel discrete or continuous rods (or mixtures thereof), including arrays of relatively long, parallel scintillator rods, can implement readout photodetectors at one or both ends of the array. Encoding techniques described herein for crossed scintillator rod detector modules can be used for parallel scintillator rod detector modules.

Some applications may require improvements (or can tolerate reductions) in one or more resolution parameters. If resolution improvements are required for either the one end or both ends readout configuration, then additional surfaces can be sampled with readout photodetectors (including all or parts of the ends of one or more scintillator rod arrays, all or parts of one or more sides of discrete or continuous intermediate layers, all or part of the face of a pixelated scintillator array) and/or encoding techniques can be implemented.

Any of the multi-layer rod detector module configurations described herein (including physical and virtual crossed rod, a pixel layer coupled to a rod layer, crossed rods with an intermediate layer, rods and pixels mixed within a layer, etc.) can employ readout photodetectors at one or both ends of at least one layer of rods. Multi-layer rod detector module configurations with single end or dual end readout implementations can include more than one intermediate layer and the intermediate layer or layers can be encoded (e.g., using scintillator materials with different properties, or using reflectors, scatterers, absorbers, WLS materials, Quantum dots/nanoparticles, etc.).

Suitable photodetectors include at least one of discrete pixel arrays, sparse arrays and strip detectors, as well as position sensitive detectors. Advantages may include improvements in at least one of timing resolution, spatial resolution, energy resolution, and increased rod lengths, with the potential for increased cost. For example, two layers of crossed rods could employ readout photodetectors at both ends of one layer of rods, and readout photodetectors at either one end or both ends of the crossed layer of rods. Yet another implementation of these various multi-layer rod detector module configurations employs readout photodetectors coupled to a single end of a single layer of rods, with controlled light channeling (using at least one of absorbers, reflectors, scattering materials, WLS materials, Quantum dots/nanoparticles, etc., to encode the spatial information).

Figure 15A:
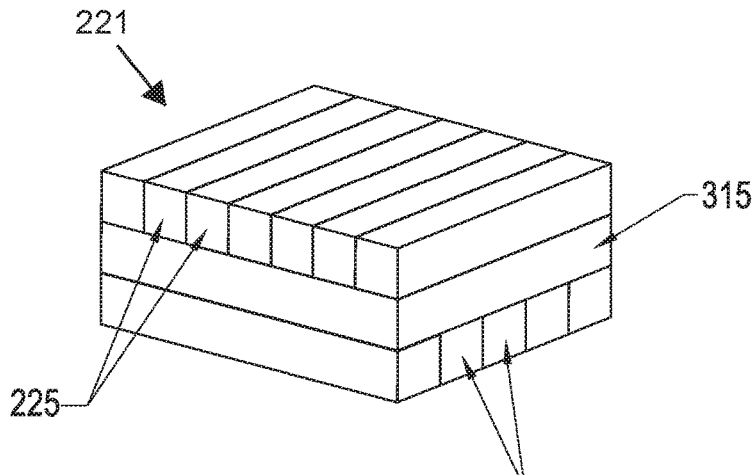
FIG. 15A is a perspective view of a discrete structured 3D scintillator detector module with crossed scintillator rods implementing a discrete intermediate layer.

FIG. 15A illustrates a discrete structured 3D scintillator detector module 221 with crossed scintillator rods 225 implementing a discrete intermediate layer 315.

Figure 15B:
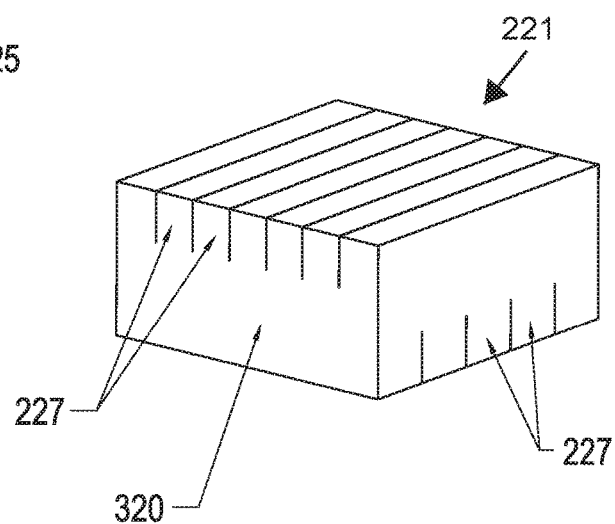
FIG. 15B is a perspective view of a double-sided, semi-continuous structured 3D scintillator detector module with crossed scintillator rods implementing a continuous intermediate layer.

FIG. 15B illustrates a double-sided, semi-continuous structured 3D scintillator detector module 221 with crossed scintillator rods 227 implementing a continuous intermediate layer 320 (a double-sided semi-continuous structured scintillator sheet with a rod structure and an intermediate layer). An alternative implementation employs a virtual pixelated intermediate layer.

Figure 15C:
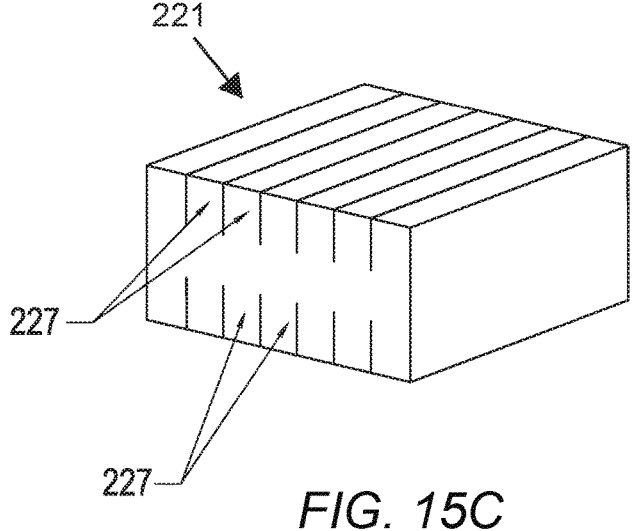
FIG. 15C is a perspective view of a double-sided, semi-continuous structured 3D scintillator detector module with parallel scintillator rods implementing a continuous intermediate layer.

FIG. 15C illustrates a double-sided, semi-continuous structured 3D scintillator detector module 221 with parallel scintillator rods implementing a continuous intermediate layer. Alternative implementations employ a virtual pixelated or crossed scintillator rods intermediate layer.

A conventional 2D scintillator rod parallel array detector module (face-on geometry) employs an array of discrete scintillator rods with a photodetector readout on one end (the bottom side or bottom end) of the array. Spatial resolution can be increased from 2D to 3D (adding depth-of-interaction (DOI) resolution for a face-on geometry or sub-aperture resolution (SAR) for the edge-on geometry) by positioning photodetectors (at least one photodetector may implement 2D spatial resolution) at both ends of the scintillator parallel array (using signal weighting between opposite photodetectors at the ends of a scintillator rod to compare signal strength at both ends) with reduced requirements for coincidence measurements between photodetectors at the two ends of the rods. Alternatively, photodetectors can be employ at one or both ends of the array of scintillator rods and light sharing and other encoding techniques described herein can be employed to provide 3D spatial resolution.

As previously described herein, weighting can also be employed with TOF resolution for a photodetector at both ends of a scintillator rod array (comprised of discrete rods or rods within a scintillator sheet or a combination of discrete rods and rods within a scintillator sheet). Alternatively, photodetectors with TOF resolution can be employed at only one end of a scintillator rod array using a comparison between the initial pulse and a direct reflected pulse or an effective reflected pulse (a delayed signal) from the opposite end (for example, a WLS reflected pulse) and/or encoding techniques, including segmentation, as described herein. One end (one-sided) and both end (two-sided) readout configurations can take advantage of previously described encoding techniques in order to implement 3D detector modules. For example, one or more scintillator properties of a scintillator rod such as temporal decay distribution, spectral distribution, conversion efficiency can be varied spatially along the length of a scintillator rod according to an encoded pattern. (Spatially-varying scintillator properties can also be used as a technique for encoding scintillator sheets.) Another technique for improving TOF resolution is to utilize the gamma ray interaction positional information along the length of the scintillator rod to correct for the position-dependent propagation time of the optical signal.

Continuous or discrete (encoded) patterns of WLS materials can be applied along the length of a rod such that wavelength and/or pulse shape properties vary with position. Both encoding techniques can be used together. (If the area of a rod face is sufficiently large 3D resolution within the rod is possible.) The top side of the 2D face-on detector design (one end readout) could employ a reflector (focused or planar) or one or more WLS materials (with or without a reflector). A 3D face-on detector design (or a 3D edge-on detector design) employing a parallel array of scintillator rods with a photodetector readout positioned along at least one of the top and bottom (or positioned along at least one of the two sides for the edge-on geometry) can implement these encoding techniques, as described for 2D face-on or edge-on detectors. Potential benefits include enhanced DOI spatial resolution (sub-aperture resolution (SAR) for the edge-on geometry), energy resolution and reduced ambiguity.

Two or more scintillator rods (including all rods) within a single row or within multiple rows of the parallel array of scintillator rods can be replaced by scintillator sheets (including structured scintillator sheets with a rod structure, continuous scintillator sheets, single sided and double-sided semi-continuous structured scintillator sheets with a rod structure). The encoding techniques described herein for use with scintillator rods can be implemented with scintillator sheets.

It should be noted that 2D/3D edge-on and face-on readout geometries are not limited to the ends of scintillator rods. 2D/3D edge-on and face-on (or combinations of edge-on and face-on) readout geometries also include, but are not limited to, the sides of scintillator rods, the sides and ends of scintillator rods, one or more sides of a scintillator sheet (including thick scintillator sheets/blocks).

The discrete structured 3D scintillator detector module design, as well as the variations taught herein, have described planar geometry implementations. There are radiation imaging applications (medical imaging, inspection, security, astronomy, high energy physics, etc.) that would benefit from the implementation of a focused detector geometry such as focused discrete structured or semi-continuous structured 3D scintillator detector modules (which can be employed in face-on or edge-on orientation). Consider the example of a face-on orientation of focused 3D scintillator detectors suitable for deployment in a spherical/cylindrical imaging geometry (other geometries can be implemented).

The focused discrete structured 3D scintillator detectors can be implemented by using crossed top and bottom spherical/cylindrical shell layers of parallel arrays of discrete and/or virtual scintillator rods in which the parallel rods in each layer are cut/sawed/etched/ion-implanted/laser-engraved using a scintillator spherical/cylindrical shell (sheet) segment. In a similar manner, focused double-sided semi-continuous structured 3D scintillator detectors can be implemented by using a single spherical/cylindrical shell layer and forming parallel arrays of semi-continuous discrete and/or virtual scintillator rods. All of the 3D detector module implementations previously discussed herein (double sided or single-sided, semi-continuous structured 3D scintillator detector modules, discrete structured 3D scintillator detector modules and semi-continuous structured 3D scintillator detector modules with at least one intermediate layer, etc.) can be implemented with a focused geometry. If acceptable ionizing radiation stopping power is maintained, one or more scintillator rods (up to and including all the rods) within any detector layer described herein can be replaced by conventional or encoded scintillator fibers or fiber optics (light pipes).

An alternative implementation is to approximate the shape of scintillator spherical/cylindrical shell segments with planar segments in which the arrays of discrete and/or virtual scintillator rods (or semi-continuous discrete and/or virtual scintillator rods) follow the curvature of the spherical/cylindrical geometry. The edges of the planar segments can be tapered if desired to form a close fit with nearest neighbor planar segments.

Note that in the case of a face-on or edge-on structured 3D scintillator detectors employed in a cylindrical geometry focusing in the radial direction is beneficial whereas focusing in the axial direction may be of reduced benefit in some applications relative to the cost of implementation. The benefit of axial focusing (see FIG. 3, FIG. 11) is readily apparent when point-like or relatively small radiation sources are used for imaging (e.g. x-ray radiography applications including, but not limited to, tomosynthesis, CT, cone beam CT, chest x-ray). Focusing can be implemented in PET, SPECT, probes/mini-PET or mini-Gamma cameras. An alternative for PET imaging is to implement only a subset of 3D detectors to implement axial focusing, thus reduced cost while allowing improved imaging over smaller regions of interest.

Focusing can be implemented with face-on structured mold detectors (semiconductor, scintillator, gas, etc.) used in single layer or multiple layer flat panel ionizing radiation detector applications (e.g., chest x-ray, cone beam CT, tomosynthesis, etc.) by varying the slant angle that holes (containing the detector material) make with respect to the flat panel surface. When used with a point-like radiation source the slant angle of the holes typically increases away from the flat panel center in order to compensate for the divergence of the point-like radiation source at the location of the flat panel. Optionally, for implementations using semiconductor materials the anodes (and/or cathodes) can be segmented (providing energy resolution and/or DOI capability for a face-on orientation and SAR for an edge-on orientation). Anode and cathode slant angles can be implemented with structured 3D silicon, 3D GaAs, 3D CdTe, 3D CIT, 3D Ge, 3D GaP, 3D GaSe, 3D diamond, 3D carbon nanotubes, 3D Se, 3D PbS, 3D InP, 3D $PbI_2$, 3D $HgI_2$, 3D PbO, 3D CdS, 3D TlBr, etc. (including doped semiconductors and other doped implementations of these materials).

Figure 16:
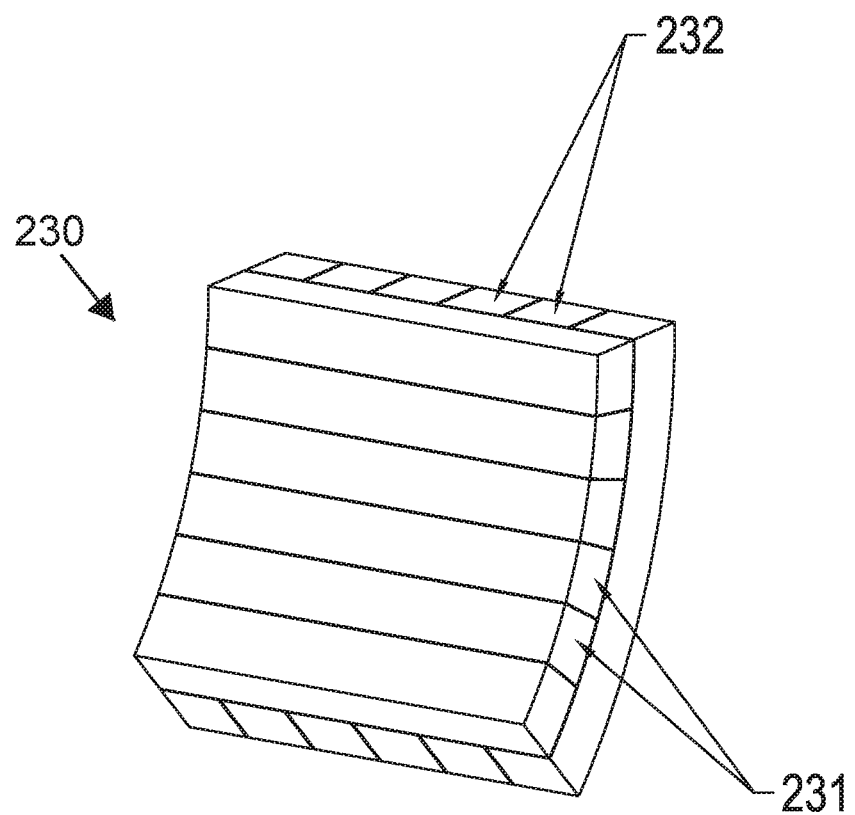
FIG. 16 is a perspective view of a focused discrete structured 3D scintillator detector module with crossed top and bottom cylindrical shell layers of parallel arrays of discrete scintillator rods.

FIG. 16 illustrates a focused discrete structured 3D scintillator detector module 230 with crossed top and bottom cylindrical shell layers of parallel arrays of discrete scintillator rods 231, 232. Other geometries (including, but not limited to, spherical layers) can also be implemented depending on the application. One or more discrete scintillator rods can be replaced with virtual scintillator rods. The 3D detector module implementations previously discussed herein can be implemented with a focused geometry, including implementations with intermediate layers.

3D Scintillator and Optical Fiber Detectors

Another implementation is a discrete structured 3D scintillator fiber detector module that implements one or more independent layers of 1D parallel arrays of scintillator fibers and/or at least one set of crossed coupled top and bottom (planar, spherical, cylindrical, etc.) layers of 1D parallel arrays of scintillator fibers (previously herein-described encoding techniques can be employed in order to enhance resolution. Including spatially-varying the properties of the scintillator fiber materials and the use of WLS materials and patterned WLS materials). (Note that these encoding techniques can also be employed with 2D arrays of scintillator fibers.)

One of the crossed scintillator fiber layers can be replaced by an optical fiber layer (which can implement WLS materials and patterned WLS materials). Spatial positioning within scintillator fiber (or fiber optic) layers can be determined by implementing one or more encoding techniques and/or employing photodetectors at both ends (using signal weighting to compare signal strength at both ends and/or TOF resolution techniques to compare initial pulse arrival times at both ends or measuring a delayed signal at both ends) or at one end (using TOF resolution to compare arrival times of the initial pulse with the direct reflected pulse or an effective reflected pulse (a delayed signal) from the opposite end (such as a WLS reflected pulse) of the independent layers (this is also applicable for 2D arrays of scintillator fibers, layers or arrays of non-scintillator fibers, crossed layers of scintillator fibers, crossed layer of non-scintillator fibers).

One or more non-scintillator supporting layers (as previously described herein) can be employed. The properties of the scintillator fibers (temporal decay, fluorescence efficiency, spectral distribution, energy-dependent and/or particle-dependent stopping power) within a parallel array as well as between crossed parallel arrays can be selected based on the application. For example, a fast scintillator fiber may be used for TOF applications. Previously herein-described readout geometries (photodetectors at one end or both ends) can be implemented for each layer of scintillator fibers (or optical fibers). One or more encoding techniques can be employed with the scintillator fibers, including, but not limited to, modifications to surface properties (reflective, roughness, absorptive, WLS coating, index of refraction coating, or coupling material properties), and/or embedding selected materials as a function of position, and/or assembling a scintillator fiber from scintillator fiber segments with the same or different properties.

A variation of the discrete structured 3D scintillator fiber detector module enhances detection efficiency by incorporating additional sheet, 2D or 3D scintillator (or semiconductor) detectors (which may also function as converters) which can be positioned behind, in front of, or behind and in front of the discrete structured 3D scintillator fiber detector module (depending on the application) in a stacked configuration. A discrete structured 3D scintillator fiber detector module can be manufactured with an area comparable to or greater than at least one sheet, 2D, or 3D scintillator detector (it can span multiple detectors).

A scintillator layer or layers (structured or continuous, comprised of discrete scintillator rods/pixels and/or scintillator sheets) can be coupled to one or more scintillator or optical fiber layers. A scintillator layer can be positioned between and coupled to crossed layers or parallel layers of scintillator fibers or optical fibers. A scintillator fiber or optical fiber layer can be shared between (top and bottom) scintillator layers and a scintillator or optical fiber layer can be coupled to and span multiple scintillator layers. The structured or continuous scintillator layer(s) can employ one or more photodetectors on one or more sides to enhance resolution.

If the scintillator or optical fibers are transparent to the scintillator detector fluorescence (or employ WLS materials to convert scintillator fluorescence to wavelengths that can be transmitted through the scintillator or optical fibers) then photodetectors can be coupled to scintillator layer sides coupled to the scintillator or optical fibers. Detection efficiency gains can be realized by incorporating additional sheet, 2D or 3D scintillator (or semiconductor) detectors (which may also function as converters). For example, a simple area photodetector (providing energy resolution and/or temporal resolution) could be coupled to one surface (crossing the Z axis) of a scintillator sheet/block (or an array of uniform or non-uniform scintillator sheets which may be optically-coupled, partially coupled, or optically-isolated) to provide energy resolution while crossed layers of scintillator or optical fibers (or a combination of both) are coupled to two surfaces (crossing an X axis and a Y axis).

One or both layers of scintillator fiber or optical fibers (or a combination of both) can be coupled to one or more scintillator sheets/blocks. Improvements in spatial resolution and/or a reduction in the number of scintillator and/or optical fiber layers can be achieved by replacing the simple area photodetector with an area detector with a readout at its four corners, a strip array photodetector, a 2D array photodetector.

A scintillator fiber layer (or an optical fiber layer) can be shared between (or coupled to) two adjacent intermediate scintillator layers within a stack geometry or other configurations. For example, the intermediate layers could be arrays of scintillator rods in parallel in a stack configurations. In another example, intermediate layers of sheets/blocks could share a scintillator fiber layer (or an optical fiber layer) in a stack geometry or adjacent sheets/blocks could share a scintillator fiber layer (optical fiber layer) in a different configuration (or one scintillator fiber layer (optical fiber layer) can be shared between two layers of sheets/blocks while the other scintillator fiber layer (optical fiber layer) is shared between two adjacent sheets/blocks. A scintillator fiber layer (optical fiber layer) can span one or more sheets/blocks. The structured or unstructured scintillator detector(s) can employ one or more photodetectors on one or more sides not coupled to the scintillator fibers in order to enhance resolution.

The choice of a scintillator fiber core is not limited to glass and plastic scintillators (including embedded nanoparticles), scintillator fiber cores can also be made from scintillator materials. Furthermore, by varying one or more scintillator properties of the scintillator fiber core (temporal decay distribution, spectral distribution, conversion efficiency, energy-dependent and/or particle-dependent stopping power) along its length according to a predetermined pattern then positional information can be encoded into the scintillator fiber core. Patterns can also be imposed using WLS materials.

Implementations of encoded scintillator fiber cores may be used to enhance resolution for the case of crossed fiber layers (with or without an intermediate scintillator detector layer) or (if encoding permits sufficient accuracy) alternatively allow the use of uncrossed fiber layers. Cherenkov radiation can also be recorded. Readout photodetectors are coupled to one end or both ends of each array of crossed scintillator fibers. If the readout photodetectors are only coupled to one end then the opposite end is typically covered with a reflector material and/or a WLS material. This represents an alternative to reading out both ends of each single layer of scintillator fibers.

A variation of the discrete structured 3D scintillator fiber detector module coupled to at least one intermediate scintillator layer (structured or unstructured, including scintillator rods and/or pixels, scintillator sheets/blocks, continuous scintillator sheets) implements a layer of optical fibers (including WLS materials) in place of one or both layers of scintillator fibers that are cross couple to the at least one intermediate scintillator layer (a discrete structured 3D scintillator fiber-fiber optic detector or a discrete structured 3D fiber optic-fiber optic detector, respectively). Each layer of optical fibers is separated from its nearest crossed neighbor layer of scintillator fibers or optical fibers by an intermediate scintillator detector layer.

These scintillator and/or fiber optic layers can span multiple intermediate scintillator detectors or a single intermediate scintillator detector. A scintillator fiber layer or a fiber optic layer can be shared between (coupled to) two adjacent intermediate (discrete or continuous) scintillator layers within a stack configuration. The structured or unstructured scintillator detector(s) can employ one or more photodetectors on one or more sides not coupled to the scintillator fiber layer or the optical fiber layer in order to enhance resolution (at additional cost).

Figure 17:
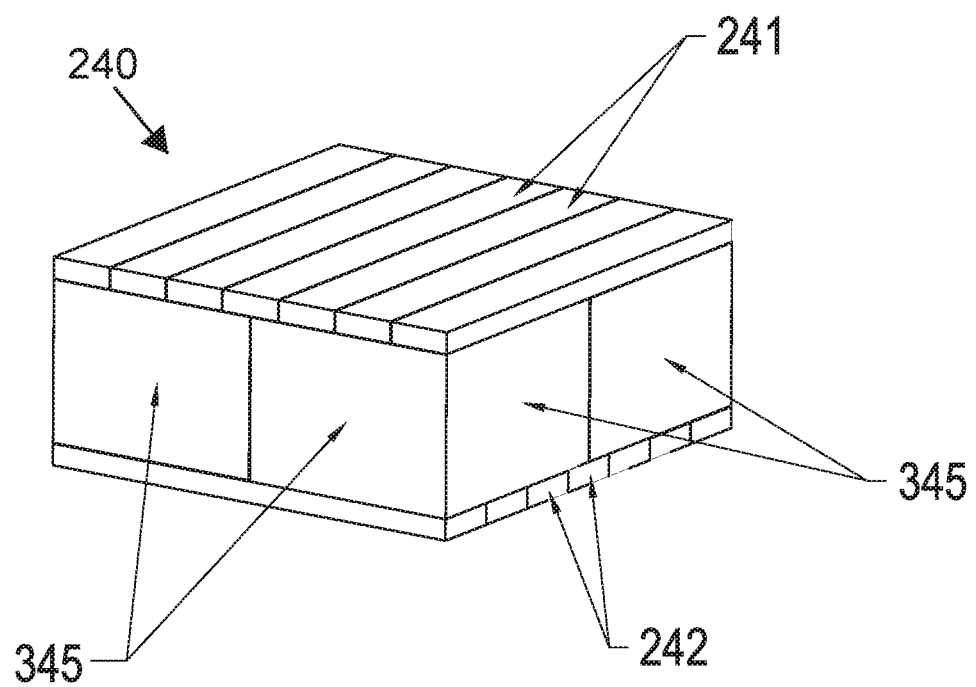
FIG. 17 is a perspective view of a discrete structured 3D scintillator fiber detector module in which a structured intermediate scintillator layer (comprised of multiple scintillator detector blocks is positioned between and coupled to crossed planar layers of scintillator fibers.

FIG. 17 illustrates a discrete structured 3D scintillator fiber detector module 240 in which a structured intermediate scintillator layer (comprised of multiple scintillator detector sheets/blacks 345) is positioned between and coupled to crossed planar layers of scintillator fibers 241, 242. A scintillator fiber layer (or, alternatively a fiber optic layer) is not constrained to terminate at the outer boundary of a structured intermediate scintillator layer (as shown in FIG. 17) or an unstructured intermediate scintillator layer.

It should be noted that the 3D particle detectors that implement light-sharing designs may have both positive benefits and negative potential consequences. Positive benefits, depending on the design, typically include features such as cost-savings and detector design flexibility. Negative potential consequences, depending on the design, typically impact one or more features such as: detection rates, energy resolution, temporal resolution, coincidence detection.

Consider the following example of a double-sided semi-continuous structured 3D scintillator detector module. A 4 mm thick, square-shaped (other geometric shapes such as rectangles, circles, etc. can be implemented according to detector requirements) scintillator sheet (a double-sided semi-continuous structured scintillator sheet with a rod structure) has a parallel array of semi-continuous discrete scintillator rods, each 2 mm deep and 2 mm wide, cut/sawed/etched/ion-implanted into the top surface. An identical parallel array of semi-continuous discrete scintillator rods (2 mm deep, 2 mm wide) is cut/sawed/etched/ion-implanted/laser-engraved into the bottom surface but in a crossed direction (typically 90 degrees) to the orientation of the top surface array of rods.

The ends of the cut/sawed/etched/ion-implanted/laser-engraved semi-continuous discrete scintillator rods (or discrete scintillator rods) not coupled to photodetectors) can be shaped, patterned, coated, etc. as desired to provide good optical coupling to photodetectors. One or more coatings can be applied to any accessible semi-continuous discrete scintillator rod walls (specular reflective, diffuse reflective, low index, WLS, etc.). For example, a two-layer coating (or covering) could include a diffuse reflector such as Teflon tape backed by an aluminum specular reflector layer (as an alternative to a multiple Teflon tape layers of greater thickness), and may be beneficial for TOF PET as well as conventional PET imaging. Coatings can be continuous or applied in patterns. Accessible semi-continuous discrete scintillator rod walls can be completely or partially polished (smooth), etched or roughened (patterns can be implemented). Internal structures can be introduced into the scintillator sheet. Previously herein-described encoding techniques (including varying one or more scintillator properties of a scintillator rod along its length) can be employed in order to enhance resolution. Readout photodetectors are coupled to at least one end of at least one array of scintillator rods comprising the top and bottom layers.

Discrete and Semi-Continuous Structured 3D Scintillator Detectors with Intermediate Layers Nelson (U.S. Pat. No. 7,635,848) has previously taught the implementation of at least one additional intermediate layer of crossed arrays of discrete scintillator rods. For the case of one intermediate layer the discrete scintillator rod arrays of the top and bottom layers are parallel to each other and crossed with respect to the discrete rod array of the one intermediate layer. An alternative is to replace the at least one additional intermediate layer of an array of discrete scintillator rods with at least one non-scintillator or scintillator sheet (or spacer).

Consider the case of a scintillator sheet intermediate layer in which the intermediate layer scintillator material(s) can be different from the scintillator materials implemented in the top and bottom layers. Coatings (including structured/patterned coatings, WLS coatings, coupling materials, etc.) can be added to the surfaces and internal structures can be introduced into the intermediate scintillator sheet layer (as well as the top and bottom layers) as needed to enhance optical coupling and/or to direct the propagation of optical signals (fluorescence and in some instances Cherenkov radiation). Previously herein-described encoding techniques can be employed in order to enhance resolution for the intermediate scintillator sheet layer as well as the top and bottom layers.

The thickness of the intermediate layer of scintillator material is typically chosen to be one times the thickness of the top or bottom layer although other multiples greater than or less than one may also be chosen as advantageous based on a factors such as energy resolution, temporal resolution, spatial resolution, stopping power, cost of materials and cost of readout electronics. In one implementation the scintillator sheet intermediate layer implements a discrete or virtual array of rods or pixels. In another implementation the scintillator sheet intermediate layer is continuous. In yet another implementation the scintillator sheet intermediate layer is semi-continuous (single-sided, double-sided, double-sided with an intermediate layer).

The result of adding an intermediate layer is that in some implementations the readout optical signals will be more spread-out (dispersed). If spreading out of optical signals is determined to be desirable independent of using an intermediate scintillator layer then an alternative is to implement a transparent non-scintillator sheet (fiber array, plastic, epoxy, gel, fluid, air) which may have an internal structure. The thickness of the transparent non-scintillator intermediate layer can be selected to control the spread of the optical signal. The index of refraction (IOR) of the non-scintillator intermediate layer material can be selected (within limits) to improve at least one of spatial resolution, temporal resolution, optical signal collection. The non-scintillator intermediate layer can have one or more internal structures including, but not limited to, physical pixels, virtual pixels, patterns of embedded microstructures such as low IOR microspheres (or microellipsoids, etc.) for the purpose of redirecting optical signals propagating between the top and bottom layers.

Consider the example of a semi-continuous, double-sided with an intermediate layer structured 3D scintillator detector module wherein the scintillator sheet/block has dimensions of W=L=N1 mm, thickness=6 mm. (In this example assume N1 is an integer multiple of 2 for convenience.) An array of (N1×0.5) semi-continuous discrete or virtual scintillator rods with dimensions of 2 mm×N1 mm and a consistent depth (thickness) of 2 mm are cut/sawed/etched/ion-implanted/laser-engraved into each of the top and bottom surface. (Note that other semi-continuous discrete or virtual rod depths can be implemented to modify light propagation and the rod depth can be varied spatially between rods and along the length of a rod.) For the case of a consistent rod depth of 2 mm the effective intermediate layer has a consistent effective thickness of 2 mm (other effective thickness can be implemented). In some implementations the effective intermediate layer can be readout from one or more sides or not at all (relying exclusively on the readout detectors coupled to at least one end of at least one array of semi-continuous discrete scintillator rods comprising the top and bottom layers. The result of adding an intermediate layer is that the readout optical signals will generally be more dispersed.

Detector Stack Configurations

The Nelson (U.S. Pat. No. 7,635,848) discrete structured 3D scintillator detector module designs as well as the variations taught herein can be implemented in a detector configuration with a depth of 1 module or a depth of at least 2 modules (a stack). A stack configuration of 3D detector modules extends the flexibility inherent to a single module implementation. Properties of modules within a stack can range from being identical to being highly dissimilar. Individual layer thickness, module thickness, individual layer spatial resolution, individual layer scintillator material(s) as well as optional conversion materials can be tailored for specific imaging (and/or tracking) applications including single and multiple radiation fields encountered in x-ray radiography and CT imaging, nuclear medicine and PET imaging, radiation therapy (of all types), probes, high energy physics, astronomy, industrial imaging, homeland security, etc.

The stack configuration offers significant flexibility in the choice of detectors and therefor is not limited to implementing only structured 3D scintillator detector modules. Face-on and edge-on scintillator and/or semiconductor detectors (included structured scintillator and semiconductor detectors as well as scintillating fibers or WLS fibers) can be incorporated into a stack configuration. A stack configuration may enable the use of scintillator materials with one or more properties such as stopping power, fluorescence efficiency, temporal decay, manufacturability that would otherwise limit their use in a conventional PET detector implementation. Additional variations on the 3D scintillator detector module stack introduce at least one semiconductor or structured detector layer between at least two adjacent 3D scintillator detector modules within a stack and/or replace at least one 3D scintillator detector module with at least one semiconductor or structured detector layer within a stack.

For example, consider the case of a detector stack implemented for SPECT and PET imaging. The at least one front-end structured 3D scintillator detector module in the stack can be adapted for low energies such as 140.5 keV (Tc-99m) used in SPECT imaging while the back-end structured 3D scintillator detector module(s) can be adapted for PET imaging. Alternatively, at least one of the front-end and back-end structured 3D scintillator detector modules can be integrated into a single structured 3D scintillator detector module. Slower scintillators may be acceptable for SPECT whereas faster scintillators would be preferred for PET. Alternatively, the same or a different PET scintillator may be employed for SPECT imaging.

Furthermore, consider the case of a detector stack implemented for CT (ring CT, cone beam CT, tomosynthesis) and PET imaging. The front-end detector module(s) could implement an edge-on or face-on scintillator or semiconductor detector module(s) offering at least one of energy integration, photon counting, photon counting with energy resolution capability suitable for CT (including tomosynthesis). Optional energy-dependent radiation attenuation filter layers can be inserted between one or more layers within the front-end modules(s) and/or an energy-dependent radiation attenuation filter layer can be inserted between the front-end module(s) and the back-end module(s) to modify the spatially-dependent radiation spectrum (non-scattered and scattered photons, characteristic x-rays, bremsstrahlung, electrons) in order to enhance energy resolution and/or reduce the detection of undesirable radiation. If photon counting with energy resolution is implemented and excessive count rates that significantly degrade energy resolution are experienced then the electronics can automatically implement either photon counting or energy integration capability. The back-end detector module(s) could implement optional edge-on or face-on scintillator or semiconductor detector modules including structured 3D scintillator detector modules, axial scintillator fiber arrays, etc. as described herein.

Multi-Energy CT, CT with Pet/Spect

Consider the case of a planar or focused edge-on detector array module implemented for single or multiple x-ray source CT (ring CT, cone beam CT, split-beam CT, or tomosynthesis) with or without a stack detector implemented for PET (or SPECT) imaging. An edge-on, n-level multispectral CT detector module (aligned with the axial direction) implements one or more CT scintillators for the n levels with photodetector readouts. Optional energy-dependent radiation attenuation filter layers can be inserted between one or more CT scintillator layers. If an additional back-end detector module (for example, a SPECT and/or PET detector module), separate or integrated directly with the CT detector module, is employed behind the n-level multispectral CT detector module then an optional energy-dependent radiation attenuation layer can be inserted between the CT detector module and the additional back-end detector module.

The choice of detector element scintillator and/or the depth of the scintillator (in the radial direction) can be adjusted to compensate for x-ray beam hardening as it propagates through each of the n levels of scintillator material (and any optional attenuation filters), constituting a "poor man's" n-level multispectral CT scintillator detector implementing one or more x-ray sources (also applicable for cone beam CT, split-beam CT and tomosynthesis). Energy calibration will be implemented.

For the case of n=1 there is only one energy level (conventional, single spectrum CT detector). A simple example of a multispectral CT detector is the n=2 case (dual energy). The top scintillator level (level 1) would implement a low-Z x-ray/gamma ray scintillator (or a reduced thickness of a high-Z x-ray/gamma ray scintillator) and the bottom scintillator level (level 2) would implement a high-Z x-ray/gamma ray scintillator with 2 levels of photodetectors providing signal readout. An x-ray energy filter can be positioned between the two levels of scintillator and optionally in front of the top level (level 1) scintillator.

Each two-level edge-on detector array is aligned with the axial direction and distributed in a circle or semi-circle (full ring or partial ring CT detectors, respectively). Similar dual energy (multi-energy) configurations can be implemented for planar cone beam CT and tomosynthesis detectors (optionally, focusing can be implemented in the radial and/or axial direction) as well as curved cone beam and tomosynthesis detector implementations. The distribution of scintillator levels and/or scintillator materials can be varied in the axial direction to accommodate different x-rays spectrums (from a single filtered x-ray source or from multiple x-ray sources distributed in the axial direction). This variation along the axial direction can also be implemented if an n-level multispectral CT semiconductor detector is employed. The spectral CT designs described herein may also be implemented for cone beam CT and tomosynthesis. Focused collimators or focused collimators with a curved geometry can be implemented in order to reduce x-ray scatter.

The flexibility of the multilayer design includes the use of edge-on and/or face on detectors, one or more detector materials, at least one of energy resolution, PC capability, energy integration capability. Some designs involve sharing one or more layers of detectors for two or more imaging modalities (CT, SPECT, PET, Compton). Although conventional CT benefits from the use of a point-like x-ray source (with implied directionality) the typical broad x-ray energy spectrum and high x-ray count rates per pixel may impose a financial and engineering burden on the multi-spectral CT designers.

A variation of the previously herein-described "poor man's" n-level multispectral CT scintillator detector sacrifices the x-ray stopping power of the layer 1 scintillator with a higher quality (such as a semiconductor) energy-resolving detector layer(s) while emphasizing the stopping power of the energy-integrating detector layer(s) (which may be shared, for example, with a PET detector system). A thinner version of a detector (with respect to the direction of the incident radiation) typically offer lower stopping power but with potential advantages such as faster response, better energy resolution, a lower count rate and a lower cost.

For example, in one implementation, a dual layer spectral CT detector employs a first layer comprised of relatively thin (in terms of x-ray stopping power) pixelated, face-on semiconductor detectors and the second layer implements a relatively thick (in terms of x-ray stopping power) pixelated, face-on (or edge-on) scintillator detector. The first layer offers sufficient stopping power to ascertain the incident x-ray spectral distribution (within the guidelines established for patient radiation) while limiting pulse pile up effects. The second layer (which could, for example be based on a pixelated, face-on CT detector array) offers substantial stopping power and functions as an energy integrator.

The total detector energy for pairs (or multiple pairs) of aligned detector pixels can be summed. Spectral data from individual or neighboring detector pixels of the first layer can be evaluated. Corrections can be applied to account for scattering within and between detector layers as well as the responses of the first and second layer detectors. The spectral and total detector energy data can then be evaluated with respect to calibration data in order to implement multi-spectral CT reconstruction. Pixels sizes of the first and second layer detectors can be the same or they can be different (as previously described herein for the case of CT-PET).

Other variations of this two layer spectral CT design employ edge-on detectors in the first and second layers or a combination of edge-on and face-on detectors in the two layers. The first layer is not limited to semiconductor detectors. One alternative is structured semiconductor detectors.

The second layer is not limited to scintillators. Semiconductor or structured semiconductor detectors (or other detector types) can be employed.

This multi-spectral CT design can be extended to three or more layers including one or more relatively thin layers (multiple thin layers can use the same or different semiconductor or structured semiconductor detector materials) followed by one or more relatively thick layers (which can be of the same or different scintillator, semiconductor, structured semiconductor, etc.) detector materials. For example, one or more relatively thin semiconductor detector layers could be combined (as the top layer or layers) with a "poor man's" n-level multispectral CT scintillator detector.

In yet another example, one or more layers of a relatively low-Z semiconductor (for efficient sampling of lower energy x-rays with energy resolution or photon counting) could be followed by a relatively moderate-Z (or high-Z) semiconductor layer (for efficient sampling of higher energy x-rays with energy resolution or photon counting), followed by a moderate-to-high Z scintillator layer (with energy integration capability) or a semiconductor layer (with at least one of energy resolution or photon counting or energy integration capability). These designs may also be employed with cone beam CT detectors, split-beam CT detectors and tomosynthesis detectors.

Multispectral CT detectors (including ring CT, cone beam CT and tomosynthesis detectors) can be implemented in scanner systems with one or more x-ray sources (x-ray tubes, scanning electron beams) and the x-ray sources can be operated at one or more (switched) voltage levels providing one or more x-ray spectrums and/or temporal pulse properties and sequences. Ring CT geometries include full ring and partial ring configurations. A partial ring CT geometry employs at least one partial ring and at least one x-ray source. A full ring CT geometry typically employs multiple x-ray sources or a scanning electron beam source, permitting faster acquisition times with reduced mechanical wear. Focused collimators or focused collimators with a curved geometry can be implemented in order to reduce x-ray scatter.

CT data (as well as PET data) can be correlated with other patient monitoring data (such as EKG data) for purposes of gating. CT scanners (and tomosynthesis scanners) typically include at least one of collimators and/or numerical techniques to provide x-ray scatter reduction and/or to correct for scatter. An external collimator can be made mobile if desired. The edge-on detector design will typically include external collimation and may incorporate internal collimation to reduce x-ray cross talk and/or shield readout ASICs from direct radiation.

Figure 18A:
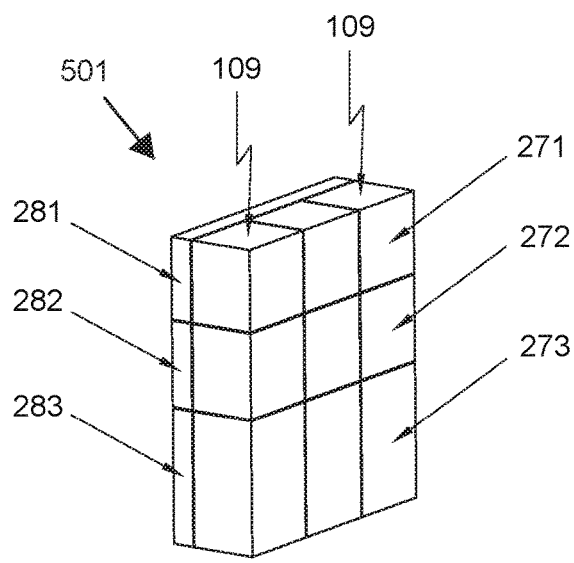
FIG. 18A is a perspective view of an edge-on, planar n-level (n=3) multispectral CT detector comprised of an array of detector elements which implement photodetectors coupled to the side faces of scintillators which may differ in at least one of different scintillator material, different scintillator depths.

FIG. 18A illustrates an edge-on, planar n-level (n=3) multispectral CT (ring CT, cone beam CT, split-beam CT, tomosynthesis) scintillator detector 501 comprised of an array of detector elements which implement photodetectors 281-283 coupled to the side faces of scintillators 271-273 with incident radiation 109. FIG. 18A illustrates only 3 detector elements in each row for illustrative purposes. The number of detector elements per row can greatly exceed 3 for many applications. Detector element scintillator materials and/or depths can be the same or they can be different depending on the application.

Figure 18B:
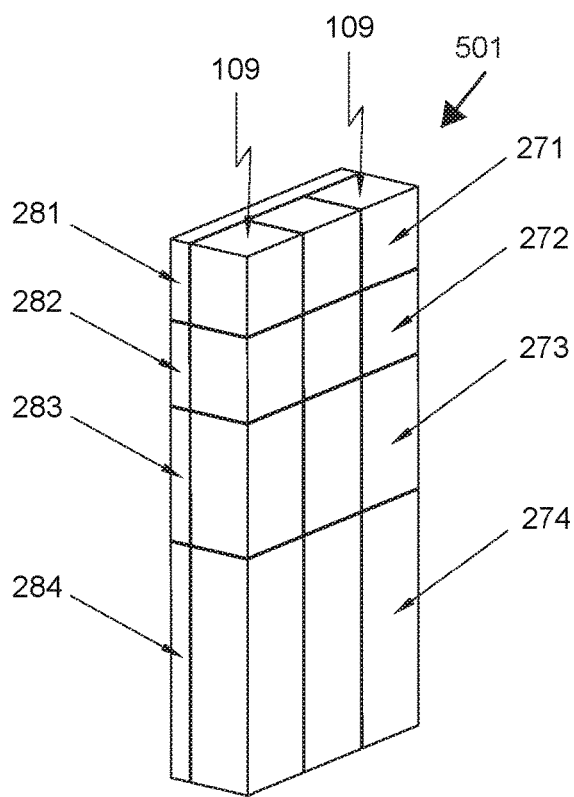
FIG. 18B is a perspective view of an edge-on, planar n-level (n=4) multispectral CT detector comprised of an array of detector elements which implement photodetectors coupled to the side faces of scintillators which may differ in at least one of different scintillator material, different scintillator depths.

FIG. 18B illustrates an edge-on, planar n-level (n=4) multispectral CT (ring CT, cone beam CT, split-beam CT, tomosynthesis) scintillator detector 501 comprised of an array of detector elements which implement photodetectors 281-284 coupled to the side faces of scintillators 271-274 with incident radiation 109. For each value of n (1-4) the scintillator materials and/or scintillator depths can be the same or different. The value of n within each column can be same or can be varied along the direction of the rows of detector elements. An x-ray energy filter can optionally be positioned between one or more adjacent levels of scintillators. Furthermore an energy filter can optionally be positioned in front of the top level (level 1) scintillator.

Although FIG. 18A illustrates individual rows of uniform detector elements (along the axial direction) the flexibility of this design permits n to be varied along the axial direction according to the application requirements. One implementation butts independent edge-on, planar multispectral CT detectors with different values of n in the axial direction. Another implementation involves electronically (or during post-processing) combining two or more adjacent photodetectors (pixel merging) and thereby reduces the local value of n. For example, the n=4 multispectral CT (ring or cone beam CT, split-beam CT, tomosynthesis) detector elements could be positioned to cover the volume of the patient requiring maximum spectral resolution whereas other patient volumes could be covered by n<4 multispectral CT (or tomosynthesis) detector elements.

The edge-on, n-level scintillator detector (or a section thereof) can be replaced by an edge-on, n-level semiconductor detector (including a structured semiconductor detector). Furthermore, one or more edge-on scintillator detector levels can be replace by edge-on or face-on semiconductor (or structured semiconductor) detector levels. Optionally, at least one energy-dependent radiation attenuation filter can be included with the edge-on, n-level semiconductor detector (with or within the structured semiconductor detector) or combinations of edge-on scintillator detector layers and semiconductor (structured semiconductor) detector layers.

Continuous or discrete patterns of WLS materials can be implemented with face-on scintillator CT detectors and edge-on (single energy or multispectral) scintillator CT detectors described herein, providing at least one of spatial encoding, spatial redistribution of shifted-fluorescence signals, wavelength shifting, temporal shifting in dedicated CT scanners or scanners in which CT is integrated with at least one of a SPECT, PET or Compton camera. For example (as previously described herein), a scintillator with an emission spectrum that offers a poor optical match to the spectral response of a photodetector may be suitable for x-ray and/or gamma ray imaging with the application on appropriate surfaces of one or more WLS materials of a more desirable emission spectrum(s). The spatial redistribution of shifted-fluorescence signals can be used to reduce light trapping of a fraction of the scintillator fluorescence signal emitted within the scintillator volume.

The n-level, multispectral CT (ring CT, cone beam CT, tomosynthesis) detector can be integrated with a PET and/or SPECT and/or Compton detector (the back-end detector) and/or a radiation therapy system, including the PET and/or SPECT and/or Compton detectors described herein, implementing at least one of simultaneous or sequential acquisition of CT and PET and/or SPECT images. One or multiple x-ray sources (x-ray tubes, scanning electron beams, etc.) can be employed. Multiple x-ray sources can be distributed along the circumference of a ring and/or along the axial direction. Multiple x-ray sources can be used to provide at least one of: reduced acquisition times (improved temporal resolution), multiple x-ray spectrums.

In general, if gaps within the PET and/or SPECT and/or Compton detectors are due to the presence of one or more x-ray sources then more complete sampling can be achieved by inserting removable PET and/or SPECT detector modules (electronically linked to the existing detector modules) into the gaps when the x-ray sources are no longer needed or existing PET detector modules can be temporarily rotated into the position of the gaps. The extent of the CT detector and PET and/or SPECT and/or Compton detector along the circumference or in the axial direction can be the same or different. If a partial ring geometry CT implementation is preferred to a full ring geometry implementation then the properties of any external PET and/or SPECT and/or Compton detectors used to implement a functional PET and/or SPECT scanner can be the same or different from the properties of the integrated CT-PET and/or SPECT detectors.

For example, the external PET and/or SPECT and/or Compton detectors could employ non-functional substitutes for front end CT detector materials employed with the integrated CT-PET and/or SPECT detectors in order to reproduce the scatter and absorption properties of the front end. CT detector. Similar principles apply for the cases of cone beam CT and tomosynthesis imaging detectors. Previously herein-described energy calibration techniques can be employed. Positioning stacked structured 3D scintillator detectors (or other 2D/3D PET and/or SPECT and/or Compton detectors including edge on and/or face on high-Z scintillator or semiconductor detectors or structured semiconductor or axial scintillator fiber array detectors) beneath this edge-on, n-level multispectral CT detector for PET and/or SPECT imaging is one option.

Another option is to extend the edge-on, n-level multispectral CT scintillator detector in depth to include m-levels of edge-on PET and/or SPECT scintillator(s) detectors (edge-on, n/m-level CT-PET, CT-SPECT or CT-SPECT-PET detector) in place of the 2D or 3D scintillator detectors, etc. The dimensions of the back-end readout pixels as well as the scintillator elements used for PET and/or SPECT and/or Compton detectors can be different from the dimensions of the readout pixels and scintillator elements used for CT (and tomosynthesis) detectors. (Note that, as previously described herein, Compton detectors can be used as PET and/or SPECT detectors and vice versa. If only PET and/or SPECT detectors are described then in at least one implementation they can incorporate Compton detector features).

The edge-on, n/m-level CT-PET, CT-SPECT or CT-SPECT-PET (including ring and cone beam CT, split-beam CT, tomosynthesis) detector allows for many configurations (including Compton implementations of PET and/or SPECT). For example, replace one level (level n) of the n-level multispectral CT detector with one additional level of a PET scintillator (along with any appropriate changes in the readout photodetector and electronics) in either the extended edge-on detector array configuration or the n-level edge-on detector array configuration followed by a 3D scintillator detector stack). If the level n CT scintillator employed integrating readout electronics with a photodiode then these items can be replaced with a photodetector offering gain (such as SiPMs, silicon nanowires, APDs, etc.) and readout electronics capable of at least one of energy integration or photon counting as well as photon counting with energy resolution. The collimated CT radiation is preferably incident on an entry side face whereas gamma radiation typically experiences limited or no collimation and can be incident on multiple side faces (including the photodetector-coupled side face).

In general, the depth of the additional level of PET scintillator can be implemented so as to provide acceptable detection efficiency (stopping power, fluorescence light collection) for the CT spectrum present at that level and thus can be different from the old level n CT scintillator depth as well as any of the m levels of PET scintillator depths. The limiting case involves replacing all n levels of CT scintillators (including the case n=1) with n levels of PET scintillators of appropriate depths. The PET scintillator(s) employed with the m-levels of PET scintillators need not be the same as the PET scintillator(s) employed with the replaced level(s) of CT scintillators.

The implementation of one or more PET scintillator materials is typically based on various physical properties such as energy-dependent stopping power, fluorescence efficiency, fluorescence spectrum, transparency and index of refraction, temporal decay, radiation hardness, hydroscopic nature, etc. as well as cost The edge-on design will typically include some internal collimation to reduce x-ray cross talk and shield readout electronics (such as ASICs) from direct CT (or tomosynthesis) radiation. An external collimator (which can be made mobile if desired) is typically used for CT to provide x-ray scatter reduction although an alternative is to implement numerical algorithms may be employed to estimate and correct for x-ray scatter. In some implementations PET detectors implement internal collimation. The presence of any internal as well as any external detector collimation should be accounted for when acquiring simultaneous or sequential CT (or tomosynthesis) and PET images.

Figure 19A:
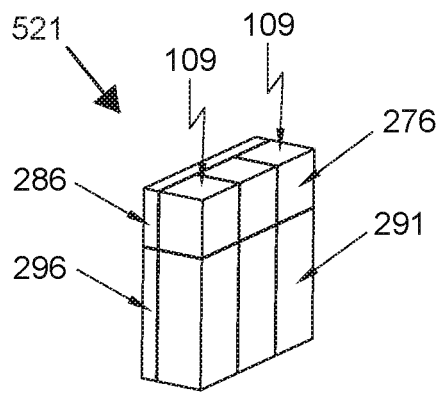
FIG. 19A is a perspective view of an edge-on, n/m-level CT-PET detector for n=1 and m=1 in which the PET detector implements photodetectors coupled to the side faces of scintillators.

FIG. 19A illustrates an edge-on, n/m-level CT-PET detector 521 for n=1 (photodetectors 286 coupled to the side face of scintillators 276) and m=1 in which the PET detector implements photodetectors 296 coupled to the side face of scintillators 291.

Figure 19B:
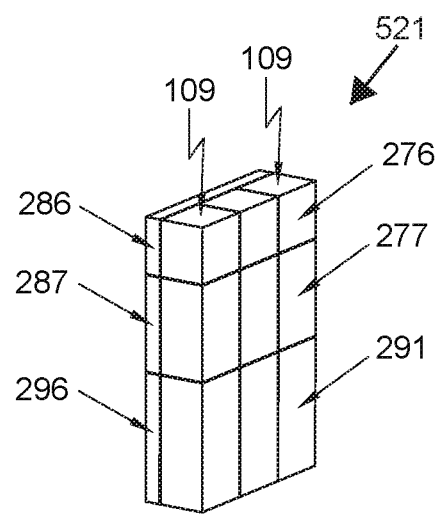
FIG. 19B is a perspective view of an edge-on, n/m-level CT-PET detector for n=2 and m=1 in which the PET detector implements photodetectors coupled to the side faces of scintillators.

FIG. 19B illustrates an edge-on, n/m-level CT-PET detector 521 for n=2 (photodetectors 286, 287 coupled to the side faces of scintillators 276, 277) and m=1 in which the PET detector implements photodetectors 296 coupled to the side face of scintillators 291.

Figure 19C:
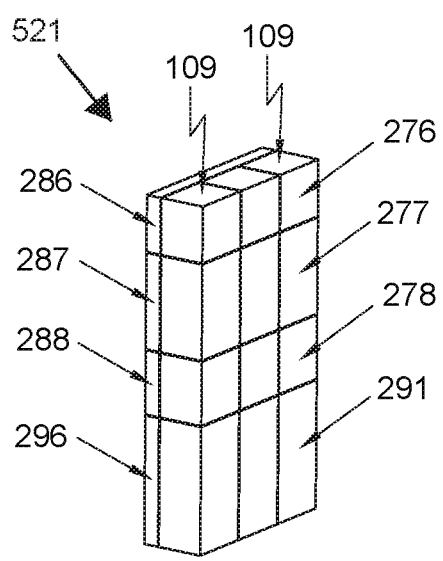
FIG. 19C is a perspective view of an edge-on, n/m-level CT-PET detector for n=3 and m=1 in which the PET detector implements photodetectors coupled to the side faces of scintillators.

FIG. 19C illustrates an edge-on, n/m-level CT-PET detector 521 for n=3 (photodetectors 286, 287, 288 coupled to the side face of scintillators 276, 277, 278) and m=1 in which the PET detector implements photodetectors 296 coupled to the side face of scintillators 291.

Figure 19D:
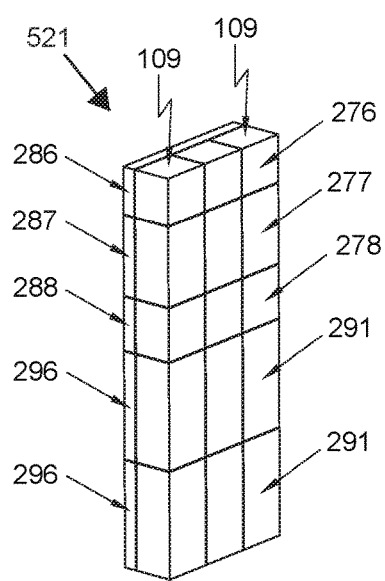
FIG. 19D is a perspective view of an edge-on, n/m-level CT-PET detector for n=3 and m=2 in which the PET detector implements photodetectors coupled to the side faces of scintillators.

FIG. 19D illustrates an edge-on, n/m-level CT-PET detector 521 for n=3 (photodetectors 286, 287, 288 coupled to the side face of scintillators 276, 277, 278) and m=2 in which the PET detector implements photodetectors 296 coupled to the side face of scintillators 291.

Figure 19F:
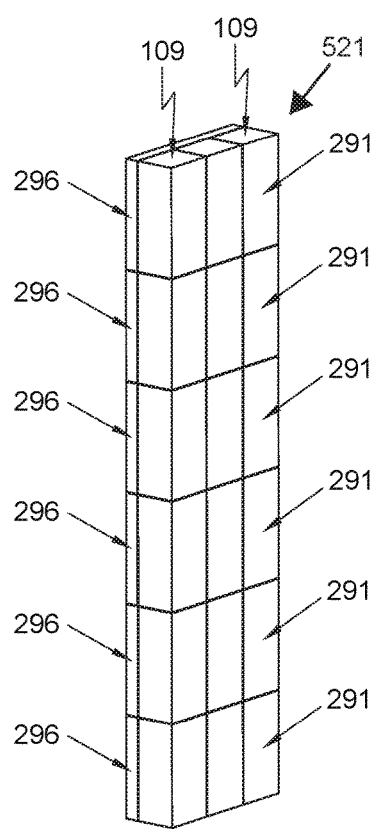
FIG. 19F is a perspective view of an edge-on, n/m-level CT-PET detector for n=2 at least 1 up to 6 and m=6 in which the PET detector implements photodetectors coupled to the side faces of scintillators.
Figure 19E:
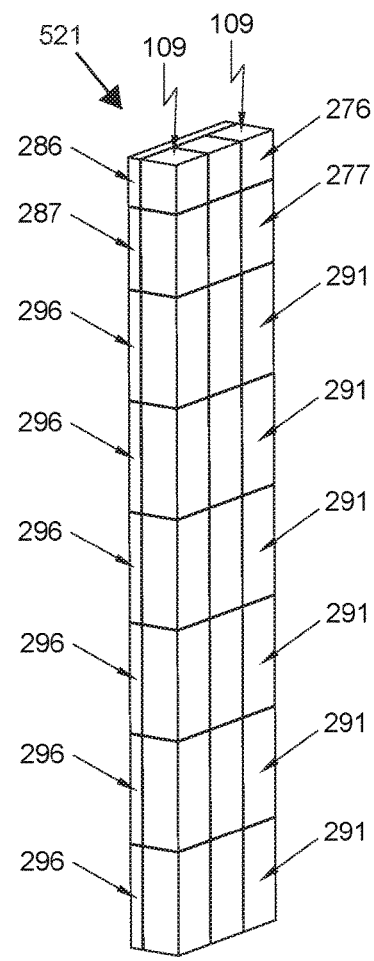
FIG. 19E is a perspective view of an edge-on, n/m-level CT-PET detector for n=2 and m=6 in which the PET detector implements photodetectors coupled to the side faces of scintillators.

FIG. 19E illustrates an edge-on, n/m-level CT-PET detector 521 for n=2 (photodetectors 286, 287 coupled to the side faces of scintillators 276, 277) and m=6 in which the PET detector implements photodetectors 296 coupled to the side face of scintillators 291.

FIG. 19F illustrates an edge-on, film-level CT-PET detector 521 for n=1 up to 6 (photodetectors 291 coupled to the side faces of scintillators 291) and m=6 in which the PET detector implements photodetectors 296 coupled to the side face of scintillators 291. One or more PET detector layers are therefore employed as CT detector layers.

Figure 19G:
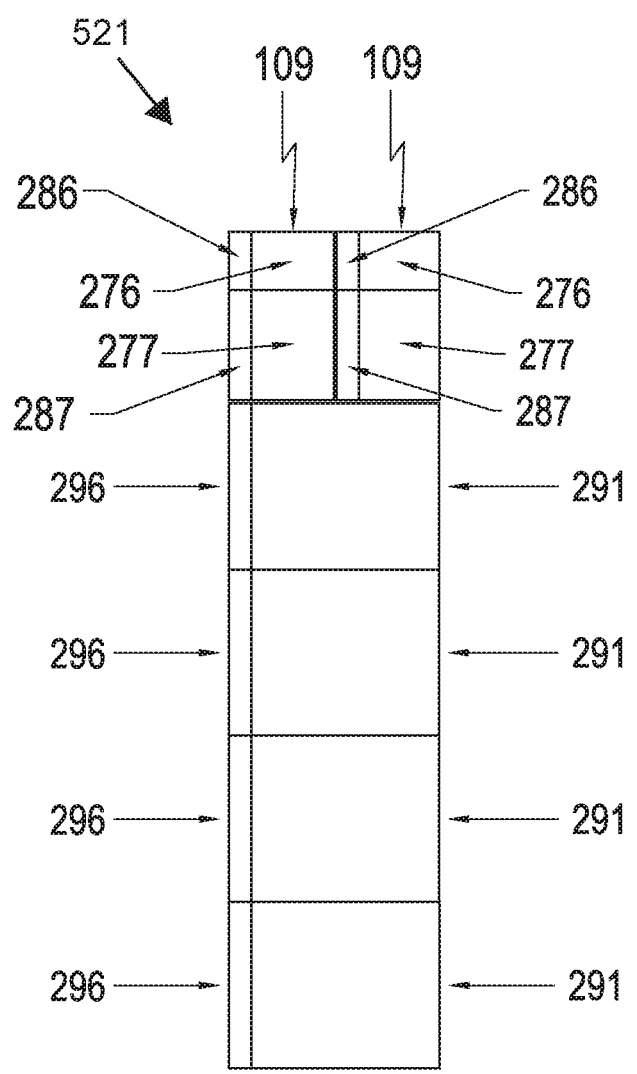
FIG. 19G is a perspective view (from an end perspective) of a shared edge-on, n/m-level CT-PET detector n=2, m=4) in which the PET detector elements are preceded by two adjacent edge-on CT detector elements.

FIG. 19G illustrates (from an end perspective) a shared edge-on, n/m-level CT-PET detector 521 for n=2 (photodetectors 286, 287 coupled to the side faces of scintillators 276, 277 in a photodetector-scintillator, photodetector-scintillator symmetric arrangement) and m=4 in which the PET detector implements photodetectors 296 coupled to the side face of scintillators 291.

A gap can be implemented between the two adjacent photodetector-scintillators. An alternative implementation employs the two adjacent edge-on, dual layer CT detector elements in a photodetector-scintillator, scintillator-photodetector asymmetric arrangement (enabling different maintenance and cooling techniques). The PET detector elements are positioned behind the two adjacent edge-on, dual layer CT detector elements (in contrast to FIG. 19E).

The CT and PET detector depths shown in FIGS. 19A-19G are for illustrative purposes and therefore are not necessarily to scale. Optionally, one or more PET detector layers can be employed as CT detector layers in an edge-on, n/m-level CT-PET detector. Furthermore, one or more CT detector layers can be employed as PET detector layers in an edge-on, n/m-level CT-PET detector.

Sharing one or more PET and CT detector layer without modifications may, depending on the properties of the shared layers, resulting in poorer performance for at least one of the CT and/or PET detectors. If deemed beneficial detector element properties within a shared detector layer (such as scintillator dimensions, materials, coatings, photodetectors and readout electronics) can be selected to provide improved detector results for CT and/or PET. For example, one or more parameters such as a smaller scintillator volume, a brighter scintillator phosphor, a more efficient photodetector, configurable readout electronics (spectral or PC, integration), etc. could be adjusted in order to compensate for the lower photon energies used in x-ray CT versus PET.

Although FIGS. 19A-G show PET detector layers with uniform properties concerning scintillators and photodetectors (PET detector elements) it should be understood, in general, that these. PET detector elements are not constrained to possess uniform properties. The PET photodetectors can be implemented as pixelated, strip, or area photodetectors depending on cost and performance requirements. The edge-on n-level scintillator detector can be replaced by an edge-on n-level semiconductor detector (including a structured mold semiconductor detector). Yet another implementation replaces the edge-on m-level scintillator detector with an edge-on m-level semiconductor detector (including a structured mold semiconductor detector).

Yet another implementation replaces both of the edge-on n-level and m-level scintillator detectors with edge-on n-level and in-level semiconductor detectors (including structured mold semiconductor detectors). Yet another implementation replaces at least one of the edge-on n-level or m-level scintillator detector layers with an edge-on or face-on semiconductor detector (including structured mold semiconductor detector) layer. Optionally, at least one energy-dependent radiation attenuation filter can be included with these scintillator-scintillator, scintillator semiconductor and semiconductor-semiconductor detector implementations. Structured mold semiconductor detectors, as previously described, can incorporate one or more energy-dependent radiation attenuation filters.

If cost is an issue the edge-on, n/m-level CT-PET detector can be implemented with an m=1 PET detector in an edge-on geometry or an m=1 PET detector in a face-on geometry. For example, the m=1 PET detector in an edge-on geometry can implement SAR resolution by implementing photodetectors at one or both ends of scintillator rods or scintillator fiber arrays (including encoded implementations as described herein). The m=1 PET detector in a face-on geometry can implement DOI resolution by implementing photodetectors at both ends of the scintillator rods. Encoded alternatives that can provide DOI resolution with photodetectors at one end of the scintillator rods include, but are not limited to, a discrete or continuous phoswich design, various light sharing designs between adjacent discrete or virtual rods (including the, 3D scintillator designs described herein) or applying a pattern of WLS materials to the scintillator rod surface such that wavelength and/or pulse shape properties vary with position along the lengths of the scintillator rods. A previous implementation used m=2 in which 2 discrete scintillator rods segments (segmented rods) with different pulse properties were optically-coupled to form individual phoswich scintillator rods with two level DOI resolution (this configuration can also be described as an m=1 PET detector). If multi-energy CT is not required then an n=1 CT detector in an edge-on geometry or an n=1 CT detector in a face-on geometry can be implemented.

The design principles detailed herein of integrated CT-PET, CT-SPECT and CT-SPECT-PET (ring or cone beam CT, tomosynthesis) detector modules with simultaneous or sequential acquisition can be readily extended to include integrated SPECT-PET detector modules with simultaneous or sequential acquisition. Full ring and partial ring geometries of detectors can be implemented for ring CT. Integrated SPECT-PET detector modules can implement one or more levels of scintillator(s) with 2D or 3D resolution suitable for use with one or more SPECT radionuclides (with lower energies than 511 keV) backed by stacked structured 3D scintillator PET detectors (or other 2D/3D PET detectors). Variations of SPECT-PET detector modules include implementations with one or more levels of semiconductors (or structured semiconductors) or a combination of scintillator and semiconductor (structured semiconductor) levels. For example, a scintillator level used for SPECT or SPECT and CT could be replaced by a semiconductor level. A conventional SPECT detector typically implements a collimator. An alternative (when employing suitable detectors) is to implement a Compton-SPECT detector (or a Compton-SPECT-PET detector) with or without a Compton collimator.

As described earlier herein, in one implementation detectors such as stacked structured 3D scintillators can incorporate both SPECT and PET scintillators (or only PET scintillators) within a stack since the extreme count rates associated with x-ray CT are not an issue. Another implementation modifies the (extended) edge-on, n/m-level CT-PET detector design taught earlier herein such that the n levels of edge-on SPECT scintillator(s) are appropriate for the one or more SPECT radionuclide energies backed by m levels of edge-on PET scintillator(s) (an edge-on, n/m-level SPECT-PET detector) as an alternative to stacked structured 3D scintillator PET detectors (or other 2D/3D PET detectors). One or more scintillator levels can be replaced by one or more semiconductor (or structured semiconductor) levels. While ring or partial ring (or cylindrical/spherical) detector geometries are often desirable, alternative detector geometries can employ planar implementations of the detectors described herein (e.g. positron emission mammography) and in some cases a ring, etc. detector geometry can be simulated by moving the planar detectors or arrangements of planar detectors (e.g. cone beam CT, SPECT).

Integrated CT-SPECT-PET imaging detectors can implement a combination of one or more levels of scintillator(s) suitable for appropriate CT x-ray spectrum(s) with one or more SPECT radionuclides (with lower energies than 511 keV) backed by stacked structured 3D scintillator PET detectors (or other 2D/3D PET detectors). One or more scintillator levels can be replaced by one or more semiconductor levels. As described previously herein, in one implementation detectors such as stacked structured 3D scintillators can incorporate both SPECT and PET scintillators (or only PET scintillators) within a stack since the extreme count rates associated with x-ray CT are not an issue.

Yet another implementation modifies the (extended) edge-on, n/m-level CT-PET detector design taught earlier herein in which one or more of the n levels of edge-on CT scintillator(s) are appropriate for the one or more SPECT radionuclide energies backed by in levels of edge-on PET scintillator(s) detectors (an edge-on, n/m-level SPECT-PET detector) as an alternative to stacked structured 3D scintillator PET detectors (or other 2D/3D PET detectors). The choice of CT scintillators and SPECT scintillators (and pixel depths) may in some instances represent a compromise since the most common SPECT radionuclide (Tecnetium-99 140 keV gamma ray) has an energy at or above the energy limit for typical CT beam spectra. Higher SPECT radionuclide energies can be covered by PET scintillator detectors.

As taught earlier herein, at least one level (level n) of the n-level multispectral CT/SPECT or SPECT detector can be replaced with one additional level of a PET scintillator (along with any appropriate changes in the readout photodetector and electronics) either the (extended) edge-on detector array configuration or the n-level edge-on detector array configuration followed by a 3D scintillator detector stack. Shared edge-on, n/m-level SPECT-PET, CT-PET, CT-SPECT and CT-SPECT-PET detector configurations can be implemented.

Implementations of CT-SPECT-PET detector modules include designs in which SPECT and/or PET detector resolution are comparable to, or coarser than CT detector resolution for patient imaging (or small animal imaging). SPECT and PET detectors can be shared (rather than only PET detectors). The edge-on design can include internal collimation to shield photodetectors and/or electronics from direct CT radiation. Internal shielding can be implemented in order to limit radiation cross talk. External collimation (which can be made mobile if desired) can be implemented for CT imaging as well as SPECT imaging. In some implementations PET detectors implement internal collimation. The presence of any internal as well as any external detector collimation should be accounted for when acquiring simultaneous or sequential SPECT-PET, CT-PET, CT-SPECT or CT-SPECT-PET images.

Energy-dependent MTF (Modulation Transfer Function) or MTF(E) calibration techniques have been previously described (Nelson, U.S. Pat. No. 6,583,420) for various x-ray detectors used in slit scan x-ray mammography, tomosynthesis, area imaging and CT (ring, cone beam), whether the energy resolution is inherent to the detector (spectroscopic capability), is the result of the detector geometry or both. When energy resolution is only the result of the detector geometry then one or more detector elements function as energy integrators or photon counters and energy resolution is inferred for those detector elements according to the energy-dependent attenuation properties of detector elements and the energy spectrum of the incident radiation field upon the detector elements.

An example of a detector in which energy resolution is only the result of the detector geometry include a scintillator-based, edge-on, n-level CT detector operating in the energy integrating or photon counting mode. An example of a detector in which energy resolution is both inherent and the result of detector geometry is an edge-on n-level CT (or tomosynthesis or slit/slot) semiconductor/structured semiconductor detector (with energy resolution) followed by at least one level of a scintillator (or semiconductor/structured semiconductor) detector operating in an energy integrating or photon counting mode.

MTF(E) calibration techniques can be applied for dedicated multi-energy CT (and tomosynthesis, slit/slot, area) detectors as well as integrated CT-PET, CT-SPECT or CT/SPECT/PET detectors. Calibration of the SPECT and/or PET detectors present in an integrated detector using conventional or unconventional SPECT and/or PET calibration phantoms and sources (Nelson, U.S. Pat. No. 6,583,420) should include effects from nearby detectors (including CT detectors) and any collimation that will be present during SPECT and/or PET imaging. In addition, if any detectors incorporate radioactive materials then their impact needs to be accounted for if deemed significant.

Ionizing Radiation Detectors Employing Multiple Information Carriers

When a detector interacts with ionizing radiation such as x-rays, gamma rays, charged particles, neutral particles one or more local electric, magnetic, optical, acoustic, thermal properties of the detector material may be altered. For example, phenomena such as x-ray induced photoacoustics, magnetoacoustics, etc. are well-documented in the literature. Ionizing radiation detector encoding techniques (implemented with appropriate readout sensors) for properties such as spatial and/or temporal resolution are not limited to optical passive methods such as light sharing, the use of WLSs, etc.

Ionizing radiation detectors can employ one or more active and/or passive encoding techniques that utilize electromagnetic (EM) and/or non-EM information carriers (introducing radiation including, but not limited to, acoustic radiation, electromagnetic radiation, an applied electric or magnetic field into the detector material). Active encoding techniques include modifying at least one of local or global atomic, electric, magnetic, EM, acoustic and thermal ionizing radiation detector properties (with applications including, but not limited to, the ionizing radiation detectors described herein, such as edge-on and face-on rod, fiber, sheet, slab, block, pixelated, array and structured detectors).

Passive encoding techniques include introducing at least one type of radiation and/or field (electromagnetic, acoustic, neutral particles, an electric field, a magnetic field) into the direct (or indirect) ionizing radiation detector material, without significantly modifying the properties of the material, and recording changes to the introduced radiation (and/or changes to another type of radiation) due to an ionizing radiation event. Passive encoding techniques can implement recording of a radiation signature resulting from an interaction between the ionizing radiation and the material. For example, one passive EM (acoustic) encoding technique introduces at least one EM (acoustic) waveform into at least one surface of the detector medium, without modifying significantly the EM (acoustic) property of the material.

For example, an EM (acoustic) beam or array of beams with a single frequency band waveform or with a spatially-encoded frequency band waveform can be introduced at a single detector surface, or at least two (preferably) perpendicular detector surfaces, forming a crossed-beam arrangement. EM (acoustic) sensors would be coupled to the opposing detector face(s). Preferably, the EM (acoustic) beams used to encode the medium have minimal or no interaction with the conventional readout of the radiation detector medium, for the case of a direct ionizing radiation detector material.

The EM (acoustic) waveform can be made to interfere with itself, or another coherent EM (acoustic) waveform, and thereby create an interference pattern that can be monitored (often, e.g., by recirculating the waveform internally or externally to the material medium). The EM (UV, visible, infrared, terahertz, microwave) waveforms (or acoustic waveforms) can be encoded using one or more formats including, but not limited to, continuous, pulsed, wavelength, modulated (patterned), polarized, interference and spatially patterned EM (acoustic) radiation fields. Modifications to the propagation of the encoded EM (acoustic) radiation by an ionizing radiation event in the material can then be recorded (e.g., a change in intensity, polarization, interference pattern, modulation, spatial distribution), providing at least one of temporal information, spatial information, and energy information.

For example, if the propagation of an EM waveform through a detector medium is disrupted due to an ionizing radiation event, then event timing can be estimated based on knowing the maximum propagation length to the EM readout sensor and the speed of the EM wave through the detector medium. If event position information within the detector medium is available, event timing resolution can be corrected based on the distance from the event location to the EM readout sensor. If the disrupted EM waveform can be measured by separated detectors with sufficient timing resolution, then the event timing resolution estimate can be improved and the event position along the propagation path can be estimated.

Modifications to the encoded EM radiation properties and/or the spatial extent of the modified encoded EM radiation can be used to estimate the energy deposited in the detector medium. For some ionizing radiation detector implementations, this can reduce the conventional readout complexity and cost by reducing the number of readout detector elements since their individual contribution to event location determination is reduced or eliminated.

Note that optical pump and pump-probe techniques described herein are examples of encoding techniques. These active and/or passive encoding techniques are not limited to use with the direct ionizing radiation detectors as described herein, and can also be applied to the interrogation of material samples including human tissue (typically using at least one of ionizing or non-ionizing radiation detectors). Furthermore, interrogated material samples can function as indirect ionizing radiation detectors (local material properties are at least temporarily modified as a result of ionization, but signal carriers such as fluorescent photons or electrons and holes are typically not collected), and therefor can be incorporated into detector modules with or without direct detectors.

For example, the output from an optically-pumped laser rod or a laser fiber can be modified through an interaction with one or more ionizing radiation events (including through the generation of Cherenkov radiation). A piece of glass or plastic or other material (the same is true for a piece of scintillator or semiconductor ionizing radiation detector) can experience a measurable change in at least one local property, including, but not limited to, the index of refraction, the polarization, the acoustic impedance through an interaction with one or more ionizing radiation events. In addition, Cherenkov radiation can also be generated and detected (for appropriate materials).

One or more properties of ionizing radiation structured detector materials (including nanoparticle properties if employed) and even the structured detector frames (including features such as hole or trench size, shape, surface properties, coatings, anode and/or cathode properties (if present), the incorporation of embedded sensors) can be modified or enhanced in order to support the use of one or more than one type of information carrier. For example, in one implementation anode and/or cathode materials used in an ionizing radiation structured detector could incorporate both conductive and acoustic properties (enabling the use of both charge and acoustic information carriers). In another implementation, a hole or trench anode (for example) could be segmented along its depth providing DOI (as well as energy and/or particle sensitivity as a function of depth) in a face-on geometry or SAR in an edge-on geometry.

The dimensions of the hole or channel can be selected in order to achieve a desired balance between temporal resolution, spatial resolution, radiation stopping power, and energy resolution (including noise properties). A channel can be treated as a single extended pixel, or it can be segmented along its length to form a linear array of pixels. An alternative to employing a single semiconductor or nanoparticle material in a segmented hole or trench in a face-on geometry is to enhance energy and/or particle detection sensitivity by filling successive hole or trench segments with a specific semiconductor or nanoparticle material with favorable energy or particle interaction capabilities for at least a part of the incident radiation spectrum. A related concept is employed in dual energy CT in which a low Z phosphor top layer preferentially detects low energy x-rays followed by a high Z phosphor bottom layer for detection of moderate-to-high energy x-rays.

In another implementation, holes and channels (with or without depth segmentation) are incorporated into the ionizing radiation structured (conductive mold) detector. In yet another implementation, holes and/or channels (with or without depth segmentation) are incorporated into both sides of the ionizing radiation structured detector. The holes and/or channels on one side of the semiconductor substrate (such as Si) of the ionizing radiation structured detector can be aligned or offset with respect to the holes and/or channels on the other side of the semiconductor substrate. An offset format for holes and/or channels between the two sides of the semiconductor substrate can be used to reduce ionizing radiation transmission losses through the semiconductor substrate walls that separate adjacent holes and/or channels. Detector systems that employ one or more structured detector modules, including conductive mold structured detector modules, can implement within at least one detector module (and/or a material sample) the active and/or passive encoding techniques described herein including, but not limited to, optical pump encoding, optical pump-probe encoding, an applied electric field encoding, an applied magnetic field encoding, passive electromagnetic encoding, active electromagnetic encoding, active acoustic encoding and passive acoustic encoding, active thermal encoding.

An active encoding technique is to embed or couple individual and/or arrays of sensors (probes) within or on the surface(s) of an ionizing radiation detector (including, but not limited to, the ionizing radiation detectors (scintillator, semiconductor, structured, gas, superconductor) described herein with configurations such as rod, fiber, sheet, slab, block, pixelated, array, structured, 3D structured, layered, etc.). The sensors could be at least one of: electrically-sensitive, magnetically-sensitive, electromagnetically-sensitive, acoustically-sensitive, temperature-sensitive, particle-sensitive. The sensors could provide at least one of: temporal information, spatial information, temperature information, energy deposition information, polarity information, particle identity information, detector health information in addition to detector readout information.

For example, an embedded sensor array could implement at least one of a single-sided readout format, a double-sided readout format, an autonomous readout format. A single-sided readout could have one or more sensor elements positioned at the end or along the length of a cable/wire at known positions and thereby encode spatial resolution information. One or more cable/wires could extend to select distances within the detector volume or traverse the detector volume. A double-sided readout format could employ sensor cables/wires that traverse the detector volume from one side of a detector to the other side (in one version employing a signal processing technique such as signal division to determine the position of an ionizing event with respect to an individual sensor cable/wire). 2D and 3D arrays of cables/wires can be implemented.

Wired and/or wireless readout capabilities can be implemented. Signal strength (energy resolution) and timing information (temporal resolution), as well as other signal event information, may also be available depending on the capabilities of the sensor cable/wire. If multiple sensor cables/wires are present then readout information from the various sensor cables/wires can be combined or correlated, potentially enhancing spatial resolution, etc. and (in some instances) enabling tracking and/or a more detailed analysis of the event. Passive and/or active encoding techniques can be employed with, but are not limited to, the ionizing radiation detectors described herein.

An additional active encoding technique is to introduce one or more static or dynamic virtual structure within or on the surface of the detector. Sources of static or dynamic virtual structures can be the result of applied external magnetic fields, electric fields, electromagnetic fields, acoustic fields, and/or temperature variations. For example, optical source(s) and/or an acoustic source(s) can impose a static or dynamic wave form pattern within an ionizing radiation detector (a simple pattern is a repetition of pulses). When the pattern is disrupted due to an ionizing event the change in the pattern can be detected optically and/or acoustically, providing at least one of spatial resolution, temporal resolution, energy resolution or other properties of the ionizing event.

Optical and/or acoustic elements or arrays that generate a wave form pattern can be coupled to one or more surfaces of an ionizing radiation detector including, but not limited to, semiconductor or scintillator ionizing radiation detectors and used to reconstruct the location and/or timing of an ionizing event from the disruption of the pattern (note that an acoustic source may also be used as a receiver). If the imposed external radiation pattern is dynamic then information concerning parameters such as position or timing may be encoded into the waveform imposed on the ionizing radiation detector and thus extracted when the dynamic pattern is modified by an ionization event. For example, acousto-optic modulators are used to modulate light beam intensity by varying (encoding) the refractive index within a material. The art of encoding propagating acoustic and electromagnetic wave forms is also adaptable to the fields of acoustics, optical communications, radar, seismology, etc. The application of one or more external EM, acoustic, electric and magnetic fields can be used to encode and/or alter the properties of direct and indirect ionizing radiation detectors.

Multiple active encoding techniques can be employed simultaneously with ionizing radiation detectors. Furthermore, active encoding techniques and passive encoding techniques (including passive techniques described in this specification) can be employed simultaneously with ionizing radiation detectors. It should be understood that optical source and detectors include not only visible but also near-infrared, infrared and terahertz sources and detectors.

Ionizing radiation detectors that incorporate active and/or passive encoding techniques that employ at least two types of information carriers to detect ionizing radiation represent an alternative to conventional ionizing radiation detectors that typically use a single type of information carrier (one exception is liquid Xenon which can generate measurable electronic signals and a fluorescence signals). For example, acoustic/ultrasound elements or arrays can be coupled to one or more surfaces of an ionizing radiation detector including, but not limited to microchannel plate, structured (mold, 3D, straw, etc.), optically-pumped, gas, liquid, superconducting, semiconductor or scintillator ionizing radiation detectors and used to reconstruct the location of an ionizing event by listening to acoustic sounds (the pressure signature) generated by the photoacoustic event.

The types of ionizing radiation detectors that can be coupled to acoustic/ultrasound elements or arrays include, but are not limited to, the 1D, 2D, 3D, Compton camera, Compton-PET, CT-PET, CT, SPECT, SPECT-PET, CT-Compton-PET, etc. radiation detectors described herein. Applications include medical, industrial, homeland security and scientific imaging and/or analysis.

Figure 20A:
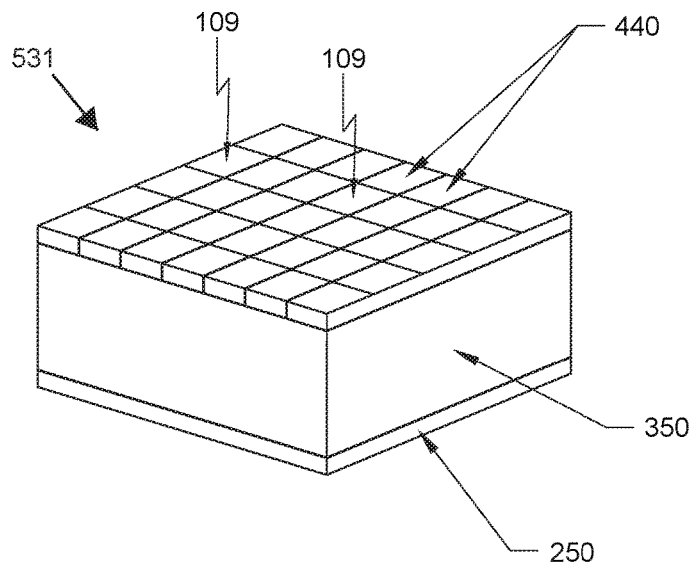
FIG. 20A is a perspective view of a discrete 3D scintillator and photoacoustic PET detector module irradiate face-on in which a scintillator block 350 is coupled to a photodetector 250 and an acoustic array 440.

FIG. 20A illustrates a perspective of a discrete 3D scintillator and photoacoustic PET detector module 531 irradiated with ionizing radiation 109 face-on in which a scintillator block 350 is coupled to a photodetector 250 on one surface and an acoustic array 440 is coupled to a different surface.

Figure 20B:
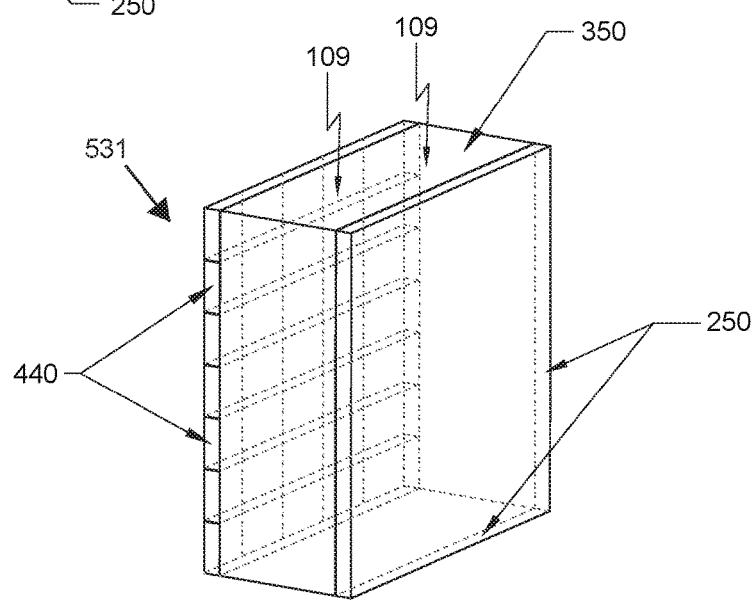
FIG. 20B is a perspective view of a discrete 3D scintillator and photoacoustic PET detector module irradiated edge-on in which a scintillator block 350 is coupled to a photodetector 250 and an acoustic array 440.

FIG. 20B illustrates a perspective of a discrete 3D scintillator and photoacoustic PET detector module irradiated with ionizing radiation 109 edge-on in which a scintillator block 350 is coupled to a photodetector 250 on one surface and an acoustic array 440 is coupled to a different surface.

Figure 20C:
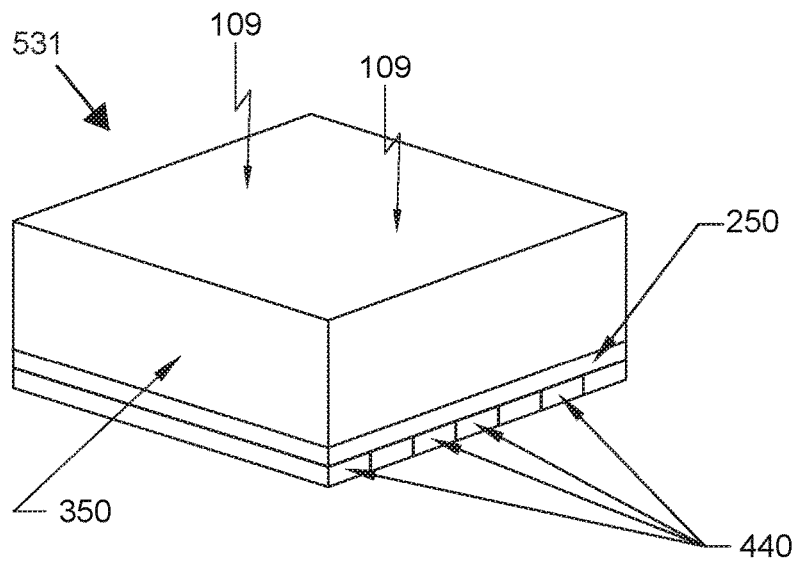
FIG. 20C is a perspective view of a discrete 3D scintillator and photoacoustic PET detector module irradiate face-on in which a scintillator block 350 is coupled to a photodetector 250 and an acoustic array 440 at the same interface.

In yet another implementation the photodetector and acoustic array are both coupled to the same surface of the scintillator block. FIG. 20C illustrates a perspective of a discrete 3D scintillator and photoacoustic PET detector module 531 irradiated with ionizing radiation 109 face-on ill which a scintillator block 350 is coupled to a photodetector 250 and an acoustic array 440 at the same surface.

Figure 20D:
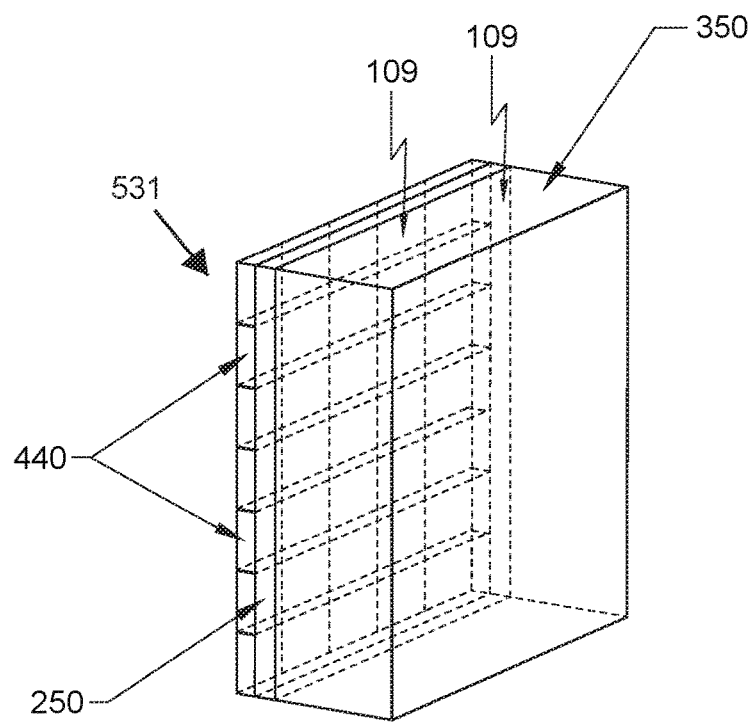
FIG. 20D is a perspective view of a discrete 3D scintillator and photoacoustic PET detector module irradiated edge-on in which a scintillator block 350 is coupled to a photodetector 250 and an acoustic array 440 at the same interface.

FIG. 20D illustrates a perspective of a discrete 3D scintillator and photoacoustic PET detector module 531 irradiated with ionizing radiation 109 edge-on in which a scintillator block 350 is coupled to a photodetector 250 and an acoustic array 440 at the same surface.

Alternative implementations include reversing the order of the photodetector array and acoustic array (if acceptable photodetection efficiency is achieved) or employing a single readout device offering both acoustic and photodetection capability.

In FIG. 20A the single photodetector provides information concerning at least one of energy resolution and/or temporal resolution whereas the acoustic array provides information concerning at least one of spatial resolution, temporal resolution, energy resolution. The use of a single photodetector may offer advantages in terms of overall cost and/or improved performance. Spatial resolution can be modified by one or more techniques including, but not limited to: selecting a different surface to couple the photodetector and/or acoustic array to, implementing an acoustic array element density that ranges from coarse to fine, employing one or more additional acoustic arrays coupled to additional surfaces, implementing a 1D or 2D photodetector, employing one or more additional photodetectors (including 1D or 2D photodetectors) coupled to additional surfaces (in some configurations enabling SAR or DOI measurements). Although scintillator blocks are depicted in FIG. 20A-20D, other scintillator geometries including, but not limited to, scintillator arrays can be implemented. At least one of area, strip, and pixel array photodetector geometries can also be employed. The photodetectors may be used to provide spatial resolution, and photodetectors and/or acoustic arrays may be coupled to more than one surface. Furthermore, acoustic/ultrasound elements or arrays can be coupled to the other detector materials described herein, including semiconductor detectors, structured detectors, gas detectors, etc.

The use of acoustic/ultrasound elements or arrays is not limited to implementing only receiver (passive) capabilities. Optionally, acoustic/ultrasound transmitter (active) capabilities can also be implemented. Alternatively, acoustic/ultrasound elements or arrays could be integrated directly into the ionizing radiation detector (consider the case of a silicon-based radiation detector wherein the technology of silicon CMOS ultrasound transmitter and/or receiver chips is applied). Furthermore, acoustic/ultrasound transmitters that can be employed with ionizing radiation detectors can also be used with tissue (the sample) to create stationary or dynamic tissue density variations within a tissue volume that can be evaluated by employing x-ray or gamma ray (or other ionizing radiation) phase imaging techniques using at least one ionizing radiation detector module (including, but not limited to, the ionizing radiation detector modules described herein). Conventional radiological and phase images can be acquired and compared. The ionizing radiation source can be external and/or internal to the tissue). This method is readily extended to include the analysis of samples composed of materials other than tissue for non-medical imaging applications in science, industry and inspection.

In general, one or more surfaces of a scintillator array, sheet, slab or block can be coupled to one or more acoustic/ultrasound elements or arrays (to measure acoustic information carriers) and one or more photodetectors (to measure optical information carriers). The acoustic/ultrasound elements or arrays would provide information relevant for at least one of spatial resolution, temporal resolution, energy resolution (wherein at least one of spectral resolution, PC, energy integration can be implemented).

The photodetector(s), such as single photodetectors, position-sensitive photodetectors and photodetector arrays, would provide at least one of energy resolution (alternatively, PC and/or energy integration can be implemented), temporal resolution, spatial resolution. These photodetectors can be positioned in previously herein-described detector configurations including, but not limited to, edge-on, face-on, edge-on with SAR, face-on with DOI, edge-on with encoding, face-on with encoding, discrete and semi-continuous structured 3D scintillators. This represents a flexible detector format since specific resolution capabilities for the acoustic/ultrasound elements or arrays or the photodetectors can be emphasized or de-emphasized according to the performance requirements of an application such as SPECT imaging, PET imaging, x-ray imaging, Compton imaging, particle detection, industrial imaging, homeland security.

In some instances resolution information from both acoustic and optical information carriers can be combined beneficially. For example, if spatial resolution information (even if limited) is available from photodetectors this information can, in some cases, augment spatial resolution information provided by the acoustic/ultrasound elements or arrays. If spatial resolution is largely or entirely determined by the acoustic/ultrasound elements or arrays then the number of photodetector elements could be reduced, simplifying photodetector and readout electronics design and/or cost. Then the scintillator detector could be adapted for one or more features such as stopping power, energy resolution, temporal resolution either without the constraint of optically-determining spatial resolution or while allowing for reduced optically-determining spatial resolution. (the acoustic/ultrasound elements or arrays are used to augment the spatial resolution capabilities of the photodetectors).

Non-imaging optics designs can be implemented in some cases. In some cases the use of fewer photodetectors or even a single photodetector can result in lower photodetector (and readout electronics) costs and/or the use of higher performance photodetectors (in some instances with simplified features). For example, in some implementations 1D or 2D PMTs, micro-channel plates, SiPMs, etc. could be employed with much larger pixel sizes than are currently employed for use in small animal and human SPECT and/or PET imaging.

The use of one or more acoustic/ultrasound elements or arrays to provide spatial resolution (and/or temporal resolution, energy resolution) information is not limited to scintillator detectors. Other ionizing radiation detector materials including, but not limited to, semiconductor detectors, super conductors, storage phosphors, nanoparticles, gases, liquids, etc. (and even traditional non-detector solid, liquid and gas materials) can be used with an acoustic/ultrasound elements or arrays in order to provide (or augment) at least one of spatial resolution, temporal resolution, energy resolution. The ionizing radiation detector may be tuned to enhance its response for a specific information carrier.

For example, the acoustic response and/or acoustic transport of an ionizing radiation detector can be enhanced by various techniques including the selection of detector materials with inherent (or that can be engineered) favorable acoustic properties (acoustic resonances, channeling) or the implementation of structured detector with enhanced acoustic properties. These passive encoding techniques, as described early, can be combined with active encoding techniques. Traditional non-detector materials include, but are not limited to, metals, ceramics, glasses, various forms of carbon, plastics, water, ice, etc. which can all function as ionizing radiation detectors. Optionally, uniform or non-uniform temperature control of detector materials and/or non-detector materials can be implemented to enhance photoacoustic response. Imposing a non-uniform temperature distribution within the material volume could be used to spatially-modify the photoacoustic response of the material.

Transformer Pet

Various implementations of PET scanners (uniform and non-uniform detectors; ring, ring with flat detectors, split-ring, dual-ring/open-ring, slant-ring, flat panel (or other) detector geometries; PET, CT-PET, SPECT-PET, CT-SPECT-PET, Compton-PET, CT-Compton-PET, Compton-PET-SPECT, CT-Compton-PET-SPECT) can be implemented. For example, an open-ring PET scanner designed for radiation therapy with PET or CT with PET implements two identical, fixed PET detector rings that are used cooperatively (coincidences can be detected within the individual ring detectors as well as between ring detectors). There is a gap between ring detectors in order to accommodate a radiation therapy or CT source and an opposing detector (and/or a beam stop). Sections of the gap that are not exposed to the radiation source can be filled-in with PET detector arrays.

The open-ring PET scanner design can lack flexibility in some respects. A more flexible PET system design employs two or more PET scanners (which may implement the same or different detector geometries and/or detector properties) that can operate independently or cooperatively (referred to as transformer PET or T-PET). Gaps between adjacent PET scanners (if deemed undesirable) can be reduced by implementing removable cowling from one or both sides of adjacent PET scanners.

For example, a T-PET system comprised of at least two ring PET scanners (for the case of two ring PET scanners one can be fixed and one can be mobile or both can be mobile) could be used simultaneously to image a single region of a patient with greater detector efficiency or an extended region of a patient (an extended axial field of view). An extended region of a patient may include sub-regions with different PET detector requirements (such as a patient's chest/heart and head or neck/head). Two or more ring PET scanners can be employed in place of a dedicated whole body PET scanner. The ring PET scanners can be the same or they can be different (for example, different diameters and/or different detector properties). None, one or more ring PET scanners can be employed with one or more non-ring PET scanners (planar, square cylinder, rectangular cylinder, etc. geometries) to form a T-PET system.

A special case of a two ring (or multiple ring) T-PET system directly integrates PET detector rings with different properties (e.g., DOI, SAR, temporal response, scintillator and/or non-scintillator detector materials, spatial resolution, readout electronics, photodetectors, etc.). For example, a TOF PET detector ring could be integrated with a conventional (temporal resolution) PET detector ring (or between conventional, temporal resolution PET detector rings). The TOF PET detector ring could then be positioned over the region of the patient which would benefit the most from TOF resolution. Note that this technique of mixing detectors of different properties can be used for any diagnostic ionizing radiation imaging system, including, but not limited to, PET, SPECT, CT, x-ray radiography.

The at least two ring PET scanners of the T-PET system could operate independently (with the same patient or different patients) or cooperatively with coincidence detection implemented between ring PET scanners. Cooperative coincidence event processing can be implemented electronically (detected event information can be shared dynamically between PET scanners) or through off-line processing using detected event information. Whether the at least two PET scanners operate independently or cooperatively with the same patient, optional shielding can be positioned between the PET scanners to reduce their effective field of view of radiation sources within the imaged volume.

Figure 21:
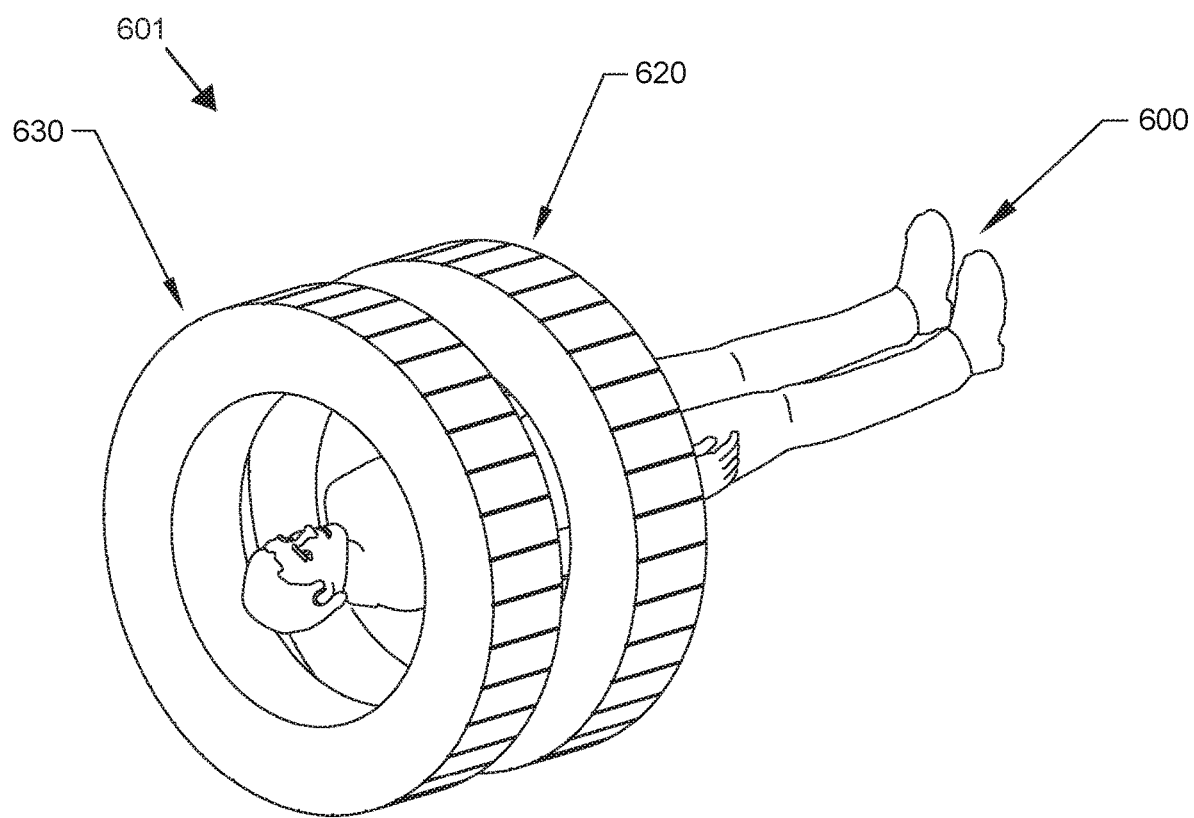
FIG. 21 illustrates a T-PET system in which a heart/chest PET scanner 620 and a head/neck PET scanner 630 operate cooperatively to simultaneously acquire PET cardiac and brain images of a patient 600.

FIG. 21 illustrates a T-PET system 601 in which a heart/chest PET scanner 620 and a head/neck PET scanner 630 operate cooperatively to simultaneously acquire PET cardiac and brain images of a patient 600. When the two ring PET scanners are operated independently with the same patient then optional stationary and/or adaptive shielding can be employed to help limit the field of view for each PET scanner. Furthermore, the two ring PET scanners can operate cooperatively when only one region of the patient is imaged and thereby continue to benefit from the inherent improvement of overall detection efficiency (potentially reducing patient imaging time and/or the amount of radioactivity given to patient).

If three or more PET scanners are present all PET scanners can be operated cooperatively or independently as well as various combinations of cooperative and independent PET scanners. If one or more of the PET scanners is to be operated independently the PET scanner(s) can optionally be shielded from the other PET scanners using stationary and/or adaptive shielding (extendable/retractable) to help limit the field of view for the independently-operated PET scanner(s).

The improved flexibility of the T-PET system allows for the (at least) two ring PET scanners to be employed to image one patient's chest/heart and another patient's brain (or neck brain) independently. The two PET scanners could offer the same or different levels of performance. For example, the brain or neck/brain PET scanner could optionally implement: detectors offering higher spatial resolution (including non-uniform spatial resolution), different detector orientations, materials, energy resolution, temporal resolution; a smaller ring diameter, different readout electronics, etc. than the chest/cardiac PET scanner.

Implementations of the T-PET system are not limited to ring detector geometries (including partial ring geometries) and can be readily implemented with other PET detector geometries as previously described herein (including, but not limited, to flat panel geometries). Furthermore, T-PET systems can implement multiple PET detector geometries and detector properties (for example, mixing ring and flat panel (or other) detector geometries; uniform and non-uniform detectors; the implementation of at least one of CT-PET, SPECT-PET, CT-SPECT-PET in at least one of the PET scanners).

A limiting case for T-PET system employs two or more stationary PET scanners which can operate cooperatively or independently or a combination thereof. If one or more of the PET scanners is to be operated independently that (those) PET scanner(s) can optionally be shielded from the other PET scanners using stationary and/or adaptive shielding to help limit the field of view for the independently-operated PET scanner(s). If SPECT capabilities are present in the T-PET system then various combinations of SPECT-PET imaging can be implemented: all scanners implement only PET, all scanners implement only SPECT, all scanners implement only SPECT-PET, at least one scanner implements PET, at least one scanner implements SPECT, at least one scanner implements SPECT-PET. Collimation and shielding can be employed as needed. The flexibility of the T-PET system allows for (at least) two SPECT-PET scanners to be employed to image (at least) two patient independently using at least one of SPECT, PET or SPECT-PET functionality.

Gas-Based Compton Scatter Pet Detectors

The use of gas-based, multilayer straw detectors as Compton scatter detectors for PET imaging was described earlier herein. An advantage is that multilayer straw detectors are straightforward to implement using existing technology. The Compton scattering geometry for a face-on (or an edge-on) multilayer straw detector can be improved by requiring that the lower (bottom) surface wall of a layer of straws utilizes the upper (top) surface wall of the straws that define the next layer within a stack and that side walls within a layer of straws are shared, forming a monolithic multilayer straw detector.

In another implementation, the gas is replaced with a liquefied gas including, but not limited to, liquid Xenon (providing Compton scatter and photoelectric event detection, and thus can be used for CT-Compton-PET, CT-PET, Compton-PET and direct PET imaging, as described herein). The choice of straw wall materials can be expanded, since the walls can be employed to provide at least one of photoelectric interactions, Compton interactions or minimal interactions with the incident radiation. In one implementation, the fast fluorescence signal can be detected by coupling (directly or indirectly) a photodetector to one or both ends of a straw (providing at least one of event temporal resolution, energy resolution, spatial resolution). The anode signal can be read out at both ends, providing information concerning energy deposited and the spatial location of the event along the anode. The information provided by the fluorescence signal, and anode signal information, including time delays between the fluorescence and anode signals, can be correlated to further refine at least one of the temporal, energy and spatial resolution (including the radial distance of the event from the anode wire). The encoding techniques described herein for scintillator rods and scintillator fibers can also be employed with straw detectors.

Figure 22A:
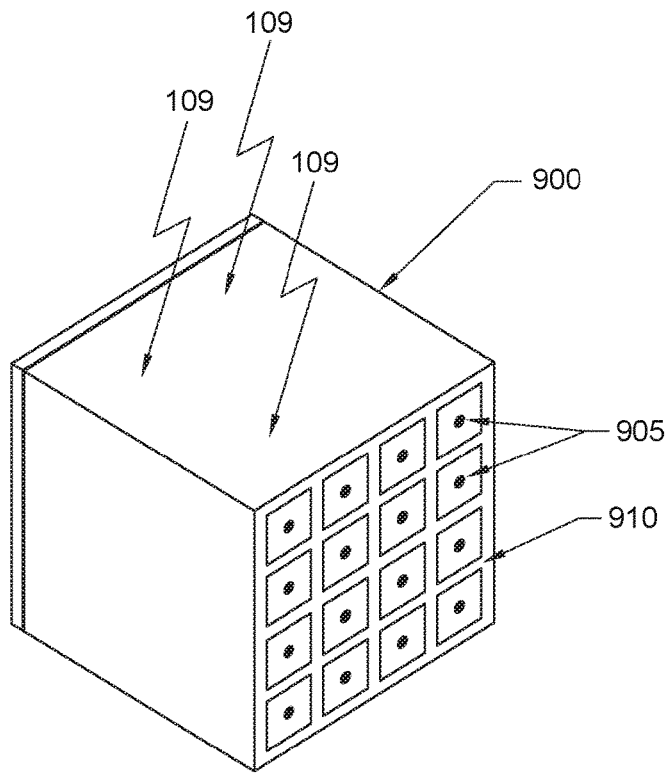
FIG. 22A is a cutaway view of a planar, face-on implementation of a monolithic multilayer straw detector comprised of straw fibers with square cross sections and shared walls.

FIG. 22A illustrates a planar, face-on implementation of a monolithic multilayer straw detector 900 comprised of straw fibers with square cross sections and shared walls and incident ionizing photon radiation 109. Wires 905 function as anodes. The walls 910 function as a Compton scattering material and as a cathode. Event location along a wire can be determined by charge division or timing techniques.

The side walls of the straw fibers used in a monolithic multilayer straw detector can be thinned or eliminated entirely. Eliminating side walls simplifies manufacturing but (as is the case of thinning side walls) reduces the total volume of low-Z material available for Compton scattering. If the sidewalls within a layer are eliminated entirely the result is a monolithic multilayer, multiwire proportional counter detector with anode wires and cathode upper and lower surface walls defining each layer.

Figure 22B:
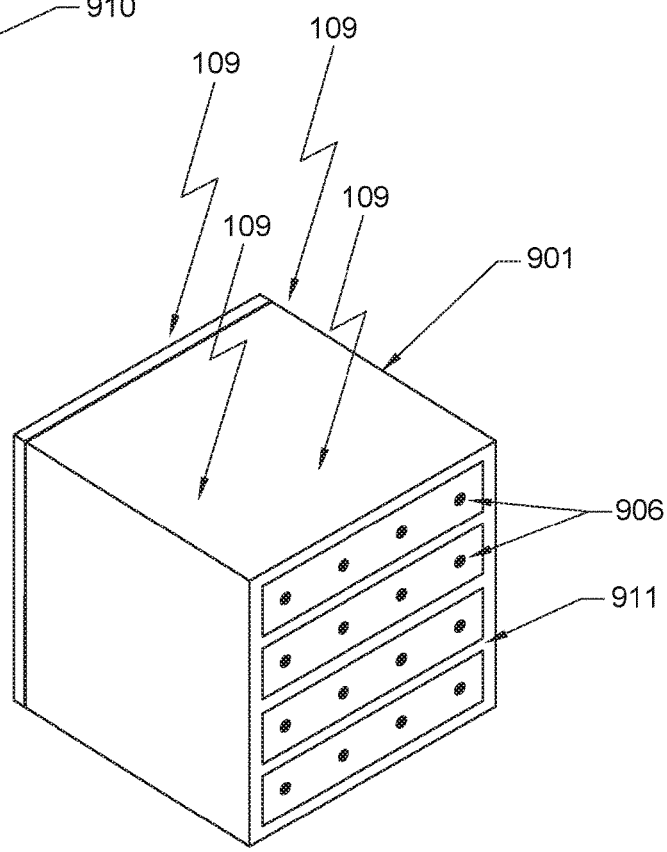
FIG. 22B is a cutaway view of a planar, face-on implementation of a monolithic multilayer multiwire proportional counter detector.

FIG. 22B illustrates a planar, face-on implementation of a monolithic multilayer multi wire proportional counter detector 901 and incident ionizing photon radiation 109. Wires 906 function as anodes. The walls 911 function as a Compton scattering material and as a cathode. Monolithic single layer multiwire proportional counter detectors can also be implemented.

An alternative implementation (that employs much shorter anode wires between crossed cathode strips) is a monolithic multilayer crossed strips multiwire proportional counter detector. Yet another implementation is to replace the array of wires in each layer with a gas electron multiplier (GEM) foil or a micromegas mesh with a 2D anode plane readout. Although more expensive than arrays of wires, improvements in spatial and timing resolution (and event rate capability) are possible. Yet another implementation is a monolithic multilayer microstrip gas chamber (including position-sensing microstrip gas chamber variations).

Conventional RPCs, microstrip gas chambers, multiwire proportional counters and crossed strips multilayer proportional counters (including readout techniques to impose spatial resolution along the length or a wire or strip), GEM and micromegas detectors are described. Monolithic single layer and multilayer straw, multilayer multiwire proportional counter (including crossed strips, GEM and micromegas variations) and microstrip gas chamber (including position-sensing microstrip gas chamber variations) detectors (including arrays) can be employed as stand-alone PET detectors or as front-end detectors along with one or more layers of back-end detectors for PET imaging. Planar and/or curved geometries can be employed in edge-on and/or face-on orientation.

Monolithic single layer and multilayer straw detectors (as well as multilayer multiwire proportional counter (including crossed strips, GEM and micromegas variations) and microstrip gas chamber (including position-sensing microstrip gas chamber variations) detectors) can be employed as PET detectors in edge-on and/or face-on orientation. For example, a ring (or an approximation thereof) PET detector geometry could be implemented using multiple monolithic single layer straw detectors oriented edge-on along the axial direction or using multiple curved monolithic multilayer straw detectors oriented face-on or edge-on (alternatively, multiple planar monolithic multilayer straw detectors oriented in the axial direction could be distributed about the circumference of the ring).

Typically, the straw, multiwire, microstrip, GEM, micromegas and RPC gas detectors employed for Compton scattering offer at least one of: good-to-excellent spatial resolution and/or temporal resolution but with only marginal or limited energy resolution for events originating outside the gas medium. Energy losses experienced by individual photoelectric, Compton and secondary electrons that escape from the low-Z scattering material into the gas are not predictable.

If excellent temporal resolution is available then TOF PET (offering improved image reconstruction resolution and reduced background noise) can be implemented on some level. Structured straw detectors (as well as other gas-filled detectors such as multiwire, microstrip and RPC detectors) employing low-Z materials (glass, bakelite, plastic, Aluminum, etc.) are candidates for front-end detectors in extended axial field of view whole body PET (with or without TOF capability) as well as PET (with or without TOF capability) since large area detectors can be manufactured directly as a single detector piece or assembled from multiple detector pieces.

The properties of the back-end detector can be customized to compensate for any weakness of the structured straw, multiwire, microstrip, GEM, micromegas or RPC gas detector. For example, in one implementation, an RPC detector offers good-to-excellent spatial and temporal resolution but poor energy resolution. A back-end detector with adequate temporal resolution then should offer good-to-excellent energy resolution and spatial resolution.

For example, assume that tracking is implemented within and between the front-end Compton scattering detector material (with poor energy resolution) and the back-end detector (with good energy resolution) and reasonable estimates for scattering angles (aside from Doppler effects) can be made, then the Compton equation can be applied one or more times to approximate the incident energy of the gamma ray at the front-end detector (which is relevant when an energy discrimination window is employed). This method is particularly useful for the simplest case of a single Compton-scattered photon event in the front-end detector that terminates as a photoelectric event in the back-end detector since the accuracy of any energy and spatial position measurements are limited.

Variants of these detector designs described herein can be further customized for imaging charged and neutral particles with appropriate changes to the front-end detectors and/or the back-end detectors (if present). The use of these gas-based Compton scatter detectors is not limited to PET imaging and they can be employed in any imaging application involving ionizing radiation including, but not limited to, nuclear medicine imaging (SPECT, PET-SPECT, Compton, Compton-PET, Compton-SPECT, Compton-PET-SPECT), medical x-ray imaging, homeland security imaging, industrial imaging, and scientific imaging.

High Resolution Detectors for Dental Imaging

Structured detectors such as structured 3D semiconductor detectors and structured mold semiconductor detectors and transparent nanoparticle storage phosphor plate detectors can be employed in a face-on orientation for high spatial resolution (typically greater than 7-10 lp/mm) applications such as intraoral dental x-ray imaging (see Nelson, U.S. Pat. No. 9,384,864 and U.S. patent application Ser. No. 13/199,612, U.S. Publication No. 2012/0181437). Structured 3D semiconductor detectors (including amplified, co-doped and high resistivity variations) including, but not limited to, 3D Si, 3D GaAs, 3D CdTe, 3D CZT, 3D Ge, 3D TlBr, 3D Se, 3D HgI$_2$, etc. (including doped versions) as well as structured mold semiconductor detectors that can be employed in various face-on and/or edge-on implementations of Compton, PET, SPECT, CT, slit, slot, and area x-ray imaging (including diagnostic and radiation therapy imaging) as described herein are also suitable for applications including, but not limited to, high spatial resolution intraoral dental x-ray imaging, dental cone beam CT imaging, dental 3D tomosynthesis (single tooth) intraoral imaging and x-ray fluorescence imaging. Structured 3D semiconductor detectors can also be referred to as 3D semiconductor detectors.

For intraoral dental imaging, the structured 3D semiconductor detector or structured mold semiconductor detector would be employed in a face-on geometry. The same protective shell (frame) and electronic readout system described previously by Nelson (U.S. patent application Ser. No. 13/199,612, U.S. Publication No. 2012/0181437) can be employed while the high resolution structured mold semiconductor detector array is replaced with a high resolution structured 3D semiconductor detector array. The structured 3D semiconductor detector or structured mold semiconductor detector can be implemented in at least one of integrating, photon counting and spectral resolution detection modes.

The structured 3D semiconductor detector can offer advantages, in some cases, with respect to structured mold semiconductor detectors in terms of materials that can be utilized and manufacturability (including materials with limited electron and/or hole mobility). Detectors of reduced thickness compared to SPECT, PET or CT imaging can be employed due to the relatively low x-ray energies used in dental intraoral imaging. The anode and cathode 3D structures created by drilling holes into the semiconductor detector material allows for the creation of very small pixels in contrast to the manufacturing difficulty associated with structured mold semiconductor detector which requires filling very small holes with semiconductor or nanoparticle detector materials.

The components of a digital x-ray camera for intraoral dental imaging are shown in FIGS. 23A-23D.

Figure 23A:
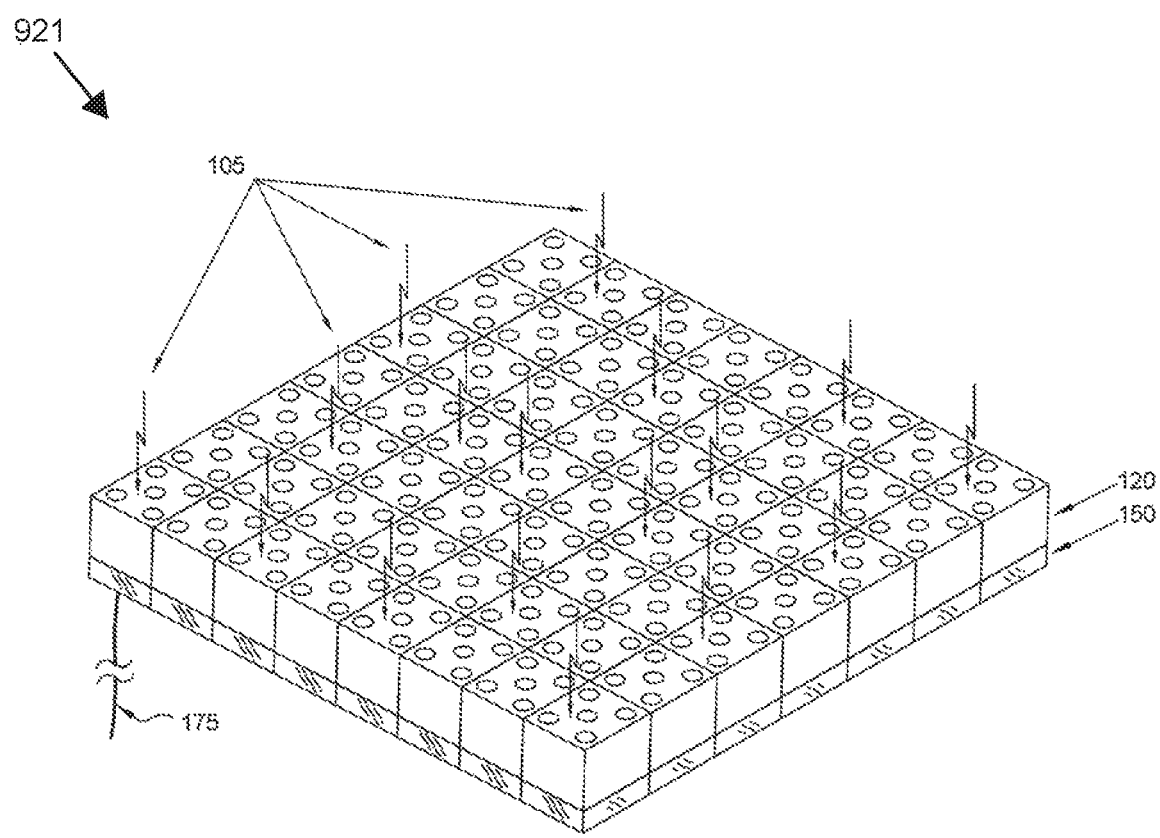
FIG. 23A is a perspective view of a structured 3D semiconductor x-ray detector with an array of electrode holes that is electronically-coupled to an attached substrate incorporating readout circuitry with a power and communication link for connection to a computer.

FIG. 23A illustrates a perspective of a structured 3D semiconductor x-ray detector 921 with an array of holes 120 (anodes and cathodes) that are electronically-coupled to an attached substrate incorporating readout circuitry 150 with a power and communication link 175 for connection to a computer with incident radiation field 105. Alternatively, a structured mold semiconductor detector can be employed with an array of holes, e.g., filled with at least one of polycrystalline, amorphous, and nan-particle semiconductor materials.

Figure 23B:
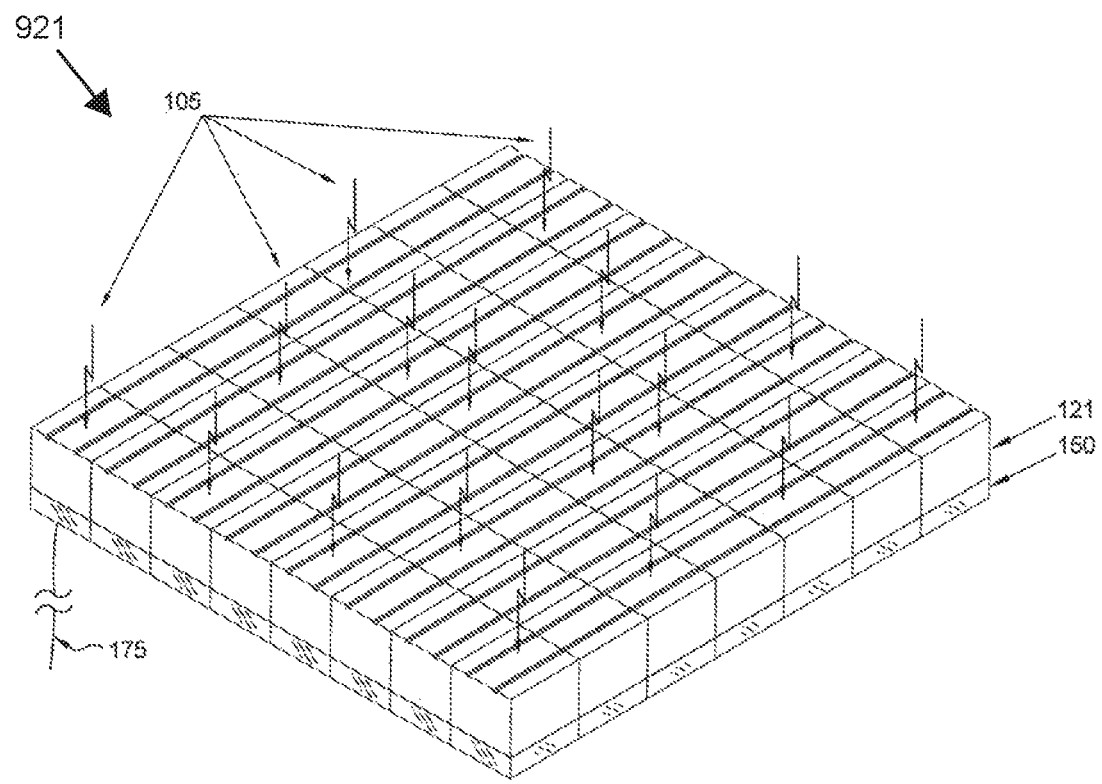
FIG. 23B is a perspective view of a structured 3D semiconductor x-ray detector with an array of electrode channels that is electronically-coupled to an attached substrate incorporating readout circuitry with a power and communication link for connection to a computer.

FIG. 23B illustrates a perspective of a structured 3D semiconductor x-ray detector 921 with an array of segmented anode and cathode channels 121 (rather than holes) that are electronically-coupled to an attached substrate incorporating readout circuitry 150 with a power and communication link 175 for connection to a computer with incident radiation field 105. Alternatively, a structured mold semiconductor detector with an array of holes and/or channels (including segmented holes and/or channels) filled with at least one of polycrystalline, amorphous, and nan-particle semiconductor materials can be employed.

Channels can be continuous (spanning the length, width or diagonal length of the active detector area) or discontinuous (spanning a length, width or diagonal length less than that of the active detector area). The hole dimensions and channel dimensions as well as the number of holes and channels shown are for illustrative purposes only. Both channels and holes can be employed within a structured 3D semiconductor detector or a structured mold semiconductor detector.

Figure 23C:
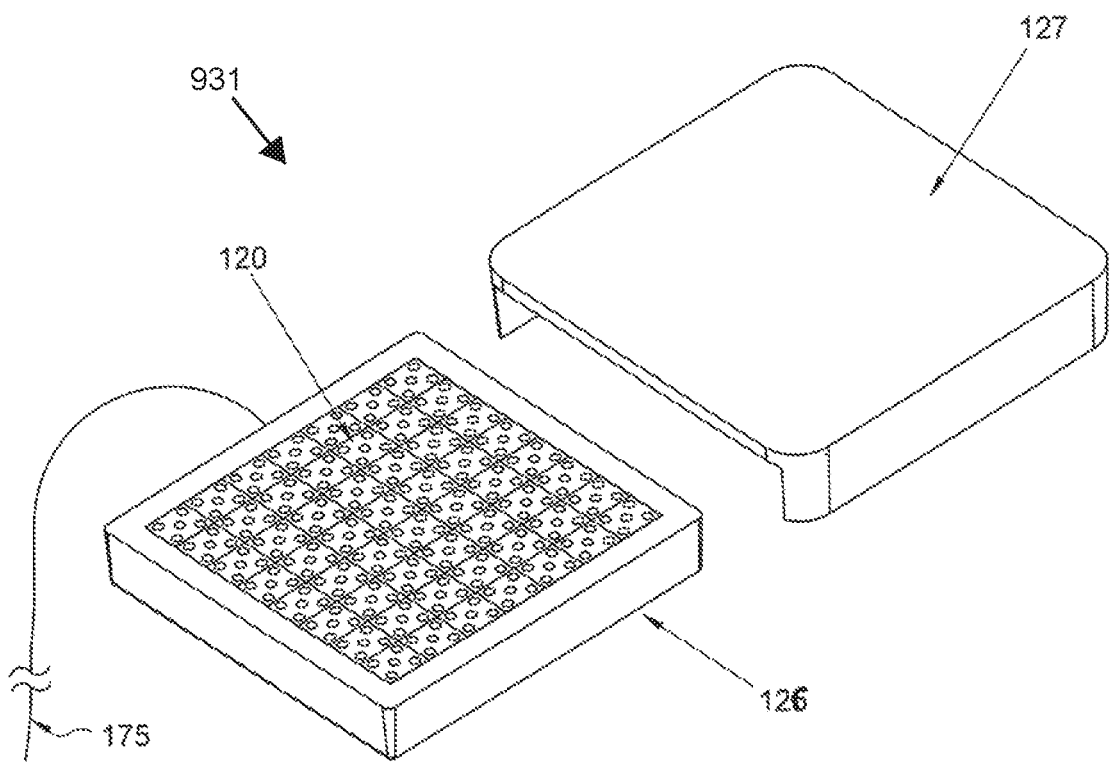
FIG. 23C is a perspective view of a movable protective cover that slides onto a protective frame holding a structured 3D semiconductor x-ray detector with an attached substrate incorporating readout circuitry including a power and communication link.

FIG. 23C illustrates a perspective of a movable protective cover 127 that can slide onto the protective shell or frame 126 holding a structured 3D semiconductor x-ray detector 921 with holes 120 and attached substrate incorporating readout circuitry as well as a power and communication link 175 connected to a computer. Alternatively, protective shell or frame 126 can hold a structured 3D semiconductor x-ray detector with channels 121. Optionally, the power source and communication link can be contained within the protective cover e.g. a battery, a wireless link).

Figure 23D:
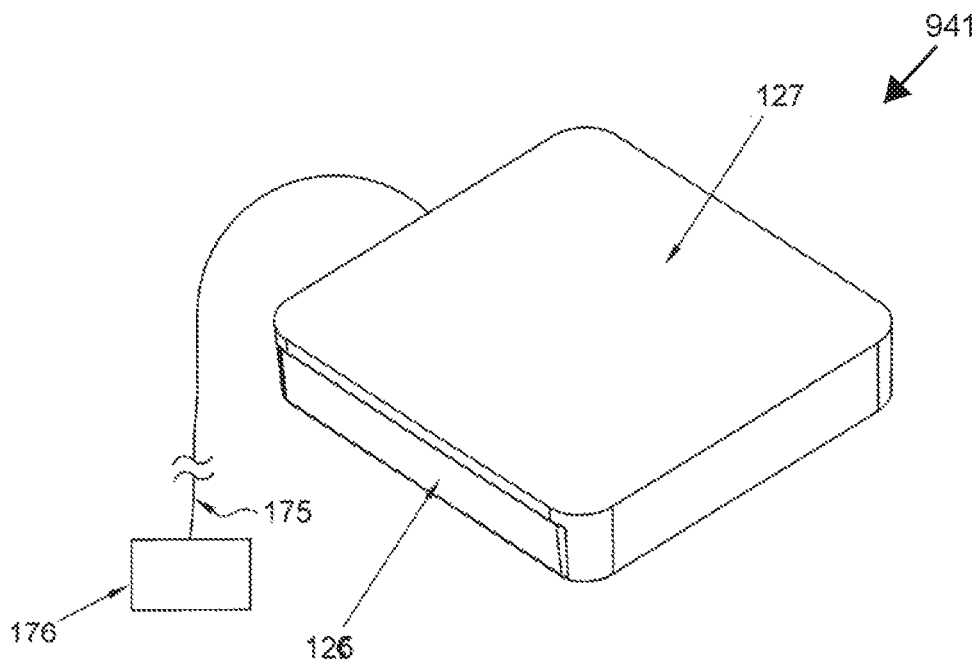
FIG. 23D is a perspective view of a movable protective cover in place over the protective frame holding a structured 3D semiconductor x-ray detector and attached substrate incorporating readout circuitry forming a digital x-ray camera for intraoral dental imaging with a power and communication link connected to computer.

FIG. 23D illustrates a perspective of a movable protective cover 127 in place over the protective frame 126 forming a digital x-ray detector or camera 941 for intraoral dental imaging with a power and communication link 175 connected to computer 176.

High resolution transparent nanoparticle storage phosphor sheets detectors (mounted on a base or plate) offer advantages compared to scintillator on CMOS/CCD detectors for intraoral dental imaging (greater x-ray stopping power, greater spatial resolution). However, the density of nanoparticles embedded within a transparent medium such as a glass ceramic is often low. This requires thicker storage phosphor sheets (approximately 400-1,000 microns or more depending on desired x-ray stopping power) to improve x-ray stopping power which in turn requiring a thicker protective shell (frame) that increases patient discomfort).

Yields often decrease as transparent nanoparticle storage phosphor detector sheet thickness increases. Uniform dispersion of nanoparticle storage phosphors within the transparent medium can be problematic and the nanoparticle storage phosphors make the transparent medium brittle which in turn requires a thicker protective shell (frame) or the use of expensive rigid materials in the shell (frame) to increase its rigidity. Furthermore, fluorescence efficiency of nanoparticle storage phosphors may typically be substantially less than for a more conventional storage phosphor, often potentially increasing patient radiation dose unnecessarily.

An alternative to the nanoparticle storage phosphor sheet detector that decreases detector sheet thickness (thickness of approximately 50-200 microns are suitable for many intraoral dental imaging applications) while restoring fluorescence efficiency is to employ a conventional storage phosphor deposited as a transparent, continuous thin film or layer (which can be applied with good uniformity) on a rigid plate or support or glued to a rigid plate or support (a substrate). The rigid plate or support can be implemented as a removable structure from the protective shell (frame) or as an integral part of the protective shell (frame) which then requires a moveable protective shell lid or cover for scanning and readout. The rigid plate surface adjacent to the storage phosphor layer can implement at least one of reflectors, absorbers, scatterers, and WLS materials.

The same protective shell (frame), nanoparticle storage phosphor detector scanning mechanism and electronic readout system can be employed as well as modifications (etchings, coatings, etc.) to one or both of the transparent storage phosphor film surfaces and/or the storage phosphor film rigid plate or support (previously described herein for one or both surfaces of the nanoparticle storage phosphor plates as well as the supporting surface). The protective shell (frame)

thickness can be kept the same or decreased (which improves patient comfort) due to the reduced thickness of the storage phosphor film compared to the nanoparticle storage phosphor plate.

A dual energy implementation of the storage phosphor film detector employs transparent storage phosphor film detectors (of the same storage phosphor material or different storage phosphor materials) mounted on both sides of support plate. If two different storage phosphor materials are employed the material with the lower effective Z is typically positioned to intercept the x-ray beam first. If only one storage phosphor material is employed the layer that intercepts the x-ray beam first is typically of the same or reduced thickness relative to the second layer. The two surfaces can be scanned and read out at the same time (e.g., using two independent readout systems), or sequentially. Optionally, the support plate can provide energy filtration by selective adsorption of the incident radiation, so that the energy spectrum is modulated on passage through the support plate. An alternative implementation (which may limit the choice of storage phosphors) employs a stack of at least two different transparent storage phosphor films (different stimulating wavelengths and/or different emission spectrums), minimizing registration issues and reducing the thickness of the protective frame. Multi-energy implementations employ at least one additional transparent storage phosphor film layer on at least one side of the support plate. Furthermore, variations of dual energy (or multi-energy) implementations include, but are not limited to, replacing a continuous transparent storage phosphor film layer with either a granular storage phosphor layer or a transparent nano-particle storage phosphor layer or a pixelated storage phosphor layer or a structured storage phosphor layer.

Figure 24A:
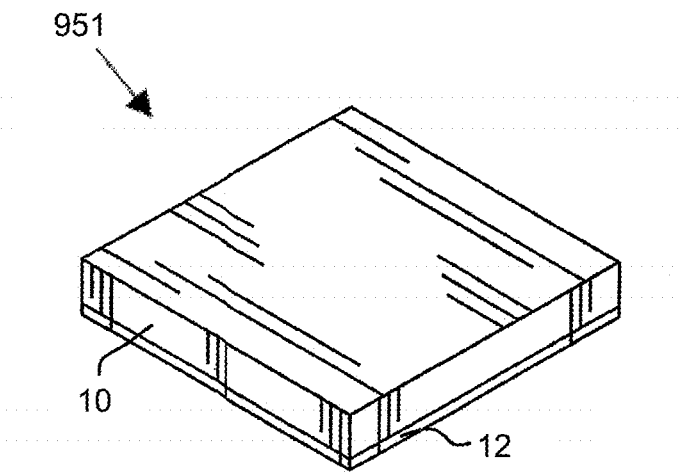
FIG. 24A is a perspective view of a flat, small area transparent storage phosphor film on a support plate (a transparent storage phosphor film plate) that can be mounted within a protective frame.

FIG. 24A illustrates a perspective of a flat, small area transparent storage phosphor film 10 on a support plate 12 (a transparent storage phosphor film support plate) that can be mounted within a protective frame to provide a detector system 951.

Figure 24B:
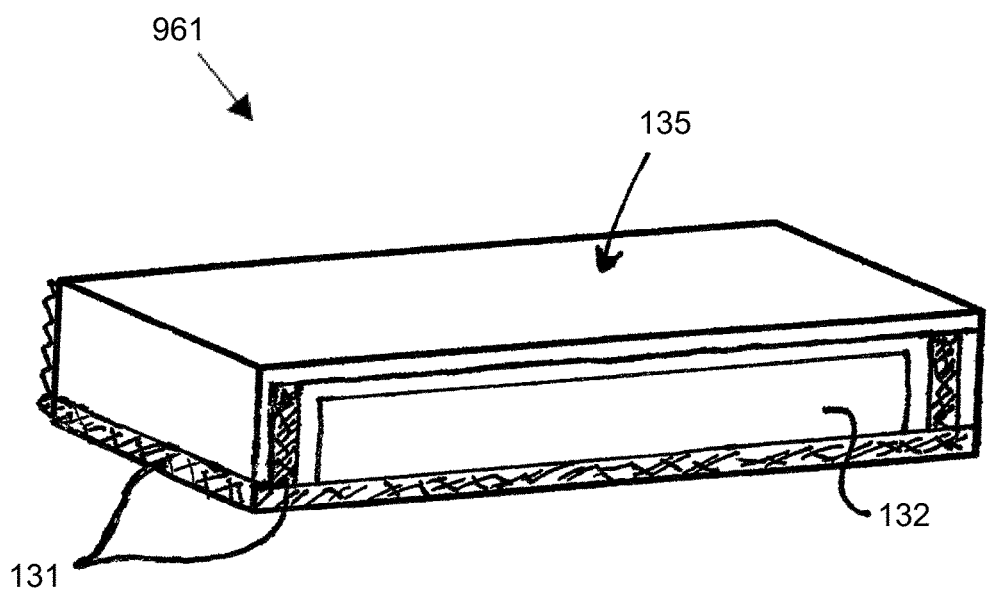
FIG. 24B is a perspective view of a movable protective layer that can slide onto the protective frame of a transparent storage phosphor film plate.

FIG. 24B illustrates a perspective (transparent edge-on) of a transparent storage phosphor film support plate 132 attached to a protective frame 131 with a movable protective layer 135 that slides onto the protective frame to provide a detector system 961.

Figure 24C:
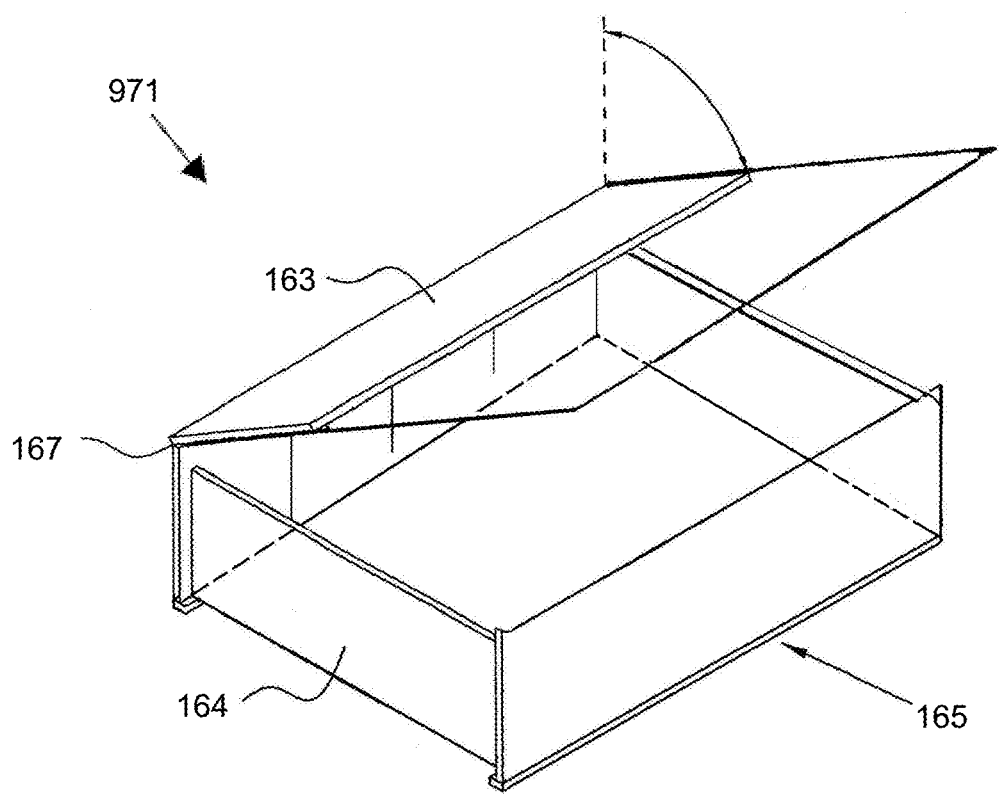
FIG. 24C is a perspective view of a movable protective layer that is attached to the protective frame of a transparent storage phosphor film plate by a hinge mechanism.

FIG. 24C illustrates a perspective of a protective frame with a base 165, sidewalk 164 and a rotatable movable protective layer or cover 163 attached by a hinge 167 to the protective frame. A transparent storage phosphor film support plate can be made separable from the frame or it can be integrated into the frame to provide a detector system 971.

EXAMPLES

Suitable examples and embodiments of the invention include, but are not limited to, any one or more of the following. Individual features of these examples and embodiments can be provided in any order or combination suitable to radiation imaging, as described herein.

A detector module comprising: a first layer of scintillator rods, each scintillator rod in the first layer extending in a first direction; and a second layer of scintillator rods stacked on or adjacent the first layer, each scintillator rod in the second layer extending in a second direction; wherein the first and second directions are transversely oriented, such that the first and second layers of scintillator rods are crossed to define a region of light sharing between the scintillator rods of the first layer and the scintillator rods of the second layer.

In particular examples and embodiments, the scintillator rods in the first layer have at least one of different dimension or different scintillator materials with respect to the scintillator rods in the second layer, such that the first and second layers have one or more of different spatial, timing and energy resolution. Scintillator rods within at least one of the first and second layers have at least one of different dimensions or different scintillator materials. At least some of the scintillator rods have different cross-sectional area transverse to at least one of the first and second directions, respectively. At least some of the scintillator rods have different longitudinal dimension along at least one of the first and second directions, respectively.

The detector module, further comprising encoding features disposed at least one of in, on and between one or both of the scintillator rods of the first layer and the scintillator rods of the second layer, wherein the encoding features are configured to modulate propagation of optical signals along one or both of the layers of scintillator rods, or between the layers of scintillator rods. In various examples and embodiments, the scintillator rods are configured to generate the optical signals in response to one or more of x-ray radiation, gamma radiation, or particle radiation.

The detector module, further comprising a pattern applied to one or both of the first and second layers of scintillator rods, or between the scintillator rods, the pattern comprising at least one of a reflective, diffusive, absorptive, WLS, photonic crystal, nano-layered metamaterials (including nanocavities), refracting, diffracting and lens optical surface adapted to modulate propagation of optical signals along one or both of the layers of scintillator rods, or between the layers of scintillator rods. In various examples and embodiments, the pattern comprises a grid of optical features having a spacing corresponding to that of the crossed scintillator rods in the first and second layers, the grid of optical features configured to modulate lateral light flow therebetween.

The detector module, further comprising an offset portion of one or both of the layers of scintillator rods with respect to the other, wherein the offset portion is defined by an extension of the respective scintillator rods beyond a periphery of the other layer, outside the region of light sharing between the first and second layer.

The detector module, further comprising a photodetector element coupled to the offset portion of one of both of the layers, wherein the photodetector element is configured to sense optical signals from the extension of the respective scintillator rods, outside the region of light sharing between the first and second layer. In various examples and embodiments, the scintillator rods in the first layer and the scintillator rods in the second layer have at least one of a substantially same cross sectional dimension, a substantially same longitudinal dimension, and a substantially same scintillator material with a substantially same response.

A detector module comprising: a layer of scintillator rods, each scintillator rod extending in a longitudinal direction therein; a pixel structured scintillator layer stacked on or adjacent the layer of scintillator rods, the pixel structured scintillator layer extending transversely to the longitudinal direction; and a light sharing region defined between the layer of scintillator rods and the pixel structured scintillator layer.

A detector module comprising: a layer of scintillator rods, each scintillator rod extending in a longitudinal direction therein; a continuous scintillator layer stacked on or adjacent the layer of scintillator rods, the continuous scintillator layer extending transversely to the longitudinal direction; and a light sharing region defined between the layer of scintillator rods and the continuous scintillator layer.

A detector module comprising: at least first and second layers of crossed scintillator rods configured to generate optical signals in response to ionizing radiation, the crossed scintillator rods extending in first and second transverse directions in the first and second layers, respectively; a light sharing region defined between the first and second layers, wherein the optical signals are transmitted between the respective crossed scintillator rods; and a plurality of photodetector elements configured to convert the optical signals into output characterizing the radiation.

In various examples and embodiments, the first and second layers of scintillator rods are defined in discrete, stacked scintillator elements having the light sharing region defined therebetween. The first and second layers of scintillator rods are defined in a unitary scintillator element having the light sharing region defined therein.

The detector module, further comprising a plurality of dividers extending in the first and second directions in the first and second layers respectively, the dividers defining the scintillator rods in the respective layers. In various examples and embodiments, dividers extend into the unitary scintillator element from a first major surface of the first layer and from a second major surface of the second layer, respectively, each of the dividers having a depth less than a thickness of the unitary scintillator element between the first and second major surfaces. The depth of the dividers varies between different scintillator rods in one or both of the first and second layers. The dividers comprise at least one of physical or virtual gaps formed in the unitary scintillator element, between the respective scintillator rods. The dividers comprise at least one of a reflective, diffusive, absorptive or WLS optical feature or material disposed between the respective scintillator rods.

The detector module, further comprising an encoding pattern configured to modulate the transmission of the optical signals between the first and second layers of scintillator rods. In various examples and embodiments, the photodetector elements are disposed at ends of the scintillator rods, the ends defining an end face having a cross sectional area transverse to the first and second direction in the first and second layers, respectively.

A detector module comprising: at least first and second layers comprising scintillator rods and a pixel structured scintillator, respectively, configured to generate optical signals in response to ionizing radiation, wherein the scintillator rods extend in a longitudinal direction and the pixel structured scintillator extends transversely thereto; a light sharing region defined between the first and second layers, wherein the optical signals are transmitted between the scintillator rods and the pixel structured scintillator; and a plurality of photodetector elements configured to convert the optical signals into output characterizing the radiation.

In various examples and embodiments, the first layer comprises a plurality of discrete scintillator rod elements coupled to the second layer; and the second layer comprises a plurality of discrete pixel structured scintillator elements coupled to the first layer.

In various examples and embodiments, the first and second layers are formed of a unitary scintillator element having a first major surface of the first layer and a second major surface of the second layer, in which: the first layer comprises a plurality of virtual rod elements defined by a first set of dividers extending into the unitary scintillator element from the first major surface thereof; the second layer comprises a plurality of virtual pixel structured scintillator elements defined by a second set of dividers extending into the unitary scintillator element from the second major surface thereof; and each of the first and second sets of dividers has a depth less than a thickness of the unitary scintillator element between the first and second major surfaces.

The detector module of claim 25, wherein: the first layer comprises a unitary scintillator element coupled to the second layer, the unitary scintillator element having a set of dividers defining the scintillator rods as a plurality of virtual rod elements therein; and the second layer comprises of a plurality of discrete pixel structured scintillator elements coupled to the first layer. In various examples and embodiments, the first layer comprises a plurality of discrete scintillator rod elements coupled to the second layer; and the second layer comprises a unitary scintillator element coupled to the first layer, the unitary scintillator element having a set of dividers defining the pixel structured scintillator as a plurality of virtual pixel elements therein.

A detector module comprising: at least a first layer of scintillator rods or a pixel structured scintillator coupled to a second layer of semi-continuous structured scintillator sheet, each of the layers extending in first and second transverse directions and configured to generate optical signals in response to ionizing radiation; a light sharing region defined between the first and second layers, wherein the optical signals are transmitted therebetween; and a plurality of photodetector elements configured to convert the optical signals into output characterizing the radiation.

A detector module comprising: a first layer of scintillator defining a plurality of scintillator elements, each of the scintillator elements extending in a longitudinal direction along the first layer; a second layer of scintillator defining a substantially continuous scintillator element extending adjacent the first layer defining the plurality of scintillator elements; a plurality of photodetector elements configured to convert optical signals generated by the scintillator into output characterizing radiation interacting in one or both of the first and second layers.

In various examples and embodiments, the plurality of scintillator elements are defined by dividers extending into the scintillator from a first major surface of the first layer, wherein a depth of the dividers defines a thickness of the first layer. Dividers are formed by at least one of a reflective, absorptive or WLS optical feature or material disposed between the respective scintillator rods. The depth of the dividers is nonuniform and defines a corresponding nonuniform thickness of the first layer. The depth of the dividers is selected to define a curved or arcuate boundary between the first and second layers.

Any such detector module, further comprising an encoding pattern configured to modulate light sharing between the first and second layers of the scintillator.

A scintillator detector module comprising: a first layer of elongate scintillator elements, each extending in a first longitudinal direction along the first layer; a second layer of elongate scintillator elements, each extending in a second longitudinal direction along the second layer; and a plurality of photodetectors configured to generate output characterizing optical signals generated by the scintillator elements in response to radiation interacting in one or both of the first and second layers.

A scintillator detector module comprising: a first layer of elongate scintillator elements, each extending in a longitudinal direction along the first layer; a second layer of pixel structured scintillator elements extending in first and second transverse directions along the second layer; and a plurality of photodetectors configured to generate output characterizing optical signals generated by the scintillator elements in response to radiation interacting in one or both of the first and second layers.

A detector module comprising: a first layer comprising a plurality of one or both of: elongate scintillator elements extending in a longitudinal direction along the first layer, and pixel structured scintillator elements extending in first and second transverse directions along the first layer; a plurality of photodetectors configured to generate output characterizing optical signals generated by the scintillator elements in response to radiation interacting therein; a second layer comprising one or more semiconductor detector elements oriented edge on or face on with respect to the radiation.

A detector module, further comprising an intermediate layer of scintillator disposed between the first and second layers. In various examples and embodiments, one, two or more of the first, second and intermediate layers are formed of a unitary scintillator material and further comprising a plurality of dividers formed in the unitary scintillator material, the dividers defining the scintillator elements therein. One, two or more of the first, second and intermediate layers are formed of discrete scintillator materials joined together to form the detector module. The intermediate layer comprises a plurality of elongate scintillator elements. The elongate scintillator elements in the intermediate layer are disposed at a skew angle with respect to the elements of the first or second layer. The intermediate layer comprises a plurality of pixel structured scintillator elements. The intermediate layer comprises a continuous scintillator layer.

The detector module, further comprising an intermediate layer disposed between the first and second layers, wherein the intermediate layer comprises a non-scintillator material. In various examples and embodiment, the intermediate layer is configured to modulate light sharing between the scintillator elements in the first and second layers. The elements in the second layer are oriented transverse to the elements in the first layer such that the elements in the first and second layers are crossed. The elements in the second layer are oriented along the elements in the first layer such that the elements in the first and second layers are parallel.

Any such detector module, further comprising wavelength shifting material disposed at least one of in, on and between the scintillator elements and the photodetector elements, wherein the wavelength shifting material is adapted to shift an emission spectrum of the scintillator elements to match a spectral response of the photodetector elements. In various examples and embodiments, the wavelength shifting material is adapted to shift the emission spectrum of Cherenkov light emitted by the scintillator elements in response to the radiation to match the spectral response of the photodetector elements. The wavelength shifting material is adapted to reduce light trapping of a fluorescence signal generated by the scintillator elements in response to the radiation. The wavelength shifting material is adapted to modulate the optical signals as a function of position along the scintillator elements.

The detector module, further comprising an optical coating applied between the wavelength shifting material and a surface of one or more of the scintillator elements, the optical coating having an index of refraction selected to enhance internal reflection at the surface. In various examples and embodiments, the photodetector elements are disposed to detect the optical signals emitted at a single side or end or at opposite sides or ends of one or more of the scintillator elements. The photodetector elements are disposed to detect optical signals emitted at sides or ends of the scintillator elements and have timing resolution adapted to distinguish signals reflected from opposite sides or ends thereof.

Any such detector module, wherein the layers are curved or generally arcuate to provide a focused geometry of the scintillator module with respect to a radiation source. In various examples and embodiments, the layers define one or more generally cylindrical shell segments oriented along an axial direction transverse to a direction of the radiation source. The layers define one or more generally spherical shell segments disposed generally transverse to a direction of the radiation source.

A detector module comprising: a first layer of scintillator elements, each extending in a first direction along the first layer; a second layer of scintillator elements, each extending in a second direction along the second layer, wherein the second direction is oriented transverse to the first direction such that the scintillator elements in the first and second layers are crossed; an intermediate layer disposed between the first and second layers; and a plurality of photodetectors configured to convert optical signals generated by the scintillator elements into output characterizing radiation interacting in at least one of the first, second and intermediate layers.

A detector module comprising: a first layer of scintillator elements, each extending in a first direction along the first layer; a plurality of photodetectors configured to convert optical signals generated by the scintillator elements into output characterizing radiation interacting therein; a second layer of one or more semiconductor detector elements oriented edge on or face on with respect to the radiation; and an intermediate layer between the first and second layers.

In various examples and embodiments, the intermediate layer comprises a plurality of scintillator blocks positioned between and optically coupled to the first and second layers of crossed scintillator elements. The optical signals are transmitted through the intermediate layer between the first layer and the second layer. The intermediate layer is encoded to modulate transmission of the optical signals as a function of position along the scintillator elements. The first, second and intermediate layers are formed of a unitary scintillator element. The intermediate layer has internal structure. The intermediate layer is formed of a different scintillator material from the scintillator elements of one or both of the first and second layers. The intermediate layer is substantially transparent. The intermediate layer is configured to transmit the optical signals from a scintillator element in the first layer to multiple scintillator elements in the second layer. The photodetector elements are configured for the output to characterize radiation of different energy spectra interacting in the first and second layers. The thicknesses of the first and second layers are selected to compensate for beam hardening.

Any such detector module, wherein one or more layers of the scintillator elements comprise scintillator fibers or optical fibers. In various examples and embodiments, at least one of the layers comprises scintillator material having optical fibers embedded therein. At least one of the layers comprises a plurality of scintillator fibers or optical fibers coupled to a scintillator sheet or block. At least some of the fibers comprise encoded cores. At least some of the fibers comprise wavelength shifting materials provided in an encoded pattern.

Any such detector module, wherein event localization information is employed to correct for optical signal propagation time within the detector module utilizing at least one of a direct event signal, a reflected signal, a cross-coupled signal, a wavelength shifted signal, and an indirect signal responsive to the event localization in the detector module.

An edge-on, multispectral CT scintillator detector system comprising a plurality of such detector modules, wherein the radiation is incident on end faces of the scintillator elements in at least one of the layers.

In various examples and embodiments, the photodetector elements are optically coupled to side faces of the scintillator elements in the at least one of the layers. The first and second layers are responsive to different energy ranges of the radiation. The first and second layers have different energy responses. The first and second layers have a same energy response.

The detector system, further comprising at least a third layer of scintillator elements having a different energy response from at least one of the first and second layers. The detector system, further comprising at least a third layer of scintillator elements having a same energy response as at least one of the first and second layers. In various examples and embodiments, the radiation comprises a combination of x-ray radiation from an x-ray source and gamma radiation from a gamma source.

The detector system, further comprising readout electronics coupled to the photodetector elements, wherein the readout electronics are adapted for a combination of CT and at least one of PET, SPECT, PET-SPECT and Compton imaging. In various examples and embodiments, the radiation comprises x-ray radiation from plural x-ray sources. Scintillator elements in the first and second layers comprise different, relatively lower-Z and relatively higher-Z scintillator materials, respectively.

The detector system, further comprising a collimator disposed with respect to the first and second layers, wherein the collimator is configured to modulate scattering of the radiation. The detector system, further comprising readout electronics coupled to the photodetector elements, wherein the readout electronic are configured for one or more of energy integration, photon counting, and photon counting with energy resolution. In various examples and embodiments, the detector system is configured for at least one of ring CT, cone beam CT, and tomosynthesis imaging.

An edge-on, integrated PET-CT detector system comprising a plurality of any such detector modules, wherein the radiation is incident on end faces of the scintillator elements in at least one of the layers and the photodetector elements are optically coupled to side faces thereof. In various examples and embodiments, the radiation comprises a combination of x-ray radiation from an x-ray source and gamma radiation from a gamma source. The first and second layers have different energy response to the radiation. The first and second layers have a same energy response to the radiation.

The detector system, further comprising at least a third layer of scintillator elements having a different energy response to the radiation than at least one of the first and second layers. The detector system, further comprising at least a third layer of scintillator elements having a same energy response to the radiation as at least one of the first and second layers. The detector system, further comprising readout electronics configured for determination of an interaction position of the radiation within the scintillator elements.

In various examples and embodiments, scintillator elements in different layers have different cross sectional geometry. The detector modules define a full ring geometry with respect to a source of the radiation. The detector modules define a partial ring geometry with respect to a source of the radiation. The detector modules define a planar geometry.

Any such detector system, further comprising an encoding pattern configured to modulate light sharing between the first and second layers, wherein the encoding pattern is adapted to modulate the optical signals as a function of position along the first and second layers. Any such detector system, further comprising a pattern of wavelength shifting material applied to the scintillator elements, wherein the pattern of wavelength shifting material is adapted to modulate the optical signals as a function of position along the first and second layers. Any such detector system, further comprising readout electronics coupled to the photodetector elements, wherein the readout electronics are adapted for a combination of at least two of CT, PET, SPECT and Compton imaging.

A radiation detector module comprising: a scintillator element configured to generate optical signals in response to incident radiation; a photodetector coupled to at least a first surface of the scintillator element, the photodetector configured to convert the optical signals into output characterizing the radiation; and an acoustic array coupled to at least a second surface of the scintillator element, the acoustic array configured to convert acoustic signals generated in the scintillator element into output characterizing acoustic energy deposited therein.

In various examples and embodiments, the radiation is incident face on-to the scintillator element, along a major surface thereof. The radiation is incident edge-on to the scintillator element, along an edge defined transverse to first and second major opposing surfaces thereof. The photodetector and the acoustic array are disposed on opposing surfaces of the scintillator element. The photodetector and the acoustic array are disposed on a same surface of the scintillator element. The photodetector and the acoustic array are disposed on non-parallel surfaces of the scintillator element. At least one of the photodetector and the acoustic array is coupled to more than one surface of the scintillator element.

The detector module, further comprising readout electronics coupled to the photodetector, the readout electronics configured to characterize the incident radiation based on one or more of energy resolution, spatial resolution or temporal resolution of the optical signals. The detector module, further comprising readout electronics coupled to the acoustic array, wherein the readout electronics are configured to characterize the incident radiation based on one or more of spatial resolution, temporal resolution or energy resolution of the acoustic signals. In various examples and embodiments, the acoustic array comprises an acoustic transceiver configured for generating audio or ultrasound signals.

An imaging system comprising any such radiation detector module adapted to image at least one of an external or internal radiation field, and further comprising: a sample acoustically coupled to the detector module; an acoustic transceiver configured to generate density variations in the sample; and a processor in data communication with the radiation detector module, the processor configured to evaluate the sample based on the first and second outputs. In various examples and embodiments, the radiation detector module is configured for the imaging system to acquire conventional radiological images of the sample based on the output characterizing the radiation and phase images of the sample based further on the output characterizing the acoustic energy.

A radiation detector module comprising: a detector element configured to generate electronic and acoustic signals in response to incident radiation passing through a sample;

and an acoustic array or transceiver coupled to the detector element and acoustically coupled to the sample, wherein the acoustic array or transceiver is configured to convert the acoustic signals into output characterizing the incident radiation. In various examples and embodiments, the detector element comprises a solid state detector medium. In various examples and embodiments, the detector element comprises a scintillator.

INCORPORATED REFERENCES

These references are expressly incorporated by reference herein:

Bornefalk Hans, Danielsson Mats, Svensson Christer, Image Quality in Photon Counting-Mode Detector Systems, U.S. Publication No. 2010/0215230 (U.S. Pat. No. 8,378,310).

Cherry Simon, Sorenson James, Phelps Michael, Physics in Nuclear Medicine, third edition, Saunders, N.Y., 2003.

Danielsson Mats, Karlsson Staffan, Silicon Detector Assembly for X-ray Imaging, U.S. Publication No. 2010/0204942 (U.S. Pat. No. 8,183,535).

Da Via C., et al., Dual Readout—Strip/Pixel Systems, Nucl. Instr. Meth. A594, p. 7 (2008).

Knoll, G., Radiation Detection and Measurement, 4th edition, Wiley, pp. 50-51, 189-202, 230, 238, 492 (2010).

Kroeger R., et al., Three-Compton Telescope: Theory, Simulations, and Performance, IEEE Trans. Nucl. Sci., Vol. 49(4), pp. 1887-1892 (August 2002).

Kronberger Matthias, Auffray Etiennette, Lecoq Paul, Probing the Concepts of Photonic Crystals on Scintillating Materials, IEEE Transactions on Nuclear Science, Vol. 55, No. 3, June 2008

Nagarkar Vivek, Gaysinskiy Valeriy, Gelfandbein Vladimir, Miller Stuart, Cool Steven, Kudrolli Haris, and Barber H., Continuous Phoswich Detector for Molecular Imaging, IEEE NSS/MIC, Knoxville, Tenn., Oct. 30-Nov. 6, 2010.

Nelson R., Barbaric Z., High Efficiency X-Radiation Converters, U.S. Pat. No. 4,560,882.

Nelson R., X-ray Detector for Radiographic Imaging, U.S. Pat. No. 4,937,453.

Nelson R., Method for Manufacturing a High Resolution Structured X-ray Detector, U.S. Pat. No. 5,258,145.

Nelson R., Nelson W., Device and System for Improved Imaging in Nuclear Medicine and Mammography, U.S. Pat. No. 6,583,420.

Nelson R., Nelson W., Device and System for Enhanced SPECT, PET, and Compton Scatter Imaging in Nuclear Medicine, U.S. Pat. No. 7,291,841.

Nelson R., Devices and Systems for Enhanced SPECT, PET, and Compton Gamma Cameras, U.S. Pat. No. 7,635,848.

Nelson R., Nelson W., Slit and Slot Scan, SAR, and Compton Devices and Systems for Radiation Imaging, U.S. Pat. No. 8,017,906.

Nelson R., Edge-on SAR Scintillator Devices and Systems for Enhanced SPECT, PET, and Compton Gamma Cameras, U.S. Pat. No. 8,115,174.

Nelson R., Edge-on SAR Scintillator Devices and Systems for Enhanced SPECT, PET, and Compton Gamma Cameras, U.S. Pat. No. 8,115,175.

Nelson R., Edge-on SAR Scintillator Devices and Systems for Enhanced SPECT, PET, and Compton Gamma Cameras, U.S. Pat. No. 8,183,533.

Nelson R., Nelson W., High Resolution Imaging System for Digital Dentistry, U.S. patent application Ser. No. 13/199,612, filed Sep. 6, 2011 (U.S. Publication No. 2012/0181437).

Nelson R., Nelson W., Enhanced Resolution Imaging Systems for Digital Radiography, U.S. Pat. No. 9,347,893.

Nelson R., Nelson W., Detector Systems for Radiation Imaging, U.S. patent application Ser. No. 14/804,777, filed Jul. 21, 2015 (U.S. Publication No. 2016/0021674).

Nelson R., Nelson W., Detector Systems for Radiation Imaging, U.S. patent application Ser. No. 14/804,838, filed Jul. 21, 2015 (U.S. Publication No. 2015/0331115).

Nelson W., Nelson R., Device and System for Improved Imaging in Nuclear Medicine, U.S. Pat. No. 7,015,460.

Parker S., et al., 3DX: an X-ray pixel array detector with active edges, IEEE Trans. Nucl. Sci. 53 1676-1688 (2006).

Parker S., et al., Increased speed: 3D silicon sensors; Fast current amplifiers, IEEE Trans. Nucl. Sci. 58, pp. 404-417 (2011).

Phelps Michael, PET Physics, Instrumentation, and Scanners, Springer, N.Y., 2006.

Singh, M., An electronically collimated gamma camera for single photon emission computed tomography. Part I: Theoretical considerations and design criteria, Medical Physics Vol. 10(4), pp. 421-427 (July/August 1983).

Singh, M., Doria D., An electronically collimated gamma camera for single photon emission computed tomography. Part Image reconstruction and preliminary experimental measurements, Medical Physics Vol. 10(4), pp. 428-435 (July/August 1983).

Yu, H. and Wang, G., Compressed sensing based interior tomography, Phys. Med. Biol., Vol. 54(9): pp. 2791-2805 (2009).

Urdaneta, M., et al., Quantum dot composite radiation detectors, IEEE Nuclear Science Symposium (2010).

While this invention has been described with reference to exemplary embodiments, it will be understood by those skilled in the art that various changes can be made and equivalents may be substituted without departing from the spirit and scope thereof. Modifications may also be made to adapt the teachings of the invention to particular problems, technologies, materials, applications and materials, without departing from the essential scope thereof. The invention is not limited to the particular examples that are disclosed herein, but encompasses all embodiments falling within the scope of the appended claims.

The invention is thus susceptible to various modifications and alternative forms, specific examples thereof having been shown by way of example in the drawings and described in detail. It is understood that the invention is not limited to the particular forms or methods disclosed, but to the contrary, the invention encompasses all modifications, equivalents, and alternatives falling within the spirit and scope of the claims.

The invention claimed is:

1. A detector module comprising:
   a first layer of scintillator rods, each scintillator rod in the first layer extending in a first direction; and
   a second layer of scintillator rods adjacent the first layer, each scintillator rod in the second layer extending in a second direction;
   wherein the first and second directions are transversely oriented or parallel,
   such that the first and second layers of scintillator rods are crossed and implement a single-sided photodetector readout in one of the first and second layers and a double-sided photodetector readout in another of the first and second layers, or such that the first and second layers of scintillator rods implement a sparse or reduced sparse dual-sided photodetector readout; and
  a region of light sharing defined between the scintillator rods of the first layer and the scintillator rods of the second layer;
  wherein one or more of the scintillator rods implement light sharing within one or both of the first and second layers, or have at least one different detector property selected from a different detector material, decay time, emission spectrum or dimension with respect to at least one other of the scintillator rods in the first or second layer, and wherein the one or more scintillator rods in one or both of the first and second layers have one or more of different spatial, timing or energy resolution with respect to the at least one other scintillator rod in the first or second layer; and
  wherein the scintillator rods are configured to generate optical signals in response to one or more of x-ray radiation, gamma radiation, or particle radiation.

2. The detector module of claim 1, wherein the scintillator rods in the first layer include at least one different scintillator material from the scintillator rods in the second layer.

3. The detector module of claim 1, wherein one or more of the scintillator rods in one or both of the first and second layers have at least one of different cross-sectional areas transverse to either the first or second direction, or different longitudinal dimensions along either the first or second direction, with respect to at least one other of the scintillator rods in the first or second layer.

4. The detector module of claim 1, further comprising an offset portion defined by an extension of one or more of the scintillator rods in one or both of the first and second layers, the offset portion extending beyond a periphery of an adjacent layer of the first and second layers of scintillator rods, outside the region of light sharing defined between the first and second layers of scintillator rods.

5. The detector module of claim 4, wherein the photodetector readout comprises a photodetector coupled to the offset portion of at least one of the scintillator rods, and wherein the photodetector is configured to sense optical signals from the extension of the at least one respective scintillator rod, outside the region of light sharing.

6. The detector module of claim 4, wherein the offset portion defined by the extension of one or more of the detector elements beyond the periphery of the adjacent layer is sufficiently large so as to define one or more pixels by an absence of direct light sharing, outside the region of light sharing defined between the first and second layers of scintillator rods.

7. An imaging system comprising one or more detector modules configured to interrogate a material sample by detecting ionizing radiation according to claim 1, and further comprising an image processor in communication with the one or more detector modules, the image processor configured to generate images of the material sample based on the ionizing radiation and the encoding technique.

8. The imaging system of claim 7, wherein the material sample includes biological tissue and the image processor is configured for medical imaging of the biological tissue.

9. The imaging system of claim 7, wherein the encoding features comprise non-optical information carriers.

10. The imaging system of claim 7, wherein the one or more detector modules comprise structured ionizing radiation detector elements and the encoding features are implemented with the structured ionizing radiation detector elements.

11. The detector module of claim 1, further comprising encoding features disposed in, on or between at least some of the scintillator rods of one or both of the first and second layer, wherein the encoding features are configured to modulate propagation of the optical signals along or between or out of one or both of the layers.

12. The detector module of claim 11, wherein the encoding features comprise a pattern of at least one photonic crystal material, and wherein the pattern is adapted to modulate the propagation of optical signals along or between one or both of the layers of scintillator rods.

13. The detector module of claim 11, wherein the encoding features comprise a grid of optical features having a spacing corresponding to that of the scintillator rods in the first and second layers, the grid of optical features configured to modulate light flow between the first and second layers.

14. The detector module of claim 11, wherein the encoding features comprise a pattern of nano-layered metamaterials or nanocavities, wherein the pattern is adapted to modulate the propagation of optical signals along or between one or both of the layers of scintillator rods.

15. The detector module of claim 14, wherein the first and second directions are transversely oriented such that the first and second layers of scintillator rods are crossed and the pattern is adapted to modulate the propagation of optical signals along or between one or both of the layers of crossed scintillator rods.

16. The detector module of claim 11, wherein the encoding features comprise a pattern of a refracting, diffracting or lens optical surface, wherein the pattern is adapted to modulate the propagation of optical signals along or between one or both of the layers of scintillator rods.

17. The detector module of claim 1, wherein the first and second directions are transversely oriented such that the first and second layers of scintillator rods are crossed and implement double-sided photodetector readout.

18. The detector module of claim 17, wherein the scintillator rods implement light sharing within one or both of the first and second crossed layers.

19. The detector module of claim 1, wherein the first and second layers of scintillator rods implement the sparse or reduced sparse dual-sided photodetector readout with different sets of photodetectors coupled to the scintillator rods on opposite sides of the detector module, each scintillator rod having one and only one photodetector readout, with one and only one photodetector readout per each scintillator rod.

20. The detector module of claim 19, wherein the scintillator rods implement light sharing within one or both of the first and second layers and some of the scintillator rods have the at least one different detector property selected from a different detector material, decay time, emission spectrum or dimension with respect to at least some others of the scintillator rods in the first or second layer.

21. The detector module of claim 1, further comprising an offset portion defined by an overhang of one or more of the scintillator rods in one or both of the first and second layers, wherein the one or more of the scintillator rods extend to overhang the region of light sharing defined between the scintillator rods of the first layer and the scintillator rods of the second layer.

22. The detector module of claim 1, further comprising an offset portion defined by an underhang of one or more of the scintillator rods in one or both of the first and second layers, the underhang extending within a periphery of an adjacent layer of the first and second layers of scintillator rods, wherein one or more photodetectors are coupled to an end of the one or more scintillator rods in the underhang, recessed with respect to the adjacent scintillator layer.

23. A detector module comprising:
a first layer of scintillator rods, each scintillator rod in the first layer extending in a first direction; and
a second layer of scintillator rods adjacent the first layer, each scintillator rod in the second layer extending in a second direction;
wherein the first and second directions are transversely oriented or parallel,
such that the first and second layers of scintillator rods are crossed and implement a single-sided photodetector readout in one of the first and second layers and a double-sided photodetector readout in another of the first and second layers, or
such that the first and second layers of scintillator rods implement a sparse or reduced sparse dual-sided photodetector readout; and
a region of light sharing defined between the scintillator rods of the first layer and the scintillator rods of the second layer;
wherein one or more of the scintillator rods implement light sharing within one or both of the first and second layers;
wherein the scintillator rods are configured to generate optical signals in response to one or more of x-ray radiation, gamma radiation, or particle radiation; and
wherein the first and second layers of scintillator rods comprise at least one of virtual or semi-continuous discrete scintillator elements having the light sharing region defined between the virtual or semi-continuous discrete scintillator elements of the first and second layers.

24. The detector module of claim 23, wherein the photodetector readout includes at least one of strip photodetectors with readout at both ends or continuous area photodetectors with readout at four corners or 1D or 2D photodetector arrays, wherein the photodetector readouts are disposed at end faces of the scintillator rods, the end faces having a cross sectional area transverse to the first or second direction of the scintillator rods within the respective first and second layers.

25. The detector module of claim 23, wherein the photodetector readout is configured to generate output characterizing radiation of first and second different energy spectra interacting in the first and second layers, respectively.

26. The detector module of claim 23, further comprising at least one intermediate scintillator layer comprising one or more of pixel, rod, block or sheet scintillator elements disposed between the first and second layers of scintillator rods, wherein the intermediate scintillator layer defines the region of light sharing between the first and second layers of scintillator rods.

27. The detector module of claim 26, wherein one or more of the first and second layers of scintillator rods or the intermediate scintillator layer implements the sparse or reduced sparse dual-sided photodetector readout.

28. An edge-on, multispectral CT detector system comprising:
a plurality of multilayer detector modules extending along an axial direction of the detector system, each multilayer detector module comprising at least first and second layers of scintillator or semiconductor or structured semiconductor or structured mold detector elements extending in first and second directions,
wherein the first and second directions are transversely oriented or parallel,
such that the first and second layers of detector elements are crossed or parallel and implement a single-sided readout or a double-sided readout in at least one of the first and second layers, or
such that the first and second layers of detector elements comprise scintillator detector elements and implement a sparse or reduced sparse dual-sided photodetector readout;
wherein the detector elements are configured to generate signals in response to one or more of x-ray radiation, gamma radiation, or particle radiation incident on the multilayer detector modules from at least one source;
wherein at least one of the layers of detector elements is oriented edge-on such that the radiation is incident from the at least one source on end faces of the detector elements in the at least one of the layers; and
wherein the readout is configured to generate output from the signals with at least one of the layers of the multilayer detector modules providing energy resolution, such that the output characterizes the radiation interacting with different energy spectra in the at least first and second layers, respectively.

29. The detector system of claim 28, wherein the detector elements in the at least one of the layers of the multilayer detector module comprise scintillator detector elements and the readout comprises photodetectors optically coupled to side faces or end faces of the scintillator detector elements in the at least one of the layers.

30. The detector system of claim 28, wherein the first and second layers of the multilayer detector modules are responsive to different energy ranges of the radiation and the first and second layers have different energy responses to the radiation.

31. The detector system of claim 28, at least some of the multilayer detector modules further comprising at least a third layer of detector elements having a different energy response to the radiation from at least one of the first and second layers, wherein a number of layers of the detector elements in at least some multilayer detector modules varies with respect to others of the multilayer detector modules.

32. The detector system of claim 28, wherein the radiation incident on the multilayer detector modules comprises a combination of x-ray radiation from an x-ray source and gamma radiation from a gamma source.

33. The detector system of claim 32, wherein the multilayer detector modules of the detector system are adapted for a combination of CT and at least one of PET, SPECT, PET-SPECT and Compton imaging.

34. The detector system of claim 28, wherein the detector elements of the multilayer detector modules comprise scintillator rods in at least the first and second layers, and wherein the scintillator rods in at least the first and second layers comprise different, relatively lower-Z and relatively higher-Z scintillator materials, respectively.

35. The detector system of claim 28, further comprising a collimator disposed with respect to at least the first and second layers of the multilayer detector modules, wherein the collimator is configured to modulate scattering of the radiation.

36. The detector system of claim 28, wherein the first and second layers of detector elements of the multilayer detector modules of the detector system are configured for at least one of ring CT, partial ring CT, cone beam CT, and tomosynthesis imaging.

37. The detector system of claim 28, wherein the detector elements of the multilayer detector modules comprise scintillator detectors in at least the first and second layers and further comprise semiconductor detectors or structured semiconductor detectors or structured mold detectors in at least one of the first and second layers, or in another layer of the multilayer detector modules.

38. The detector system of claim 28, wherein the multilayer detector modules are uniform along the axial direction of the detector system.

39. The detector system of claim 28, wherein the multilayer detector modules are non-uniform along the axial direction of the detector system.

40. The detector system of claim 39, wherein a number of layers of the detector elements in the multilayer detector modules varies along the axial direction, or wherein a material composition of the detector elements varies along the axial direction, or wherein both the number of layers and the material composition vary along the axial direction.

41. The detector system of claim 40, wherein the number of layers or material composition are selected based on different spectra of the radiation along the axial direction, or wherein both the number of layers and the material composition are selected based on the different spectra.

42. The detector system of claim 41, wherein the material composition varies to compensate for beam hardening of the radiation as it propagates through the layers of the detector elements.

43. The detector system of claim 28, further comprising one or more detector modules with n layers of detector elements configured to generate signals in response to the radiation incident on the n layers of the detector modules, wherein n is one, two, three or four.

44. The detector system of claim 43, wherein n varies along the axial direction.

* * * * *

UNITED STATES PATENT AND TRADEMARK OFFICE
CERTIFICATE OF CORRECTION

PATENT NO. : 11,073,625 B2
APPLICATION NO. : 16/284776
DATED : July 27, 2021
INVENTOR(S) : Robert Sigurd Nelson and William Bert Nelson Page 1 of 5

It is certified that error appears in the above-identified patent and that said Letters Patent is hereby corrected as shown below:

On the Title Page

Item (57) Abstract, Line 1 reads:
"Detector module designs for radiographic include"
Should be:
--Detector module designs for radiographic imaging include--

In the Specification

Column 4, Line 6 reads:
"CT-PET detector for n=2 at least 1 up to 6"
Should be:
--CT-PET detector for n= at least 1 up to 6--

Column 7, Line 33 reads:
"detect radiation such as changed particles"
Should be:
--detect radiation such as charged particles--

Column 8, Line 60 reads:
"sub-aperture resolution (SIR)"
Should be:
--sub-aperture resolution (SAR)--

Column 10, Line 37 reads:
"Krueger R, et al."
Should be:
--Kroeger R, et al.--

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,073,625 B2

Column 11, Line 34 reads:
"crystal scintillator fibers LuAG or Lutetium Aluminum Garnet"
Should be:
--crystal scintillator fibers (e.g., LuAG or Lutetium Aluminum Garnet--

Column 13, Lines 58-59 read:
"optical pump wavelenth band or interest the pump-probe wavelength bands)."
Should be:
--optical pump wavelength band of interest (or the pump-probe wavelength bands).--

Column 31, Line 39 reads:
"Possible scintillators with at east one"
Should be:
--Possible scintillators with at least one--

Column 32, Line 42 reads:
"electron multiplier CODs"
Should be:
--electron multiplier CCDs--

Column 36, Line 28 reads:
"semiconductor arrays chiding"
Should be:
--semiconductor arrays (including--

Column 37, Line 49 reads:
"intensity of x-ray's"
Should be:
--intensity of x-rays--

Column 45, Line 61 reads:
"AN implementations described"
Should be:
--All implementations described--

Column 48, Line 12 reads:
"Pace-on and edge-on"
Should be:
--Face-on and edge-on--

Column 51, Line 6 reads:
"or CLT, scintillators"
Should be:
--or CZT, scintillators--

CERTIFICATE OF CORRECTION (continued)
U.S. Pat. No. 11,073,625 B2

Column 61, Line 33 reads:
"of Ha 9."
Should be:
--of FIG. 9.--

Column 62, Line 33 reads:
"for at east one"
Should be:
--for at least one--

Column 68, Line 28 reads:
"implementations described herein rods,"
Should be:
--implementations described herein (e.g., rods,--

Column 69, Line 43 reads:
"detector) module."
Should be:
--detector module.--

Column 70, Line 50 reads:
"Pulse shape discrimination (PSI))"
Should be:
--Pulse shape discrimination (PSD)--

Column 71, Line 55 reads:
"Furthermore, be employed"
Should be:
--Furthermore, it can be employed--

Column 81, Line 67 reads:
"M rod array"
Should be:
--1D rod array--

Column 82, Line 27 reads:
"distribution fluorescence"
Should be:
--distribution of fluorescence--

Column 87, Line 46 reads:
"CIT"
Should be:
--CZT--

Column 90, Line 22 reads:
"sheets/blacks"
Should be:
--sheets/blocks--

Column 99, Line 42 reads:
"in-level semiconductor detectors"
Should be:
--m-level semiconductor detectors--

Column 101, Line 7 reads:
"backed by in levels"
Should be:
--backed by m levels--

Column 101, Line 21 reads:
"either the (extended)"
Should be:
--in either the (extended)--

Column 106, Line 38 reads:
"face-on ill"
Should be:
--face-on in--

Column 111, Lines 3-4 read:
"(or neck brain)"
Should be:
--(or neck/brain)--

Column 111, Line 27 reads:
"monolithic multilayer multi wire proportional counter"
Should be:
--monolithic multilayer, multiwire proportional counter--

Column 112, Line 26 reads:
"The properties of the hack-end detector"
Should be:
--The properties of the back-end detector--

Column 114, Line 16 reads:
"cover e.g. a battery, a wireless link)."
Should be:
--cover (e.g. a battery, a wireless link).--

Column 115, Line 46 reads:
"sidewalk 164"
Should be:
--sidewalls 164--

Column 124, Line 26 reads:
"Part Image reconstruction"
Should be:
--Part II: Image reconstruction--